(12) United States Patent
Genkin et al.

(10) Patent No.: US 11,905,522 B2
(45) Date of Patent: Feb. 20, 2024

(54) TREATMENT OF DISEASES BY LIVER EXPRESSION OF AN ENZYME WHICH HAS A DEOXYRIBONUCLEASE (DNASE) ACTIVITY

(71) Applicant: CLS THERAPEUTICS LIMITED, Saint Peter Port (GG)

(72) Inventors: Dmitry Dmitrievich Genkin, Saint Petersburg (RU); Georgy Viktorovich Tets, Saint Petersburg (RU); Viktor Veniaminovich Tets, Saint Petersburg (RU)

(73) Assignee: CLS THERAPEUTICS LIMITED, Saint Peter Port (GG)

( * ) Notice: Subject to any disclaimer, the term of this patent is extended or adjusted under 35 U.S.C. 154(b) by 107 days.

(21) Appl. No.: 16/248,245

(22) Filed: Jan. 15, 2019

(65) Prior Publication Data
US 2019/0241908 A1    Aug. 8, 2019

Related U.S. Application Data

(60) Provisional application No. 62/617,879, filed on Jan. 16, 2018.

(51) Int. Cl.
| | |
|---|---|
| *A61K 48/00* | (2006.01) |
| *C07H 21/04* | (2006.01) |
| *C12N 15/63* | (2006.01) |
| *C12N 15/00* | (2006.01) |
| *C12N 15/86* | (2006.01) |
| *C12N 9/22* | (2006.01) |
| *A61K 38/46* | (2006.01) |
| *A61P 35/04* | (2006.01) |
| *A61P 25/28* | (2006.01) |
| *A61P 1/16* | (2006.01) |
| *C07K 14/005* | (2006.01) |
| *G01N 33/53* | (2006.01) |
| *C12Q 1/68* | (2018.01) |
| *A01K 67/00* | (2006.01) |
| *A61B 5/00* | (2006.01) |
| *A61B 17/00* | (2006.01) |

(52) U.S. Cl.
CPC ............ *C12N 15/86* (2013.01); *A61K 38/465* (2013.01); *A61K 48/005* (2013.01); *A61K 48/0058* (2013.01); *A61P 1/16* (2018.01); *A61P 25/28* (2018.01); *A61P 35/04* (2018.01); *C07K 14/005* (2013.01); *C12N 9/22* (2013.01); *C12Q 1/68* (2013.01); *G01N 33/5308* (2013.01); *A01K 2207/12* (2013.01); *A01K 2227/105* (2013.01); *A01K 2267/0331* (2013.01); *A61B 5/4848* (2013.01); *A61B 2017/00893* (2013.01); *C12N 2750/14122* (2013.01); *C12N 2750/14143* (2013.01); *C12N 2750/14145* (2013.01); *C12N 2830/008* (2013.01); *G01N 2333/435* (2013.01); *G01N 2800/7028* (2013.01)

(58) Field of Classification Search
CPC .. A61K 48/005; A61K 48/0058; C12N 15/86; C12N 9/22; C12N 2750/14143; C12N 2750/14145; C12N 2830/008
See application file for complete search history.

(56) References Cited

U.S. PATENT DOCUMENTS

| | | |
|---|---|---|
| 3,224,942 A | 12/1965 | Martin |
| 4,485,095 A | 11/1984 | Fujisaki et al. |
| 5,484,589 A | 1/1996 | Salganik |
| 5,656,589 A | 8/1997 | Stossel et al. |
| 5,830,744 A | 11/1998 | Rosen et al. |
| 5,855,920 A | 1/1999 | Chein |
| 5,889,153 A | 3/1999 | Suzuki et al. |
| 5,952,170 A | 9/1999 | Stroun et al. |
| 6,033,846 A | 3/2000 | Fournie |
| 6,156,504 A | 12/2000 | Gocke et al. |
| 6,391,607 B1 | 5/2002 | Lazarus et al. |
| 6,428,785 B1 | 8/2002 | Gokcen |
| 6,455,250 B1 | 9/2002 | Aguilera et al. |
| 6,465,177 B1 | 10/2002 | Hoon |
| 6,521,409 B1 | 2/2003 | Gocke et al. |
| 7,297,526 B2 | 11/2007 | Shak |
| 7,402,724 B2 | 7/2008 | Conover |
| 7,612,032 B2 | 11/2009 | Genkin et al. |

(Continued)

FOREIGN PATENT DOCUMENTS

| | | |
|---|---|---|
| CA | 2184582 A1 | 9/1995 |
| CA | 2394856 A1 | 6/2001 |

(Continued)

OTHER PUBLICATIONS

Sugihara S, Yamamoto T, Tanaka H, Kambara T, Hiraoka T, Miyauchi Y. Deoxyribonuclease treatment prevents blood-borne liver metastasis of cutaneously transplanted tumour cells in mice. British journal of cancer. Jan. 1993;67(1):66-70. (Year: 1993).*
Garley M, Jabłońska E, Dbrowska D. NETs in cancer. Tumor Biology. Nov. 2016;37(11):14355-61. (Year: 2016).*
Hawes MC, Wen F, Elquza E. Extracellular DNA: a bridge to cancer. Cancer research. Oct. 15, 2015;75(20):4260-4. (Year: 2015).*
Kattenhorn LM, Tipper CH, Stoica L, Geraghty DS, Wright TL, Clark KR, Wadsworth SC. Adeno-associated virus gene therapy for liver disease. Human gene therapy. Dec. 1, 2016;27(12):947-61. (Year: 2016).*

(Continued)

*Primary Examiner* — Quang Nguyen
(74) *Attorney, Agent, or Firm* — ENTRALTA PLLC; Peter D. Weinstein; James F. Fleming

(57) ABSTRACT

The invention relates to the liver-specific delivery and/or expression of an enzyme which has a deoxyribonuclease (DNase) activity for enhanced clearance of cell free DNA (cfDNA) accumulated in hepatic porto-sinusoidal circulation and the use of such liver-specific delivery and/or expression for treatment of various diseases and conditions, including cancer and neurodegeneration.

6 Claims, 34 Drawing Sheets
(15 of 34 Drawing Sheet(s) Filed in Color)
Specification includes a Sequence Listing.

(56) References Cited

U.S. PATENT DOCUMENTS

| | | | |
|---|---|---|---|
| 8,388,951 B2 | 3/2013 | Genkin et al. | |
| 8,431,123 B2 | 4/2013 | Genkin et al. | |
| 8,535,663 B2 | 9/2013 | Genkin et al. | |
| 8,710,012 B2 | 4/2014 | Genkin et al. | |
| 8,759,004 B2 | 6/2014 | Coy | |
| 8,796,004 B2 | 8/2014 | Genkin et al. | |
| 8,871,200 B2 | 10/2014 | Genkin et al. | |
| 9,238,682 B2 | 1/2016 | Rosner | |
| 9,695,220 B2 | 4/2017 | Vandenberghe et al. | |
| 10,988,745 B2* | 4/2021 | Posada | C12Y 301/21001 |
| 2002/0076798 A1* | 6/2002 | Miao et al. | |
| 2003/0044403 A1 | 3/2003 | Shak | |
| 2004/0001817 A1 | 1/2004 | Giampapa | |
| 2004/0157239 A1 | 8/2004 | Tanuma et al. | |
| 2006/0228347 A1 | 10/2006 | Sunaga et al. | |
| 2006/0233780 A1 | 10/2006 | Genkin et al. | |
| 2007/0104702 A1 | 5/2007 | Genkin et al. | |
| 2008/0004561 A1 | 1/2008 | Genkin et al. | |
| 2009/0047272 A1 | 2/2009 | Appelbaum et al. | |
| 2009/0053200 A1 | 2/2009 | Genkin et al. | |
| 2010/0061971 A1 | 3/2010 | Genkin et al. | |
| 2010/0150903 A1 | 6/2010 | Genkin et al. | |
| 2010/0303796 A1 | 12/2010 | Genkin et al. | |
| 2011/0033438 A1 | 2/2011 | Bartoov et al. | |
| 2011/0070201 A1 | 3/2011 | Shaaltiel et al. | |
| 2011/0189156 A1 | 8/2011 | Genkin et al. | |
| 2012/0252750 A1 | 4/2012 | Shea et al. | |
| 2013/0183283 A1 | 7/2013 | Genkin et al. | |
| 2013/0183284 A1 | 7/2013 | Genkin et al. | |
| 2013/0209443 A9 | 8/2013 | Genkin et al. | |
| 2013/0216516 A1 | 8/2013 | Genkin et al. | |
| 2014/0193389 A1 | 7/2014 | Genkin et al. | |
| 2015/0010523 A1 | 1/2015 | Genkin et al. | |
| 2015/0010527 A1 | 1/2015 | Shaaltiel et al. | |
| 2015/0110769 A1 | 4/2015 | Genkin et al. | |
| 2016/0130570 A1 | 5/2016 | Genkin et al. | |
| 2016/0303204 A1 | 10/2016 | Genkin et al. | |
| 2017/0216456 A1 | 8/2017 | Alexander et al. | |
| 2019/0151365 A1 | 5/2019 | Anak et al. | |
| 2020/0323917 A1 | 10/2020 | Fuchs et al. | |
| 2020/0399623 A1 | 12/2020 | Baik et al. | |

FOREIGN PATENT DOCUMENTS

| | | | |
|---|---|---|---|
| DE | 4024530 A1 | 2/1992 | |
| DE | 10221194 A1 | 12/2003 | |
| EP | 0325191 A2 | 7/1989 | |
| EP | 1431762 A1 | 6/2004 | |
| EP | 1655036 A1 | 5/2006 | |
| EP | 1661579 A2 | 5/2006 | |
| EP | 1666055 A1 | 6/2006 | |
| EP | 1880733 A1 | 1/2008 | |
| EP | 2057465 A2 | 5/2009 | |
| EP | 2095825 A1 | 9/2009 | |
| EP | 2497488 A1 | 9/2012 | |
| GB | 984464 A | 2/1965 | |
| GB | 1005985 A | 9/1965 | |
| IL | 199005 B | 4/2012 | |
| JP | 61293927 A | 12/1986 | |
| JP | 2000-229881 A | 8/2000 | |
| JP | 2006290769 A | 10/2006 | |
| JP | 2010511039 A | 4/2010 | |
| NZ | 299257 A | 7/2000 | |
| RU | 2099080 C1 | 12/1997 | |
| RU | 2001129826/14 C1 | 11/2001 | |
| RU | 2202109 C1 | 4/2003 | |
| RU | 2207876 C1 | 7/2003 | |
| RU | 2003127898/14 | 9/2003 | |
| RU | 2227029 C2 | 4/2004 | |
| RU | 2239404 C1 | 11/2004 | |
| RU | 2239442 C1 | 11/2004 | |
| RU | 2004108060/14 A | 9/2005 | |
| RU | 2267329 C2 | 1/2006 | |
| RU | 2269356 C2 | 2/2006 | |
| RU | 2269357 C2 | 2/2006 | |
| RU | 2269358 C2 | 2/2006 | |
| RU | 2269359 C2 | 2/2006 | |
| RU | 2308968 C2 | 10/2007 | |
| WO | 1993/03709 A1 | 3/1993 | |
| WO | 1995/00170 A1 | 1/1995 | |
| WO | 1997/28266 A1 | 8/1997 | |
| WO | 1997/47751 A1 | 12/1997 | |
| WO | WO-9747751 A1 * | 12/1997 | C12N 9/22 |
| WO | 199904632 A1 | 2/1999 | |
| WO | 2000/003709 A1 | 1/2000 | |
| WO | 2000/031238 A2 | 6/2000 | |
| WO | 2001/074905 A1 | 10/2001 | |
| WO | 2001/82949 A1 | 11/2001 | |
| WO | 2003/068254 A1 | 8/2003 | |
| WO | 2005004789 A2 | 1/2005 | |
| WO | 2005004903 A1 | 1/2005 | |
| WO | 2005004904 A1 | 1/2005 | |
| WO | 2005007187 A1 | 1/2005 | |
| WO | WO 2005/000220 * | 1/2005 | |
| WO | 2005/115444 A2 | 12/2005 | |
| WO | 2006/130034 A1 | 12/2006 | |
| WO | 2008/039989 A2 | 4/2008 | |
| WO | 2008047364 A2 | 4/2008 | |
| WO | 2008/066403 A1 | 6/2008 | |
| WO | WO 2010/042654 * | 4/2010 | |
| WO | 2011/073665 A1 | 6/2011 | |
| WO | 2012/075506 A2 | 6/2012 | |
| WO | 2013114373 A1 | 8/2013 | |
| WO | 2013123503 A1 | 8/2013 | |
| WO | 2014/020564 A1 | 2/2014 | |
| WO | 2014193716 A2 | 12/2014 | |
| WO | 2015054653 A2 | 4/2015 | |
| WO | WO-2015139093 A1 * | 9/2015 | A61K 48/0041 |
| WO | 2016081811 A1 | 5/2016 | |
| WO | 2016108244 A1 | 7/2016 | |
| WO | 2016190780 A1 | 12/2016 | |
| WO | 2017015102 A1 | 1/2017 | |
| WO | 2017019876 A1 | 2/2017 | |
| WO | WO-2017019876 A1 * | 2/2017 | A61K 38/46 |
| WO | 2017074211 A1 | 5/2017 | |
| WO | 2017077451 A1 | 5/2017 | |
| WO | 2017100791 A1 | 6/2017 | |
| WO | 2017/147446 A1 | 8/2017 | |
| WO | 2019036719 A2 | 2/2019 | |
| WO | 2020076817 A1 | 4/2020 | |

OTHER PUBLICATIONS

Santiago-Ortiz JL, Schaffer DV. Adeno-associated virus (AAV) vectors in cancer gene therapy. Journal of Controlled Release. Oct. 28, 2016;240:287-301. (Year: 2016).*

Cools-Lartigue J, Spicer J, McDonald B, Gowing S, Chow S, Giannias B, Bourdeau F, Kubes P, Ferri L. Neutrophil extracellular traps sequester circulating tumor cells and promote metastasis. J Clin Invest. 2013;123:3446-5. (Year: 2013).*

Anatomy of the Portal Circulation; https://www.le.ac.uk/pa/teach/va/anatomy/case5/5_3.html; retrieved from on Sep. 3, 2021 (Year: 2021).*

Shak S, Capon DJ, Hellmiss R, Marsters SA, Baker CL. Recombinant human DNase I reduces the viscosity of cystic fibrosis sputum. Proceedings of the National Academy of Sciences. Dec. 1, 1990;87(23):9188-92. (Year: 1990).*

Grimm D, Pandey K, Nakai H, Storm TA, Kay MA. Liver transduction with recombinant adeno-associated virus is primarily restricted by capsid serotype not vector genotype. Journal of virology. Jan. 1, 2006;80(1):426-39 (Year: 2006).*

Alignment of GenBank Accession: M55983 with instant SEQ ID No. 5 and 30 (Year: 2022).*

Pan et al. Improved potency of Hyperactive and Actin-resistant human DNase I variants for treatment of Cystic Fibrosis and Systemic Lupus Erythematosus. J. Biol. Chem. 273:18374-18381, (Year: 1998).*

Otsenka mukoliticheskogo effekta pulmozima u bolnykh mukovistsidozom, Ekaterinburg, 1999, PhD dissertation in medicine, (Reference in Russian and English Translation).

Shah, P.L., et al., "Medium Term Treatment of Stable Stage Cystic Fibrosis with Recombinant Human Dnase I," Thorax, 1995, vol. 50, pp. 333-338.

(56) References Cited

OTHER PUBLICATIONS

Shak, S., et al., "Recombinant Human DNAse I Reduces the Viscosity of Cystic Fibrosis Sputum," Proc. Natl. Acad. Sci. USA, 1990, vol. 87, pp. 9188-9192.
Sherry, S., et al., "Presence and Significance of Desoxyribose Nucleoprotein in the Purulent Pleural Exudates of Patients," Experiemtnal Biology and Medicine, 1948, vol. 68, Issue 1, pp. 179-184.
Shevchuk, N.A., Vremyarazreshenniy Immunofluorescentniy Analiz na DNK i Issledovanie Soderzhaniya DNK v Syvoroike Cheloveka, Voprosi Medicinskoi Khimii, No. 4, 2001 (Reference in Russian and English Translation).
Shimony, A., et al., "Cell Free DNA Detected by a Novel Method in Acute ST-Elevation Myocardial Infarction Patients," Acute Cardiac Care, 2010, vol. 12, Issue 3, pp. 109-111.
Shuster, A.M., et al., "DNA Hydrolyzing Autoantibodies," Science, 1992, vol. 256, Issue 5057, pp. 665-667.
Sigma Product Information Sheet for Deoxyribonuclease I from Bovine Pancreas, 2006.
Simpson, G., et al., "Successful Treatment of Empyema Thoracis with Human Recombinant Deoxyribonuclease," Thorax, 2003, vol. 58, No. 4, pp. 365-366.
Sugihara, S., et al., "Deoxyribonuclease Treatment Prevents Blood-Borne Liver Metastasis of Cutaneously Transplanted Tumour Cells in Mice," British Journal of Cancer, 1993, vol. 67, No. 1, pp. 66-70.
Tetz, G.V., et al., "Effect of DNase and Antibiotics on Biofilm Characteristics," Antimicrobial Agents and chemotherapy, 2009, vol. 53, No. 3, pp. 1204-1209.
Tetz, GV, et al., "Effect of Nucleolytic, Proteolytic, and Lipolytic Enzymes on Transfer of Antibiotic Resistance Genes in Mixed Bacterial Communities," Universal Journal of Medicine and Dentistry, 2012, vol. 1, No. 4, pp. 46-50.
Tetz, V.V., et al., "Effect of Extracellular DNA Destruction by DNase I on Characteristics of Forming Biofilms," DNA and Cell Biology, 2010, vol. 29, No. 8, pp. 399-405.
Tolkoff-Rubin, N.E., et al., "Recent Advances in the Diagnosis and Management of Infection in the Organ Transplant Receipient," Seminars of Nephrology, 2000, vol. 20, No. 2, pp. 148-163.
Treshalin, I.D., et al., "Modification of antitumor drugs toxicity as a method of enhancing anticancer chemotherapeutic efficacy," Possiiskii bioterapeuticheskii zhurnal, 2005, tom 4, No. 3, pp. 87-94.
Ulrich, R., et al., "Toxicogenomics and Drug Discovery: Will New Technologies Help us Produce Better Drugs?," Nature, 2002, vol. 1, pp. 84-88.
Van Der Vaart, M., et al., "A Method of Characterization of Total Circulating DNA," Annals of the New York Academy of Sciences, 2008, vol. 1137, pp. 92-97.
Varidase Buccal Tablets product information from Lederle Laboratories Inc., Canad. M. A. J., 1961, vol. 84, pp. 867-868.
Varidase product information from EPGOnline, accessed on Dec. 12, 2011, total 2 pages.
VIJG, J., "Somatic Mutations, Genome Mosaicism, Cancer and Aging," Current Opinion in Genetics & Development, 2014, vol. 26, pp. 141-149.
Vonmoos, P.L., et al., "Absorption and Hematologic Effect of Streptokinase-Streptodornase (varidase) After Intracavital or Oral Administration," Schweiz Med Wochenschr, 1979, vol. 109, pp. 1538-1544, Abstract.
Whitchurch, C.B., et al., "Extracellular DNA Required for Bacterial Biofilm Formation," Science, 2002, vol. 295, Issue 5559, pp. 1487.
Whitfield, J.F., et al., "The Effects of X-Radiation on Lactate Metabolism of Mammalian Cells," Experiemental Cell Research, 1964, vol. 37, Issue 3, pp. 637-649.
WHO Laboratory Manual for the Examination of Human Semen and Sperm-cervical Mucus Interaction, 4th ed., Cambridge University Press, 1999, pp. 128.
Written Opinion issued International Application No. PCT/RU2015/000721 dated Aug. 18, 2016, 4 pages.
Written Opinion issued International Application No. PCT/RU2016/000284 dated Oct. 7, 2016, 5 pages.

Yastrebova / Yaserova N.E., "Razrabotka I Izuchenie diagnosticheskikh vozmozhnostei immunofermentnykh test-sistem na osnove antigennykh preparatov zolotistogo stafilokokka I DNK," Avtoreferat dissertatsii na soiskanie uchenoi stepeni kandidata meditsinskikh nauk (author's abstract of PhD thesis in medical sciences), M., 1988, pp. 17-18, (Reference in Russian and English language translation).
Yasuda, T., et al., "Activity Measurement for Deoxyribonucleases I and II with Picogram Sensitivity Based on DNALSYBR Green I Fluorescence," Analytical Biochemistry, 1998, vol. 255, Issue 2, pp. 274-276.
Ye, L., et al., "Quantification of Circulating Cell-Free DNA in the Serum of Patients with Obstructive Sleep Apnea-Hypopnea Syndrome," Lung, 2010, vol. 188, Issue 6, pp. 469-474.
Youssoufian, H., et al., "Mechanisms and Consequences of Somatic Mosaicism in Humans," Nature Reviews Genetics, 2002, vol. 3, pp. 748-758.
Zaman, S., et al., "Direct Amplification of Entamoeba Histolytica DNA from Amoebic Liver Abscess Pus Using Polymerase Chain Reaction," Parasitology Research, 2000, vol. 86, Issue 9, pp. 724-728.
Zaravinos, A., et al., "Levosimendan Reduces Plasma Cell-Free DNA Levels in Patients with Ischemic Cardiomyopathy," J. Thromb. Thrombolysis, 2011, vol. 31, pp. 180-187.
Zhong, S., et al., "Presence of Mitochondrial tRNA(leu(UUR) A to G 3243 Mutation in DNA Extracted from Serum and Plasma of Patients with Type 2 Diabetes Mellitus," Journal of Clinical Pathology, 2000, vol. 53, pp. 466-469.
Communication issued in European Search Report for European Patent Appl. No. EP04775224, dated Jul. 5, 2011.
International Preliminary Report on Patentability issued by the International Searching Authority in International Application No. PCT/RU2015/000721, dated May 1, 2018, 5 pages total.
Song, L. et al., "NLRP3 Inflammasome in Neurological Diseases, from Functions to Therapies" Front. Cell. Neurosci., 2017, vol. 11, No. 63.
Tohme, S. et al., "Neutrophil Extracellular Traps Promote the Development and Progression of Liver Metastases after Surgical Stress" Cancer Res., Mar. 15, 2016, 76(6): 1367-1380.
Demers, M. at al., "Cancers predispose neutrophils to release extracellular DNA traps that contribute to cancer-associated thrombosis" PNAS, 2012, 109(32):13076-13081.
Dan Li, DNase I Treatment Reduces GVHD in Mice. Biology of Blood and Marrow Transplantation (2015) vol. 21, Issue 2, p. S339.
Sawyers 2008 C.L., "The cancer biomarker problem" Nature ,2008, 452(7187):548-552.
Wen, F. et al., "Extracellular DNA in Pancreatic Cancer Promotes Cell Invasion and Metastasis" Cancer Res., 2013, 73:4256-4266.
Emilien, G., et al., "Pharmacological Management of Diabetes: Recent Progress and Future Perspective in Daily Drug Treatment," Pharmacology & Therapeutics, 1999, vol. 81, No. 1, pp. 37-51.
Epstein, S.E., et al., "Infection and Atherosclerosis: Potential Roles of Pathogen Burden and Molecular Mimicry," Arterioscler Thrombosis Vascular Biology, 2000, vol. 20, No. 6, pp. 1417-1420.
Erickson, R.P., "Somatic Gene Mutation and Human Disease Other than Cancer," Mutation Research, 2003, vol. 543, Issue 2, pp. 125-136.
Erickson, R.P., "Somatic Gene Mutation and Human Disease Other than Cancer: An Update," Mutation Research, 2010, vol. 705, Issue 2, pp. 96-106.
Favorov, P.V., "Issledovanie kinetiki prevrashcheny DNK pod deystviem DNK-topoizomeraz I DNK-abzimov, author's abstract of PhD thesis in biological sciences, M.," 1999, pp. 3-4, (Reference in Russian and English-language translation).
Finlay, B.J., "The Global Diversity Protozoa and Other Small Species," International Journal of Parasitology, 1998, vol. 28, Issue 1, pp. 29-48.
Freshney, R. I., "Culture of Animal Cells: A Manual of Basic Technique," Alan R. Liss, Inc., 1983, pp. 3-4.
Funakoshi, A., et al., "Clinical Investigation of Serum Deoxyribonuclease: II. Clinical Studies of Serum Deoxyribonuclease Activity in Pancreatic Disease, " Gastroenterologia Japonica, 1979, vol. 14, Issue 5, pp. 436-440.

(56) References Cited

OTHER PUBLICATIONS

Gal, S., et al., "Detection and Quantification of Circulating Plasmodium Falciparum DNA by Polymerase Chain Reaction," Methods in Molecular Biology, 2006, vol. 336, pp. 155-162.
Gannushkina, I.V., et al., "Plasma DNA Levels in Patients with Atherosclerotic Involvement of the Major Arteries of the Head and lateral Amyotrophic Sclerosis, Bulletin of Experimental Biology and Medicine," 1997, vol. 124, Issue 6, pp. 1164-1166 (Translated from: Gannushkina LV et al., 'Uroven DNK v plazme krovi bolnykh s arteroskloticheskim porazheniem magistralnykh artery golovy I bokovym amiotroficheskim sklerozom, Byulleten' Experimental'noi Biologii i Meditsiny, Moscow, Meditsina, No. 12, pp. 610-612, 1997).
Gibbs, J.B., "Mechanism-Based Target Identification and Drug Discovery in Cancer Research Science," Science, 2000, vol. 287, pp. 1969-1973.
Gibson, R.L., "Pathophysiology and Management of Pulmonary Infections in Cystic Fibrosis," American Journal of Respiratory and Critical Care Medicine, 2003, vol. 168, No. 8, pp. 918-951.
Glebova, K.V., et al., "Properties of Extracellular DNA from the Cerebrospinal Fluid and Blood Plasma during Parkinson's Disease," Bulletin of Experimental Biology and Medicine, 2014, vol. 156, Issue 6, pp. 826-828.
Gluhov, B.M., "Znachenije nukleaz v patogeneze neirovirusnyh zabolevanij, Avtoreferat dissertatsii na soiskanie uchenoi stepeni doktora medicinskikh nauk (author's abstract of MD thesis in medical sciences)," Novosibirsk, pp. 15-16, 21-26, 1996 (Reference in Russian and English-language translation of pp. 14-17 and 20-27).
Gormally, E., et al., "Circulating Free DNA in Plasma or Serum as Biomarker of Carcinogenesis: Practical Aspects and Biological Significance," Mutation Research, 2007, vol. 635, Issues 2-3, pp. 105-117.
Gorrini, C., et al., "Effect of Apoptogenic Stimuli on Colon Carcinoma Cell Lines with a Different c-myc Expression Level," International Journal of Molecular Medicine, 2003, vol. 11, No. 6, pp. 737-742.
Gould, K.L., "New Concepts and Paradigms in Cardiovascular Medicine: The Noninvasive Management of Coronary Artery Disease," The American Journal of Medicine, 1998, vol. 104, pp. 2s-17s.
Graham, R.M., "Cyclosporine: Mechanisms of Action and Toxicity," Cleaveland Clinic Journal of Medicine, 1994, vol. 61, No. 4, pp. 308-313.
Gura, T., "Systems for Identifying New Drugs Are Often Faulty," Science, 1997, vol. 278, pp. 1041-1042.
Hakkim, A., et al., "Impairment of Neutrophil Extracellular Trap Degradation is Associated with Lupus Nephritis," PNAS, 2010, vol. 107, No. 21, pp. 9813-9818.
Hann, B., et al., "Building 'Validated' Mouse Models of Human Cancer," Current Opinion in Cell Biology, 2001, vol. 13, Issue 6, pp. 778-784.
Harley, C., "Telomere Loss: Miotic Clock or Genetic Time Bomb?," Mutation Resrarch/DNAging, 1991, vol. 256, Issue 2-6, pp. 271-281.
Hawes, M.C., et al., "Extracellular DNA: A Bridge to Cancer," Cancer Research, 2015, vol. 75, No. 20, pp. 1260-4264.
Hayflick, L., "Aging Under Glass," Department of Medical Microbiology, Stanford University School of Medicine, 1970, pp. 291-303.
Hayflick, L., "The Limited in Vitro Lifetime of Human Diploid Cell Stains," Experimental Cell Research, 1965, vol. 37, pp. 614-635.
Hayflick, L., et al., "The Serial Cultivation of Human Diploid Cell Stains," Experimental Cell Research, 1961, vol. 25, pp. 585-621.
Holterhus, P-M., et al., "Mosaicism Due to a Somatic Mutation of the Androgen Receptor Gene Determines Phenotype in Androgen Insensitivity Syndrome," Journal of Clinical Endocrinology & Metabolism, 1997, vol. 82, Issue 11, pp. 3584-3589.
Horlitz, M., et al., "Optimized Quantification of Fragmented, Free Circulating DNA in Human Blood Plasma Using a Calibrated Duplex Real-Time Pcr," PLoS One, 2009, vol. 4, Issue 9, e7207, total 6 pages.
Hursting, S.D., et al., "Calorie Restriction, Aging and Cancer Prevention: Mechanisms of Action and Applicability to Humans," Annual Review of Medicine, 2003, vol. 54, pp. 131-152.
Huttunen, R., et al., "Fatal Outcome in Bacteremia is Characterized by High Plasma Cell Free DNA Concentration and Apoptotoc DNA Fragmentation: A Prospective Cohort Study," PLoS One, 2011, vol. 6, e21700, total 8 pages.
International Search Report and Written Opinion for PCT/RU2015/000721, dated Aug. 25, 2016.
International Search Report and Written Opinion for PCT/RU2016/000284, dated Nov. 10, 2016.
International Search Report for PCT/GB2011/051557, dated Feb. 27, 2012.
International Search Report for PCT/RU2003/000304, dated Mar. 25, 2004.
International Search Report for PCT/RU2004/000260, dated Dec. 9, 2004.
International Search Report for PCT/RU2004/000261, dated Oct. 21, 2004.
International Search Report for PCT/RU2004/000262, dated Oct. 21, 2004.
International Search Report for PCT/RU2005/000236, dated Nov. 24, 2005.
International Search Report for PCT/RU2006/000642, dated Aug. 2, 2007.
International Search Report for PCT/US2011/043290, dated Dec. 9, 2011.
Irvine, D., et al., "DNA Integrity in Human Spermatozoa: Relationships with Semen Quality," Journal of Andrology, 2000, vol. 21, No. 1, pp. 33-44.
Juncosa, B., "DNA on the Loose: Next-Gen Blood Tests Tap Free-Floating Genetic Material," Scientific American, 2009, total 5 pages.
Jylhava, J., et al., "Aging is associated with quantitative and qualitative changes in circulating cell-free DNA: the Vitality 90+ study," Mechanisms of Ageing and Development, 2011, vol. 132, Issues 1-2, pp. 20-26.
Kadioglu, E., et al., "Detection of oxidative DNA damage in lymphocytes of patients with Alzheimer's disease," Biomarkers, 2004, vol. 9, Issue 2, pp. 203-209.
Kagan, V.E., et al., "Toward Mechanism-based Antioxidant Interventions," Annals of the New York Academy of Sciences, 2002, vol. 959, pp. 188-198.
Kalandarishvili, F., "Nakoplenie spontanno povrezhdennoj DNK v ne-i postgepatjektomirovannoj pecheni u staryh krys," Med. Novosti Gruzii, No. 5, pp. 11-12, 1998 (Reference in Russian and English-language translation).
Kaprin, et al., "Prognoz i lechenie bol'nih poverhnostnim rakom mochevogo puziria visokoi stepeni riska, Visokie Tehnologii v Onkologii," Rostov-na-Donu, vol. 3, pp. 149-150, 2000 (Reference in Russian and English-language translation).
Kawane, K., et at, "DNAse II Deficiency Causes Chronic Polyarthritis in Mice," Nature Clinical Practice Rheumatology, 2007, vol. 3, pp. 192.
Kenyon, C., "A Conserved Regulatory System for Aging", Cell, 2001, vol. 105, pp. 165-168.
Krapf, F., et al., "The Estimation of Circulating Immune Complexes, C3d, and Anti-ds-DNA-Antibody Serum Levels in the Monitoring of Therapeutic Plasmapheresis in a Patient with Systemic Lupus Erythematosus: A Case Report," Clinical and Experimental Rheumatology, 1985, vol. 3, No. 2, pp. 159-162.
Communication (International Search Report) mailed in International Application No. PCT/US2020/41574 dated Dec. 18, 2020, 7 pages total.
Communication (International Search Report) mailed in International Application No. PCT/US2020/41579 dated Dec. 22, 2020, 6 pages total.
Communication (Written Opinion) mailed in International Application No. PCT/US2020/41574 dated Dec. 18, 2020, 11 pages total.

(56) References Cited

OTHER PUBLICATIONS

Communication (Written Opinion) mailed in International Application No. PCT/US2020/41579 dated Dec. 22, 2020, 8 pages total.
Cooke, M.S. et al., "Oxidative DNA Damage: Mechanisms, Mutation, and Disease" The FASEB Journal (2003) vol. 17, pp. 1195-1214.
Klein, C et al., "Genetics of Parkinson's Disease" Cold Spring Harbor Perspectives in Medicine (2012) vol. 2, 15 pages total.
Migliore L., et al., "Chromosome and Oxidative Damage Biomarkers in Lymphocytes of Parkinson's Disease Patients" International Jounal of Hygiene and Environmental Health (2001) vol. 204, pp. 61-66.
Zhang, J. et al., "Parkinson's Disease is Associated with Oxidative Damage to Cytoplasmic DNA and RNA in Substantia Nigra Neurons" American Journal of Pathology (1999) vol. 154, No. 5, pp. 1423-1429.
Anunobi, R. et al., "Extracellular DNA Promotes Colorectal Tumor Cell Survival after Cytotoxic Chemotherapy" Journal of Surgical Research (2018) vol. 226, pp. 181-191.
Communication (Extended European Search report) issued by the Europe Patent Office in European application No. 15907392.3 dated May 24, 2019, 8 pages total.
Esposito, S. et al., "The Place of Desoxyribonuclease in the Treatment of Chronic Lymphatic Leukemia" Database EMBASE, Elsevier Science Publishers (1972) 1 page total.
Foote, M., "The Importance of Planned Dose of Chemotherapy on Time: Do We Need to Change our Clinical Practice?" The Oncologist: Physician Education (1998) vol. 3, pp. 365-368.
García-Olmo D.C. and García-Olmo, D. "Biological role of cell-free nucleic acids in cancer: the theory of genometastasis" Crit Rev Oncolog., 2013, 18:153-161.
Communication (Japanese Notice of Grounds for Rejection) issued by the Japanese Patent Office in Japanese Application No. 2018-519282, dated Jun. 27, 2019, 9 pages total.
Kanyshkova, TG et al., "Multiple enzymic activities of human milk lactoferrin" European Journal of Biochemistry (2003) vol. 270, No. 16, pp. 3353-3361.
Lelbach, A. et al., "Current Perspectives of Catabolic Mediators of Cancer Cachexia" Med Sci Monit (2007) vol. 13, No. 9, pp. RA168-173.
Meirovitz, A. et al., "Novel Formation of Rnase and DNAse Employing Unique Nanospheres to Allow Oral Drug Delivery and Demonstrate Anticancer Activity" ASCO University (2015) Abstract, 2 pages total.
Mittal, B. et al., "Effect of Recombinant Human Deoxyriboneclease on Oropharyngeal Secretions in Patients with Head-and-Neck Cancers Treated with Radiochemotherapy" International Journal of Radiation Onocology Bioloy Physics (2013) vol. 87, No. 2, pp. 282-289.
Mittra, I. et al., "Prevention of Chemotherapy Toxicity by Agents that Neutralize or Degrade Cell-Free Chromatin" Annals of Oncology (2017) vol. 28, pp. 2119-2127.
Patutina, O. et al., Inhibition of metastasis development by daily administration of ultralow doses of RNase A and DNase I. Biochimie., Apr. 2011, 93(4): 689-96.
Petruzzelli, M. et al., "Mechanisms of Metabolic Dysfunction in Cancer-Associated Cachexia" Genes & Development (2016) vol. 30, pp. 489-501.
Schwarzenbach H. et al., "Detection and monitoring of cell-free DNA in blood of patients with colorectal cancer" Ann. N.Y. Acad. Sci., 2008, 1137:190-196.
Amendment filed in U.S. Appl. No. 10/564,861 dated Jun. 24, 2008.
Anderson, G.P., et al., "Acquired Somatic Mutations in the molecular Pathogenesis of COPD," Trends in Pharmacological Sciences, 2003, vol. 24, Issue 2, pp. 71-76.
Andreassi, M.G., "Coronary Atherosclerosis and Somatic Mutations: An Overview of the Contributive Factors for Oxidative DNA Damage," Mutation Research, 2003, vol. 543, Issue 1, pp. 67-86.
Anker, P., et al., "Tumor-related Alterations in Circulating DNA, Potential for Diagnosis, Prognosis and Detection of Minimal Residual Disease," Leukemia, 2001, vol. 15, No. 2, pp. 289-291.
Arinchina, N.I., et al., "Cellular and Humoral Mechanisms of Immunity Changing," 1982, pp. 280-282.
Ashton, G., "Growing Pains for Biopharmaceuticals," Nature Biotechnology, 2001, vol. 19, pp. 307-311.
Aung, K.L., et al., "Current Status and Future Potential of Somatic Mutation Testing from Circulating Free DNA in Patients with Solid Tumours," HUGO Journal, 2010, vol. 4, No. 1-4, pp. 11-21.
Barrett, J.P., et al., "A Systematic Review of the Antifungal Effectiveness and Tolerability of Amphotericin B Formulations," Clinical Therapeutics, 2003, vol. 25, Issue 5, pp. 1295-1320.
Beckman, J.A., et al., "Diabetes and Atherosclerosis Epidemiology, Pathophysiology, and Management," JAMA, 2002, vol. 287, No. 19, pp. 2570-2581.
Beishon, M., "What Can We Learn from Liquid Biopsies? Early Detection, Disease Prognosis, A Guide to Treatment, A Key to Unlocak the Secrets of How Cancers Evolve. Researchers have High Hopes for What They Can Learn from the Biological Detritus Shed by Primary Tumours and Metastases," CancerWorld, 2015, No. 68, pp. 12-17.
Bertoni, A.G., et al., "Diabetes and the Risk of Infection-Related Mortality in the U.S.," Diabetes Care, 2001, vol. 6, Issue 6, pp. 1044-1049.
Botto, N., et al., "Elevated Levels of Oxidative DNA damage in Patients with Coronary Artery Disease," Coronary Artery Disease, 2002, vol. 13, No. 5, pp. 269-274.
Boyko, M., et al., "Cell-free DNA-A Marker to Predict Ischemic Brain Damage in a Rat Stroke Experimental Model," Journal of Neurosurgical Anesthesiology, 2011, vol. 23, No. 3, pp. 222-228.
Burt, M., et al., "Detection of Circulating Donor Deoxyribonucleic Acid By Microsatellite Analysis in a Liver Transplant Recipient," Liver Transplantation and Surgery, 1996, vol. 2, No. 5, pp. 391-394.
Campisi, J., "Cancer and Ageing: Rival Demons?," Nature Reviews Cancer, 2003, vol. 3, pp. 339-349.
Campisi, J., et al., "Cellular Senescence: When Bad Things Happen to Good Cells," Nature Reviews, 2007, vol. 8, pp. 729-740.
Canudas-Romo, V., "Three Measures of Longevity: Time Trends and Record Values," Demography, 2010; vol. 47, Issue 2, pp. 299-312.
Canuto, M.M., et al., "Antifungal Drug Resistance to Azoles and Polyenes," Lancet Infectious Dieases, 2002, vol. 2, No. 9, pp. 550-563.
Cizman, M., "The Use and Resistance of Antibiotics in the Community," International Journal of Antimicrobial Agents, 2003, vol. 21, Issue 4, pp. 297-307.
Clearfield, M.B., "Statins: Balancing Benefits, Efficacy and Safety," Expert Opinion on Pharmacotherapy, 2002, vol. 3, Issue 5, pp. 469-477.
Communication European Office Action, dated Jun. 12, 2013, which issued during the prosecution of European Patent Application No. 05745412.6, which corresponds to the present application.
Communication Extended European Search Report for European Patent Appl. No. EP12170750 dated Aug. 3, 2012.
Communication Extended European Search Report for European Patent Appl. No. EP12170754 dated Aug. 3, 2012.
Communication Extended European Search Report for European Patent Appl. No. EP12170757 dated Aug. 3, 2012.
Communication issued by the European Patent Office in European Application No. 04 775 224.1, dated Jul. 22, 2010.
Communication issued by the European Patent Office in European Application No. 04748955.4, dated Jan. 11, 2011.
Communication issued by the European Patent Office in European Application No. 04748955.4, dated May 21, 2010.
Communication issued by the Japanese Patent Office in Japanese Application No. 2009-539202, dated Feb. 22, 2013.
Communication issued by the Japanese Patent Office in Japanese Application No. 2009-539202, dated Mar. 13. 2012.
Communication Supplementary European Search Report for European Patent Appl. No. EP03796243, dated Jan. 12, 2010.
Communication Supplementary European Search Report for European Patent Appl. No. EP04748955, dated May 19, 2009.

(56) References Cited

OTHER PUBLICATIONS

Communication Supplementary European Search Report for European Patent Appl. No. EP04775224, dated Oct. 28, 2009.
Communication Supplementary European Search Report for European Patent Appl. No. EP05745412, dated Jul. 10, 2009.
Communication Supplementary European Search Report for European Patent Appl. No. EP06843990, dated Nov. 23, 2009 and cf Form 1507.
Communication Translation of International Preliminary Report on Patentability for PCT/RU2003/000304, dated Nov. 1, 2005.
Communication Translation of International Preliminary Report on Patentability for PCT/RU2004/000260, dated Jan. 14, 2006.
Communication Translation of International Preliminary Report on Patentability for PCT/RU2004/000261, dated Dec. 2, 2005.
Communication Translation of International Preliminary Report on Patentability for PCT/RU2004/000262, dated Apr. 12, 2006.
Communication Translation of International Preliminary Report on Patentability for PCT/RU2005/000236, dated Feb. 13, 2008.
Communication Translation of International Preliminary Report on Patentability for PCT/RU2006/000642, dated Jul. 7, 2009.
Coppe, J-P., et al., "Secretion of Vascular Endothelial Growth Factor by Primary Human Fibroblasts at Senescence," Journal of Biological Chemistry, 2006, vol. 281, No. 40, pp. 29568-29574.
Davis, B.R., et al., "Somatic Mosaicism in the Wiskott-Aldrich Syndrome: molecular and Functional Characterization of Genotypic Revetants," Clinical Immunology, 2010, vol. 135, pp. 72-83.
Davis, J.C., et al., "Recombinant Human Dnase I (rhDNase) in Patients with Lupus Nephritis," LUPUS, 1999, vol. 8, Issue 1, pp. 68-76.
Dayan, A.D., "Forward: Pharmacological-Toxicological (Expert Report on Recombinant Human Deoxyribonuclease I (rhDNase; PulmozymeTm)," Human and Experimental Toxicology, 1994, vol. 3:S2, pp. 41 pages total.
Deitsch, K.W., et al., "Transformation of Malaria Parasites by the Spontaneous Uptake and Expression of DNA from Human Erythrocytes," Nucleic Acids Research, 2001, vol. 29, No. 3, pp. 850-853.
Deocharan B., et al., "Alpha-Actinin is a Cross-Reactive Renal Target for Pathogenic Anti-DNA Antibodies," Journal of Immunology, 2002, vol. 168, pp. 3072-3078.
Department of Health and Human Services Food and Drug Administration, Federal Register, Dec. 13, 1985, vol. 50, No. 240.
Dewitt, D.E., et al., "Outpatient Insulin Therapy in Type 1 and Type 2 Diabetes Mellitus: Scientific Review," JAMA, 2003, vol. 289, No. 17, pp. 2254-2264.
Dittmar, M., et al., "A Novel Mutation in the DNASE1 Gene is Related with Protein Instability and Decreased Enzyme Activity in Thyroid Autoimmunity," Journal of Autoimmunity, 2009, vol. 32, pp. 7-13.
El Hassan, N.O., et al., "Rescue Use of Dnase in Critical Lung Atelectasis Mucus Retention in Premature Neonates," Pediatrics., 2001, vol. 108, pp. 468-470.
Krtolica, A., et al., "Senescent Fibroblasts Promote Epithelial Cell Growth and Tumorigenesis: A Link Between Cancer and Aging," PNAS, 2001, vol. 98, No. 21, pp. 12072-12077.
Lachmann, P.J., "Lupus and Desoxyribonuclease," Lupus, 2003, vol. 12, vol. 12, pp. 202-206.
Lecompte, T., et al., "Detection of Free-Circulating Tumor-Associated DNA in Plasma of Colorectal Cancer Patients and its Association with Prognosis," International Journal of Cancer, 2002, vol. 100, Issue 5, pp. 542-548.
Lee, D., "Continued Marketing of a Useless Drug ('Varidase') in Panama," Lancet, 1990, vol. 335, pp. 667.
Leland, P.A., et al., "Cancer Chemotherapy—Ribonucleases to the Rescue," Chemistry & Biology, 2001, vol. 8, pp. 405-413.
Leon et al., Free DNA in the Serum of Cancer Patients and the Effect of Therapy, Cancer Research, vol. 37, pp. 646-650, 1977.
Li, L.-Q., et al., "The Haemophilus Ducreyi Cytolethal Distending Toxin Activates Sensors of DNA Damage and Repair Complexes in Proliferating and Non-Proliferating Cells," Cellular Microbiology, 2002, vol. 4, No. 2, pp. 87-99.
Li, X., et al., "Systemic Diseases Caused by Oral Infection," Clinical Microbiology Reviews, 2000, vol. 13, No. 4, pp. 547-558.
Liggett, T., et al., "Methylation Patterns of Cell-Free Plasma DNA in Relapsing-Remitting Multiple Sclerosis," Journal of Neurological Sciences, 2010, vol. 290, pp. 16-21.
Macanovic, M., et al., "The Treatment of Systemic Lupus-Erythematosus (SLE) in NZB/W FI-Hybrid Mice-Studies with Recombinant Murine DNase and with Dexamethasone," Clinical and Experimental Immunology, 1996, vol. 106, pp. 243-252.
Malickova, K., et al., "Decreased Activity of DNase-I Predisposes to Immune-Mediated Complications in IBD Patients During Anti-TNFA Treatment," Gastroenterology, 2010, Abstract 202, vol. 138 (5 Supplement 1), pp. S-37.
Martinod, K., et al., "Peptidylarginine Deiminase 4 Promotes Age-Related Organ Fibrosis," Journal of Experimental Medicine, 2017, vol. 214, No. 2, pp. 439-458.
Maurer, H.R., "Bromelain: Biochemistry, Pharmacology and Medical Use," Cellular and Molecular Life Sciences, 2001, vol. 58, pp. 1234-1245.
Mel'Nikov, D., et al., "Voprosy onkologicheskoi pomoschi na etape reformirovaniya zdravookhraneniya," Ekaterinburg, 1996, pp. 159-161 (Reference in Russian and English-language translation).
Merkus, P.J.F.M., et al., "DNase Treatment for Atelectasis in Infants with Severe Respiratory Syncytial Virus Bronchiolitis," European Respiratory Journal, 2001, vol. 18, pp. 734-737.
Moghadasian, M.H., et al., "A Safety Look at Currently Available Statins," Expert Opinion on Drug Safety, 2002, vol. 1, Issue 3, pp. 269-274.
Moreira, V.G., et al., "Usefulness of Cell-Free Plasma DNA, Procalcitonin and C-Reactive Protein as Markers of Infection in Febrile Patients," Annals of Clinical Biochemistry, 2010, vol. 47, pp. 253-258.
Morton, C.O., et al., "Dynamics of Extracellular Release of Aspergillus Fumigatus DNA and Galactomannan During Growth in Blood and Serum," Journal of Medical Microbiology, 2010, vol. 59, pp. 408-413.
Mosca, M., et al., "Cell-Free DNA in the Plasma of Patients with Systemic Sclerosis," Clinical Rheumatology, 2009, vol. 28, pp. 1437-1440.
Mueller, G.M., "Fungal Biodiversity: What Do We Know? What Can We Predict?," Biodiversity and Conservation, 2007, vol. 16, Issue 1, pp. 1-5.
Mutirangura, A., "Serum/Plasma Viral DNA: Mechanisms and Diagnostic Applications to Nasopharyngeal an Cervical Carcinoma," Annals of the New York Academy of Sciences, 2001, vol. 945, pp. 59-67.
National Institute On Aging, "Can We Prevent Aging? Tips from the National Institute on Aging," 2012, pp. 1-8.
Nestle, M., et al., "An Extracellular Nuclease from Serratia Marcescens," Journal of Biological Chemistry, 1969, vol. 244, No. 19, pp. 5213-5218.
Ngan, R.K.C., et al., "Remarkable Application of Serum EBV EBER-1 in Monitoring Response of Nasopharyngeal Cancer Patients to Salvage Chemotherapy," Annals New York Academy of Sciences, 2001, vol. 945, pp. 73-79.
Tikunova., Sozdanie rekombinantnykh antitel 17 protiv virusa kleschevogo entsefalita i izuchenie ikh svoysty, Avtoreferat dissertatsii na soiskanie uchenoi stepeni kandidata biologicheskikh nauk (author's abstract of PhD thesis in biological sciences), Koltsovo, pp. 1-2, 19, 1999 (Reference in Russian and English-language translation).
Oliven, A., et al., "Orally and Rectally Administered Streptokinase," Pharmacology, 1981, vol. 22, pp. 135-138.
Osivac, et al., Reorganizacija DNK i biologicheskoje starenije, Biohimija, 1997, vol. 62, pp. 1491-1502, (Reference in Russian and English-language translation).
Parrinello, S., et al., "Stromal-Epithelial Interactions in Aging and Cancer: Senescent Fibroblasts alter Epithelial Cell Differentiation," Journal of Cell Science, 2004, vol. 118, No. 3, pp. 485-496.
Perel'Man Mi, et al., Molekuljarnaj a medicina i lechenie tuberkuleza, Problemi tuberkuleza, No. 5, pp. 5-7, 2001 (Reference in Russian and English-language translation).

(56) References Cited

OTHER PUBLICATIONS

Perl, T.M., "The Threat of Vancomycin Resistance," The American Journal of Medicine, 1999, vol. 106, Issue 5, pp. 26s-37s.
Pietropalol, M., et al., "Evidence of Islet Cell Autoimmunity in Elderly Patients with Type 2 Diabetes Mellitus," Diabetes, 2000, vol. 49, pp. 32-38.
Pisetsky, D., "Immune Response to DNA in Systemic Lupus Erythematosus," Isr. Med. Assoc. J., 2001, vol. 3, pp. 850-853.
Ponticelli, C., "Renal Transplantation, Past, Present, and Future," Journal of Nephrology, 1999, vol. 12, Suppl. 2, pp. S105-S110.
Pressler, T., "Review of Recombinant Human Deoxyribonuclease (rhDNase) in the Management of Patients with Cystic Fibrosis," Biologics: Targets & Therapy, 2008, vol. 2, No. 4, pp. 611-617.
Prince, W.S., et al., "Pharmacodynamics of Recombinant Human DNase I in Serum," Clin Exp Immunol, 1998, vol. 113, pp. 289-296.
Pulmozyme® (dornase alfa) Inhalation Solution product leaflet, Genetech, Inc., 2005.
Rao, K.S., et al., "Studies on the Synthesis and Degradation of DNA in Developing and Old Chick Cerebellum," Journal of Neurochemistry, 1976, vol. 27, pp. 1205-1210.
Raz, E., et al., "Anti-DNA antibodies bind directly to renal antigens and induce kidney dysfunction in the isolated perfused rat kidney," J. Immunol., 1989, vol. 142, No. 9, pp. 3076-3082.
Riches, A.C., et al., "Blood vol. Determination in the Mouse," Journal of Physiology, 1973, vol. 228, Issue 2, pp. 279-284.
Robertson, D., et al., "The Microbiology of the Acute Dental Abscess," Journal of medical Microbiology, 2009, vol. 58, pp. 155-162.
Roche, Pulmozyme®, Dornase alfa solution for inhalation 1.0 mg/ml, Data Sheet, 2008.
Roper, N.A., "Cause-Specific Mortality in a Population with Diabetes: South Tees Diabetes Mortality Study," Diabetes Care, 2002, vol. 25, No. 1, pp. 43-48.
Ross, K.A., "Evidence of Somatic Gene Conversion and Deletion in Bipolar Disorder, Crohn's Disease, Coronary Artery Disease, Hypertension, Rheumatoid Arthritis, Type-1 Diabetes, and Type-2 Diabetes," BMC Medicine, 2011, vol. 9, No. 12, pp. 1-29.
Rowe P., et al., "WHO Manual for the Standardized Investigation and Diagnosis of the Infertile Couple," Cambridge University Press, 1993, pp. 83.
Rowlatt, C., et al., "Lifespan, Age Changes and Tumour Incidence in an Ageing C57BL Mouse Colony," Laboratory Animals, 1976, vol. 10, pp. 419-442.
Schapira, A.H.V., "Mitochondrial disease," Lancet, 2006, vol. 368, pp. 70-82.
Schloss, P.D., et al., "Status of the Microbial Census," Microbiology and Molecular Biology Reviews, 2004, vol. 68, No. 4, pp. 686-691.
Schmitz, K.H., et al., "The Intersection of Cancer and Aging: Establishing the Need for Breast Cancer Rehabilitation," Cancer Epidemiology, Biomarkers & Prevention, 2007, vol. 16, No. 5, pp. 866-872.
Scoble, J.E., et al., "Athersclerotic Renovascular Disease Causing Renal Impairment—A Case for Treatment," Clinical Nephrology, 1989, vol. 31, No. 3, pp. 119-122.
Sefton, A.M., "Mechanisms of Antimicrobial Resistance," Drugs, 2002, vol. 62, Issue 4, pp. 557-566.
Frain et al., "Binding of a Liver-Specific Factor to the Human Albumin Gene Promoter and Enhancer", Molecular and Cellular Biology, 1990, vol. 10, No. 3, pp. 991-999.
Manderson et al., "The in vivo expression of actin/salt-resistant hyperactive DNase I inhibits the development of anti-ssDNA and anti-histone autoantibodies in a murine model of systemic lupus erythematosus", Arthritis Research & Therapy, 2006, 8:R68. (doi: 10.1186/ar1936).
Tedcastle et al., "Actin-resistant DNAse I Expression from Oncolytic Adenovirus Enadenotucirev Enhances Its Intratumoral Spread and Reduces Tumor Growth", Molecular Therapy, 2016, vol. 24, No. 4, pp. 796-804.

Colella, P. et al., "AAV Gene Transfer with Tandem Promoter Design Prevents Anti-Transgene Immunity and Provides Persistent Efficacy in Neonate Pompe Mice" Methods & Clinical Development (2019) vol. 12, pp. 85-101.
Communication (International Preliminary Report on Patentability) mailed in International Application No. PCT/RU2019/050003 dated Jul. 21, 2020, 8 pages total.
Communication (International Search Report) mailed in International Application No. PCT/RU2019/050003 dated May 7, 2019, 4 pages total.
Communication (Japanese Notice of Grounds for Rejection) issued by the Japanese Patent Office in Japanese Application No. 2018-519282, dated Apr. 23, 2020, 6 pages total.
Communication (Written Opinion) mailed in International Application No. PCT/RU2019/050003 dated May 7, 2019, 7 pages total.
Eun, H-M. et al., "Nucleases" Enzymology Primer for Recombinant DNA Technology (1996) Chapter 3, pp. 145-159.
Fani, L. et al., "Helicobacter Pylori and the Risk of Dementia: A Population-Based Study" Alzheimer's & Dementia (2018) vol. 14, pp. 1377-1382.
Gieffers, J. et al., "Failure to Detect Chlamydia Pneumoniae in Brain Sections of Alzheimer's Disease Patients" Journal of Clinical Microbiology (2000) vol. 38, No. 2, pp. 881-882.
Li, W. et al., "Helicobacter Pylori Infection is a Potential Protective Factor Against Conventional Multiple Sclerosis in the Japanese Population" Journal of Communication (2007) vol. 184, pp. 227-231.
Marques, A.R. et al., "Lack of Evidence of Borrelia Involvement in Alzheimer's Disease" Journal of Infectious Diseases: To the Editor (2000) vol. 182, pp. 1006-1007.
Meng H. et al., "Clinical Application of Polysialylated Deoxyribonuclease and Erythropoietin" Recent Patents on Drug Delivery and Formulation, 2018, vol. 12, pp. 212-222.
Migliore L., et al., Oxidative DNA damage in peripheral leukocytes of mild cognitive impairment and AD patients. Neurobiol Aging. May 2005; 26(5):567-73.
Morell, A.G. et al., "The Role of Sialic Acid in Determining the Survival of Glycoproteins in the Circulation" The Journal of Biological Chemistry (1971) vol. 246, No. 5, pp. 1461-1467.
Nicolson, G.I. et al., "Role of Chronic Bacterial and Viral Infection in Neurodegenerative, Neurobehavioural, Psychiatric, Autoimmune and Fatiguing Illnesses: Part 2" British Journal of Medical Practitioners (2010) vol. 3, No. 1, pp. 24-33.
Nicolson, G.I., "Chronic Bacterial and Viral Infections in Neurodegenerative and Neurobehavioral Diseases" Lab Medicine (2008) vol. 39, No. 5, pp. 291-299.
Podolski, J.L. et al., "Association of Deoxyribonuclease I with the Pointed Ends of Actin Filaments in Human Red Blood Cell Membrane Skeletons" The Journal of Biological Chemistry (1988) vol. 263, No. 2, pp. 638-645.
Ring, R.H. et al., "Failure to Detect Chlamydia Pneumoniae in the Late-Onset Alzheimer's Brain" Journal of Clinical Microbiology (2000) vol. 38, No. 7, pp. 2591-2594.
Scalzo, P.L. et al., "Quantitative Plasma DNA Analysis in Parkinson's Disease" Neuroscience Letters (2009) vol. 452, pp. 5-7.
Smalheiser, N.R., "Mining Clinical Case Reports to Identify New Lines of Investigation in Alzheimer's Disease: The Curious Case of DNase I" Journal of Alzheimer's Disease Reports (2019) vol. 3, pp. 71-76.
Taylor, G.S. et al., "Failure to Correlate C. Pneumoniae with Late Onset Alzheimer's Disease" Neurology (2002) vol. 59, pp. 142-143.
Trysberg, E. et al., "Cerebral Inflammation and Degeneration in Systemic Lupus Erythematosus" Current Opinion in Rheumatology (2004) vol. 16, pp. 527-533.
Victor Tetz et al. Effect of deoxyribonuclease I treatment for dementia in end-stage Alzheimer's disease: a case report. Journal of Medical Case Reports. vol 10, No. 1, May 28, 2016.
Weintraub, K., "Tau Shows Promis as Achilles' Heel for Alzheimer's and Similar Diseases" Neurological Health (2020) https://www.scientificamerican.com/article/tau-shows-promise-as-achilles-heel-for-alzheimers-and-similar-diseases/, 9 pages total.

(56) References Cited

OTHER PUBLICATIONS

Yao, G. et al., "Meta-Anaylsis of Association Between Helicobacter Pylori Infection an Multiple Sclerosis" Neuroscience Letters (2016) vol. 620, pp. 1-7.
Communication (Extended European Search report) issued by the Europe Patent Office in European application No. 19741177.0 dated Sep. 23, 2021, 8 pages total.
Communication (Russian Office Action) issued by the Russia Patent Office in Russian application No. 2020126929, dated Sep. 29, 2021, 12 pages total.
Pakula A.A. et.al., Genetic analysis of protein stability and function, Anna. Rev. Genet, 1989, No. 23, pp. 289-310 (pp. 305-306).
Soussain C. et al. CNS complications of radiotherapy and chemotherapy. The Lancet, vol. 374, Issue 9701, Nov. 7-13, 2009, pp. 1639-1651. https://doi.org/10.1016/S0140-6736(09)61299-X.
Witkowski A. et al. Conversion of a B-Ketoacyl Synthase to a Malonyl Decarboxylase by Replacement of the Active-Site Cysteine with Glutamine. Biochemistry, Jul. 2, 1999, 38, 11643-11650, abstract table. 1.
International Search Report and Written Opinion dated Apr. 1, 2022 for International Patent Application No. PCT/US22/11648, which was filed Jan. 7, 2022 (12 pages).
Kramer, et al., In Vitro and in Vivo Comparative Study of Chimeric Liver-Specific Promoters, Molecular Therapy, Mar. 2003, pp. 375-385, vol. 7, No. 3, The American Society of Gene Therapy, USA.

\* cited by examiner

Organs and structures drained by portal vein

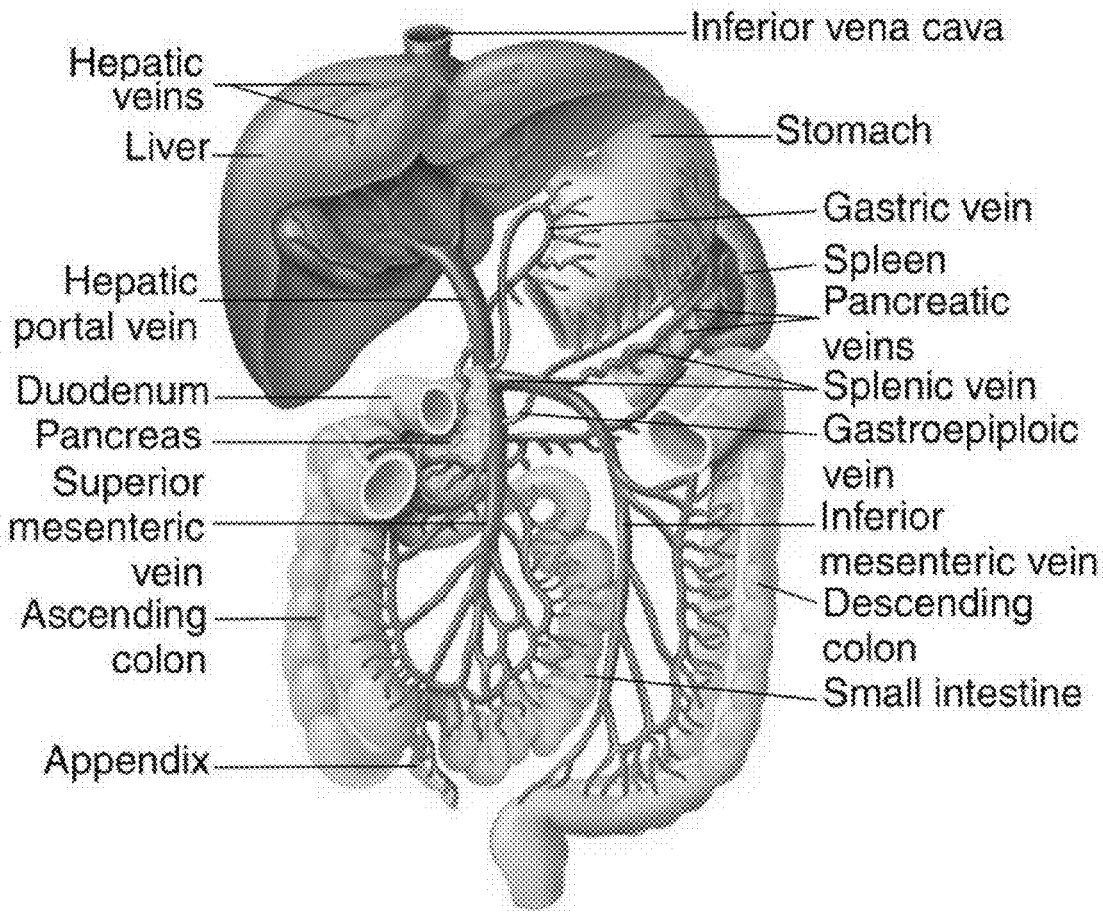

Adapted from Mosby's Medical Dictionary, 9th edition, 2009. (available at https://medical-dictionary.thefreedictionary.com/Portal+venous+system)

Lower part of esophagus
Stomach
Pancreas
Gallbladder
Spleen
Small and large intestine
Upper part of bladder
Liver Tumors
Any carcinoma, sarcoma, lymphoma originating from organs above
Peritoneal carcinomatosis
Metastatic sites in any of organs above

Fig. 1

| Disease summary | Recurrent rectal carcinoma, multiple liver and lung metastasis. T4N3M1. PI | | |
|---|---|---|---|
| Time points | Admission | End of week II | End of week III |
| Electrophoretic profile of circulating cell free DNA in plasma | | | |
| RECIST outcome | The sum of evaluable diameters has 12% increase | | |

| Disease summary | Recurrent renal cancer, multiple bone metastasis. T4NXM1.PVII | | |
|---|---|---|---|
| Time points | Admission | End of week II | End of week III |
| Electrophoretic profile of circulating cell free DNA in plasma | 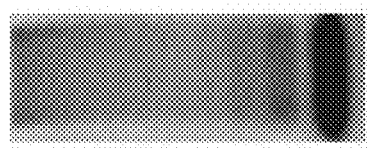 | 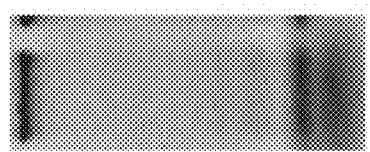 | 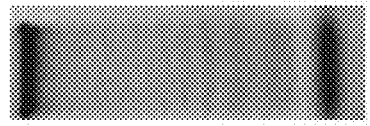 |
| RECIST outcome | The sum of evaluable diameters has 5.5% increase | | |
Fig. 2G

Group 7
Liver of MIA PaCa-2 mice treated by gemcitabine. Intensive diffuse staining for primary anti DNA IgM antibody

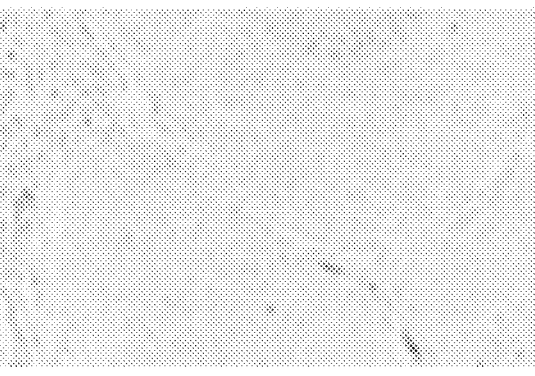

Group 6
Liver of MIA PaCa-2 mice treated by gemcitabine and recombinant DnaseI at 50 mg/kg twice daily for two weeks. Staining for primary anti DNA IgM antibody is less intensive but still significant

Group 3
Liver of MIA PaCa-2 mice treated by gemcitabine and single injection of DnaseI CMVE/CAG AAV8 vector. Staining for primary anti DNA IgM antibody is less intensive vs. group 7 but still significant.

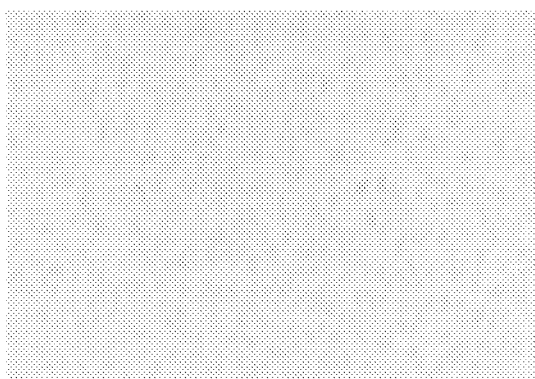

Group 2
Liver of MIA PaCa-2 mice treated by gemcitabine and and single injection of DnaseI mAFP/Alb AAV8 vector. No staining for primary anti DNA IgM antibody.

Fig. 4

Adapted from Zinn et al., "In Silico Reconstruction of the Viral Evolutionary Lineage Yields a Potent Gene Therapy Vector" Cell Reports, 2015, 12, 1-13.

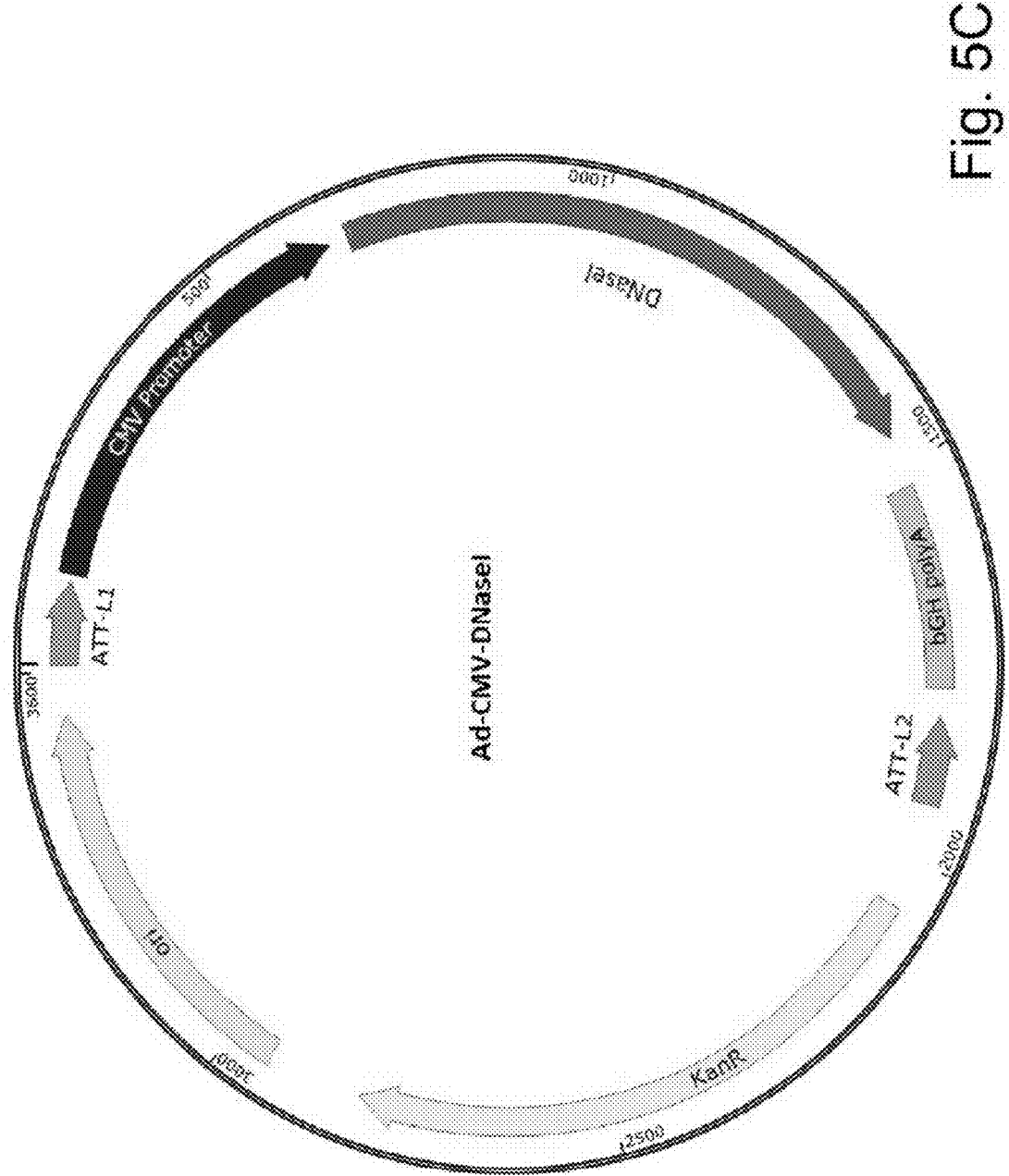

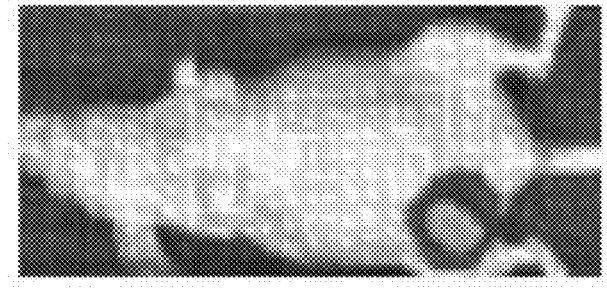
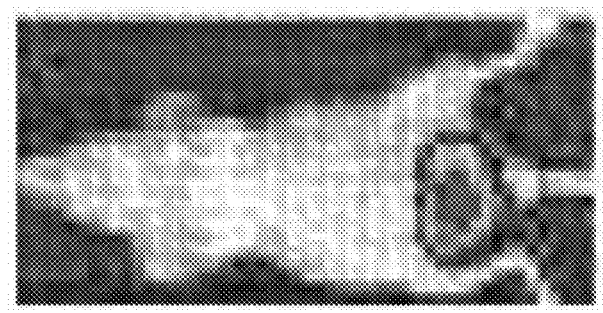
Mice with non-orthotopic pancreatic cancer:
Left Mplacebo
Right MDnaseI mAFP/Alb AAV8
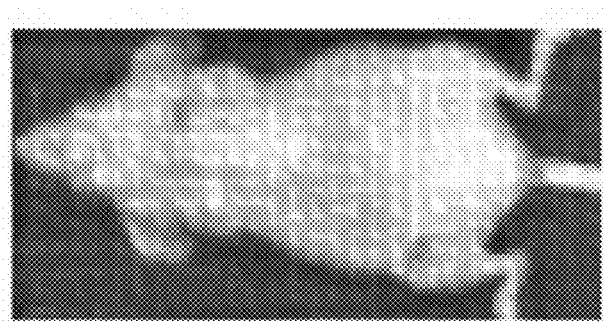
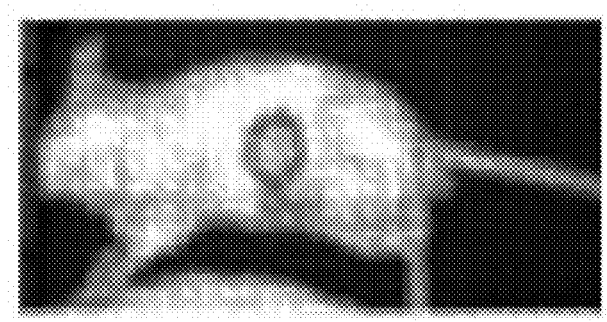
Mice with orthotopic pancreatic cancer:
Left Mplacebo
Right - DnaseI mAFP/Alb AAV8
Fig. 6

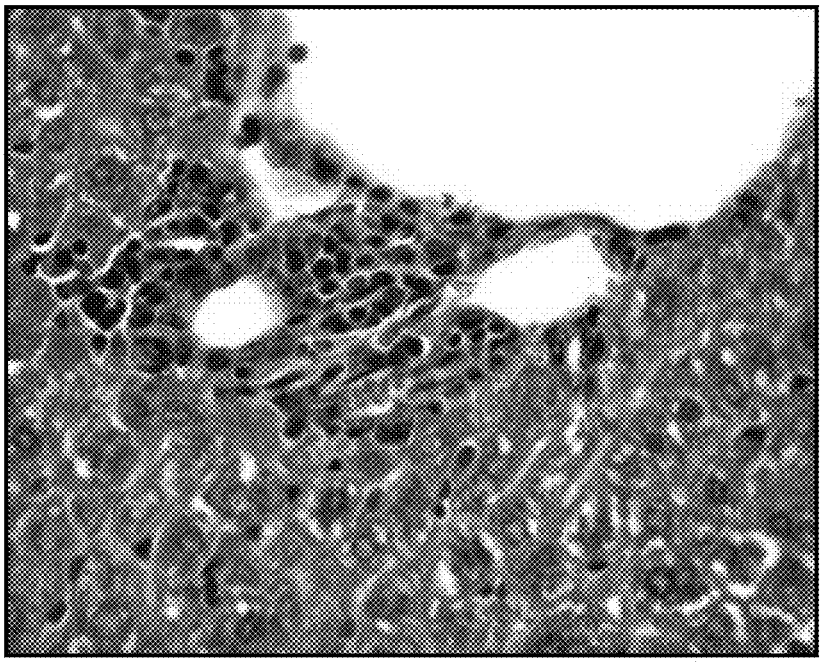
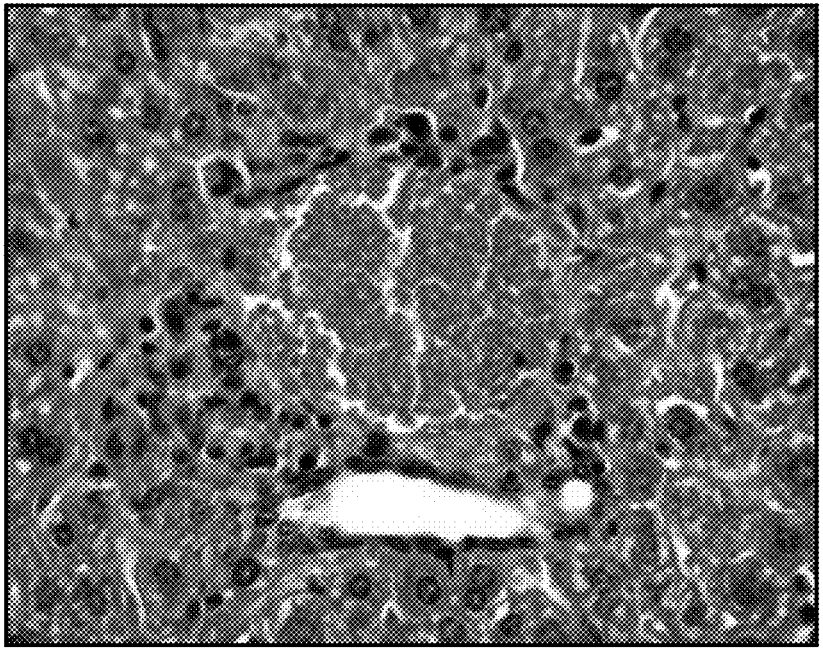

Liver : DNAse I treated (left) and DnaseI mAFP/Alb AAV8 treated (right)

Lymphoplasmacytic infiltration of portal tracts, segmental loss of bile duct epithelial cells, areas of focal necrosis of hepatocytes and significant amount of nucleiphilic material at the vascular interface on the left slide. On the right slide Inflammatory cell density is much lower; no necrosis and much less nucleiphilic material at the vascular interface.

Fig. 7

Significant reduction of total numbers of donor-derived T cells, donor-derived CD4+ and CD8+ T cells in the PLN, MLN and PP in DnaseI mAFP/Alb AAV8 treated recipients compared with recombinant DnaseI treated recipients Complete sequence of ApoEHCR enhancer-hAAT promoter-hDNaseI (hyperactive) correct leader-WPRE Xinact:

aggctcagaggcacacaggagtttctgggctcaccctgcccccttccaaccccctcagttcccatcctccagcagctgtttgtgtgctgcct
ctgaagtccacactgaacaaacttcagcctactcatgtccctaaaatgggcaaacattgcaagcagcaaacagcaaacacacagc
cctccctgcctgctgaccttggagctggggcagaggtcagagacctctctgggcccatgccacctccaacatccactcgacccttgg
aatttcggtggagaggagcagaggttgtcctggcgtggtttaggtagtgtgagagg*atcttgctaccagtggaacagccactaagga*
*ttctgcagtgagagcagagggccagctaagtggtactctcccagagactgtctgactcacgccacccctccaccttggacacagga*
*cgctgtggtttctgagccaggtacaatgactcctttcggtaagtgcagtggaagctgtacactgcccaggcaaagcgtccgggcagcg*
*taggcgggcgactcagatcccagccagtggacttagccctgtttgctcctccgataactgggtgaccttggttaatattcaccagcag*
*cctccccgttgccctctggatccactgcttaaatacggacgaggacagggccctgtctcctcagcttcaggcaccaccactgacctg*
*ggacagtgaat*GCCGCCACCatgaggggcatgaagctgctgggggcgctgctggcactggcggccctactgcagg
gggccgtgtcctgaagatcgcagccttcaacatcaggacatttgggaggaccaagatgtccaatgccaccctcgtcagc
tacattgtgcagatcctgagccgctatgacatcgccctggtccaggaggtcagagacagccacctgactgccgtggggaa
gctgctggacaacctcaatcaggatgcaccagacacctatcactacgtggtcagtgagccactgggacggaagagctata
aggagcgctacctgttcgtgtacaggcctgaccaggtgtctgcggtggacagctactactacgatgatggctgcgagccct
gcgggaacgacaccttcaaccgagagccattcattgtcaggttcttctcccggttcacagaggtcagggagtttgccattgtt
cccctgcatgcggccccggggg acgcagtagccgagatcgacgctctctatgacgtctacctggatgtccaagagaaat
ggggcttggaggacgtcatgttgatgggcgacttcaatgcgggctgcagctatgtgagaccctcccagtggtcatccatcc
gcctgtggacaagccccaccttccagtggctgatccccgacagcgctgacaccacagctacacccacgcactgtgcctat
gacaggatcgtggttgcagggatgctgctccgaggcgccgttgttcccgactcggctcttcccttaacttccaggctgcct
atggcctgagtgaccaactggcccaagccatcagtgaccactatccagtggaggtgatgctgaagtgaagtggcggccgct
cgagctagcggccgctctagaagataatcaacctctggattacaaaatttgtgaaagattgactggtattcttaactatgttgctccttttac
gctatgtggatacgctgctttaatgcctttgtatcatgctattgcttcccgtatggctttcattttctcctccttgtataaatcctggttgctgtctcttt
atgaggagttgtggcccgttgtcaggcaacgtggcgtggtgtgcactgtgtttgctgacgcaacccccactggttggggcattgccacc
acctgtcagctcctttccgggactttcgctttccccctccctattgccacggcggaactcatcgccgcctgccttgcccgctgctggacag
gggctcggctgttgggcactgacaattccgtggtgttgtcggggaaatcatcgtcctttccttggctgctcgcctgtgttgccacctggattct
gcgcgggacgtccttctgctacgtcccttcggccctcaatccagcggaccttccttcccgcggcctgctgccggctctgcggcctcttccg
cgtcttcgccttcgccctcagacgagtcggatctcccttgggccgcctccccgcatcggactag APOE HCR enhancer: 1-320 bases (underlined)

human alpha-1-antitrypsin promoter: 321-717 (italics)

Kozak sequence: 718-726 (capitalized)

human DNaseI hyperactive variant with natural leader sequence: 727-1575 (bold)

WPRE X protein inactivated: 1576-2212 (plain text)

Fig. 10A

40   AAV2/8.CMV.EGFP WPRE.bGH
75   AAV2/Anc80 AAP.APOE.hAAT.hDNaseI-WT WPRE.pA

Cells count and viability 5 days after transduction

| GC/cell | HEP G2 mut | HEP G2 WT | SK-HEP-1 MUT | SK-HEP-1 WT |
|---|---|---|---|---|
| $10^5$ | Live = 85%<br>Cell = $7.1 \times 10^5$ | 83%<br>$7.2 \times 10^5$ | 82%<br>$4.6 \times 10^5$ | 80%<br>$4.7 \times 10^5$ |
| $10^5$ | 90%<br>$7.9 \times 10^5$ | 92%<br>$7.8 \times 10^5$ | 92%<br>$4.8 \times 10^5$ | 93%<br>$4.7 \times 10^5$ |
| $10^4$ | 89%<br>$7.8 \times 10^5$ | 88%<br>$7.7 \times 10^5$ | 89%<br>$5.0 \times 10^5$ | 87%<br>$5.1 \times 10^5$ |
| $10^3$ | 86%<br>$7.5 \times 10^5$ | 83%<br>$7.4 \times 10^5$ | 88%<br>$5.2 \times 10^5$ | 86%<br>$5.1 \times 10^5$ |
| $10^2$ | 85%<br>$7.7 \times 10^5$ | 84%<br>$7.8 \times 10^5$ | 82%<br>$5.6 \times 10^5$ | 82%<br>$5.2 \times 10^5$ |
| 0 | 81%<br>$6.9 \times 10^5$ | 85%<br>$7.0 \times 10^5$ | 89%<br>$4.7 \times 10^5$ | 84%<br>$4.8 \times 10^5$ |

Fig. 13B

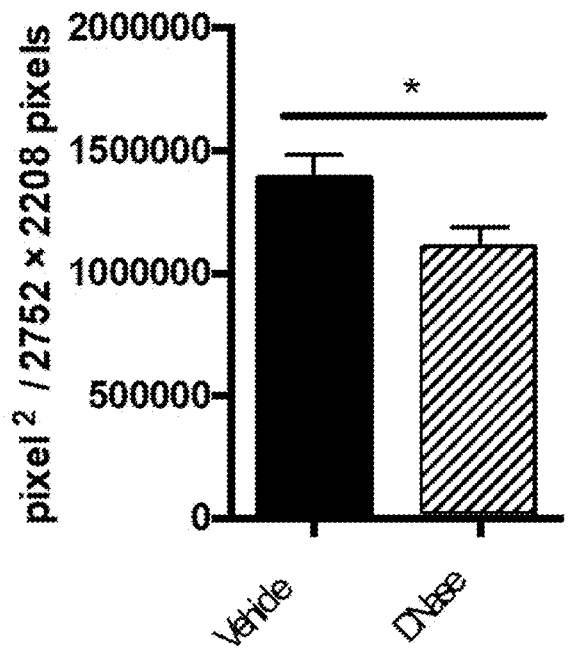
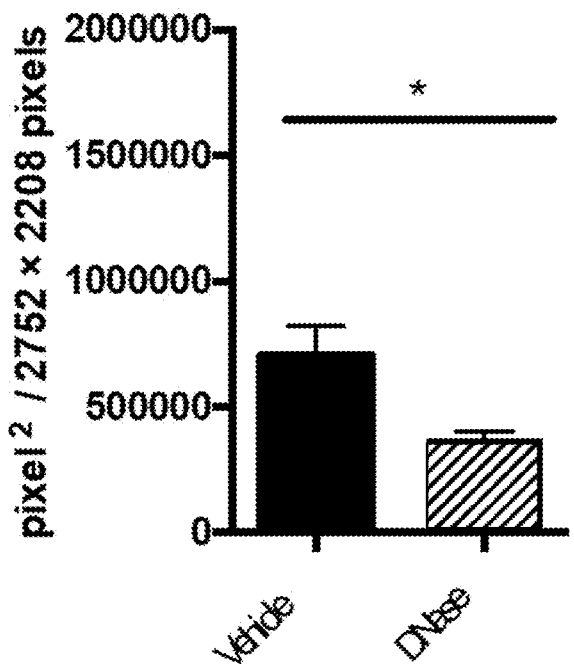
Fig. 18

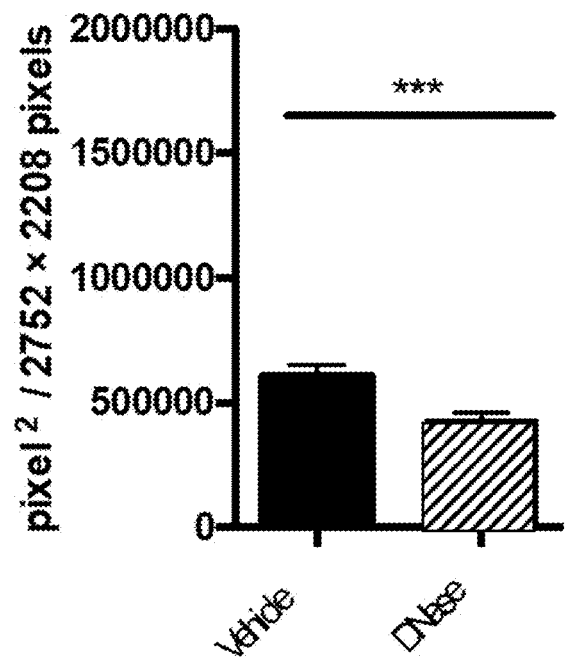
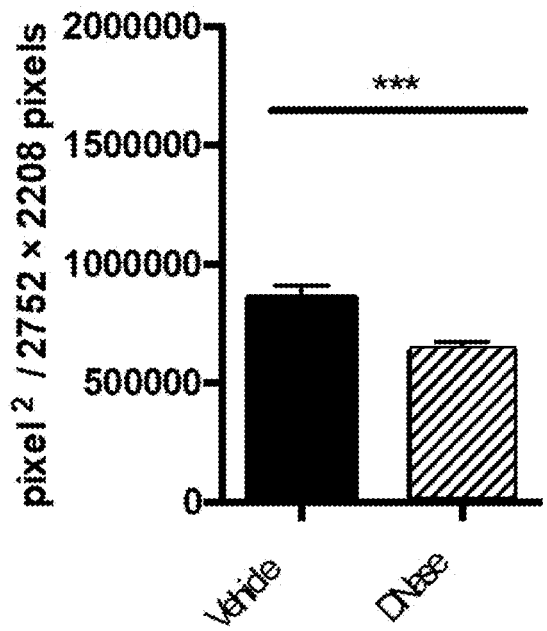
Fig. 18 (cont.)

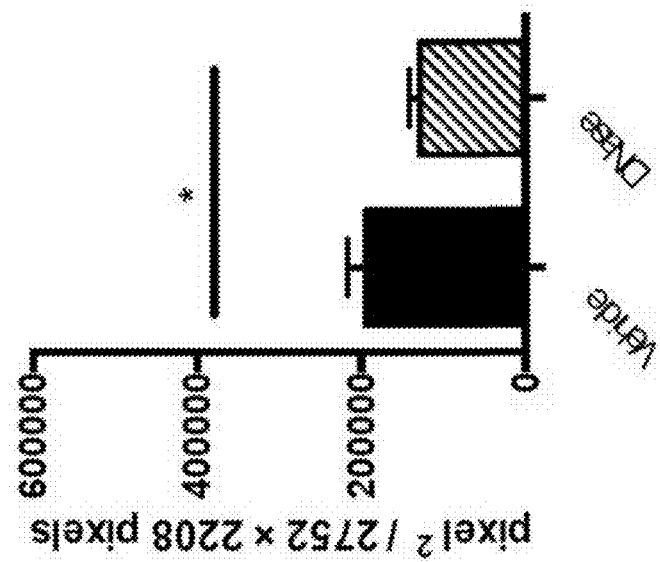
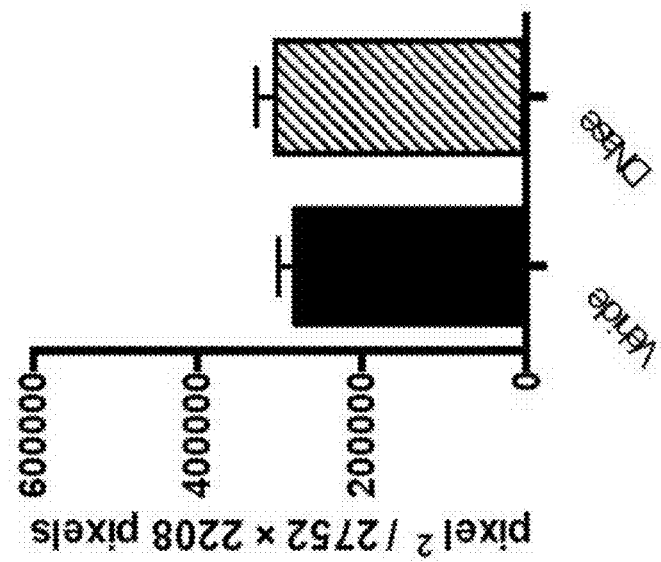
Fig. 19

SEQUENCE LISTING

<160> NUMBER OF SEQ ID NOS: 43

<210> SEQ ID NO 1
<211> LENGTH: 282
<212> TYPE: PRT
<213> ORGANISM: Homo sapiens

<400> SEQUENCE: 1

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
        275                 280

<210> SEQ ID NO 2
<211> LENGTH: 282
<212> TYPE: PRT

<213> ORGANISM: Homo sapiens

<400> SEQUENCE: 2

```
Met Arg Gly Met Lys Leu Leu Gly Ala Leu Ala Leu Ala Ala Leu
1               5                   10                  15

Leu Gln Gly Ala Val Ser Leu Lys Ile Ala Ala Phe Asn Ile Arg Thr
            20                  25                  30

Phe Gly Arg Thr Lys Met Ser Asn Ala Thr Leu Val Ser Tyr Ile Val
            35                  40                  45

Gln Ile Leu Ser Arg Tyr Asp Ile Ala Leu Val Gln Glu Val Arg Asp
        50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Lys
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Phe Ile Val Arg Phe Phe Ser Arg Phe
130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
            275                 280
```

<210> SEQ ID NO 3
<211> LENGTH: 732
<212> TYPE: PRT
<213> ORGANISM: Artificial Sequence
<220> FEATURE:
<223> OTHER INFORMATION: Description of Artificial Sequence: Synthetic
      Anc80 AAV capsid protein
<220> FEATURE:
<221> NAME/KEY: MOD_RES
<222> LOCATION: (166)..(166)
<223> OTHER INFORMATION: Lys or Arg
<220> FEATURE:
<221> NAME/KEY: MOD_RES
<222> LOCATION: (202)..(202)
<223> OTHER INFORMATION: Ala or Ser
<220> FEATURE:
<221> NAME/KEY: MOD_RES
<222> LOCATION: (263)..(263)
<223> OTHER INFORMATION: Ala or Gly
<220> FEATURE:

```
<221> NAME/KEY: MOD_RES
<222> LOCATION: (308)..(308)
<223> OTHER INFORMATION: Arg or Lys
<220> FEATURE:
<221> NAME/KEY: MOD_RES
<222> LOCATION: (408)..(408)
<223> OTHER INFORMATION: Glu or Gln
<220> FEATURE:
<221> NAME/KEY: MOD_RES
<222> LOCATION: (456)..(456)
<223> OTHER INFORMATION: Thr or Glu
<220> FEATURE:
<221> NAME/KEY: MOD_RES
<222> LOCATION: (489)..(489)
<223> OTHER INFORMATION: Ala or Thr
<220> FEATURE:
<221> NAME/KEY: MOD_RES
<222> LOCATION: (558)..(558)
<223> OTHER INFORMATION: Ser or Asn
<220> FEATURE:
<221> NAME/KEY: MOD_RES
<222> LOCATION: (572)..(572)
<223> OTHER INFORMATION: Gln or Glu
<220> FEATURE:
<221> NAME/KEY: MOD_RES
<222> LOCATION: (583)..(583)
<223> OTHER INFORMATION: Ser or Ala
<220> FEATURE:
<221> NAME/KEY: MOD_RES
<222> LOCATION: (605)..(605)
<223> OTHER INFORMATION: Asn or Asp

<400> SEQUENCE: 3

Ala Ala Asp Gly Tyr Leu Pro Asp Trp Leu Glu Asp Asn Leu Ser Glu
1               5                   10                  15

Gly Ile Arg Glu Trp Asp Leu Lys Pro Gly Ala Pro Lys Pro Lys Ala
            20                  25                  30

Asn Gln Gln Lys Gln Asp Asp Gly Arg Gly Leu Val Leu Pro Gly Tyr
        35                  40                  45

Lys Tyr Leu Gly Pro Phe Asn Gly Leu Asp Lys Gly Glu Pro Val Asn
    50                  55                  60

Ala Ala Asp Ala Ala Ala Leu Glu His Asp Lys Ala Tyr Asp Gln Gln
65                  70                  75                  80

Leu Lys Ala Gly Asp Asn Pro Tyr Leu Arg Tyr Asn His Ala Asp Ala
                85                  90                  95

Glu Phe Gln Glu Arg Leu Gln Glu Asp Thr Ser Phe Gly Gly Asn Leu
            100                 105                 110

Gly Arg Ala Val Phe Gln Ala Lys Lys Arg Val Leu Glu Pro Leu Gly
        115                 120                 125

Leu Val Glu Glu Gly Ala Lys Thr Ala Pro Gly Lys Lys Arg Pro Val
130                 135                 140

Glu Gln Ser Pro Gln Glu Pro Asp Ser Ser Gly Ile Gly Lys Lys
145                 150                 155                 160

Gly Gln Gln Pro Ala Xaa Lys Arg Leu Asn Phe Gly Gln Thr Gly Asp
                165                 170                 175

Ser Glu Ser Val Pro Asp Pro Gln Pro Leu Gly Glu Pro Pro Ala Ala
            180                 185                 190

Pro Ser Gly Val Gly Ser Asn Thr Met Xaa Ala Gly Gly Ala Pro
        195                 200                 205

Met Ala Asp Asn Asn Glu Gly Ala Asp Gly Val Gly Asn Ala Ser Gly
210                 215                 220

Asn Trp His Cys Asp Ser Thr Trp Leu Gly Asp Arg Val Ile Thr Thr
225                 230                 235                 240
```

-continued

```
Ser Thr Arg Thr Ala Leu Pro Thr Tyr Asn Asn His Leu Tyr Lys Gln
                245                 250                 255

Ile Ser Ser Gln Ser Gly Xaa Ser Thr Asn Asp Asn Thr Tyr Phe Gly
            260                 265                 270

Tyr Ser Thr Pro Trp Gly Tyr Phe Asp Phe Asn Arg Phe His Cys His
        275                 280                 285

Phe Ser Pro Arg Asp Trp Gln Arg Leu Ile Asn Asn Asn Trp Gly Phe
    290                 295                 300

Arg Pro Lys Xaa Leu Asn Phe Lys Leu Phe Asn Ile Gln Val Lys Glu
305                 310                 315                 320

Val Thr Thr Asn Asp Gly Thr Thr Thr Ile Ala Asn Asn Leu Thr Ser
                325                 330                 335

Thr Val Gln Val Phe Thr Asp Ser Glu Tyr Gln Leu Pro Tyr Val Leu
            340                 345                 350

Gly Ser Ala His Gln Gly Cys Leu Pro Pro Phe Pro Ala Asp Val Phe
        355                 360                 365

Met Ile Pro Gln Tyr Gly Tyr Leu Thr Leu Asn Asn Gly Ser Gln Ala
    370                 375                 380

Val Gly Arg Ser Ser Phe Tyr Cys Leu Glu Tyr Phe Pro Ser Gln Met
385                 390                 395                 400

Leu Arg Thr Gly Asn Asn Phe Xaa Phe Ser Tyr Thr Phe Glu Asp Val
                405                 410                 415

Pro Phe His Ser Ser Tyr Ala His Ser Gln Ser Leu Asp Arg Leu Asn
            420                 425                 430

Pro Leu Ile Asp Gln Tyr Leu Tyr Tyr Leu Ser Arg Thr Gln Thr Thr
        435                 440                 445

Ser Gly Thr Ala Gly Asn Arg Xaa Leu Gln Phe Ser Gln Ala Gly Pro
    450                 455                 460

Ser Ser Met Ala Asn Gln Ala Lys Asn Trp Leu Pro Gly Pro Cys Tyr
465                 470                 475                 480

Arg Gln Gln Arg Val Ser Lys Thr Xaa Asn Gln Asn Asn Asn Ser Asn
                485                 490                 495

Phe Ala Trp Thr Gly Ala Thr Lys Tyr His Leu Asn Gly Arg Asp Ser
            500                 505                 510

Leu Val Asn Pro Gly Pro Ala Met Ala Thr His Lys Asp Asp Glu Asp
        515                 520                 525

Lys Phe Phe Pro Met Ser Gly Val Leu Ile Phe Gly Lys Gln Gly Ala
    530                 535                 540

Gly Asn Ser Asn Val Asp Leu Asp Asn Val Met Ile Thr Xaa Glu Glu
545                 550                 555                 560

Glu Ile Lys Thr Thr Asn Pro Val Ala Thr Glu Xaa Tyr Gly Thr Val
                565                 570                 575

Ala Thr Asn Leu Gln Ser Xaa Asn Thr Ala Pro Ala Thr Gly Thr Val
            580                 585                 590

Asn Ser Gln Gly Ala Leu Pro Gly Met Val Trp Gln Xaa Arg Asp Val
        595                 600                 605

Tyr Leu Gln Gly Pro Ile Trp Ala Lys Ile Pro His Thr Asp Gly His
    610                 615                 620

Phe His Pro Ser Pro Leu Met Gly Gly Phe Gly Leu Lys His Pro Pro
625                 630                 635                 640

Pro Gln Ile Leu Ile Lys Asn Thr Pro Val Pro Ala Asn Pro Pro Thr
                645                 650                 655

Thr Phe Ser Pro Ala Lys Phe Ala Ser Phe Ile Thr Gln Tyr Ser Thr
```

```
              660                 665                 670
Gly Gln Val Ser Val Glu Ile Glu Trp Glu Leu Gln Lys Glu Asn Ser
            675                 680                 685
Lys Arg Trp Asn Pro Glu Ile Gln Tyr Thr Ser Asn Tyr Asn Lys Ser
        690                 695                 700
Thr Asn Val Asp Phe Ala Val Asp Thr Asn Gly Val Tyr Ser Glu Pro
705                 710                 715                 720
Arg Pro Ile Gly Thr Arg Tyr Leu Thr Arg Asn Leu
                725                 730

<210> SEQ ID NO 4
<211> LENGTH: 260
<212> TYPE: PRT
<213> ORGANISM: Homo sapiens

<400> SEQUENCE: 4

Leu Lys Ile Ala Ala Phe Asn Ile Gln Thr Phe Gly Glu Thr Lys Met
1               5                   10                  15
Ser Asn Ala Thr Leu Val Ser Tyr Ile Val Gln Ile Leu Ser Arg Tyr
                20                  25                  30
Asp Ile Ala Leu Val Gln Glu Val Arg Asp Ser His Leu Thr Ala Val
            35                  40                  45
Gly Lys Leu Leu Asp Asn Leu Asn Gln Asp Ala Pro Asp Thr Tyr His
        50                  55                  60
Tyr Val Val Ser Glu Pro Leu Gly Arg Asn Ser Tyr Lys Glu Arg Tyr
65                  70                  75                  80
Leu Phe Val Tyr Arg Pro Asp Gln Val Ser Ala Val Asp Ser Tyr Tyr
                85                  90                  95
Tyr Asp Asp Gly Cys Glu Pro Cys Gly Asn Asp Thr Phe Asn Arg Glu
            100                 105                 110
Pro Ala Ile Val Arg Phe Phe Ser Arg Phe Thr Glu Val Arg Glu Phe
        115                 120                 125
Ala Ile Val Pro Leu His Ala Ala Pro Gly Asp Ala Val Ala Glu Ile
    130                 135                 140
Asp Ala Leu Tyr Asp Val Tyr Leu Asp Val Gln Glu Lys Trp Gly Leu
145                 150                 155                 160
Glu Asp Val Met Leu Met Gly Asp Phe Asn Ala Gly Cys Ser Tyr Val
                165                 170                 175
Arg Pro Ser Gln Trp Ser Ser Ile Arg Leu Trp Thr Ser Pro Thr Phe
            180                 185                 190
Gln Trp Leu Ile Pro Asp Ser Ala Asp Thr Thr Ala Thr Pro Thr His
        195                 200                 205
Cys Ala Tyr Asp Arg Ile Val Val Ala Gly Met Leu Leu Arg Gly Ala
    210                 215                 220
Val Val Pro Asp Ser Ala Leu Pro Phe Asn Phe Gln Ala Ala Tyr Gly
225                 230                 235                 240
Leu Ser Asp Gln Leu Ala Gln Ala Ile Ser Asp His Tyr Pro Val Glu
                245                 250                 255
Val Met Leu Lys
            260

<210> SEQ ID NO 5
<211> LENGTH: 260
<212> TYPE: PRT
<213> ORGANISM: Homo sapiens
```

-continued

```
<400> SEQUENCE: 5

Leu Lys Ile Ala Ala Phe Asn Ile Arg Thr Phe Gly Arg Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
50                  55                  60

Tyr Val Val Ser Glu Pro Leu Gly Arg Lys Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 6
<211> LENGTH: 22
<212> TYPE: PRT
<213> ORGANISM: Homo sapiens

<400> SEQUENCE: 6

Met Arg Gly Met Lys Leu Leu Gly Ala Leu Leu Ala Leu Ala Ala Leu
1               5                   10                  15

Leu Gln Gly Ala Val Ser
            20

<210> SEQ ID NO 7
<211> LENGTH: 20
<212> TYPE: PRT
<213> ORGANISM: Homo sapiens

<400> SEQUENCE: 7

Met Tyr Arg Met Gln Leu Leu Ser Cys Ile Ala Leu Ser Leu Ala Leu
1               5                   10                  15

Val Thr Asn Ser
```

<210> SEQ ID NO 8
<211> LENGTH: 214
<212> TYPE: DNA
<213> ORGANISM: Homo sapiens

<400> SEQUENCE: 8

```
actagttcca gatggtaaat atacacaagg gatttagtca aacaattttt tggcaagaat    60
attatgaatt ttgtaatcgg ttggcagcca atgaaataca aagatgagtc tagttaataa   120
tctacaatta ttggttaaag aagtatatta gtgctaattt ccctccgttt gtcctagctt   180
ttctcttctg tcaaccccac acgcctttgg cacc                               214
```

<210> SEQ ID NO 9
<211> LENGTH: 726
<212> TYPE: PRT
<213> ORGANISM: Artificial Sequence
<220> FEATURE:
<223> OTHER INFORMATION: Description of Artificial Sequence: Synthetic
      Anc80 VP3 capsid protein
<220> FEATURE:
<221> NAME/KEY: MOD_RES
<222> LOCATION: (165)..(165)
<223> OTHER INFORMATION: Lys or Arg
<220> FEATURE:
<221> NAME/KEY: MOD_RES
<222> LOCATION: (201)..(201)
<223> OTHER INFORMATION: Ala or Ser
<220> FEATURE:
<221> NAME/KEY: MOD_RES
<222> LOCATION: (261)..(261)
<223> OTHER INFORMATION: Ala or Gly
<220> FEATURE:
<221> NAME/KEY: MOD_RES
<222> LOCATION: (306)..(306)
<223> OTHER INFORMATION: Arg or Lys
<220> FEATURE:
<221> NAME/KEY: MOD_RES
<222> LOCATION: (406)..(406)
<223> OTHER INFORMATION: Glu or Gln
<220> FEATURE:
<221> NAME/KEY: MOD_RES
<222> LOCATION: (454)..(454)
<223> OTHER INFORMATION: Thr or Glu
<220> FEATURE:
<221> NAME/KEY: MOD_RES
<222> LOCATION: (486)..(486)
<223> OTHER INFORMATION: Ala or Thr
<220> FEATURE:
<221> NAME/KEY: MOD_RES
<222> LOCATION: (554)..(554)
<223> OTHER INFORMATION: Ser or Asn
<220> FEATURE:
<221> NAME/KEY: MOD_RES
<222> LOCATION: (568)..(568)
<223> OTHER INFORMATION: Gln or Glu
<220> FEATURE:
<221> NAME/KEY: MOD_RES
<222> LOCATION: (579)..(579)
<223> OTHER INFORMATION: Ser or Ala
<220> FEATURE:
<221> NAME/KEY: MOD_RES
<222> LOCATION: (600)..(600)
<223> OTHER INFORMATION: Asn or Asp

<400> SEQUENCE: 9

```
Ala Ala Asp Gly Tyr Leu Pro Asp Trp Leu Glu Asp Asn Leu Ser Glu
1               5                   10                  15

Gly Ile Arg Glu Trp Asp Leu Lys Pro Gly Ala Pro Lys Pro Lys Ala
            20                  25                  30
```

-continued

```
Asn Gln Gln Lys Gln Asp Asp Gly Arg Gly Leu Val Leu Pro Gly Tyr
             35                  40                  45

Tyr Leu Gly Pro Phe Asn Gly Leu Asp Lys Gly Glu Pro Val Asn Ala
 50                  55                  60

Ala Asp Ala Ala Ala Leu Glu His Asp Lys Ala Tyr Asp Gln Gln Leu
 65                  70                  75                  80

Lys Ala Gly Asp Asn Pro Tyr Leu Arg Tyr Asn His Ala Asp Ala Glu
                 85                  90                  95

Phe Gln Glu Arg Leu Gln Glu Asp Thr Ser Phe Gly Gly Asn Leu Gly
            100                 105                 110

Arg Ala Val Phe Gln Ala Lys Lys Arg Val Leu Glu Pro Leu Gly Leu
            115                 120                 125

Val Glu Glu Gly Ala Lys Thr Ala Pro Gly Lys Lys Arg Pro Val Glu
130                 135                 140

Gln Ser Pro Gln Glu Pro Asp Ser Ser Ser Gly Ile Gly Lys Lys Gly
145                 150                 155                 160

Gln Gln Pro Ala Xaa Lys Arg Leu Asn Phe Gly Gln Thr Gly Asp Ser
                165                 170                 175

Glu Ser Val Pro Asp Pro Gln Pro Leu Gly Glu Pro Ala Ala Pro
            180                 185                 190

Ser Gly Val Gly Ser Asn Thr Met Xaa Ala Gly Gly Ala Pro Ala
            195                 200                 205

Asp Asn Asn Glu Gly Ala Asp Gly Val Gly Asn Ala Ser Gly Asn Trp
            210                 215                 220

His Cys Asp Ser Thr Trp Leu Gly Asp Arg Val Ile Thr Thr Ser Thr
225                 230                 235                 240

Arg Thr Ala Leu Pro Thr Tyr Asn Asn His Leu Tyr Lys Gln Ile Ser
                245                 250                 255

Ser Gln Ser Gly Xaa Ser Thr Asn Asp Asn Thr Tyr Phe Gly Tyr Ser
                260                 265                 270

Thr Pro Trp Gly Tyr Phe Asp Phe Asn Arg Phe His Cys His Phe Ser
            275                 280                 285

Pro Arg Asp Trp Gln Arg Leu Ile Asn Asn Asn Trp Gly Phe Arg Pro
            290                 295                 300

Lys Xaa Leu Asn Phe Lys Leu Phe Asn Ile Gln Val Lys Glu Val Thr
305                 310                 315                 320

Thr Asn Asp Gly Thr Thr Thr Ile Ala Asn Asn Leu Thr Ser Thr Val
                325                 330                 335

Gln Val Phe Thr Asp Ser Glu Tyr Gln Leu Pro Tyr Val Leu Gly Ser
            340                 345                 350

Ala His Gln Gly Cys Leu Pro Pro Phe Pro Ala Asp Val Phe Met Ile
            355                 360                 365

Pro Gln Tyr Gly Tyr Leu Thr Leu Asn Asn Gly Ser Gln Ala Val Gly
370                 375                 380

Arg Ser Ser Phe Tyr Cys Leu Glu Tyr Phe Pro Ser Gln Met Leu Arg
385                 390                 395                 400

Thr Gly Asn Asn Phe Xaa Phe Ser Tyr Thr Phe Glu Asp Val Pro Phe
                405                 410                 415

His Ser Ser Tyr Ala His Ser Gln Ser Leu Asp Arg Leu Asn Pro Leu
            420                 425                 430

Ile Asp Gln Tyr Leu Tyr Tyr Leu Ser Arg Thr Gln Thr Thr Ser Gly
            435                 440                 445

Thr Ala Gly Asn Arg Xaa Leu Gln Phe Ser Gln Ala Gly Pro Ser Ser
```

```
            450                 455                 460
Ala Asn Gln Ala Lys Asn Trp Leu Pro Gly Pro Cys Tyr Arg Gln Gln
465                 470                 475                 480

Arg Val Ser Lys Thr Xaa Asn Gln Asn Asn Ser Asn Phe Ala Trp
                485                 490                 495

Thr Gly Ala Thr Lys Tyr His Leu Asn Gly Arg Asp Ser Leu Val Asn
                500                 505                 510

Pro Gly Pro Ala Met Ala Thr His Lys Asp Asp Glu Asp Lys Phe Phe
            515                 520                 525

Pro Met Ser Gly Val Leu Ile Phe Gly Lys Gln Gly Ala Gly Asn Ser
        530                 535                 540

Asn Val Asp Leu Asp Asn Val Ile Thr Xaa Glu Glu Glu Ile Lys Thr
545                 550                 555                 560

Thr Asn Pro Val Ala Thr Glu Xaa Tyr Gly Thr Val Ala Thr Asn Leu
                565                 570                 575

Gln Ser Xaa Asn Thr Ala Pro Ala Thr Gly Thr Val Asn Ser Gln Gly
                580                 585                 590

Ala Leu Pro Gly Val Trp Gln Xaa Arg Asp Val Tyr Leu Gln Gly Pro
        595                 600                 605

Ile Trp Ala Lys Ile Pro His Thr Asp Gly His Phe His Pro Ser Pro
610                 615                 620

Leu Met Gly Gly Phe Gly Leu Lys His Pro Pro Gln Ile Leu Ile
625                 630                 635                 640

Lys Asn Thr Pro Val Pro Ala Asn Pro Pro Thr Thr Phe Ser Pro Ala
                645                 650                 655

Lys Phe Ala Ser Phe Ile Thr Gln Tyr Ser Thr Gly Gln Val Ser Val
                660                 665                 670

Glu Ile Glu Glu Leu Gln Lys Glu Asn Ser Lys Arg Trp Asn Pro Glu
                675                 680                 685

Ile Gln Tyr Thr Ser Asn Tyr Asn Lys Ser Thr Asn Val Asp Phe Ala
            690                 695                 700

Val Asp Thr Asn Gly Val Tyr Ser Glu Pro Arg Pro Ile Gly Thr Arg
705                 710                 715                 720

Tyr Leu Thr Arg Asn Leu
                725

<210> SEQ ID NO 10
<211> LENGTH: 20
<212> TYPE: DNA
<213> ORGANISM: Homo sapiens

<400> SEQUENCE: 10
caacttcatc cacgttcacc                                          20

<210> SEQ ID NO 11
<211> LENGTH: 21
<212> TYPE: DNA
<213> ORGANISM: Homo sapiens

<400> SEQUENCE: 11
gttctgagct ccaaccattc t                                        21

<210> SEQ ID NO 12
<211> LENGTH: 21
<212> TYPE: DNA
<213> ORGANISM: Homo sapiens
```

```
<400> SEQUENCE: 12
cactgtgggt ccttcatctt t                                               21

<210> SEQ ID NO 13
<211> LENGTH: 50
<212> TYPE: DNA
<213> ORGANISM: Homo sapiens
<220> FEATURE:
<221> NAME/KEY: modified_base
<222> LOCATION: (42)..(42)
<223> OTHER INFORMATION: a, c, t, or g

<400> SEQUENCE: 13
tcgtcggcag cgtcagatgt gtataagaga cagcctacgg gnggcwgcag                50

<210> SEQ ID NO 14
<211> LENGTH: 55
<212> TYPE: DNA
<213> ORGANISM: Homo sapiens

<400> SEQUENCE: 14
gtctcgtggg ctcggagatg tgtataagag acaggactac hvgggtatct aatcc          55

<210> SEQ ID NO 15
<211> LENGTH: 397
<212> TYPE: DNA
<213> ORGANISM: Homo sapiens

<400> SEQUENCE: 15
gatcttgcta ccagtggaac agccactaag gattctgcag tgagagcaga gggccagcta    60
agtggtactc tcccagagac tgtctgactc acgccacccc ctccaccttg gacacaggac   120
gctgtggttt ctgagccagg tacaatgact cctttcggta agtgcagtgg aagctgtaca   180
ctgcccaggc aaagcgtccg ggcagcgtag gcgggcgact cagatcccag ccagtggact   240
tagcccctgt ttgctcctcc gataactggg gtgaccttgg ttaatattca ccagcagcct   300
cccccgttgc ccctctggat ccactgctta aatacggacg aggacagggc cctgtctcct   360
cagcttcagg caccaccact gacctgggac agtgaat                             397

<210> SEQ ID NO 16
<211> LENGTH: 637
<212> TYPE: DNA
<213> ORGANISM: Homo sapiens

<400> SEQUENCE: 16
agtggcggcc gctcgagcta gcggccgctc tagaagataa tcaacctctg gattacaaaa    60
tttgtgaaag attgactggt attcttaact atgttgctcc ttttacgcta tgtggatacg   120
ctgctttaat gcctttgtat catgctattg cttcccgtat ggctttcatt ttctcctcct   180
tgtataaatc ctggttgctg tctctttatg aggagttgtg gcccgttgtc aggcaacgtg   240
gcgtggtgtg cactgtgttt gctgacgcaa cccccactgg ttggggcatt gccaccacct   300
gtcagctcct ttccgggact ttcgctttcc cctccctat tgccacggcg gaactcatcg   360
ccgcctgcct tgcccgctgc tggacagggg ctcggctgtt gggcactgac aattccgtgg   420
tgttgtcggg gaaatcatcg tcctttcctt ggctgctcgc ctgtgttgcc acctggattc   480
tgcgcgggac gtccttctgc tacgtccctt cggccctcaa tccagcggac cttccttccc   540
gcggcctgct gccggtctg cggctcttc gcgtcttcg ccttcgccct cagacgagtc   600
ggatctccct ttgggccgcc tccccgcatc ggactag                             637
```

<210> SEQ ID NO 17
<211> LENGTH: 320
<212> TYPE: DNA
<213> ORGANISM: Homo sapiens

<400> SEQUENCE: 17

| | | |
|---|---|---|
| aggctcagag gcacacagga gtttctgggc tcaccctgcc cccttccaac ccctcagttc | 60 |
| ccatcctcca gcagctgttt gtgtgctgcc tctgaagtcc acactgaaca aacttcagcc | 120 |
| tactcatgtc cctaaaatgg gcaaacattg caagcagcaa acagcaaaca cacagccctc | 180 |
| cctgcctgct gaccttggag ctggggcaga ggtcagagac ctctctgggc ccatgccacc | 240 |
| tccaacatcc actcgacccc ttggaatttc ggtggagagg agcagaggtt gtcctggcgt | 300 |
| ggtttaggta gtgtgagagg | 320 |

<210> SEQ ID NO 18
<211> LENGTH: 840
<212> TYPE: DNA
<213> ORGANISM: Homo sapiens

<400> SEQUENCE: 18

| | | |
|---|---|---|
| atgaagctgc tgggggcgct gctggcactg gcggccctac tgcaggggc cgtgtccctg | 60 |
| aagatcgcag ccttcaacat caggacattt gggaggacca agatgtccaa tgccaccctc | 120 |
| gtcagctaca ttgtgcagat cctgagccgc tatgacatcg ccctggtcca ggaggtcaga | 180 |
| gacagccacc tgactgccgt ggggaagctg ctggacaacc tcaatcagga tgcaccagac | 240 |
| acctatcact acgtggtcag tgagccactg gacggaaga gctataagga gcgctacctg | 300 |
| ttcgtgtaca ggcctgacca ggtgtctgcg gtggacagct actactacga tgatggctgc | 360 |
| gagccctgcg ggaacgacac cttcaaccga gagccattca ttgtcaggtt cttctcccgg | 420 |
| ttcacagagg tcagggagtt tgccattgtt ccctgcatg cggccccggg ggacgcagta | 480 |
| gccgagatcg acgtctctcta tgacgtctac ctggatgtcc aagagaaatg gggcttggag | 540 |
| gacgtcatgt tgatgggcga cttcaatgcg ggctgcagct atgtgagacc ctcccagtgg | 600 |
| tcatccatcc gcctgtggac aagccccacc ttccagtggc tgatcccga cagcgctgac | 660 |
| accacagcta cacccacgca ctgtgcctat gacaggatcg tggttgcagg gatgctgctc | 720 |
| cgaggcgccg ttgttcccga ctcggctctt ccctttaact tccaggctgc ctatggcctg | 780 |
| agtgaccaac tggcccaagc catcagtgac cactatccag tggaggtgat gctgaagtga | 840 |

<210> SEQ ID NO 19
<211> LENGTH: 849
<212> TYPE: DNA
<213> ORGANISM: Homo sapiens

<400> SEQUENCE: 19

| | | |
|---|---|---|
| atgagggca tgaagctgct gggggcgctg ctggcactgg cggccctact gcaggggcc | 60 |
| gtgtccctga agatcgcagc cttcaacatc aggacatttg gaggaccaa gatgtccaat | 120 |
| gccaccctcg tcagctacat tgtgcagatc ctgagccgct atgacatcgc cctggtccag | 180 |
| gaggtcagag acagccacct gactgccgtg gggaagctgc tggacaacct caatcaggat | 240 |
| gcaccagaca cctatcacta cgtggtcagt gagccactgg acggaagag ctataaggag | 300 |
| cgctacctgt tcgtgtacag gcctgaccag gtgtctgcgg tggacagcta ctactacgat | 360 |
| gatggctgcg agccctgcgg gaacgacacc ttcaaccgag agccattcat tgtcaggttc | 420 |

-continued

| | |
|---|---|
| ttctcccggt tcacagaggt cagggagttt gccattgttc ccctgcatgc ggccccgggg | 480 |
| gacgcagtag ccgagatcga cgctctctat gacgtctacc tggatgtcca agagaaatgg | 540 |
| ggcttggagg acgtcatgtt gatgggcgac ttcaatgcgg gctgcagcta tgtgagaccc | 600 |
| tcccagtggt catccatccg cctgtggaca agccccacct tccagtggct gatccccgac | 660 |
| agcgctgaca ccacagctac acccacgcac tgtgcctatg acaggatcgt ggttgcaggg | 720 |
| atgctgctcc gaggcgccgt tgttcccgac tcggctcttc cctttaactt ccaggctgcc | 780 |
| tatggcctga gtgaccaact ggcccaagcc atcagtgacc actatccagt ggaggtgatg | 840 |
| ctgaagtga | 849 |

<210> SEQ ID NO 20
<211> LENGTH: 66
<212> TYPE: DNA
<213> ORGANISM: Homo sapiens

<400> SEQUENCE: 20

| | |
|---|---|
| atgaggggca tgaagctgct gggggcgctg ctggcactgg cggccctact gcaggggggcc | 60 |
| gtgtcc | 66 |

<210> SEQ ID NO 21
<211> LENGTH: 783
<212> TYPE: DNA
<213> ORGANISM: Homo sapiens

<400> SEQUENCE: 21

| | |
|---|---|
| ctgaagatcg cagccttcaa catcaggaca tttgggagga ccaagatgtc caatgccacc | 60 |
| ctcgtcagct acattgtgca gatcctgagc cgctatgaca tcgccctggt ccaggaggtc | 120 |
| agagacagcc acctgactgc cgtggggaag ctgctggaca acctcaatca ggatgccacca | 180 |
| gacacctatc actacgtggt cagtgagcca ctgggacgga agagctataa ggagcgctac | 240 |
| ctgttcgtgt acaggcctga ccaggtgtct gcggtggaca gctactacta cgatgatggc | 300 |
| tgcgagccct gcgggaacga caccttcaac cgagagccat tcattgtcag gttcttctcc | 360 |
| cggttcacag aggtcaggga gtttgccatt gttcccctgc atgcggcccc ggggacgca | 420 |
| gtagccgaga tcgacgctct ctatgacgtc tacctggatg tccaagagaa atggggcttg | 480 |
| gaggacgtca tgttgatggg cgacttcaat gcgggctgca gctatgtgag accctcccag | 540 |
| tggtcatcca tccgcctgtg gacaagcccc accttccagt ggctgatccc cgacagcgct | 600 |
| gacaccacag ctacacccac gcactgtgcc tatgacagga tcgtggttgc agggatgctg | 660 |
| ctccgaggcg ccgttgttcc cgactcggct cttcccttta acttccaggc tgcctatggc | 720 |
| ctgagtgacc aactggccca agccatcagt gaccactatc cagtggaggt gatgctgaag | 780 |
| tga | 783 |

<210> SEQ ID NO 22
<211> LENGTH: 846
<212> TYPE: DNA
<213> ORGANISM: Homo sapiens

<400> SEQUENCE: 22

| | |
|---|---|
| atgaggggca tgaagctgct gggggcgctg ctggcactgg cggccctact gcaggggggcc | 60 |
| gtgtccctga agatcgcagc cttcaacatc agacatttg gggagaccaa gatgtccaat | 120 |
| gccaccctcg tcagctacat tgtgcagatc ctgagccgct atgacatcgc cctggtccag | 180 |
| gaggtcagag acagccacct gactgccgtg gggaagctgc tggacaacct caatcaggat | 240 |

```
gcaccagaca cctatcacta cgtggtcagt gagccactgg gacggaacag ctataaggag    300
cgctacctgt tcgtgtacag gcctgaccag gtgtctgcgg tggacagcta ctactacgat    360
gatggctgcg agccctgcgg gaacgacacc ttcaaccgag agccagccat tgtcaggttc    420
ttctcccggt tcacagaggt cagggagttt gccattgttc ccctgcatgc ggccccgggg    480
gacgcagtag ccgagatcga cgctctctat gacgtctacc tggatgtcca agagaaatgg    540
ggcttggagg acgtcatgtt gatgggcgac ttcaatgcgg ctgcagcta tgtgagaccc    600 tcccagtggt catccatccg cctgtggaca agccccacct tccagtggct gatccccgac    660
agcgctgaca ccacagctac acccacgcac tgtgcctatg acaggatcgt ggttgcaggg    720
atgctgctcc gaggcgccgt tgttcccgac tcggctcttc cctttaactt ccaggctgcc    780
tatggcctga gtgaccaact ggcccaagcc atcagtgacc actatccagt ggaggtgatg    840
ctgaag                                                              846
```

```
<210> SEQ ID NO 23
<211> LENGTH: 780
<212> TYPE: DNA
<213> ORGANISM: Homo sapiens

<400> SEQUENCE: 23
ctgaagatcg cagccttcaa catccagaca tttggggaga ccaagatgtc caatgccacc     60
ctcgtcagct acattgtgca gatcctgagc cgctatgaca tcgccctggt ccaggaggtc    120
agagacagcc acctgactgc cgtggggaag ctgctggaca acctcaatca ggatgcacca    180
gacacctatc actacgtggt cagtgagcca ctgggacgga cagctataa ggagcgctac    240 ctgttcgtgt acaggcctga ccaggtgtct gcggtggaca gctactacta cgatgatggc    300
tgcgagccct gcgggaacga caccttcaac cgagagccag ccattgtcag gttcttctcc    360
cggttcacag aggtcaggga gtttgccatt gttcccctgc atgcggcccc ggggacgca    420 gtagccgaga tcgacgctct ctatgacgtc tacctggatg tccaagagaa atggggcttg    480
gaggacgtca tgttgatggg cgacttcaat gcggctgcag ctatgtgag accctcccag    540 tggtcatcca tccgcctgtg gacaagcccc accttccagt ggctgatccc cgacagcgct    600
gacaccacag ctacacccac gcactgtgcc tatgacagga tcgtggttgc agggatgctg    660
ctccgaggcg ccgttgttcc cgactcggct cttcccttta acttccaggc tgcctatggc    720
ctgagtgacc aactggccca agccatcagt gaccactatc cagtggaggt gatgctgaag    780
```

```
<210> SEQ ID NO 24
<211> LENGTH: 284
<212> TYPE: PRT
<213> ORGANISM: Mus musculus

<400> SEQUENCE: 24

Met Arg Tyr Thr Gly Leu Met Gly Thr Leu Leu Thr Leu Val Asn Leu
1               5                  10                  15

Leu Gln Leu Ala Gly Thr Leu Arg Ile Ala Ala Phe Asn Ile Arg Thr
            20                  25                  30

Phe Gly Glu Thr Lys Met Ser Asn Ala Thr Leu Ser Val Tyr Phe Val
        35                  40                  45

Lys Ile Leu Ser Arg Tyr Asp Ile Ala Val Ile Gln Glu Val Arg Asp
    50                  55                  60

Ser His Leu Val Ala Val Gly Lys Leu Leu Asp Glu Leu Asn Arg Asp
65                  70                  75                  80
```

```
Lys Pro Asp Thr Tyr Arg Tyr Val Val Ser Glu Pro Leu Gly Arg Lys
                85                  90                  95

Ser Tyr Lys Glu Gln Tyr Leu Phe Val Tyr Arg Pro Asp Gln Val Ser
            100                 105                 110

Ile Leu Asp Ser Tyr Gln Tyr Asp Asp Gly Cys Glu Pro Cys Gly Asn
            115                 120                 125

Asp Thr Phe Ser Arg Glu Pro Ala Ile Val Lys Phe Phe Ser Pro Tyr
        130                 135                 140

Thr Glu Val Gln Glu Phe Ala Ile Val Pro Leu His Ala Ala Pro Thr
145                 150                 155                 160

Glu Ala Val Ser Glu Ile Asp Ala Leu Tyr Asp Val Tyr Leu Asp Val
                165                 170                 175

Trp Gln Lys Trp Gly Leu Glu Asp Ile Met Phe Met Gly Asp Phe Asn
            180                 185                 190

Ala Gly Cys Ser Tyr Val Thr Ser Ser Gln Trp Ser Ser Ile Arg Leu
        195                 200                 205

Arg Thr Ser Pro Ile Phe Gln Trp Leu Ile Pro Asp Ser Ala Asp Thr
    210                 215                 220

Thr Val Thr Ser Thr His Cys Ala Tyr Asp Arg Ile Val Val Ala Gly
225                 230                 235                 240

Ala Leu Leu Gln Ala Ala Val Val Pro Asn Ser Ala Val Pro Phe Asp
                245                 250                 255

Phe Gln Ala Glu Tyr Gly Leu Ser Asn Gln Leu Ala Glu Ala Ile Ser
            260                 265                 270

Asp His Tyr Pro Val Glu Val Thr Leu Arg Lys Ile
        275                 280

<210> SEQ ID NO 25
<211> LENGTH: 22
<212> TYPE: PRT
<213> ORGANISM: Mus musculus

<400> SEQUENCE: 25

Met Arg Tyr Thr Gly Leu Met Gly Thr Leu Leu Thr Leu Val Asn Leu
1               5                   10                  15

Leu Gln Leu Ala Gly Thr
            20

<210> SEQ ID NO 26
<211> LENGTH: 262
<212> TYPE: PRT
<213> ORGANISM: Mus musculus

<400> SEQUENCE: 26

Leu Arg Ile Ala Ala Phe Asn Ile Arg Thr Phe Gly Glu Thr Lys Met
1               5                   10                  15

Ser Asn Ala Thr Leu Ser Val Tyr Phe Val Lys Ile Leu Ser Arg Tyr
            20                  25                  30

Asp Ile Ala Val Ile Gln Glu Val Arg Asp Ser His Leu Val Ala Val
        35                  40                  45

Gly Lys Leu Leu Asp Glu Leu Asn Arg Asp Lys Pro Asp Thr Tyr Arg
    50                  55                  60

Tyr Val Val Ser Glu Pro Leu Gly Arg Lys Ser Tyr Lys Glu Gln Tyr
65                  70                  75                  80

Leu Phe Val Tyr Arg Pro Asp Gln Val Ser Ile Leu Asp Ser Tyr Gln
                85                  90                  95
```

```
Tyr Asp Asp Gly Cys Glu Pro Cys Gly Asn Asp Thr Phe Ser Arg Glu
                100                 105                 110

Pro Ala Ile Val Lys Phe Phe Ser Pro Tyr Thr Glu Val Gln Glu Phe
            115                 120                 125

Ala Ile Val Pro Leu His Ala Ala Pro Thr Glu Ala Val Ser Glu Ile
        130                 135                 140

Asp Ala Leu Tyr Asp Val Tyr Leu Asp Val Trp Gln Lys Trp Gly Leu
145                 150                 155                 160

Glu Asp Ile Met Phe Met Gly Asp Phe Asn Ala Gly Cys Ser Tyr Val
                165                 170                 175

Thr Ser Ser Gln Trp Ser Ser Ile Arg Leu Arg Thr Ser Pro Ile Phe
            180                 185                 190

Gln Trp Leu Ile Pro Asp Ser Ala Asp Thr Thr Val Thr Ser Thr His
        195                 200                 205

Cys Ala Tyr Asp Arg Ile Val Val Ala Gly Ala Leu Leu Gln Ala Ala
210                 215                 220

Val Val Pro Asn Ser Ala Val Pro Phe Asp Phe Gln Ala Glu Tyr Gly
225                 230                 235                 240

Leu Ser Asn Gln Leu Ala Glu Ala Ile Ser Asp His Tyr Pro Val Glu
                245                 250                 255

Val Thr Leu Arg Lys Ile
            260

<210> SEQ ID NO 27
<211> LENGTH: 66
<212> TYPE: DNA
<213> ORGANISM: Mus musculus

<400> SEQUENCE: 27
atgcggtaca cagggctaat gggaacactg ctcaccttgg tcaacctgct gcagctggct      60
gggact                                                                66

<210> SEQ ID NO 28
<211> LENGTH: 789
<212> TYPE: DNA
<213> ORGANISM: Mus musculus

<400> SEQUENCE: 28
ctgagaattg cagccttcaa cattcggact tttggggaga ctaagatgtc caatgctacc      60
ctctctgtat actttgtgaa atcctgagt cgctatgaca tcgctgttat ccaagaggtc     120
agagactccc acctggttgc tgttgggaag ctcctggatg aactcaatcg ggacaaacct     180
gacacctacc gctatgtagt cagtgagccg ctgggccgca aaagctacaa ggaacagtac     240 cttttttgtgt acaggcctga ccaggtgtct attctggaca gctatcaata tgatgatggc     300
tgtgaaccct gtggaaatga caccttcagc agagagccag ccattgttaa gttctttttcc    360 ccatacactg aggtccaaga atttgcgatc gtgcccttgc atgcagcccc aacagaagct     420
gtgagtgaga tcgacgccct ctacgatgtt tacctagatg tctggcaaaa gtggggcctg     480
gaggacatca tgttcatggg agacttcaat gctggctgca gctacgtcac ttcctcccag     540
tggtcctcca ttcgccttcg acaagcccc atcttccagt ggctgatccc tgacagtgcg     600
gacaccacag tcacatcaac acactgtgct tatgacagga ttgtggttgc tggagctctg     660
ctccaggctc tgttgttcc caactcggct gttccttttg atttccaagc agaatacgga     720 cttttccaacc agctggctga agccatcagt gaccattacc cagtggaggt gacactcaga     780
```

```
aaaatctga                                                                789
```

<210> SEQ ID NO 29
<211> LENGTH: 855
<212> TYPE: DNA
<213> ORGANISM: Mus musculus

<400> SEQUENCE: 29

```
atgcggtaca cagggctaat gggaacactg ctcaccttgg tcaacctgct gcagctggct    60
gggactctga gaattgcagc cttcaacatt cggacttttg gggagactaa gatgtccaat   120
gctaccctct ctgtatactt tgtgaaaatc ctgagtcgct atgacatcgc tgttatccaa   180
gaggtcagag actcccacct ggttgctgtt gggaagctcc tggatgaact caatcgggac   240
aaacctgaca cctaccgcta tgtagtcagt gagccgctgg ccgcaaaag ctacaaggaa    300
cagtaccttt ttgtgtacag gcctgaccag gtgtctattc tggacagcta tcaatatgat   360
gatggctgtg aaccctgtgg aaatgacacc ttcagcagag agccagccat tgttaagttc   420
tttttccccat acactgaggt ccaagaattt gcgatcgtgc ccttgcatgc agccccaaca  480
gaagctgtga gtgagatcga cgccctctac gatgtttacc tagatgtctg gcaaaagtgg   540
ggcctggagg acatcatgtt catgggagac ttcaatgctg gctgcagcta cgtcacttcc   600
tcccagtggt cctccattcg ccttcggaca agccccatct tccagtggct gatccctgac   660
agtgcggaca ccacagtcac atcaacacac tgtgcttatg acaggattgt ggttgctgga   720
gctctgctcc aggctgctgt tgttcccaac tcggctgttc cttttgattt ccaagcagaa   780
tacggacttt ccaaccagct ggctgaagcc atcagtgacc attacccagt ggaggtgaca   840
ctcagaaaaa tctga                                                   855
```

<210> SEQ ID NO 30
<211> LENGTH: 2212
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
aggctcagag gcacacagga gtttctgggc tcaccctgcc ccttccaac ccctcagttc     60
ccatcctcca gcagctgttt gtgtgctgcc tctgaagtcc acactgaaca aacttcagcc   120
tactcatgtc cctaaaatgg gcaaacattg caagcagcaa acagcaaaca cacagccctc   180
cctgcctgct gaccttggag ctggggcaga ggtcagagac ctctctgggc ccatgccacc   240
tccaacatcc actcgacccc ttggaatttc ggtggagagg agcagaggtt gtcctggcgt   300
ggtttaggta gtgtgagagg gatcttgcta ccagtggaac agccactaag gattctgcag   360
tgagagcaga gggccagcta agtggtactc tcccagagac tgtctgactc acgccacccc   420
ctccaccttg gacacaggac gctgtggttt ctgagccagg tacaatgact cctttcggta   480
agtgcagtgg aagctgtaca ctgcccaggc aaagcgtccg ggcagcgtag gcgggcgact   540
cagatcccag ccagtggact tagccccgt ttgctcctcc gataactggg gtgaccttgg    600
ttaatattca ccagcagcct ccccgttgc ccctctggat ccactgctta aatacggacg    660
aggacagggc cctgtctcct cagcttcagg caccaccact gacctgggac agtgaatgcc   720
gccaccatga ggggcatgaa gctgctgggg gcgctgctgg cactggcggc cctactgcag   780
ggggccgtgt ccctgaagat cgcagccttc aacatcagga catttgggag gaccaagatg   840
```

```
tccaatgcca ccctcgtcag ctacattgtg cagatcctga gccgctatga catcgccctg    900
gtccaggagg tcagagacag ccacctgact gccgtgggga agctgctgga caacctcaat    960
caggatgcac cagacaccta tcactacgtg gtcagtgagc cactgggacg aagagctat    1020 aaggagcgct acctgttcgt gtacaggcct gaccaggtgt ctgcggtgga cagctactac   1080
tacgatgatg gctgcgagcc ctgcgggaac gacaccttca accgagagcc attcattgtc   1140
aggttcttct cccggttcac agaggtcagg gagtttgcca ttgttcccct gcatgcggcc   1200 ccggggacg cagtagccga gatcgacgct ctctatgacg tctacctgga tgtccaagag    1260
aaatggggct tggaggacgt catgttgatg ggcgacttca atgcgggctg cagctatgtg   1320
agaccctccc agtggtcatc catccgcctg tggacaagcc ccaccttcca gtggctgatc   1380
cccgacagcg ctgacaccac agctacaccc acgcactgtg cctatgacag gatcgtggtt   1440
gcagggatgc tgctccgagg cgccgttgtt cccgactcgg ctcttcccct taacttccag   1500
gctgcctatg gcctgagtga ccaactggcc caagccatca gtgaccacta tccagtggag   1560
gtgatgctga agtgaagtgg cggccgctcg agctagcggc cgctctagaa gataatcaac   1620
ctctggatta caaaatttgt gaaagattga ctggtattct taactatgtt gctccttta   1680 cgctatgtgg atacgctgct ttaatgcctt tgtatcatgc tattgcttcc cgtatggctt   1740
tcattttctc ctccttgtat aaatcctggt tgctgtctct ttatgaggag ttgtggcccg   1800
ttgtcaggca acgtggcgtg gtgtgcactg tgtttgctga cgcaaccccc actggttggg   1860
gcattgccac cacctgtcag ctcctttccg ggactttcgc tttccccctc cctattgcca   1920
cggcggaact catcgccgcc tgccttgccc gctgctggac aggggctcgg ctgttgggca   1980
ctgacaattc cgtggtgttg tcggggaaat catcgtcctt tccttggctg ctcgcctgtg   2040
ttgccacctg gattctgcgc gggacgtcct tctgctacgt cccttcggcc ctcaatccag   2100
cggaccttcc ttcccgcggc ctgctgccgg ctctgcggcc tcttccgcgt cttcgccttc   2160
gccctcagac gagtcggatc tccctttggg ccgcctcccc gcatcggact ag           2212
```

<210> SEQ ID NO 31
<211> LENGTH: 2212
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
aggctcagag gcacacagga gtttctgggc tcaccctgcc cccttccaac ccctcagttc     60
ccatcctcca gcagctgttt gtgtgctgcc tctgaagtcc acactgaaca aacttcagcc    120
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg gatcttgcta ccagtggaac agccactaag gattctgcag    360
tgagagcaga gggccagcta agtggtactc tcccagagac tgtctgactc acgccacccc   420
ctccaccttg gacacaggac gctgtggttt ctgagccagg tacaatgact cctttcggta    480
agtgcagtgg aagctgtaca ctgcccaggc aaagcgtccg ggcagcgtag gcgggcgact    540
cagatcccag ccagtggact tagccctgt ttgctcctcc gataactggg gtgaccttgg    600
ttaatattca ccagcagcct ccccgttgc ccctctggat ccactgctta aatacggacg    660
```

-continued

```
aggacagggc cctgtctcct cagcttcagg caccaccact gacctgggac agtgaatgcc    720
gccaccatga ggggcatgaa gctgctgggg gcgctgctgg cactggcggc cctactgcag    780
ggggccgtgt ccctgaagat cgcagccttc aacatccaga catttgggga gaccaagatg    840
tccaatgcca ccctcgtcag ctacattgtg cagatcctga ccgctatga catcgccctg     900
gtccaggagg tcagagacag ccacctgact gccgtgggga agctgctgga caacctcaat    960
caggatgcac cagacaccta tcactacgtg gtcagtgagc cactgggacg gaacagctat   1020
aaggagcgct acctgttcgt gtacaggcct gaccaggtgt ctgcggtgga cagctactac   1080
tacgatgatg gctgcgagcc ctgcgggaac gacaccttca accgagagcc agccattgtc   1140
aggttcttct cccggttcac agaggtcagg gagtttgcca ttgttcccct gcatgcggcc   1200
ccggggacg cagtagccga gatcgacgct ctctatgacg tctacctgga tgtccaagag   1260
aaatggggct tggaggacgt catgttgatg ggcgacttca atgcgggctg cagctatgtg   1320
agaccctccc agtggtcatc catccgcctg tggacaagcc ccaccttcca gtggctgatc   1380
cccgacagcg ctgacaccac agctacaccc acgcactgtg cctatgacag gatcgtggtt   1440
gcagggatgc tgctccgagg cgccgttgtt cccgactcgg ctcttccctt taacttccag   1500
gctgcctatg gcctgagtga ccaactggcc caagccatca gtgaccacta tccagtggag   1560
gtgatgctga agtgaagtgg cggccgctcg agctagcggc cgctctagaa gataatcaac   1620
ctctggatta caaaatttgt gaaagattga ctggtattct taactatgtt gctcctttta   1680
cgctatgtgg atacgctgct ttaatgcctt tgtatcatgc tattgcttcc cgtatggctt   1740
tcattttctc ctccttgtat aaatcctggt tgctgtctct ttatgaggag ttgtggcccg   1800
ttgtcaggca acgtggcgtg gtgtgcactg tgtttgctga cgcaaccccc actggttggg   1860
gcattgccac cacctgtcag ctcctttccg ggactttcgc tttcccctc cctattgcca   1920
cggcggaact catcgccgcc tgccttgccc gctgctggac aggggctcgg ctgttgggca   1980
ctgacaattc cgtggtgttg tcggggaaat catcgtcctt tccttggctg ctcgcctgtg   2040
ttgccacctg gattctgcgc gggacgtcct tctgctacgt cccttcggcc ctcaatccag   2100
cggaccttcc ttcccgcggc ctgctgccgg ctctgcggcc tcttccgcgt cttcgccttc   2160
gccctcagac gagtcggatc tccctttggg ccgcctcccc gcatcggact ag           2212
```

<210> SEQ ID NO 32
<211> LENGTH: 849
<212> TYPE: DNA
<213> ORGANISM: Homo sapiens

<400> SEQUENCE: 32

```
atgagggggca tgaagctgct ggggcgcgctg ctggcactgg cggccctact gcagggggcc     60
gtgtccctga agatcgcagc cttcaacatc cagacatttg gggagaccaa gatgtccaat    120
gccacccctcg tcagctacat tgtgcagatc ctgagccgct atgacatcgc cctggtccag    180
gaggtcagag acagccacct gactgccgtg gggaagctgc tggacaacct caatcaggat    240
gcaccagaca cctatcacta cgtggtcagt gagccactgg gacggaacag ctataaggag    300
cgctacctgt tcgtgtacag gcctgaccag gtgtctgcgg tggacagcta ctactacgat    360
gatggctgcg agccctgcgg gaacgacacc ttcaaccgag agccagccat tgtcaggttc    420
ttctcccggt tcacagaggt cagggagttt gccattgttc ccctgcatgc ggccccgggg    480
gacgcagtag ccgagatcga cgctctctat gacgtctacc tggatgtcca agagaaatgg    540
```

-continued

```
ggcttggagg acgtcatgtt gatgggcgac ttcaatgcgg ctgcagcta tgtgagaccc      600 tcccagtggt catccatccg cctgtggaca agccccacct tccagtggct gatccccgac      660
agcgctgaca ccacagctac acccacgcac tgtgcctatg acaggatcgt ggttgcaggg      720
atgctgctcc gaggcgccgt tgttcccgac tcggctcttc cctttaactt ccaggctgcc      780
tatggcctga gtgaccaact ggcccaagcc atcagtgacc actatccagt ggaggtgatg      840
ctgaagtga                                                              849
```

```
<210> SEQ ID NO 33
<211> LENGTH: 9
<212> TYPE: DNA
<213> ORGANISM: Homo sapiens

<400> SEQUENCE: 33 gccgccacc                                                                9

<210> SEQ ID NO 34
<211> LENGTH: 736
<212> TYPE: PRT
<213> ORGANISM: Artificial Sequence
<220> FEATURE:
<223> OTHER INFORMATION: Description of Artificial Sequence: Synthetic
      Anc80L65 VP1 capsid protein

<400> SEQUENCE: 34
```

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu

```
            245                 250                 255
Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
            435                 440                 445

Thr Gln Thr Thr Ser Gly Thr Ala Gly Asn Arg Thr Leu Gln Phe Ser
            450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
            515                 520                 525

Asp Asp Glu Asp Lys Phe Phe Pro Met Ser Gly Val Leu Ile Phe Gly
            530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Glu
                565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670
```

```
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
        690                 695                 700
Tyr Asn Lys Ser Thr Asn Val Asp Phe Ala Val Asp Thr Asn Gly Val
705                 710                 715                 720
Tyr Ser Glu Pro Arg Pro Ile Gly Thr Arg Tyr Leu Thr Arg Asn Leu
                725                 730                 735

<210> SEQ ID NO 35
<211> LENGTH: 730
<212> TYPE: PRT
<213> ORGANISM: Artificial Sequence
<220> FEATURE:
<223> OTHER INFORMATION: Description of Artificial Sequence: Synthetic
      Anc80L65 VP1 capsid protein variant

<400> SEQUENCE: 35

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Tyr Leu Gly Pro Phe Asn Gly Leu Asp Lys Gly Glu Pro Val
    50                  55                  60
Asn Ala Ala Asp Ala Ala Ala Leu Glu His Asp Lys Ala Tyr Asp Gln
65                  70                  75                  80
Gln Leu Lys Ala Gly Asp Asn Pro Tyr Leu Arg Tyr Asn His Ala Asp
                85                  90                  95
Ala Glu Phe Gln Glu Arg Leu Gln Glu Asp Thr Ser Phe Gly Gly Asn
            100                 105                 110
Leu Gly Arg Ala Val Phe Gln Ala Lys Lys Arg Val Leu Glu Pro Leu
        115                 120                 125
Gly Leu Val Glu Glu Gly Ala Lys Thr Ala Pro Gly Lys Lys Arg Pro
    130                 135                 140
Val Glu Gln Ser Pro Gln Glu Pro Asp Ser Ser Ser Gly Ile Gly Lys
145                 150                 155                 160
Lys Gly Gln Gln Pro Ala Arg Lys Arg Leu Asn Phe Gly Gln Thr Gly
                165                 170                 175
Asp Ser Glu Ser Val Pro Asp Pro Gln Pro Leu Gly Glu Pro Pro Ala
            180                 185                 190
Ala Pro Ser Gly Val Gly Ser Asn Thr Met Ala Ala Gly Gly Gly Ala
        195                 200                 205
Pro Ala Asp Asn Asn Glu Gly Ala Asp Gly Val Gly Asn Ala Ser Gly
    210                 215                 220
Asn Trp His Cys Asp Ser Thr Trp Leu Gly Asp Arg Val Ile Thr Thr
225                 230                 235                 240
Ser Thr Arg Thr Trp Ala Leu Pro Thr Tyr Asn Asn His Leu Tyr Lys
                245                 250                 255
Gln Ile Ser Ser Gln Ser Gly Gly Ser Thr Asn Asp Asn Thr Tyr Phe
            260                 265                 270
Gly Tyr Ser Thr Pro Trp Gly Tyr Phe Asp Phe Asn Arg Phe His Cys
        275                 280                 285
His Phe Ser Pro Arg Asp Trp Gln Arg Leu Ile Asn Asn Asn Trp Gly
```

-continued

```
                290                 295                 300
Phe Arg Pro Lys Lys Leu Asn Phe Lys Leu Phe Asn Ile Gln Val Lys
305                 310                 315                 320

Glu Val Thr Thr Asn Asp Gly Thr Thr Thr Ile Ala Asn Asn Leu Thr
                325                 330                 335

Ser Thr Val Gln Val Phe Thr Asp Ser Glu Tyr Gln Leu Pro Tyr Val
                340                 345                 350

Leu Gly Ser Ala His Gln Gly Cys Leu Pro Pro Phe Pro Ala Asp Val
                355                 360                 365

Phe Met Ile Pro Gln Tyr Gly Tyr Leu Thr Leu Asn Asn Gly Ser Gln
370                 375                 380

Ala Val Gly Arg Ser Ser Phe Tyr Cys Leu Glu Tyr Phe Pro Ser Gln
385                 390                 395                 400

Met Leu Arg Thr Gly Asn Asn Phe Gln Phe Ser Tyr Thr Phe Glu Asp
                405                 410                 415

Val Pro Phe His Ser Ser Tyr Ala His Ser Gln Ser Leu Asp Arg Leu
                420                 425                 430

Met Asn Pro Leu Ile Asp Gln Tyr Leu Tyr Tyr Leu Ser Arg Thr Gln
435                 440                 445

Thr Thr Ser Gly Thr Ala Gly Asn Arg Thr Leu Gln Phe Ser Gln Ala
450                 455                 460

Gly Pro Ser Ser Ala Asn Gln Ala Lys Asn Trp Leu Pro Gly Pro Cys
465                 470                 475                 480

Tyr Arg Gln Gln Arg Val Ser Lys Thr Thr Asn Gln Asn Asn Asn Ser
                485                 490                 495

Asn Phe Ala Trp Thr Gly Ala Thr Lys Tyr His Leu Asn Gly Arg Asp
                500                 505                 510

Ser Leu Val Asn Pro Gly Pro Ala Met Ala Thr His Lys Asp Asp Glu
                515                 520                 525

Asp Lys Phe Phe Pro Met Ser Gly Val Leu Ile Phe Gly Lys Gln Gly
                530                 535                 540

Ala Gly Asn Ser Asn Val Asp Leu Asp Asn Val Ile Thr Asn Glu Glu
545                 550                 555                 560

Glu Ile Lys Thr Thr Asn Pro Val Ala Thr Glu Tyr Gly Thr Val
                565                 570                 575

Ala Thr Asn Leu Gln Ser Ala Asn Thr Ala Pro Ala Thr Gly Thr Val
                580                 585                 590

Asn Ser Gln Gly Ala Leu Pro Gly Val Trp Gln Asp Arg Asp Val Tyr
                595                 600                 605

Leu Gln Gly Pro Ile Trp Ala Lys Ile Pro His Thr Asp Gly His Phe
610                 615                 620

His Pro Ser Pro Leu Met Gly Gly Phe Gly Leu Lys His Pro Pro Pro
625                 630                 635                 640

Gln Ile Leu Ile Lys Asn Thr Pro Val Pro Ala Asn Pro Thr Thr
                645                 650                 655

Phe Ser Pro Ala Lys Phe Ala Ser Phe Ile Thr Gln Tyr Ser Thr Gly
                660                 665                 670

Gln Val Ser Val Glu Ile Glu Glu Leu Gln Lys Glu Asn Ser Lys Arg
                675                 680                 685

Trp Asn Pro Glu Ile Gln Tyr Thr Ser Asn Tyr Asn Lys Ser Thr Asn
                690                 695                 700

Val Asp Phe Ala Val Asp Thr Asn Gly Val Tyr Ser Glu Pro Arg Pro
705                 710                 715                 720
```

-continued

```
Ile Gly Thr Arg Tyr Leu Thr Arg Asn Leu
            725                 730

<210> SEQ ID NO 36
<211> LENGTH: 734
<212> TYPE: PRT
<213> ORGANISM: Unknown
<220> FEATURE:
<223> OTHER INFORMATION: Description of Unknown:
      Anc80 VP3 protein
<220> FEATURE:
<221> NAME/KEY: MOD_RES
<222> LOCATION: (169)..(169)
<223> OTHER INFORMATION: Lys or Arg
<220> FEATURE:
<221> NAME/KEY: MOD_RES
<222> LOCATION: (204)..(204)
<223> OTHER INFORMATION: Ala or Ser
<220> FEATURE:
<221> NAME/KEY: MOD_RES
<222> LOCATION: (264)..(264)
<223> OTHER INFORMATION: Ala or Gly
<220> FEATURE:
<221> NAME/KEY: MOD_RES
<222> LOCATION: (309)..(309)
<223> OTHER INFORMATION: Arg or Lys
<220> FEATURE:
<221> NAME/KEY: MOD_RES
<222> LOCATION: (409)..(409)
<223> OTHER INFORMATION: Glu or Gln
<220> FEATURE:
<221> NAME/KEY: MOD_RES
<222> LOCATION: (458)..(458)
<223> OTHER INFORMATION: Thr or Glu
<220> FEATURE:
<221> NAME/KEY: MOD_RES
<222> LOCATION: (491)..(491)
<223> OTHER INFORMATION: Ala or Thr
<220> FEATURE:
<221> NAME/KEY: MOD_RES
<222> LOCATION: (560)..(560)
<223> OTHER INFORMATION: Ser or Asn
<220> FEATURE:
<221> NAME/KEY: MOD_RES
<222> LOCATION: (574)..(574)
<223> OTHER INFORMATION: Gln or Glu
<220> FEATURE:
<221> NAME/KEY: MOD_RES
<222> LOCATION: (585)..(585)
<223> OTHER INFORMATION: Ser or Ala
<220> FEATURE:
<221> NAME/KEY: MOD_RES
<222> LOCATION: (607)..(607)
<223> OTHER INFORMATION: Asn or Asp

<400> SEQUENCE: 36

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

```
Asn Leu Gly Arg Ala Val Phe Gln Ala Lys Lys Arg Val Leu Glu Pro
            115                 120                 125

Leu Gly Leu Val Glu Glu Ala Lys Thr Ala Pro Gly Lys Lys Arg
        130                 135                 140

Pro Val Glu Gln Ser Pro Gln Glu Pro Asp Ser Ser Gly Ile Gly
145                 150                 155                 160

Lys Lys Gly Gln Gln Pro Ala Arg Xaa Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Xaa Ala Gly Gly Gly
        195                 200                 205

Ala Pro Met Ala Asp Asn Asn Glu Asp Gly Val Gly Asn Ala Ser Gly
    210                 215                 220

Asn Trp His Cys Asp Ser Thr Trp Leu Gly Asp Arg Val Ile Thr Thr
225                 230                 235                 240

Ser Thr Arg Thr Trp Ala Leu Pro Thr Tyr Asn Asn His Leu Tyr Lys
                245                 250                 255

Gln Ile Ser Ser Gln Ser Gly Xaa Ser Thr Asn Asp Asn Thr Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Arg Leu Ile Asn Asn Asn Trp Gly
    290                 295                 300

Phe Arg Pro Lys Xaa Leu Asn Phe Lys Leu Phe Asn Ile Gln Val Lys
305                 310                 315                 320

Glu Val Thr Thr Asn Asp Gly Thr Thr Thr Ile Ala Asn Asn Leu Thr
                325                 330                 335

Ser Thr Val Gln Val Phe Thr Asp Ser Glu Tyr Gln Leu Pro Tyr Val
            340                 345                 350

Leu Gly Ser Ala His Gln Gly Cys Leu Pro Pro Phe Pro Ala Asp Val
        355                 360                 365

Phe Met Ile Pro Gln Tyr Gly Tyr Leu Thr Leu Asn Asn Gly Ser Gln
    370                 375                 380

Ala Val Gly Arg Ser Ser Phe Tyr Cys Leu Glu Tyr Phe Pro Ser Gln
385                 390                 395                 400

Met Leu Arg Thr Gly Asn Asn Phe Xaa Phe Ser Tyr Thr Phe Glu Asp
                405                 410                 415

Val Pro Phe His Ser Ser Tyr Ala His Ser Gln Ser Leu Asp Arg Leu
            420                 425                 430

Met Asn Pro Leu Ile Asp Gln Tyr Leu Tyr Tyr Leu Ser Arg Thr Gln
        435                 440                 445

Thr Thr Ser Gly Thr Ala Gly Asn Arg Xaa Leu Gln Phe Ser Gln Ala
    450                 455                 460

Gly Pro Ser Ser Met Ala Asn Gln Ala Lys Asn Trp Leu Pro Gly Pro
465                 470                 475                 480

Cys Tyr Arg Gln Gln Arg Val Ser Lys Thr Xaa Asn Gln Asn Asn Asn
                485                 490                 495

Ser Asn Phe Ala Trp Thr Gly Ala Thr Lys Tyr His Leu Asn Gly Arg
            500                 505                 510

Asp Ser Leu Val Asn Pro Gly Pro Ala Met Ala Thr His Lys Asp Asp
        515                 520                 525
```

-continued

```
Glu Asp Lys Phe Phe Pro Met Ser Gly Val Leu Ile Phe Gly Lys Gln
            530                 535                 540

Gly Ala Gly Asn Ser Asn Val Asp Leu Asp Asn Val Met Ile Thr Xaa
545                 550                 555                 560

Glu Glu Glu Ile Lys Thr Thr Asn Pro Val Ala Thr Glu Xaa Tyr Gly
                565                 570                 575

Thr Val Ala Thr Asn Leu Gln Ser Xaa Asn Thr Ala Pro Ala Thr Gly
            580                 585                 590

Thr Val Asn Ser Gln Gly Ala Leu Pro Gly Met Val Trp Gln Xaa Arg
        595                 600                 605

Asp Val Tyr Leu Gln Gly Pro Ile Trp Ala Lys Ile Pro His Thr Asp
610                 615                 620

Gly His Phe His Pro Ser Pro Leu Met Gly Gly Phe Gly Leu Lys His
625                 630                 635                 640

Pro Pro Pro Gln Ile Leu Ile Lys Asn Thr Pro Val Pro Ala Asn Pro
                645                 650                 655

Pro Thr Thr Phe Ser Pro Ala Lys Phe Ala Ser Phe Ile Thr Gln Tyr
            660                 665                 670

Ser Thr Gly Gln Val Ser Val Glu Ile Glu Trp Glu Leu Gln Lys Glu
        675                 680                 685

Asn Ser Lys Arg Trp Asn Pro Glu Ile Gln Tyr Thr Ser Asn Tyr Asn
690                 695                 700

Lys Ser Thr Asn Val Asp Phe Ala Val Asp Thr Asn Gly Val Tyr Ser
705                 710                 715                 720

Glu Pro Arg Pro Ile Gly Thr Arg Tyr Leu Thr Arg Asn Leu
                725                 730
```

<210> SEQ ID NO 37
<211> LENGTH: 735
<212> TYPE: PRT
<213> ORGANISM: Unknown
<220> FEATURE:
<223> OTHER INFORMATION: Description of Unknown:
    AAV2 VP3 protein

<400> SEQUENCE: 37

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160
```

```
Lys Ala Gly Gln Gln Pro Ala Arg Arg Leu Asn Phe Gly Gln Thr
            165                 170                 175

Gly Asp Ala Asp Ser Val Pro Asp Pro Gln Pro Leu Gly Gln Pro Pro
        180                 185                 190

Ala Ala Pro Ser Gly Leu Gly Thr Asn Thr Met Ala Ala Thr Gly Ser
            195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575
```

-continued

```
Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 38
<211> LENGTH: 736
<212> TYPE: PRT
<213> ORGANISM: Unknown
<220> FEATURE:
<223> OTHER INFORMATION: Description of Unknown:
      AAV8 VP3 protein
<220> FEATURE:
<221> NAME/KEY: MOD_RES
<222> LOCATION: (265)..(265)
<223> OTHER INFORMATION: Ala or Gly

<400> SEQUENCE: 38

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Arg Arg Leu Asn Phe Gly Gln
                165                 170                 175

Thr Gly Asp Ser Glu Ser Val Pro Asp Pro Gln Pro Leu Gly Glu Pro
```

```
            180                 185                 190
Pro Ala Ala Pro Ser Gly Val Gly Pro Asn Thr Met Ala Ala Gly Gly
            195                 200                 205
Gly Ala Pro Met Ala Asp Asn Asn Glu Asp Gly Val Gly Ser Ser Ser
            210                 215                 220
Gly Asn Trp His Cys Asp Ser Thr Trp Leu Gly Asp Arg Val Ile Thr
225                 230                 235                 240
Thr Ser Thr Arg Thr Trp Ala Leu Pro Thr Tyr Asn Asn His Leu Tyr
            245                 250                 255
Lys Gln Ile Ser Asn Gly Thr Ser Xaa Gly Ala Thr Asn Asp Asn Thr
            260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
            290                 295                 300
Trp Gly Phe Arg Pro Lys Arg Leu Ser Phe Lys Leu Phe Asn Ile Gln
305                 310                 315                 320
Val Lys Glu Val Thr Gln Asn Glu Gly Thr Lys Thr Ile Ala Asn Asn
            325                 330                 335
Leu Thr Ser Thr Ile Gln Val Phe Thr Asp Ser Glu Tyr Gln Leu Pro
            340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
            370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Gln Phe Thr Tyr Thr Phe
            405                 410                 415
Glu Asp Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Ser Arg
            435                 440                 445
Thr Gln Thr Thr Gly Gly Thr Ala Asn Thr Gln Thr Leu Gly Phe Ser
            450                 455                 460
Gln Gly Gly Pro Asn Thr Met Ala Asn Gln Ala Lys Asn Trp Leu Pro
465                 470                 475                 480
Gly Pro Cys Tyr Arg Gln Gln Arg Val Ser Thr Thr Gly Gln Asn
            485                 490                 495
Asn Asn Ser Asn Phe Ala Trp Thr Ala Gly Thr Lys Tyr His Leu Asn
            500                 505                 510
Gly Arg Asn Ser Leu Ala Asn Pro Gly Ile Ala Met Ala Thr His Lys
            515                 520                 525
Asp Asp Glu Glu Arg Phe Phe Pro Ser Asn Gly Ile Leu Ile Phe Gly
            530                 535                 540
Lys Gln Asn Ala Ala Arg Asp Asn Ala Asp Tyr Ser Asp Val Met Leu
545                 550                 555                 560
Thr Ser Glu Glu Glu Ile Lys Thr Thr Asn Pro Val Ala Thr Glu Glu
            565                 570                 575
Tyr Gly Ile Val Ala Asp Asn Leu Gln Gln Gln Asn Thr Ala Pro Gln
            580                 585                 590
Ile Gly Thr Val Asn Ser Gln Gly Ala Leu Pro Gly Met Val Trp Gln
            595                 600                 605
```

```
Asn Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 39
<211> LENGTH: 5
<212> TYPE: PRT
<213> ORGANISM: Adeno-associated virus

<400> SEQUENCE: 39

Asn Gly Thr Ser Gly
1               5

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Gly Thr His
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Asp Thr His
1

<210> SEQ ID NO 42
<211> LENGTH: 5
<212> TYPE: PRT
<213> ORGANISM: Adeno-associated virus

<400> SEQUENCE: 42

Gly Gly Thr Ala Asn
1               5

<210> SEQ ID NO 43
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 43

Asp Gly Ser Gly Leu
1               5
```

TREATMENT OF DISEASES BY LIVER EXPRESSION OF AN ENZYME WHICH HAS A DEOXYRIBONUCLEASE (DNASE) ACTIVITY

CROSS-REFERENCE TO RELATED APPLICATIONS

This application claims priority to U.S. Provisional Patent Application No. 62/617,879, filed on Jan. 16, 2018, the disclosure of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Apr. 30, 2021, is named 252732_000005_SL.txt and is 82,326 bytes in size.

FIELD OF THE INVENTION

The invention relates to the liver-specific delivery and/or expression of an enzyme which has a deoxyribonuclease (DNase) activity for enhanced clearance of cell free DNA (cfDNA) accumulated in hepatic porto-sinusoidal circulation and the use of such liver-specific delivery and/or expression for treatment of various diseases and conditions, including cancer and neurodegeneration.

BACKGROUND OF THE INVENTION

Patients with malignant tumors have elevated levels of circulating cell free DNA (cfDNA) in their plasma and serum as compared to healthy individuals (Fleischhacker, 2007). In cancer patients, circulating cfDNA originates both from dying non-tumor cells, tumor cells and neutrophils. Tumors predispose neutrophils to release extracellular DNA traps that contribute to the establishment of a pro-thrombotic state, cachexia and organ failure in cancer patients (Demmers, 2012). Tumor originated cfDNA can contribute to the development of metastasis and chemotherapy resistance (Garcia-Olmo, 2013). The quantity of circulating cfDNA increases as the tumor progresses (Sawyers, 2008) reaching the maximal levels in patients with advanced disease and metastatic disease (Butt, 2008). It has been shown that higher quantities of circulating cfDNA significantly correlate with poor patient survival (Schwarzenbach, 2008).

Neurodegeneration is a separate clinical pathological condition with progressive loss of structure and/or function of neurons, including death of neurons. Molecular pathways leading to neurodegeneration are highly disease-specific (e.g., accumulation of abnormally folded amyloid-beta and tau proteins in the brain in Alzheimer's disease patients; accumulation of alpha-synuclein in Parkinson's disease; accumulation of mutant Huntingtin in Huntington's disease; accumulation of TDP-43 and FUS protein aggregates in Amyelotropic Lateral Sclerosis (ALS); accumulation of mitochondrial DNA mutations and broken mitochondria division mechanics in aging) and result in neuronal cell death at advanced stages of disease progression. Programmed cell death including apoptosis seems to play a key role in the progression of neurodegeneration at late disease stage, as demonstrated by studies on animal models and cell lines (Radi E., et al., J Alzheimers Dis. 2014; 42).

Patients with neurodegenerative diseases have increased levels of circulating cfDNA, including cfDNA of microbial origin, which significantly contribute to the progression of neurodegeneration (see, e.g., Int. Appl. Pub. No. WO2016/190780) through different mechanisms including transfer through blood brain barrier (BBB) and direct neuronal damage, intracerebral neutrophil DNA traps release (Zenaro, 2015) and triggering cerebral thrombotic arteriopathies.

The present inventors have previously demonstrated that systemic administration of high doses of DNase protein into a patient's circulation can be useful for treatment of a number of diseases and conditions associated with increased levels of cfDNA in the blood, including cancers (e.g., carcinomas, sarcomas, lymphomas, melanoma; see, e.g., U.S. Pat. Nos. 7,612,032; 8,710,012; 9,248,166), development of somatic mosaicism (see, e.g., U.S. Pat. Appl. Pub. No. US20170056482), side effects associated with a chemotherapy or a radiation therapy (see, e.g., U.S. Pat. Appl. Pub. No. US20170100463), neurodegenerative diseases (see, e.g., Int. Appl. Pub. No. WO2016/190780), infections (see, e.g., U.S. Pat. Nos. 8,431,123 and 9,072,733), diabetes (see, e.g., U.S. Pat. No. 8,388,951), atherosclerosis (see, e.g., U.S. Pat. No. 8,388,951), stroke (see, e.g., U.S. Pat. No. 8,796,004), angina (see, e.g., U.S. Pat. No. 8,796,004), ischemia (see, e.g., U.S. Pat. No. 8,796,004), kidney damage (see, e.g., U.S. Pat. No. 9,770,492), delayed-type hypersensitivity reactions such as, e.g., graft-versus-host disease [GVHD]) (see, e.g., U.S. Pat. No. 8,535,663), reduction of fertility (see, e.g., U.S. Pat. No. 8,916,151), age-specific sperm motility impairment (see, e.g., U.S. Pat. No. 8,871,200), and aging (see, e.g., U.S. Pat. Appl. Pub. No. US20150110769). All of these patents and applications are incorporated by reference herein in their entireties.

Others have later demonstrated similar effects. (Wen, 2013; Cederval, 2015; Tohme, 2016; Patutina, 2011; Li, 2015). RhDNase I also suppressed the development of metastatic disease by 60-90% when administered daily at 0.02-2.3 mg/kg in lung carcinoma and hepatoma metastatic disease model (Patutina, 2011). Li (Li, 2015) reported successful use of DNaseI to treat GVHD in mice.

While systemic administration of DNase protein appears to be useful for treating diseases and conditions associated with increased amount of circulating cfDNA, in clinical settings systemic treatment with DNase protein showed limited effects (see, e.g., Int. Appl. Pub. No. WO2014/020564). Thus, there is a need for more efficient methods of reduction of circulating cfDNA levels so as to increase the effectiveness of treating diseases and conditions associated with increased levels of cfDNA in the blood such as, e.g., cancer, development of somatic mosaicism, side effects associated with a chemotherapy or a radiation therapy, neurodegenerative diseases, infections, delayed-type hypersensitivity reactions, diabetes, atherosclerosis, ischemia, stroke, angina, reduction of fertility, age-specific sperm motility impairment, aging, etc.

SUMMARY OF THE INVENTION

As discussed in the Background section, above, there is a need for more efficient methods of reduction of circulating cfDNA levels so as to increase the effectiveness of treating diseases and conditions associated with increased levels of cfDNA in the blood. The present invention addresses these and other needs by providing methods and compositions for liver-specific delivery and/or expression of enzymes which has a DNase activity.

In one aspect, the invention provides a recombinant adeno-associated virus (rAAV) expression vector comprising (i) a capsid protein and (ii) a nucleic acid comprising a promoter operably linked to a nucleotide sequence encoding an enzyme which has a deoxyribonuclease (DNase) activity, wherein the promoter is a liver-specific promoter. In one embodiment, the liver-specific promoter mediates a substantially increased expression of the enzyme in the liver as compared to other tissues and organs.

In another aspect, the invention provides a recombinant adeno-associated virus expression vector (rAAV) comprising (i) a capsid protein and (ii) a nucleic acid comprising a promoter operably linked to a nucleotide sequence encoding an enzyme which has a deoxyribonuclease (DNase) activity, wherein the capsid protein mediates efficient and/or preferential targeting of the vector to the liver when administered in vivo. In one embodiment, the capsid protein is VP3. In one embodiment, the capsid protein comprises one or more mutations which improve efficiency and/or specificity of the delivery of the vector to the liver as compared to the corresponding wild-type capsid protein. In one specific embodiment, the improved efficiency and/or specificity of the delivery of the vector to the liver results in a substantially increased expression of the enzyme in the liver as compared to other tissues and organs.

Non-limiting examples of enzymes having DNase activity which can be used in the vectors of the invention include, e.g., DNase I, DNase X, DNase γ, DNase1L1, DNase1L2, DNase 1L3, DNase II, DNase IIα, DNaseIIβ, Caspase-activated DNase (CAD), Endonuclease G (ENDOG), Granzyme B (GZMB), phosphodiesterase I, lactoferrin, acetylcholinesterase, or mutants or derivatives thereof. In one embodiment, the enzyme which has a DNase activity is a DNase I (e.g., human DNase I) or a mutant or derivative thereof. In one embodiment, the nucleic acid comprises the sequence of SEQ ID NO: 30 or SEQ ID NO: 31. In one embodiment, the DNase I mutant comprises one or more mutations in an actin binding site (e.g., Gln-9, Glu-13, Thr-14, His-44, Asp-53, Tyr-65, Val-66, Val-67, Glu-69, Asn-74, Ala-114, and any combinations thereof; positions indicated in relation to a mature protein sequence lacking secretory signal sequence). In one embodiment, one of the mutations in the actin-binding site is a mutation at Ala-114. In one embodiment, the DNase I mutant comprises one or more mutations increasing DNase activity (e.g., Q9R, E13R, E13K, T14R, T14K, H44R, H44K, N74K, A114F, and any combinations thereof; positions indicated in relation to a mature protein sequence lacking secretory signal sequence). In one embodiment, the DNase I mutant comprises one or more mutations are selected from the group consisting of Q9R, E13R, N74K and A114F, and any combinations thereof. In one embodiment, the DNase I mutant comprises the mutation Q9R. In one embodiment, the DNase I mutant comprises the mutation E13R. In one embodiment, the DNase I mutant comprises the mutation N74K. In one embodiment, the DNase I mutant comprises the mutation A114F.

In one embodiment, the DNase I mutant comprises a sequence having at least 80%, 81%, 82%, 83%, 84%, 85%, 86%, 87%, 88%, 89%, 90%, 91%, 92%, 93%, 94%, 95%, 96%, 97%, 98%, or 99% identity to the sequence of SEQ ID NO: 5. In one embodiment, the DNaseI mutant comprises the mutations Q9R, E13R N74K and A114F. In one embodiment, the DNase I mutant comprises the sequence of SEQ ID NO: 5.

In one embodiment, the DNase I mutant comprises a sequence having at least 80%, 81%, 82%, 83%, 84%, 85%, 86%, 87%, 88%, 89%, 90%, 91%, 92%, 93%, 94%, 95%, 96%, 97%, 98%, or 99% identity to the sequence of SEQ ID NO: 2. In one embodiment, the DNaseI mutant comprises the mutations Q9R, E13R N74K and A114F. In one embodiment, the DNase I mutant comprises the sequence of SEQ ID NO: 2.

In one embodiment, the DNase I mutant consists of the sequence of SEQ ID NO: 2 or SEQ ID NO: 5.

In one embodiment, the DNase I mutant comprises one or more mutations selected from the group consisting of H44C, H44N, L45C, V48C, G49C, L52C, D53C, D53R, D53K, D53Y, D53A, N56C, D58S, D58T, Y65A, Y65E, Y65R, Y65C, V66N, V67E, V67K, V67C, E69R, E69C, A114C, A114R, H44N:T46S, D53R:Y65A, D53R:E69R, H44A: D53R:Y65A, H44A:Y65A:E69R, H64N:V66S, H64N: V66T, Y65N:V67S, Y65N:V67T, V66N:S68T, V67N:E69S, V67N:E69T, S68N:P70S, S68N:P70T, S94N:Y96S, S94N: Y96T, and any combinations thereof. In one embodiment, the nucleotide sequence encodes a DNase I comprising the sequence SEQ ID NO: 4. In one embodiment, the nucleic acid comprises a nucleotide sequence which is at least 85% identical to SEQ ID NO: 23. In one embodiment, the nucleic acid comprises a nucleotide sequence which is at least 90% identical to SEQ ID NO: 23. In one embodiment, the nucleic acid comprises a nucleotide sequence which is at least 95% identical to SEQ ID NO: 23. In one embodiment, the nucleic acid comprises the nucleotide sequence SEQ ID NO: 23. In one embodiment, the nucleotide sequence encodes a DNase I comprising the sequence SEQ ID NO: 1. In one embodiment, the nucleic acid comprises a nucleotide sequence which is at least 85% identical to SEQ ID NO: 22. In one embodiment, the nucleic acid comprises a nucleotide sequence which is at least 90% identical to SEQ ID NO: 22. In one embodiment, the nucleic acid comprises a nucleotide sequence which is at least 95% identical to SEQ ID NO: 22. In one embodiment, the nucleic acid comprises the nucleotide sequence SEQ ID NO: 22. In one embodiment, the nucleic acid comprises a nucleotide sequence which is at least 85% identical to SEQ ID NO: 32. In one embodiment, the nucleic acid comprises a nucleotide sequence which is at least 90% identical to SEQ ID NO: 32. In one embodiment, the nucleic acid comprises a nucleotide sequence which is at least 95% identical to SEQ ID NO: 32. In one embodiment, the nucleic acid comprises the nucleotide sequence SEQ ID NO: 32. In one embodiment, the nucleotide sequence encodes a DNase I mutant comprising the sequence SEQ ID NO: 24. In one embodiment, the nucleic acid comprises a nucleotide sequence which is at least 85% identical to SEQ ID NO: 29. In one embodiment, the nucleic acid comprises a nucleotide sequence which is at least 90% identical to SEQ ID NO: 29. In one embodiment, the nucleic acid comprises a nucleotide sequence which is at least 95% identical to SEQ ID NO: 29. In one embodiment, the nucleic acid comprises the nucleotide sequence SEQ ID NO: 29. In one embodiment, the nucleotide sequence encodes a DNase I mutant comprising the sequence SEQ ID NO: 26. In one embodiment, the nucleic acid comprises a nucleotide sequence which is at least 85% identical to SEQ ID NO: 28. In one embodiment, the nucleic acid comprises a nucleotide sequence which is at least 90% identical to SEQ ID NO: 28. In one embodiment, the nucleic acid comprises a nucleotide sequence which is at least 95% identical to SEQ ID NO: 28. In one embodiment, the nucleic acid comprises the nucleotide sequence SEQ ID NO: 28. In one embodiment, the nucleotide sequence encodes a DNase I mutant comprising the sequence SEQ ID NO: 5. In one embodiment, the nucleic acid comprises a nucleotide sequence which is at least 85% identical to SEQ ID NO: 21. In one embodiment, the nucleic acid comprises a nucleotide sequence which is at least 90% identical to SEQ ID NO: 21. In one embodiment, the nucleic acid comprises a nucleotide sequence which is at least 95% identical to SEQ ID NO: 21. In one embodiment, the nucleic acid comprises the nucleotide sequence SEQ ID NO: 21. In one embodiment, the nucleotide sequence encodes a DNase I mutant comprising the sequence SEQ ID NO: 2. In one embodiment, the nucleic acid comprises a nucleotide sequence which is at least 85% identical to SEQ ID NO: 19. In one embodiment, the nucleic acid comprises a nucleotide sequence which is at least 90% identical to SEQ ID NO: 19. In one embodiment, the nucleic acid comprises a nucleotide sequence which is at least 95% identical to SEQ ID NO: 19. In one embodiment, the nucleic acid comprises the nucleotide sequence SEQ ID NO: 19.

In one embodiment, the enzyme which has a DNase activity is a fusion protein comprising (i) a DNase enzyme or a fragment thereof linked to (ii) an albumin or an Fc polypeptide or a fragment thereof. In one embodiment, the sequence encoding the enzyme which has a DNase activity comprises a sequence encoding a secretory signal sequence, wherein said secretory signal sequence mediates effective secretion of the enzyme into the hepatic sinusoidal system upon expression of the vector in the liver. Non-limiting examples of useful secretory signal sequences include, e.g., DNase I secretory signal sequence, IL2 secretory signal sequence, the albumin secretory signal sequence, the β-glucuronidase secretory signal sequence, the alkaline protease secretory signal sequence, and the fibronectin secretory signal sequence. In one specific embodiment, the secretory signal sequence comprises a sequence having at least 80%, 81%, 82%, 83%, 84%, 85%, 86%, 87%, 88%, 89%, 90%, 91%, 92%, 93%, 94%, 95%, 96%, 97%, 98%, or 99% identity to the sequence MRGMKLLGALLALAALLQGAVS (SEQ ID NO: 6). In one specific embodiment, the secretory signal sequence comprises the sequence MRGMKLLGALLALAALLQGAVS (SEQ ID NO: 6). In one specific embodiment, the secretory signal sequence consists of the sequence MRGMKLLGALLALAALLQGAVS (SEQ ID NO: 6). In one specific embodiment, the secretory signal sequence comprises a sequence having at least 80%, 81%, 82%, 83%, 84%, 85%, 86%, 87%, 88%, 89%, 90%, 91%, 92%, 93%, 94%, 95%, 96%, 97%, 98%, or 99% identity to the sequence MYRMQLLSCIALSLALVTNS (SEQ ID NO: 7). In one specific embodiment, the secretory signal sequence comprises the sequence MYRMQLLSCIALSLALVTNS (SEQ ID NO: 7). In one specific embodiment, the secretory signal sequence consists of the sequence MYRMQLLSCIALSLALVTNS (SEQ ID NO: 7). In one specific embodiment, the sequence encoding the secretory signal sequence comprises a nucleotide sequence which is at least 85% identical to SEQ ID NO: 20. In one specific embodiment, the sequence encoding the secretory signal sequence comprises a nucleotide sequence which is at least 90% identical to SEQ ID NO: 20. In one specific embodiment, the sequence encoding the secretory signal sequence comprises a nucleotide sequence which is at least 95% identical to SEQ ID NO: 20. In one specific embodiment, the sequence encoding the secretory signal sequence comprises the nucleotide sequence SEQ ID NO: 20.

In one specific embodiment, the secretory signal sequence comprises the sequence MRYTGLMGTLLTLVNLLQLAGT (SEQ ID NO: 25). In one specific embodiment, the secretory signal sequence consists of the sequence MRYTGLMGTLLTLVNLLQLAGT (SEQ ID NO: 25). In one specific embodiment, the secretory signal sequence comprises a sequence having at least 80% sequence identity to sequence MRYTGLMGTLLTLVNLLQLAGT (SEQ ID NO: 25). In one specific embodiment, the sequence encoding the secretory signal sequence comprises a nucleotide sequence which is at least 85% identical to SEQ ID NO: 27. In one specific embodiment, the sequence encoding the secretory signal sequence comprises a nucleotide sequence which is at least 90% identical to SEQ ID NO: 27. In one specific embodiment, the sequence encoding the secretory signal sequence comprises a nucleotide sequence which is at least 95% identical to SEQ ID NO: 27. In one specific embodiment, the sequence encoding the secretory signal sequence comprises the nucleotide sequence of SEQ ID NO: 27.

Non-limiting examples of promoters which can be used in the vectors of the invention include, e.g., an albumin promoter, an a1-anti-trypsin (AAT) promoter, a thyroid hormone-binding globulin promoter, an alpha fetoprotein promoter, an alcohol dehydrogenase promoter, a factor VIII (FVIII) promoter, a HBV basic core promoter (BCP), a HBV PreS2 promoter, a phosphoenol pyruvate carboxykinase (PEPCK) promoter, a thyroxin-binding globulin (TBG) promoter, an Hepatic Control Region (HCR)-ApoCII hybrid promoter, an HCR-hAAT hybrid promoter, an apolipoprotein E (ApoE) promoter, a low density lipoprotein promoter, a pyruvate kinase promoter, a phosphenol pyruvate carboxykinase promoter, a phenylalanine hydroxylase promoter, a lecithin-cholesterol acyl transferase (LCAT) promoter, an apolipoprotein H (ApoH) promoter, an apolipoprotein A-II promoter (APOA2), a transferrin promoter, a transthyretin promoter, an α-fibrinogen promoter, a β-fibrinogen promoter, an alpha 1-antichymotrypsin promoter, an α2-HS glycoprotein promoter, an haptoglobin promoter, a ceruloplasmin promoter, a plasminogen promoter, a promoter of a complement protein, α1-acid glycoprotein promoter, a LSP1 promoter, a serpin peptidase inhibitor promoter, a Glade A member 1 (SERPINA1) (hAAT) promoter, a Cytochrome P450 family 3 subfamily A polypeptide 4 (CYP3A4) promoter, a microRNA 122 (miR-122) promoter, a liver-specific IGF-II promoter P1, a transthyretin (MTTR) promoter, and an α-fetoprotein (AFP) promoter.

In one embodiment, the promoter is an albumin promoter. In one specific embodiment, the albumin promoter comprises the sequence of SEQ ID NO: 8. In one specific embodiment, the albumin promoter consists of the sequence of SEQ ID NO: 8. See also Frain et al., Mol. Cell Biol., 1990, 10(3):991-999.

In one embodiment, the promoter is an a1-anti-trypsin (AAT) promoter. In one embodiment, the promoter is a human α1-anti-trypsin (hAAT) promoter. In one specific embodiment, the anti-trypsin promoter comprises a sequence having at least 80%, 81%, 82%, 83%, 84%, 85%, 86%, 87%, 88%, 89%, 90%, 91%, 92%, 93%, 94%, 95%, 96%, 97%, 98%, or 99% identity to the sequence of SEQ ID NO: 15. In one specific embodiment, the AAT promoter comprises the sequence of SEQ ID NO: 15. In one specific embodiment, the AAT promoter consists of the sequence of SEQ ID NO: 15.

In one embodiment, the capsid protein comprises one or more mutations selected from the group consisting of S279A, S671A, K137R, T252A, and any combinations thereof. In one embodiment, the one or more mutations in the capsid protein include mutation K137R. In one embodiment, the capsid protein comprises the sequence SEQ ID NO:3 [Anc80]. In one embodiment, the capsid protein consists of the sequence SEQ ID NO:3 [Anc80]. In one embodiment, the capsid protein comprises the sequence SEQ ID NO:9 [Anc80]. In one embodiment, the capsid protein consists of the sequence SEQ ID NO:9 [Anc80]. In one embodiment, the capsid protein comprises the sequence SEQ ID NO:34 [Anc80L65]. In one embodiment, the capsid protein consists of the sequence SEQ ID NO:34 [Anc80L65]. In one embodiment, the capsid protein comprises the sequence SEQ ID NO:35 [Anc80L65 variant]. In one embodiment, the capsid protein consists of the sequence SEQ ID NO:35 [Anc80L65 variant]. In one embodiment, the capsid protein is a mutant AAV8 capsid protein such as, e.g., AAV3G1, AAVT20 or AAVTR1, or another mutant capsid protein disclosed in Int. Pat. Appl. Pub. No. WO2017/180854 (e.g., comprising VP3 mutations in amino acids 263-267 [e.g., 263NGTSG267→SGTH ("NGTSG" disclosed as SEQ ID NO: 39 and "SGTH" disclosed as SEQ ID NO: 40) or 263NGTSG267→SDTH ("NGTSG" disclosed as SEQ ID NO: 39 and "SDTH" disclosed as SEQ ID NO: 41)] and/or amino acids 457-459 [e.g., 457TAN459→SRP], and/or amino acids 455-459 [e.g., 455GGTAN459→DGSGL ("GGTAN" disclosed as SEQ ID NO: 42 and "DGSGL" disclosed as SEQ ID NO: 43)] and/or amino acids 583-597).

Non-limiting examples of AAVs which can be used in the vectors of the invention include, e.g., serotype 1 (AAV1), AAV2, AAV3 (including AAV3A and AAV3B), AAV4, AAV5, AAV6, AAV7, AAV8, AAV9, AAV10, AAV11, AAV12, AAVrh10, AAVLK03, AAVhu37, AAVrh64R1, and Anc 80. In one specific embodiment, the AAV is from serotype 8 or Anc 80.

In one embodiment, the nucleic acid of the AAV vector further comprises two AAV inverted terminal repeats (ITRs), wherein the ITRs flank the nucleotide sequence encoding the enzyme which has a DNase activity.

In one embodiment, the nucleic acid of the AAV vector further comprises one or more enhancers located upstream or downstream of the promoter. In one embodiment, the enhancer may be located immediately upstream with the promoter, e.g., where the 3' end of an enhancer sequence fused directly to the 5' end of the promoter sequence. Non-limiting examples of useful enhancers include, e.g., an apolipoprotein E (ApoE) enhancer (e.g., an ApoE hepatic control region-1 (HCR-1) enhancer or an ApoE HCR-2 enhancer), an alpha fetoprotein enhancer, a TTR enhancer, an LSP enhancer, an al-microglobulin/bikunin enhancer, an albumin gene enhancer (Ealb), and any combination thereof. In one specific embodiment, the enhancer is an ApoE enhancer. In one specific embodiment, the enhancer is an ApoE enhancer located upstream of the promoter. In one specific embodiment, the enhancer is an ApoE enhancer fused to the 5' end of the promoter. In one specific embodiment, the ApoE enhancer is a hepatic control region (HCR) enhancer. In one specific embodiment, the enhancer comprises a sequence having at least 80%, 81%, 82%, 83%, 84%, 85%, 86%, 87%, 88%, 89%, 90%, 91%, 92%, 93%, 94%, 95%, 96%, 97%, 98%, or 99% identity to the sequence of SEQ ID NO: 17. In one specific embodiment, the enhancer comprises the sequence of SEQ ID NO: 17. In one specific embodiment, the enhancer consists of the sequence of SEQ ID NO: 17.

In one embodiment, the nucleic acid of the AAV vector further comprises a polyadenylation signal operably linked to the nucleotide sequence encoding the enzyme which has a DNase activity.

In one embodiment, the nucleic acid further comprises a Kozak sequence. In one specific embodiment, the Kozak sequence comprises the sequence of 5'-GCCGCCACC-3' (SEQ ID NO: 33). In one embodiment, the nucleic acid comprises a nucleotide sequence which is at least 80% identical to SEQ ID NO: 30. In one embodiment, the nucleic acid comprises a nucleotide sequence which is at least 85% identical to SEQ ID NO: 30. In one embodiment, the nucleic acid comprises a nucleotide sequence which is at least 90% identical to SEQ ID NO: 30. In one embodiment, the nucleic acid comprises a nucleotide sequence which is at least 95% identical to SEQ ID NO: 30. In one embodiment, the nucleic acid comprises the nucleotide sequence SEQ ID NO: 30.

In one embodiment, the nucleic acid further comprises a post-transcriptional regulatory element. In one embodiment, the post-transcriptional regulatory element is a woodchuck hepatitis post-transcriptional regulatory element (WPRE). In one specific embodiment, the WPRE does not encode a functional X protein. In one embodiment, the post-transcriptional regulatory element comprises a sequence having at least 80%, 81%, 82%, 83%, 84%, 85%, 86%, 87%, 88%, 89%, 90%, 91%, 92%, 93%, 94%, 95%, 96%, 97%, 98%, or 99% identity to the sequence of SEQ ID NO: 16. In one specific embodiment, the post-transcriptional regulatory element comprises the sequence of SEQ ID NO: 16. In one specific embodiment, the post-transcriptional regulatory element consists of the sequence of SEQ ID NO: 16.

In one embodiment, the nucleic acid of rAAV vector of the invention comprises a sequence having at least 80%, 81%, 82%, 83%, 84%, 85%, 86%, 87%, 88%, 89%, 90%, 91%, 91.5%, 92%, 92.5%, 93%, 93.5%, 94%, 94.5%, 95%, 95.5%, 96%, 96.5%, 97%, 97.5%, 98%, 98.5%, 99% or 99.5% identity to the sequence of SEQ ID NO: 19. In one specific embodiment, the nucleic acid comprises the sequence of SEQ ID NO: 19. In one specific embodiment, the nucleic acid consists of the sequence of SEQ ID NO: 19. In one specific embodiment, the nucleic acid has a map shown in FIG. 10.

In one embodiment, the invention provides a recombinant adeno-associated virus (rAAV) expression vector comprising (i) a capsid protein comprising the sequence SEQ ID NO: 34 and (ii) a nucleic acid comprising a nucleotide sequence encoding the deoxyribonuclease (DNase) enzyme comprising the sequence SEQ ID NO: 4 operably linked to an albumin promoter or an α1-anti-trypsin (AAT) promoter.

In one embodiment, the invention provides a recombinant adeno-associated virus (rAAV) expression vector comprising (i) a capsid protein comprising the sequence SEQ ID NO: 34 and (ii) a nucleic acid comprising a nucleotide sequence encoding the deoxyribonuclease (DNase) enzyme comprising the sequence SEQ ID NO: 5 operably linked to an albumin promoter or an al-anti-trypsin (AAT) promoter.

In one embodiment, the invention provides a recombinant adeno-associated virus (rAAV) expression vector comprising (i) a capsid protein comprising the sequence SEQ ID NO: 34 and (ii) a nucleic acid comprising a nucleotide sequence encoding the deoxyribonuclease (DNase) enzyme comprising the sequence SEQ ID NO: 1 operably linked to an albumin promoter or an al-anti-trypsin (AAT) promoter.

In one embodiment, the invention provides a recombinant adeno-associated virus (rAAV) expression vector comprising (i) a capsid protein comprising the sequence SEQ ID NO: 34 and (ii) a nucleic acid comprising a nucleotide sequence encoding the deoxyribonuclease (DNase) enzyme comprising the sequence SEQ ID NO: 2 operably linked to an albumin promoter or an al-anti-trypsin (AAT) promoter.

In one embodiment, the invention provides a recombinant adeno-associated virus (rAAV) expression vector comprising (i) a capsid protein comprising the sequence SEQ ID NO: 34 and (ii) a nucleic acid comprising the nucleotide sequence of SEQ ID NO: 30.

In one embodiment, the invention provides a recombinant adeno-associated virus (rAAV) expression vector comprising (i) a capsid protein comprising the sequence SEQ ID NO: 34 and (ii) a nucleic acid comprising the nucleotide sequence of SEQ ID NO: 31.

In a related aspect, the invention provides pharmaceutical compositions and dosage forms comprising any of the rAAV vectors of the invention and a pharmaceutically acceptable carrier and/or excipient.

In a related aspect, the invention provides a method for delivering an enzyme which has a deoxyribonuclease (DNase) activity to the liver in a subject in need thereof, comprising administering to the subject any of the rAAV vectors or pharmaceutical compositions described above.

In another aspect, the invention provides a method for treating a disease or condition (e.g., a cancer, a neurodegenerative disease, an atherosclerosis, or a delayed-type hypersensitivity reaction) in a subject in need thereof, wherein the disease or condition is accompanied by accumulation/elevated levels of cell free DNA (cfDNA) in the hepatic porto-sinusoidal circulation of the subject, said method comprising administering to the subject a therapeutically effective amount of any of the rAAV vectors or pharmaceutical compositions described above.

In a further aspect, the invention provides a method for treating a cancer in a subject in need thereof, said method comprising administering to the subject a therapeutically effective amount of any of the rAAV vectors or pharmaceutical compositions described above. In one embodiment, the cancer originates in and/or metastasizes to organs, tissues and/or structures that drain to the portal vein. In one embodiment, the method is effective to inhibit metastasis. Non-limiting examples of cancers treatable by the methods of the invention include, e.g., a peritoneal carcinomatosis, a lymphoma, a stomach cancer, a colon cancer, an intestinal cancer, a colorectal cancer, a pancreatic cancer, a liver cancer, a cancer of the bile duct, a cancer of the gall bladder, a sarcoma, and a liver metastatic disease of any origin.

In another aspect, the invention provides a method for treating a neurodegenerative disease in a subject in need thereof, said method comprising administering to the subject a therapeutically effective amount of any of the rAAV vectors or pharmaceutical compositions described above. Non-limiting examples of neurodegenerative diseases treatable by the methods of the invention include, e.g., Alzheimer's disease, Mild Cognitive Impairment (MCI), CADASIL syndrome, Parkinson's disease, Amyotrophic Lateral Sclerosis, progressive supranuclear palsy (PSP), corticobasal degeneration (CBD), agyrophilic grain disease (AGD), Pick's disease (PiD), Huntington's disease (HD), and Frontotemporal dementia with parkinsonism-17 (FTDP-17). In one embodiment, the neurodegenerative disease is associated with the formation of a misfolded protein due to the presence of DNA. In one specific embodiment, the DNA is human DNA, microbial DNA, cell-free DNA, or intracellular DNA.

In one embodiment, the neurodegenerative disease is secondary to diabetes, rheumatoid arthritis, systemic lupus erythematosus (SLE), gout, metabolic syndrome, an amyloidosis, asthma, or prion disease. In one embodiment, the amyloidosis is an amyloidosis with a hereditary cerebral hemorrhage, a primary systemic amyloidosis, a secondary systemic amyloidosis, a serum amyloidosis, a senile systemic amyloidosis, a hemodialysis-related amyloidosis, a Finnish hereditary systemic amyloidosis, an Atrial amyloidosis, a Lysozyme systemic amyloidosis, an Insulin-related amyloidosis, or a Fibrinogen a-chain amyloidosis.

In yet another aspect, the invention provides a method for treating a delayed-type hypersensitivity reaction in a subject in need thereof, said method comprising administering to the subject a therapeutically effective amount of any of the rAAV vectors or pharmaceutical compositions described above. In one embodiment, the delayed-type hypersensitivity reaction is a graft-versus-host disease (GVHD).

In a further aspect, the invention provides a method for treating an atherosclerosis in a subject in need thereof, said method comprising administering to the subject a therapeutically effective amount of any of the rAAV vectors or pharmaceutical compositions described above.

In another aspect, the invention provides a method for preventing or ameliorating one or more side effects associated with a chemotherapy or a radiation therapy in a subject in need thereof, said method comprising administering to the subject a therapeutically effective amount of any of the rAAV vectors or pharmaceutical compositions described above. In one embodiment, said one or more side effects of the chemotherapy are selected from the group consisting of body weight loss, bone marrow toxicity, catabolic changes in blood biochemistry, cardiotoxicity (e.g., myocardial necrosis), gastrointestinal toxicity, suppression of immunity, and neutropenia. In one embodiment, the chemotherapy comprises administration of one or more compounds selected from the group consisting of antimetabolites, alkylating agents, anticancer antibiotics, microtubule-targeting agents, topoisomerase inhibitors, alkaloids, and targeted therapeutics. In one embodiment, the chemotherapy comprises administration of one or more compounds selected from the group consisting of anthracycline, doxorubicin, 5-fluorouracil (5-FU), etoposide, taxane, and cyclophosphamide. In one embodiment, said one or more side effects of the radiation therapy are selected from the group consisting of body weight loss, skin irritation, skin damage, fatigue, nausea, vomiting, fibrosis, bowel damage, memory loss, infertility, and a second cancer. In one embodiment, the radiation therapy is external beam radiation therapy or systemic radioisotope therapy. In one embodiment, the rAAV vector or the vector composition is administered during a cycle of the chemotherapy or radiation therapy. In another embodiment, the rAAV vector or the vector composition is administered after a cycle of the chemotherapy or radiation therapy. In one embodiment, chemotherapy or radiotherapy is used for treatment of a cancer selected from the group consisting of a peritoneal carcinomatosis, a lymphoma, a stomach cancer, a colon cancer, an intestinal cancer, a colorectal cancer, a pancreatic cancer, a liver cancer, a cancer of the bile duct, a cancer of the gall bladder, a sarcoma, and a liver metastatic disease of any origin.

In one embodiment of any of the above methods of the invention, the administration of the rAAV vector or the vector composition results in the expression of the enzyme which has a DNase activity and its secretion into the hepatic porto-sinusoidal circulation of the subject.

In one embodiment of any of the above methods of the invention, the rAAV vector or the vector composition is administered in a dose and regimen which is sufficient to decrease the level of the cell free DNA (cfDNA) in the porto-sinusoidal circulation of said subject.

In one embodiment of any of the above methods of the invention, the subject is human.

In another aspect, the invention provides a method for delivering an enzyme which has a deoxyribonuclease (DNase) activity to the liver in a subject in need thereof, comprising administering to the subject an expression vector comprising a nucleic acid comprising a promoter operably linked to a sequence encoding the enzyme, wherein the promoter is a liver-specific promoter.

In a further aspect, the invention provides a method for delivering an enzyme which has a deoxyribonuclease (DNase) activity to the liver in a subject in need thereof, comprising administering to the subject an expression vector comprising a nucleic acid comprising a promoter operably linked to a sequence encoding the enzyme, wherein the vector comprises one or more molecules capable of targeting the nucleic acid to liver cells when administered in vivo.

In yet another aspect, the invention provides a method for treating a disease or condition in a subject in need thereof, wherein the disease or condition is accompanied by accumulation/elevated levels of cell free DNA (cfDNA) in the hepatic porto-sinusoidal circulation of the subject, said method comprising administering to the subject an expression vector comprising a nucleic acid comprising a promoter operably linked to a sequence encoding an enzyme which has a deoxyribonuclease (DNase) activity, wherein the promoter is a liver-specific promoter. In one embodiment, the disease is selected from the group consisting of a cancer (including a liver metastatic disease), a neurodegenerative disease, an atherosclerosis, and a delayed-type hypersensitivity reaction.

In another aspect, the invention provides a method for treating a disease or condition in a subject in need thereof, wherein the disease or condition is accompanied by accumulation/elevated levels of cell free DNA (cfDNA) in the hepatic porto-sinusoidal circulation of the subject, said method comprising administering to the subject an expression vector comprising a nucleic acid comprising a promoter operably linked to a sequence encoding an enzyme which has a deoxyribonuclease (DNase) activity, wherein the vector comprises one or more molecules capable of targeting of the nucleic acid to liver cells. In one embodiment, the disease is selected from the group consisting of a cancer (including a liver metastatic disease), a neurodegenerative disease, an atherosclerosis, and a delayed-type hypersensitivity reaction.

In a further aspect, the invention provides a method for treating a cancer in a subject in need thereof, said method comprising administering to the subject an expression vector comprising a nucleic acid comprising a promoter operably linked to a sequence encoding an enzyme which has a deoxyribonuclease (DNase) activity, wherein the promoter is a liver-specific promoter. In one embodiment, the cancer originates in and/or metastasizes to organs, tissues and/or structures that drain to the portal vein.

In yet another aspect, the invention provides a method for treating a cancer in a subject in need thereof, said method comprising administering to the subject an expression vector comprising a nucleic acid comprising a promoter operably linked to a sequence encoding an enzyme which has a deoxyribonuclease (DNase) activity, wherein the vector comprises one or more molecules capable of targeting of the nucleic acid to liver cells. In one embodiment, the cancer originates in and/or metastasizes to organs, tissues and/or structures that drain to the portal vein.

In a further aspect, the invention provides a method for treating a cancer in a subject in need thereof, said method comprising administering to the subject an expression vector comprising a nucleic acid encoding an enzyme which has a deoxyribonuclease (DNase) activity, wherein said expression vector provides synthesis of the DNase enzyme in the liver of said subject and wherein the cancer originates in and/or metastasizes to organs, tissues and/or structures that drain to the portal vein.

Non-limiting examples of cancers treatable by any of the above methods for treating cancer include, e.g., a peritoneal carcinomatosis, a lymphoma, a stomach cancer, a colon cancer, an intestinal cancer, a colorectal cancer, a pancreatic cancer, a liver cancer, a cancer of the bile duct, a cancer of the gall bladder, a sarcoma, and a liver metastatic disease of any origin.

In one embodiment of any of the above methods for treating cancer, the method is effective to inhibit metastasis.

In yet another aspect, the invention provides a method for treating a neurodegenerative disease in a subject in need thereof, said method comprising administering to the subject an expression vector comprising a nucleic acid comprising a promoter operably linked to a sequence encoding an enzyme which has a deoxyribonuclease (DNase) activity, wherein the promoter is a liver-specific promoter.

In a further aspect, the invention provides a method for treating a neurodegenerative disease in a subject in need thereof, said method comprising administering to the subject an expression vector comprising a nucleic acid comprising a promoter operably linked to a sequence encoding an enzyme which has a deoxyribonuclease (DNase) activity, wherein the vector comprises one or more molecules capable of targeting of the nucleic acid to liver cells.

In another aspect, the invention provides a method for treating a neurodegenerative disease in a subject in need thereof, said method comprising administering to the subject an expression vector comprising a nucleic acid encoding an enzyme which has a deoxyribonuclease (DNase) activity, wherein said expression vector provides synthesis of the DNase enzyme in the liver of said subject and wherein the microbial cell free DNA (cfDNA) of intestinal origin is detectable in the blood of said patient.

Non-limiting examples of neurodegenerative diseases treatable by any of the above methods for treating neurodegenerative diseases include, e.g., Alzheimer's disease, Mild Cognitive Impairment (MCI), CADASIL syndrome, Parkinson's disease, Amyotrophic Lateral Sclerosis, progressive supranuclear palsy (PSP), corticobasal degeneration (CBD), agyrophilic grain disease (AGD), Pick's disease (PiD), Huntington's disease (HD), and Frontotemporal dementia with parkinsonism-17 (FTDP-17). In one embodiment, the neurodegenerative disease is secondary to diabetes, rheumatoid arthritis, systemic lupus erythematosus (SLE), gout, metabolic syndrome, an amyloidosis, asthma, or prion disease. In one embodiment, the amyloidosis is an amyloidosis with a hereditary cerebral hemorrhage, a primary systemic amyloidosis, a secondary systemic amyloidosis, a serum amyloidosis, a senile systemic amyloidosis, a hemodialysis-related amyloidosis, a Finnish hereditary systemic amyloidosis, an Atrial amyloidosis, a Lysozyme systemic amyloidosis, an Insulin-related amyloidosis, or a Fibrinogen a-chain amyloidosis.

In another aspect, the invention provides a method for treating a delayed-type hypersensitivity reaction in a subject in need thereof, said method comprising administering to the subject an expression vector comprising a nucleic acid comprising a promoter operably linked to a sequence encoding an enzyme which has a deoxyribonuclease (DNase) activity, wherein the promoter is a liver-specific promoter. In one embodiment, the delayed-type hypersensitivity reaction is a graft-versus-host disease (GVHD).

In yet another aspect, the invention provides a method for treating a delayed-type hypersensitivity reaction in a subject in need thereof, said method comprising administering to the subject an expression vector comprising a nucleic acid comprising a promoter operably linked to a sequence encoding an enzyme which has a deoxyribonuclease (DNase) activity, wherein the vector comprises one or more molecules capable of targeting of the nucleic acid to liver cells. In one embodiment, the delayed-type hypersensitivity reaction is a graft-versus-host disease (GVHD).

In a further aspect, the invention provides a method for treating an atherosclerosis in a subject in need thereof, said method comprising administering to the subject an expression vector comprising a nucleic acid comprising a promoter operably linked to a sequence encoding an enzyme which has a deoxyribonuclease (DNase) activity, wherein the promoter is a liver-specific promoter.

In yet another aspect, the invention provides a method for treating an atherosclerosis in a subject in need thereof, said method comprising administering to the subject an expression vector comprising a nucleic acid comprising a promoter operably linked to a sequence encoding an enzyme which has a deoxyribonuclease (DNase) activity, wherein the vector comprises one or more molecules capable of targeting of the nucleic acid to liver cells.

In another aspect, the invention provides a method for preventing or ameliorating one or more side effects associated with a chemotherapy or a radiation therapy in a subject in need thereof, said method comprising administering to the subject an expression vector comprising a nucleic acid comprising a promoter operably linked to a sequence encoding an enzyme which has a deoxyribonuclease (DNase) activity, wherein the promoter is a liver-specific promoter.

In a further aspect, the invention provides a method for preventing or ameliorating one or more side effects associated with a chemotherapy or a radiation therapy in a subject in need thereof, said method comprising administering to the subject an expression vector comprising a nucleic acid comprising a promoter operably linked to a sequence encoding an enzyme which has a deoxyribonuclease (DNase) activity, wherein the vector comprises one or more molecules capable of targeting of the nucleic acid to liver cells.

In one embodiment of any of the above methods for preventing or ameliorating one or more side effects associated with a chemotherapy, said one or more side effects of the chemotherapy are selected from the group consisting of body weight loss, bone marrow toxicity, catabolic changes in blood biochemistry, cardiotoxicity (e.g., myocardial necrosis), gastrointestinal toxicity, suppression of immunity, and neutropenia.

In one embodiment of any of the above methods for preventing or ameliorating one or more side effects associated with a chemotherapy, the chemotherapy comprises administration of one or more compounds selected from the group consisting of antimetabolites, alkylating agents, anticancer antibiotics, microtubule-targeting agents, topoisomerase inhibitors, alkaloids, and targeted therapeutics.

In one embodiment of any of the above methods for preventing or ameliorating one or more side effects associated with a chemotherapy, the chemotherapy comprises administration of one or more compounds selected from the group consisting of anthracycline, doxorubicin, 5-fluorouracil (5-FU), etoposide, taxane, and cyclophosphamide.

In one embodiment of any of the above methods for preventing or ameliorating one or more side effects associated with a radiation therapy, said one or more side effects of the radiation therapy are selected from the group consisting of body weight loss, skin irritation, skin damage, fatigue, nausea, vomiting, fibrosis, bowel damage, memory loss, infertility, and a second cancer.

In one embodiment of any of the above methods for preventing or ameliorating one or more side effects associated with a radiation therapy, the radiation therapy is external beam radiation therapy or systemic radioisotope therapy.

In one embodiment of any of the above methods for preventing or ameliorating one or more side effects associated with a chemotherapy or a radiation therapy, the vector is administered during a cycle of the chemotherapy or radiation therapy.

In one embodiment of any of the above methods for preventing or ameliorating one or more side effects associated with a chemotherapy or a radiation therapy, the vector is administered after a cycle of the chemotherapy or radiation therapy.

In one embodiment of any of the methods of the invention, the vector further comprises one or more molecules capable of targeting of the nucleic acid to liver cells.

In one embodiment of any of the methods of the invention, the promoter is a liver-specific promoter.

In one embodiment of any of the methods of the invention, the vector is packaged in a liposome or a nanoparticle.

In one embodiment of any of the methods of the invention, the vector is used as a naked DNA.

In one embodiment of any of the methods of the invention, the vector is a viral vector. Non-limiting examples of useful viral vectors include, e.g., adeno-associated virus vectors, adenovirus vectors, retrovirus vectors (e.g., lentivirus vectors), and hepatotropic virus vectors (e.g., hepatitis B virus (HBV) vectors).

In one embodiment of any of the methods of the invention, the enzyme which has a DNase activity is selected from the group consisting of DNase I, DNase X, DNase γ, DNase1L1, DNase1L2, DNase1L3, DNase II, DNase IIα, DNase IIβ, Caspase-activated DNase (CAD), Endonuclease G (ENDOG), Granzyme B (GZMB), phosphodiesterase I, lactoferrin, acetylcholinesterase, and mutants or derivatives thereof. In one embodiment, the DNase is DNase I (e.g., human DNase I) or a mutant or derivative thereof. In one embodiment, the DNase I mutant comprises one or more mutations in an actin binding site (e.g., Gln-9, Glu-13, Thr-14, His-44, Asp-53, Tyr-65, Val-66, Val-67, Glu-69, Asn-74, Ala-114, and any combinations thereof positions indicated in relation to a mature protein sequence lacking secretory signal sequence). In one embodiment, one of the mutations in the actin-binding site is a mutation at Ala-114. In one embodiment, the DNase I mutant comprises one or more mutations increasing DNase activity (e.g., Q9R, E13R, E13K, T14R, T14K, H44R, H44K, N74K, A114F, and any combinations thereof positions indicated in relation to a mature protein sequence lacking secretory signal sequence). In one embodiment, the DNase I mutant comprises one or more mutations are selected from the group consisting of Q9R, E13R, N74K and A114F, and any combinations thereof. In one embodiment, the DNase I mutant comprises the mutation Q9R. In one embodiment, the DNase I mutant comprises the mutation E13R. In one embodiment, the DNase I mutant comprises the mutation N74K. In one embodiment, the DNase I mutant comprises the mutation A114F.

In one embodiment, the DNase I mutant comprises one or more mutations selected from the group consisting of H44C, H44N, L45C, V48C, G49C, L52C, D53C, D53R, D53K, D53Y, D53A, N56C, D58S, D58T, Y65A, Y65E, Y65R, Y65C, V66N, V67E, V67K, V67C, E69R, E69C, A114C, A114R, H44N:T46S, D53R:Y65A, D53R:E69R, H44A: D53R:Y65A, H44A:Y65A:E69R, H64N:V66S, H64N: V66T, Y65N:V67S, Y65N:V67T, V66N:S68T, V67N:E69S, V67N:E69T, S68N:P70S, S68N:P70T, S94N:Y96S, S94N: Y96T, and any combinations thereof. In one embodiment, the DNase I mutant is a long acting form of DNase. In one embodiment, the DNase I comprises the sequence SEQ ID NO: 4. In one embodiment, the DNase I comprises the sequence SEQ ID NO: 1. In one embodiment, the DNase I mutant comprises the sequence SEQ ID NO: 5. In one embodiment, the DNase I mutant comprises the sequence SEQ ID NO: 2.

In one embodiment of any of the methods of the invention, the sequence encoding the enzyme which has a DNase activity comprises a secretory signal sequence, wherein said secretory signal sequence mediates effective secretion of the enzyme into the hepatic porto-sinusoidal circulation upon administration of the vector to the subject. In one embodiment, the secretory signal sequence is selected from the group consisting of DNase I secretory signal sequence, IL2 secretory signal sequence, albumin secretory signal sequence, β-glucuronidase secretory signal sequence, alkaline protease secretory signal sequence, and fibronectin secretory signal sequence. In one specific embodiment, the secretory signal sequence comprises a sequence having at least 80%, 81%, 82%, 83%, 84%, 85%, 86%, 87%, 88%, 89%, 90%, 91%, 92%, 93%, 94%, 95%, 96%, 97%, 98%, or 99% identity to the sequence MRGMKLLGALLA-LAALLQGAVS (SEQ ID NO: 6). In one embodiment, the secretory signal sequence comprises the sequence MRGMKLLGALLALAALLQGAVS (SEQ ID NO: 6). In one embodiment, the secretory signal sequence consists of the sequence MRGMKLLGALLALAALLQGAVS (SEQ ID NO: 6). In one specific embodiment, the secretory signal sequence comprises a sequence having at least 80%, 81%, 82%, 83%, 84%, 85%, 86%, 87%, 88%, 89%, 90%, 91%, 92%, 93%, 94%, 95%, 96%, 97%, 98%, or 99% identity to the sequence MYRMQLLSCIALSLALVTNS (SEQ ID NO: 7). In one embodiment, the secretory signal sequence comprises the sequence MYRMQLLSCIALSLALVTNS (SEQ ID NO: 7). In one embodiment, the secretory signal sequence consists of the sequence MYRMQLLSCIALSLA-LVTNS (SEQ ID NO: 7).

In one embodiment of any of the methods of the invention, the liver-specific promoter mediates a substantially increased expression of the enzyme in the liver as compared to other tissues and organs. Non-limiting examples of liver-specific promoters useful in the methods and vectors of the present invention include, e.g., an albumin promoter, an al-anti-trypsin (AAT) promoter, a thyroid hormone-binding globulin promoter, an alpha fetoprotein promoter, an alcohol dehydrogenase promoter, a factor VIII (FVIII) promoter, a HBV basic core promoter (BCP), a HBV PreS2 promoter, a phosphoenol pyruvate carboxykinase (PEPCK) promoter, a thyroxin-binding globulin (TBG) promoter, an Hepatic Control Region (HCR)-ApoCII hybrid promoter, an HCR-hAAT hybrid promoter, an apolipoprotein E (ApoE) promoter, a low density lipoprotein promoter, a pyruvate kinase promoter, a phosphenol pyruvate carboxykinase promoter, a phenylalanine hydroxylase promoter, a lecithin-cholesterol acyl transferase (LCAT) promoter, an apolipoprotein H (ApoH) promoter, an apolipoprotein A-II promoter (APOA2), a transferrin promoter, a transthyretin promoter, an α-fibrinogen promoter, a β-fibrinogen promoter, an alpha 1-antichymotrypsin promoter, an α2-HS glycoprotein promoter, an haptoglobin promoter, a ceruloplasmin promoter, a plasminogen promoter, a promoter of a complement protein, al-acid glycoprotein promoter, a LSP1 promoter, a serpin peptidase inhibitor promoter, a Glade A member 1 (SERPINA1) (hAAT) promoter, a Cytochrome P450 family 3 subfamily A polypeptide 4 (CYP3A4) promoter, a microRNA 122 (miR-122) promoter, a liver-specific IGF-II promoter P1, a transthyretin (MTTR) promoter, and an α-fetoprotein (AFP) promoter. In one embodiment, the liver-specific promoter is an albumin promoter. In one specific embodiment, the albumin promoter comprises the sequence of SEQ ID NO: 8. In one embodiment, the albumin promoter consists of the sequence of SEQ ID NO: 8. See also Frain et al., Mol. Cell Biol., 1990, 10(3):991-999.

In one specific embodiment, the liver-specific promoter is al-anti-trypsin (AAT) promoter. In one specific embodiment, the anti-trypsin promoter is a human al-anti-trypsin (AAT) promoter. In one specific embodiment, the AAT promoter comprises the sequence of SEQ ID NO: 15. In one specific embodiment, the AAT promoter comprises the sequence of SEQ ID NO: 15. In one specific embodiment, the AAT promoter consists of the sequence of SEQ ID NO: 15. In various embodiments of any of the methods of the invention, the vector comprises an enhancer. The enhancer may be a hepatic control region enhancer, such as HCR-1 or HCR-2 associated with the ApoE gene, e.g., the human ApoE gene. In one specific embodiment, the enhancer comprises the sequence of SEQ ID NO: 17. In one specific embodiment, the enhancer consists of the sequence of SEQ ID NO: 17.

In various embodiments of any of the methods of the invention, the vector comprises a Kozak sequence upstream of the DNase coding sequence. The Kozak sequence may have the sequence of 5'-GCCGCCACC-3' (SEQ ID NO: 33).

In various embodiments of any of the methods of the invention, the vector comprises a post-transcriptional regulatory element, e.g., the WPRE that does not encode a functional X protein. In one specific embodiment, the post-transcriptional regulatory element comprises the sequence of SEQ ID NO: 16. In one specific embodiment, the post-transcriptional regulatory element consists of the sequence of SEQ ID NO: 16.

In various embodiments of any of the methods of the invention, the vector comprises a sequence having at least 80%, 81%, 82%, 83%, 84%, 85%, 86%, 87%, 88%, 89%, 90%, 91%, 91.5%, 92%, 92.5%, 93%, 93.5%, 94%, 94.5%, 95%, 95.5%, 96%, 96.5%, 97%, 97.5%, 98%, 98.5%, 99% or 99.5% identity to the sequence of SEQ ID NO: 19. In one specific embodiment, the nucleic acid comprises the sequence SEQ ID NO: 19. In one specific embodiment, the nucleic acid consists of the sequence SEQ ID NO: 19. In one specific embodiment, the nucleic acid has a map shown in FIG. 10.

In one embodiment of any of the methods of the invention, the administration of the vector results in the expression of the enzyme and its secretion into the hepatic porto-sinusoidal circulation of the subject.

In one embodiment of any of the methods of the invention, the vector is administered in a dose and regimen which is sufficient to decrease the level of the cell free DNA (cfDNA) in the porto-sinusoidal circulation of said subject.

In one embodiment of any of the methods of the invention, the subject is human.

In one embodiment of any of the methods of the invention, the method further comprises selecting a subject with an elevated level of cell-free DNA (cfDNA) in the bloodstream as compared to a level of cfDNA in the bloodstream of a normal healthy subject.

In one embodiment of any of the methods of the invention, the method further comprises administering a deoxyribonuclease (DNase) enzyme to the subject (e.g., DNase I, DNase X, DNase γ, DNase1L1, DNase1L2, DNase 1L3, DNase II (including DNase IIα and DNase IIβ), Caspase-activated DNase (CAD), Endonuclease G (ENDOG), Granzyme B (GZMB), phosphodiesterase I, lactoferrin, acetylcholinesterase, and mutants or derivatives thereof). In one specific embodiment, the DNase is DNase I or a mutant or derivative thereof.

These and other aspects of the present invention will be apparent to those of ordinary skill in the art in the following description, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the organs and tissues drained by the hepatic portal vein. For example, the portal vein drains blood from the lower part of esophagus, stomach, pancreas, gall bladder, spleen, small intestine, large intestine, upper part of the bladder and liver.

FIGS. 2A-2I show patient summaries and individual blood electrophoretic data from nine patients with advanced metastatic disease who were treated with intravenous bovine DNase I. (A) rectal carcinoma, (B) lung carcinoma, (C) lung carcinoma, (D) melanoma, (E) breast cancer, (F) adenocarcinoma, (G) renal cancer, (H) rectal carcinoma, (I) breast cancer.

FIG. 4 shows IHC microphotographs of liver tissue from different groups listed in Table 3 and treated as described in Example 4. A large amount of cfDNA was seen in the liver of a mouse treated with gemcitabine (Group 7). Comparatively little cfDNA was seen in the liver of a mouse treated with DNase I mAFP/Alb AAV8, an AAV8 vector targeting a DNase I gene to liver cells for expression under an albumin promoter (Group 2).

FIG. 5C shows a map of ADV-207186 vector based on human adenovirus type 5 (dE1/E3) with human DNase I expressed under the control of the CMV promoter.

FIG. 6 shows bioluminescence data reflective of tumor size. The tumors of both mice with an orthotopic MIA PaCa-2 tumor implant and mice with a non-orthotopic MIA PaCa-2 tumor implant decreased in size when treated with hDNaseI_mut (SEQ ID NO: 5; hyperactive actin resistant DNase I mutant) mAFP/Alb AAV8.

FIG. 7 shows liver histology data indicating that animals treated with DNase I mAFP/Alb AAV8 have much lower inflammatory cell density, no necrosis, and much less nucleiphilic material at the vascular interface when treated with DNase I mAFP/Alb AAV8 expression vector instead of DNase I protein.

FIG. 10A shows the complete sequence of a construct ApoEHCR enhancer:hAAT promoter>hDNaseI (hyperactive)correct leader-WPRE Xinact, or ApoE-HCR enhancer: hAAT promoter>human DNAse I hyperactive variant with correct leader sequence (secretory sequence):Woodchuck Hepatitis virus post-transcriptional regulatory element (WPRE) that does not encode functional protein X. Figure discloses SEQ ID NO: 30.

FIGS. 13A and 13B illustrate data where ApoEHCR enhancer-hAAT promoter-hDNaseI (hyperactive)correct leader-WPRE Xinact and ApoEHCR enhancer-hAAT promoter-hDNaseI (wild type)-WPRE Xinact vectors efficiently transduce cells of hepatocyte origin only and trigger high yield expression and secretion of biologically enhanced DNase I enzyme or wild type DNase I enzyme from transduced G2 cells.

FIG. 18 shows data indicating that treatment with VR-18013AD significantly reduces amyloid deposition in VR-18013AD treated 3xTg-AD mice vs 3xTg-AD control mice.

FIG. 19 shows that treatment with VR-18013AD significantly reduces hyperphosphorylated Tau deposition in VR-18013AD treated 3xTg-AD mice vs 3xTg-AD control mice.

DETAILED DESCRIPTION OF THE INVENTION

Figure 2A:
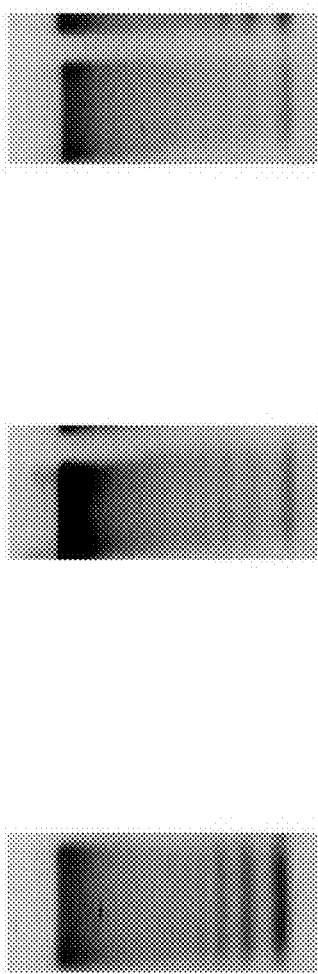
Figure 2B:
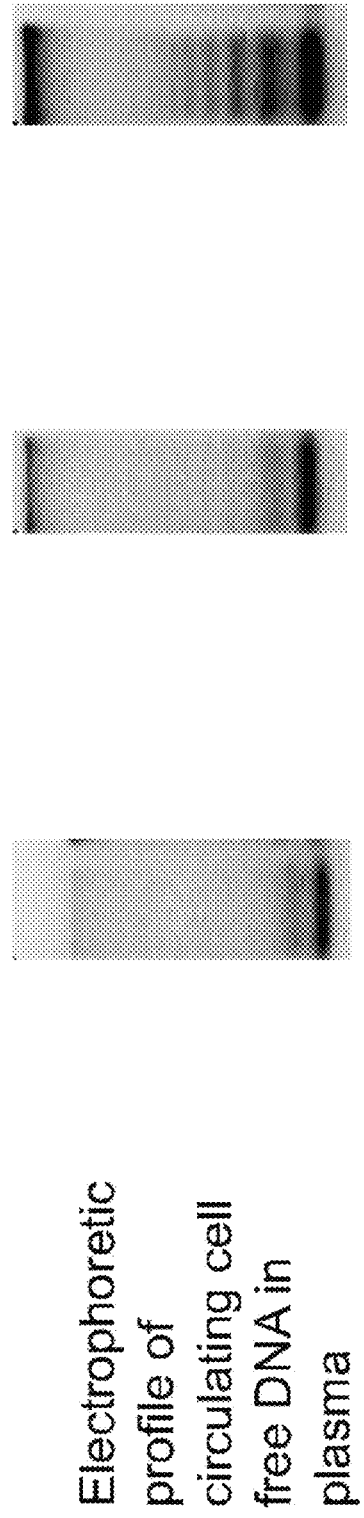
Figure 2C:
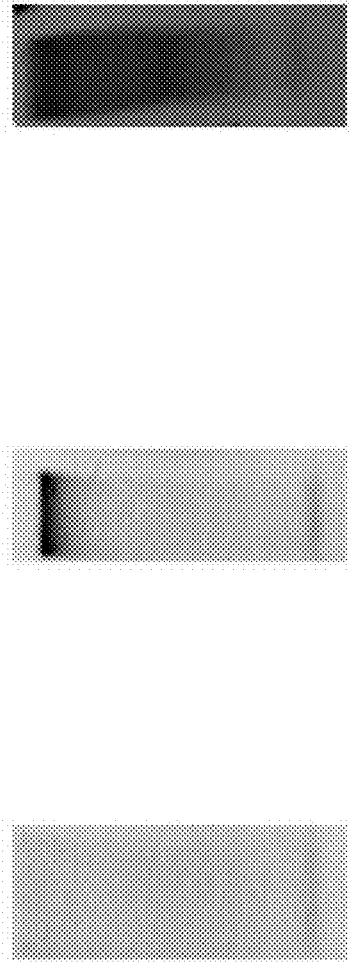
Figure 2D:
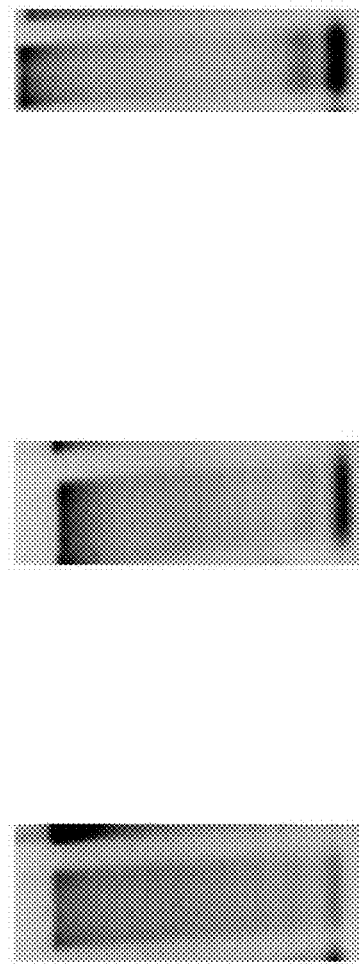
Figure 2E:
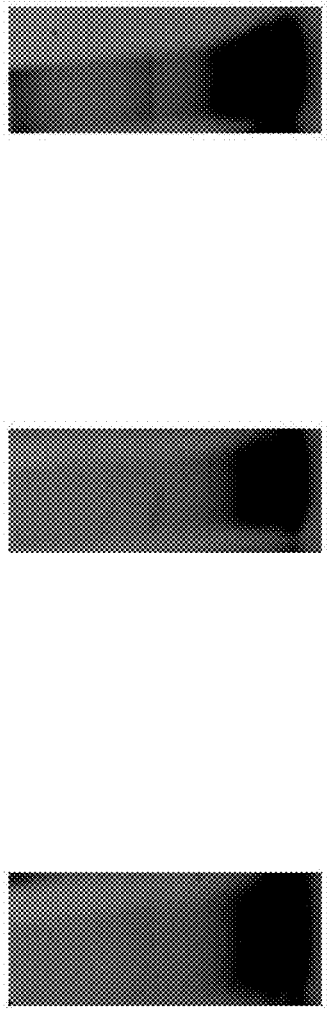
Figure 2F:
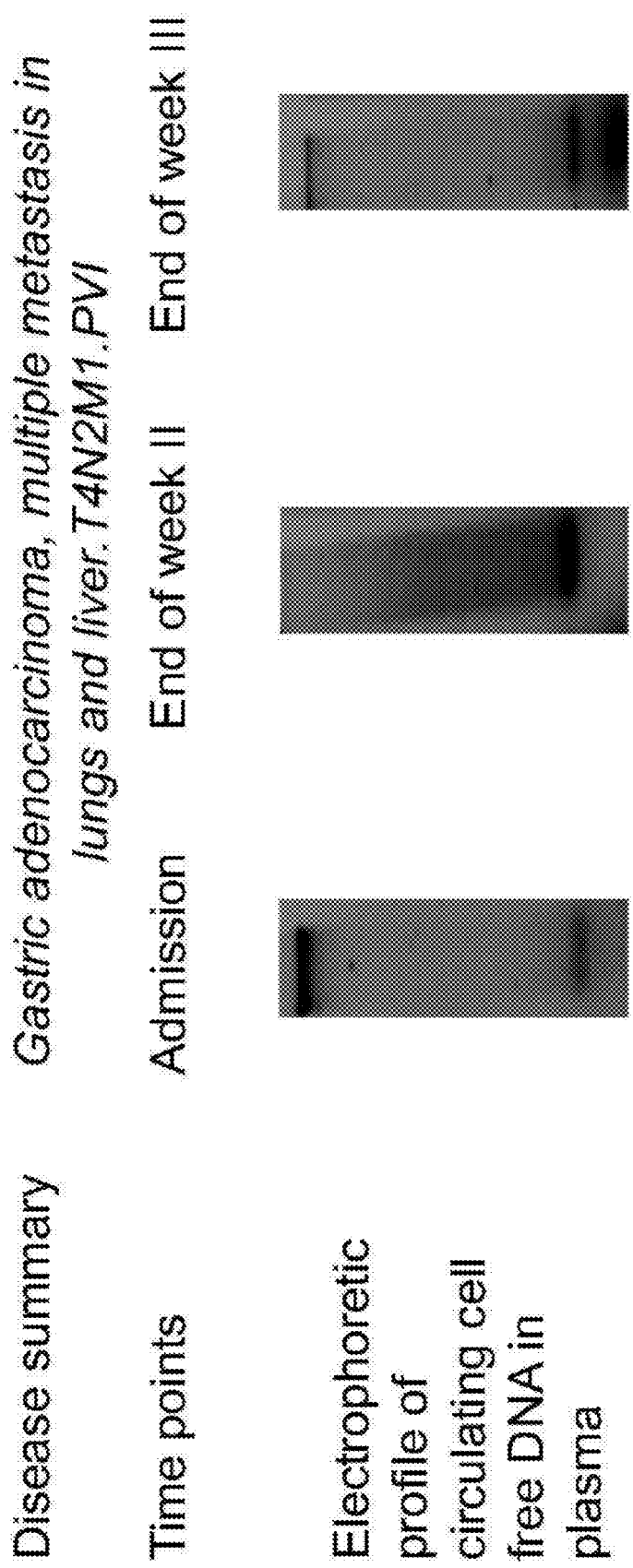
Figure 2H:
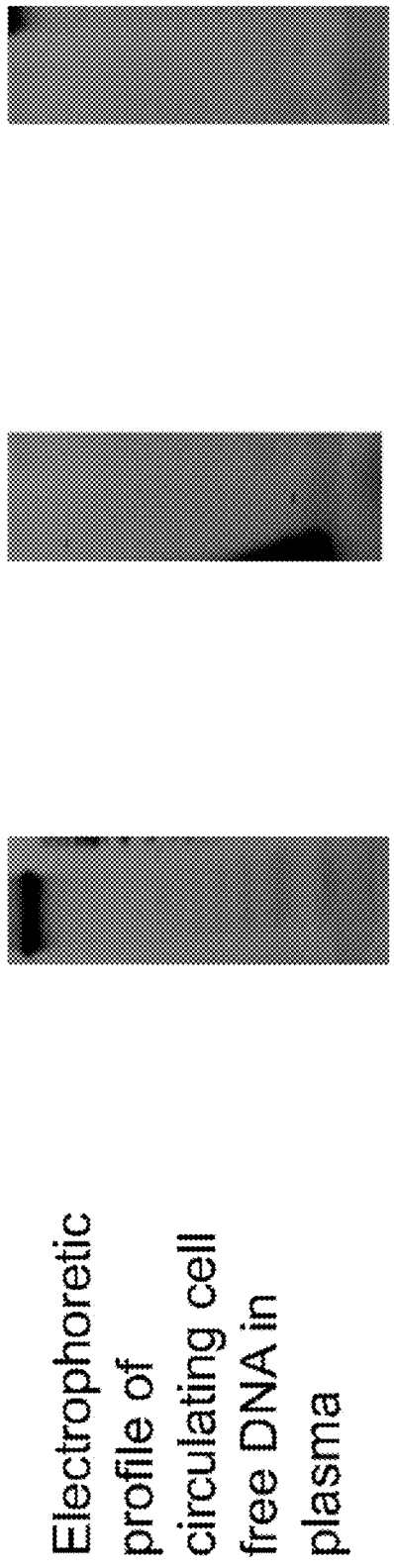
Figure 2I:
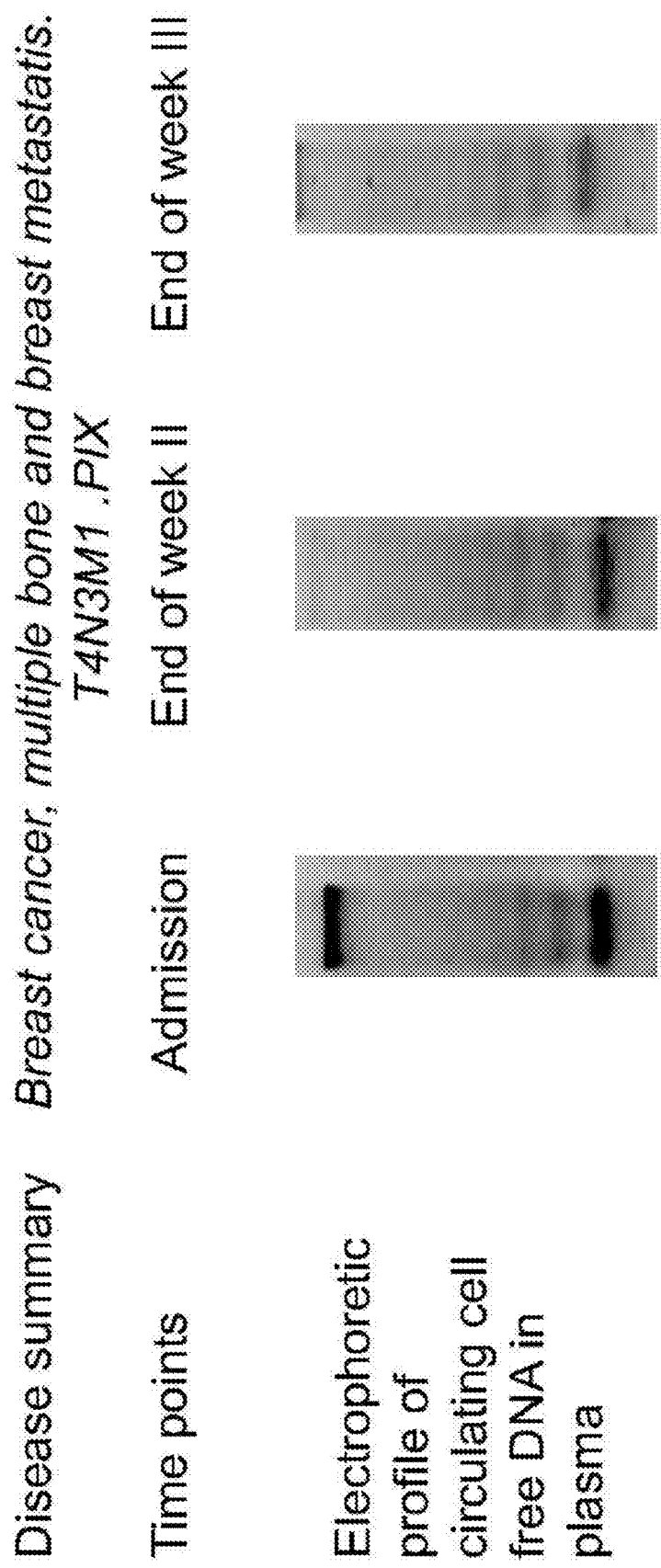

The present invention is based on an unexpected discovery that during the course of diseases and conditions characterized by elevation of circulating cfDNA level (e.g., tumor growth and progression, autoimmune and neurodegenerative diseases, infections, etc.) a significant quantity of cfDNA accumulates in the liver, mainly in the periendothelial space and space of Disse. Even high quantities of systemically administered DNase protein show limited efficacy to digest liver cfDNA. This cfDNA is continuously sourced from liver depot to hepatic portal vein and further to systemic blood circulation. As demonstrated in the Examples section, below, transgenic expression of a DNase I in the liver (e.g., using viral expression vectors) leads to almost complete clearance of cfDNA accumulated in the liver and in the porto-sinusoidal circulation when DNase is secreted to sinusoidal space of the liver. Such transgenic expression of DNase in the liver leads to significant antitumor effects (especially in tumors in organs and tissues drained by the portal vein), reduction of toxicity of anticancer chemotherapy, a slowdown in autoimmune and neurodegenerative disease progression, etc. Such transgenic expression of DNase in the liver when DNase is secreted to sinusoidal space provides even more benefits when tumor is draining by portal vein system and cfDNA generated in the tumor growth area are subject to "first pass" through portosinusoidal circulation. (FIG. 1 illustrates the organs and systems drained by the portal vein.) The same applies to neurodegenerative and autoimmune conditions facilitated by leaky gut with microbial DNA entering systemic blood circulation having respective "first pass" through portosinusoidal circulation.

The present invention provides various vectors for delivery of the DNase to the liver. Specific non-limiting examples of such vectors include AAV vectors, adenovirus vectors, retrovirus vectors (e.g., lentivirus vectors), hepatotropic virus vectors (e.g., hepatitis B virus (HBV) vectors), nanoparticles (e.g., phosphoramidite nanoparticles), liposomes (e.g., cationic liposomes such as N-[1-(2,3-dioleyloxy)propyl]-N,N,N-trimethylammonium chloride (DOTMA)), lactoferrin, poly L-lysine, polyethyleneimine, chitosan, etc.).

An enzyme which has a DNase activity may be expressed under the control of a liver-specific promoter and/or another liver-specific control element (e.g., enhancer). Specific non-limiting examples of liver-specific promoters and control elements include, e.g., an albumin promoter; human alpha-1 anti-trypsin (hAAT) promoter; TBG (thyroxine binding globulin); apolipoprotein E hepatic control region; apolipoprotein A-II promoter (APOA2); serpin peptidase inhibitor, Glade A, member 1 (SERPINA1) (hAAT) promoter; cytochrome P450 family 3, subfamily A polypeptide 4 (CYP3A4) promoter; microRNA 122 (MIR122) promoter; liver-specific IGF-II promoter P1; murine transthyretin (MTTR) promoter; and the alpha-fetoprotein (AFP) promoter. The promoter may be upstream or downstream of an enhancer. The promoter sequence may be directly fused to the enhancer sequence.

Specific non-limiting examples of enzymes which have a DNase activity that can be used in the compositions and methods of the invention include DNase I, DNase X, DNase γ, DNase1L1, DNase1L2, DNase 1L3, DNase II (e.g., DNase IIα, DNase IIβ), caspase-activated DNase (CAD), endonuclease G (ENDOG), granzyme B (GZMB), phosphodiesterase I, lactoferrin, acetylcholinesterase, and mutants or derivatives thereof.

If the enzyme which has a DNase activity is DNase I, various mutants weakening actin-binding may be used. Specific non-limiting examples of residues in wild-type recombinant human DNase I (SEQ ID NO: 4) that can be mutated include, e.g., Gln-9, Glu-13, Thr-14, His-44, Asp-53, Tyr-65, Val-66, Val-67, Glu-69, Asn-74, and Ala-114. In various embodiments, the Ala-114 mutation is used. For example, in human DNase I hyperactive mutant comprising the sequence of SEQ ID NO: 5, the Ala-114 residue is mutated. Complementary residues in other DNases may also be mutated. Specific non-limiting examples of mutations in wild-type human recombinant DNAse I include H44C, H44N, L45C, V48C, G49C, L52C, D53C, D53R, D53K, D53Y, D53A, N56C, D58S, D58T, Y65A, Y65E, Y65R, Y65C, V66N, V67E, V67K, V67C, E69R, E69C, A114C, A114R, H44N:T46S, D53R:Y65A, D53R:E69R, H44A: D53R:Y65A, H44A:Y65A:E69R, H64N:V66S, H64N: V66T, Y65N:V67S, Y65N:V67T, V66N:S68T, V67N:E69S, V67N:E69T, S68N:P70S, S68N:P70T, S94N:Y96S, S94N: Y96T.

Various DNase mutants for increasing DNase activity may be used. Specific non-limiting examples of mutations in wild-type human recombinant DNAse I include, e.g., Gln-9, Glu-13, Thr-14, His-44, Asp-53, Tyr-65, Val-66, Val-67, Glu-69, Asn-74, and Ala-114. Specific non-limiting examples of mutations for increasing the activity of wild-type human recombinant DNase I include Q9R, E13R, E13K, T14R, T14K, H44R, H44K, N74K, and A114F. For example, a combination of the Q9R, E13R, N74K and A114F mutations may be used, with such combination found at least in the hyperactive DNase I mutant comprising the sequence of SEQ ID NO: 5.

When AAV vectors are used for DNase expression, they can be derived from any serotype, e.g., from serotype 1 (AAV1), AAV2, AAV3 (e.g., AAV3A, AAV3B), AAV4, AAV5, AAV6, AAV7, AAV8, AAV9, AAV10, AAV11, AAV12, AAVrh10 (as disclosed, e.g., in U.S. Pat. No. 9,790,472, Int. Pat. Appl. Pub. Nos. WO2017/180857 and WO2017/180861), AAVLK03 (as disclosed, e.g., in Wang et al., Mol. Ther., 2015, 23(12):1877-1887), AAVhu37 (as disclosed, e.g., in Int. Pat. Appl. Pub. No. WO2017180857), AAVrh64R1 (as disclosed, e.g., in Int. Pat. Appl. Pub. No. WO2017180857), or Anc80 (Zinn et al., Cell Rep., 2015, 12(67): 1056-1068).

Point mutations can be made to the capsid protein (e.g., VP3) to improve the efficiency and/or specificity of liver-specific delivery. Specific non-limiting examples of such point mutations in the AAV8 VP3 capsid protein include, e.g., S279A, S671A, K137R, and T252A, as well as AAV8 capsid mutations disclosed in Int. Pat. Appl. Pub. No. WO2017/180854 (e.g., AAV3G1, AAVT20 or AAVTR1, VP3 mutations in amino acids 263-267 [e.g., 263NGTSG267→SGTH ("NGTSG" disclosed as SEQ ID NO: 39 and "SGTH" disclosed as SEQ ID NO: 40) or 263NGTSG267→SDTH ("NGTSG" disclosed as SEQ ID NO: 39 and "SDTH" disclosed as SEQ ID NO: 41)] and/or amino acids 457-459 [e.g., 457TAN459→SRP], and/or amino acids 455-459 [e.g., 455GGTAN459→DGSGL ("GGTAN" disclosed as SEQ ID NO: 42 and "DGSGL" disclosed as SEQ ID NO: 43)] and/or amino acids 583-597).

The vectors and compositions of the invention can be targeted to the liver in various modes. Specific non-limiting examples of routes of administration to the liver include intrahepatic injection, intravenous injection, and intra-arterial injection.

Sequences

SEQ ID NO: 1-human DNase I, wild-type (WT), precursor; Genbank Accession No. NP_005214.2; the secretory signal sequence is underlined:
MRGMKLLGALLALAALLQGAVSLKIAAFNIQTFGETKMSNATLVSYIVQILSRYDIALVQEVRDSHLTAVGKLLDNLNQDAPDTYHYVV
SEPLGRNSYKERYLFVYRPDQVSAVDSYYYDDGCEPCGNDTFNREPAIVRFFSRFTEVREFAIVPLHAAPGDAVAEIDALYDVYLDVQE
KWGLEDVMLMGDFNAGCSYVRPSQWSSIRLWTSPTFQWLIPDSADTTATPTHCAYDRIVVAGMLLRGAVVPDSALPFNFQAAYGLSDQL
AQAISDHYPVEVMLK SEQ ID NO: 2-human DNAse I mutant, precursor; the mutated residues as compared to SEQ ID NO: 1 are in bold and underlined; the secretory signal sequence is underlined:
MRGMKLLGALLALAALLQGAVSLKIAAFNIRTFGRTKMSNATLVSYIVQILSRYDIALVQEVRDSHLTAVGKLLDNLNQDAPDTYHYVV
SEPLGRKSYKERYLFVYRPDQVSAVDSYYYDDGCEPCGNDTFNREPFIVRFFSRFTEVREFAIVPLHAAPGDAVAEIDALYDVYLDVQE
KWGLEDVMLMGDFNAGCSYVRPSQWSSIRLWTSPTFQWLIPDSADTTATPTHCAYDRIVVAGMLLRGAVVPDSALPFNFQAAYGLSDQL
AQAISDHYPVEVMLK SEQ ID NO: 3-Anc80 VP1 capsid protein:
AADGYLPDWLEDNLSEGIREWDLKPGAPKPKANQQKQDDGRGLVLPGYKYLGPFNGLDKGEPVNAADAAALEHDKAYDQQLKAGDNPYL
RYNHADAEFQERLQEDTSFGGNLGRAVFQAKKRVLEPLGLVEEGAKTAPGKKRPVEQSPQEPDSSSGIGKKGQQPA$\underline{\mathbf{X^1}}$KRLNFGQTGDS
ESVPDPQPLGEPPAAPSGVGSNTM$\underline{\mathbf{X^2}}$AGGGAPMADNNEGADGVGNASGWNHCDSTWLGDRVITTSTRTALPTYNNHLYKQISSQSG$\underline{\mathbf{X^3}}$S
TNDNTYFGYSTPWGYFDFNRFHCHFSPRDWQRLINNNWGFRPK$\underline{\mathbf{X^4}}$LNFKLFNIQVKEVTTNDGTTTIANNLTSTVQVFTDSEYQLPYVL
GSAHQGCLPPFPADVFMIPQYGYLTLNNGSQAVGRSSFYCLEYFPSQMLRTGNNF$\underline{\mathbf{X^5}}$FSYTFEDVPFHSSYAHSQSLDRLNPLIDQYLY
YLSRTQTTSGTAGNR$\underline{\mathbf{X^6}}$LQFSQAGPSSMANQAKNWLPGPCYRQQRVSKT$\underline{\mathbf{X^7}}$NQNNNSNFAWTGATKYHLNGRDSLVNPGPAMATHKDDE
DKFFPMSGVLIFGKQGAGNSNVDLDNVMIT$\underline{\mathbf{X^8}}$EEEIKTTNPVATE$\underline{\mathbf{X^9}}$YGTVATNLQS$\underline{\mathbf{X^{10}}}$NTAPATGTVNSQGALPGMVWQ$\underline{\mathbf{X^{11}}}$RDVYLQG
PIWAKIPHTDGHFHPSPLMGGFGLKHPPPQILIKNTPVPANPPTTFSPAKFASFITQYSTGQVSVEIEWELQKENSKRWNPEIQYTSNY
NKSTNVDFAVDTNGVYSEPRPIGTRYLTRNL
$X^1$ = K or R; $X^2$ = A or S; $X^3$ = A or G; $X^4$ = R or K; $X^5$ = E or Q; $X^6$ = T or E; $X^7$ = A or T; $X^8$ = S or N; $X^9$ = Q or E; $X^{10}$ = S or A and $X^{11}$ = N or D.

SEQ ID NO: 4-mature wild-type (WT) human DNase I (without secretory signal sequence; Genbank Accession No. 4AWN_A:
LKIAAFNIQTFGETKMSNATLVSYIVQILSRYDIALVQEVRDSHLTAVGKLLDNLNQDAPDTYHYVVSEPLGRNSYKERYLFVYRPDQV
SAVDSYYYDDGCEPCGNDTFNREPAIVRFFSRFTEVREFAIVPLHAAPGDAVAEIDALYDVYLDVQEKWGLEDVMLMGDFNAGCSYVRP
SQWSSIRLWTSPTFQWLIPDSADTTATPTHCAYDRIVVAGMLLRGAVVPDSALPFNFQAAYGLSDQLAQAISDHYPVEVMLK SEQ ID NO: 5-mature human DNAse I mutant (without secretory signal sequence); the mutated residues as compared to SEQ ID NO: 4 are in bold and underlined:
LKIAAFNIRTFGRTKMSNATLVSYIVQILSRYDIALVQEVRDSHLTAVGKLLDNLNQDAPDTYHYVVSEPLGRKSYKERYLFVYRPDQV
SAVDSYYYDDGCEPCGNDTFNREPFIVRFFSRFTEVREFAIVPLHAAPGDAVAEIDALYDVYLDVQEKWGLEDVMLMGDFNAGCSYVRP
SQWSSIRLWTSPTFQWLIPDSADTTATPTHCAYDRIVVAGMLLRGAVVPDSALPFNFQAAYGLSDQLAQAISDHYPVEVMLK SEQ ID NO: 6-secretory signal sequence of human DNase I:
MRGMKLLGALLALAALLQGAVS SEQ ID NO: 7-secretory signal sequence of IL2:
MYRMQLLSCIALSLALVTNS SEQ ID NO: 8-human albumin promoter:
ACTAGTTCCAGATGGTAAATATACACAAGGGATTTAGTCAAACAATTTTTTGGCAAGAATATTATGAATTTTGTAATCGGTTGGCAGCC
AATGAAATACAAAGATGAGTCTAGTTAATAATCTACAATTATTGGTTAAAGAAGTATATTAGTGCTAATTTCCCTCCGTTTGTCCTAGC
TTTTCTCTTCTGTCAACCCCACACGCCTTTGGCACC SEQ ID NO: 9-Anc80 VP1 capsid protein:
AADGYLPDWLEDNLSEGIREWDLKPGAPKPKANQQKQDDGRGLVLPGYKYLGPFNGLDKGEPVNAADAAALEHDKAYDQQLKAGDNPYLR
YNHADAEFQERLQEDTSFGGNLGRAVFQAKKRVLEPLGLVEEGAKTAPGKKRPVEQSPQEPDSSSGIGKKGQQPA$\underline{\mathbf{X^1}}$KRLNFGQTGDSE
SVPDPQPLGEPPAAPSGVGSNTM$\underline{\mathbf{X^2}}$AGGGAPMADNNEGADGVGNASGWNHCDSTWLGDRVITTSTRTALPTYNNHLYKQISSQSG$\underline{\mathbf{X^3}}$STN
DNTYFGYSTPWGYFDFNRFHCHFSPRDWQRLINNNWGFRPK$\underline{\mathbf{X^4}}$LNFKLFNIQVKEVTTNDGTTTIANNLTSTVQVFTDSEYQLPYVLGS
AHQGCLPPFPADVFMIPQYGYLTLNNGSQAVGRSSFYCLEYFPSQMLRTGNNF$\underline{\mathbf{X^5}}$FSYTFEDVPFHSSYAHSQSLDRLNPLIDQYLYYL
SRTQTTSGTAGNR$\underline{\mathbf{X^6}}$LQFSQAGPSSMANQAKNWLPGPCYRQQRVSKT$\underline{\mathbf{X^7}}$NQNNNSNFAWTGATKYHLNGRDSLVNPGPAMATHKDDEDKF
FPMSGVLIFGKQGAGNSNVDLDNVIT$\underline{\mathbf{X^8}}$EEEIKTTNPVATE$\underline{\mathbf{X^9}}$YGTVATNLQS$\underline{\mathbf{X^{10}}}$NTAPATGTVNSQGALPGMVWQ$\underline{\mathbf{X^{11}}}$RDVYLQGPIWAK
IPHTDGHFHPSPLMGGFGLKHPPPQILIKNTPVPANPPTTFSPAKFASFITQYSTGQVSVEIEELQKENSKRWNPEIQYTSNYNKSTNV
DFAVDTNGVYSEPRPIGTRYLTRNL
$X^1$ = K or R; $X^2$ = A or S; $X^3$ = A or G; $X^4$ = R or K; $X^5$ = E or Q; $X^6$ = T or E; $X^7$ = A or T; $X^8$ = S or N; $X^9$ = Q or E; $X^{10}$ = S or A and $X^{11}$ = N or D SEQ ID NO: 10-human beta globin primer:
CAACTTCATCCACGTTCACC SEQ ID NO: 11-forward NLRP3 primer:
GTTCTGAGCTCCAACCATTCT SEQ ID NO: 12-reverse NLRP3 primer:
CACTGTGGGTCCTTCATCTTT SEQ ID NO: 13-forward 16S universal bacterial RNA gene primer:
TCGTCGGCAGCGTCAGATGTGTATAAGAGACAGCCTACGGGNGGCWGCAG SEQ ID NO: 14-reverse 16S universal bacterial RNA gene primer:
GTCTCGTGGGCTCGGAGATGTGTATAAGAGACAGGACTACHVGGGTATCTAATCC -continued Sequences SEQ ID NO: 15-human anti-trypsin promoter sequence:
GATCTTGCTACCAGTGGAACAGCCACTAAGGATTCTGCAGTGAGAGCAGAGGGCCAGCTAAGTGGTACTCTCCCAGAGACTGTCTGACT
CACGCCACCCCCTCCACCTTGGACACAGGACGCTGTGGTTTCTGAGCCAGGTACAATGACTCCTTTCGGTAAGTGCAGTGGAAGCTGTA
CACTGCCCAGGCAAAGCGTCCGGGCAGCGTAGGCGGGCGACTCAGATCCCAGCCAGTGGACTTAGCCCCTGTTTGCTCCTCCGATAACT
GGGGTGACCTTGGTTAATATTCACCAGCAGCCTCCCCCGTTGCCCCTCTGGATCCACTGCTTAAATACGGACGAGGACAGGGCCCTGTC
TCCTCAGCTTCAGGCACCACCACTGACCTGGGACAGTGAAT SEQ ID NO: 16-Woodchuck hepatitis virus post-transcriptional regulatory element that
does not encode functional protein X:
AGTGGCGGCCGCTCGAGCTAGCGGCCGCTCTAGAAGATAATCAACCTCTGGATTACAAAATTTGTGAAAGATTGACTGGTATTCTTAAC
TATGTTGCTCCTTTTACGCTATGTGGATACGCTGCTTTAATGCCTTTGTATCATGCTATTGCTTCCCGTATGGCTTTCATTTTCTCCTC
CTTGTATAAATCCTGGTTGCTGTCTCTTTATGAGGAGTTGTGGCCCGTTGTCAGGCAACGTGGCGTGGTGTGCACTGTGTTTGCTGACG
CAACCCCCACTGGTTGGGGCATTGCCACCACCTGTCAGCTCCTTTCCGGGACTTTGCTTTCCCCCTCCCTATTGCCACGGCGGAACTC
ATCGCCGCCTGCCTTGCCCGCTGCTGGACAGGGGCTCGGCTGTTGGGCACTGACAATTCCGTGGTGTTGTCGGGGAAATCATCGTCCTT
TCCTTGGCTGCTCGCCTGTGTTGCCACCTGGATTCTGCGCGGGACGTCCTTCTGCTACGTCCCTTCGGCCCTCAATCAGCGGACCTTC
CTTCCCGCGGCCTGCTGCCGGCTCTGCGGCCTCTTCCGCGTCTTCGCCTTCGCCCTCAGACGAGTCGGATCTCCCTTTGGGCCGCCTCC
CCGCATCGGACTAG SEQ ID NO: 17-apolipoprotein E (ApoE) enhancer, hepatic control region (HCR):
AGGCTCAGAGGCACACAGGAGTTTCTGGGCTCACCCTGCCCCCTTCCAACCCCTCAGTTCCCATCCTCCAGCAGCTGTTTGTGTGCTGC
CTCTGAAGTCCACACTGAACAAACTTCAGCCTACTCATGTCCCTAAAATGGGCAAACATTGCAAGCAGCAAACAGCAAACACACAGCCC
TCCCTGCCTGCTGACCTTGGAGCTGGGGCAGAGGTCAGAGACCTCTCTGGGCCCATGCCACCTCCAACATCCACTCGACCCCTTGGAAT
TTCGGTGGAGAGGAGCAGAGGTTGTCCTGGCGTGGTTTAGGTAGTGTGAGAGG SEQ ID NO: 18-a polynucleotide encoding human DNase I hyperactive variant of
SEQ ID NO: 5:
ATGAAGCTGCTGGGGGCGCTGCTGGCACTGGCGGCCCTACTGCAGGGGGCCGTGTCCCTGAAGATCGCAGCCTTCAACATCAGGACATT
TGGGGAGGACCAAGATGTCCAATGCCACCCTCGTCAGCTACATTGTGCAGATCCTGAGCCGCTATGACATCGCCCTGGTCCAGGAGGTCA
GAGACAGCCACCTGACTGCCGTGGGGAAGCTGCTGGACAACCTCAATCAGGATGCACCAGACACCTATCACTACGTGGTCAGTGAGCCA
CTGGGACGGAAGAGCTATAAGGAGCGCTACCTGTTCGTGTACAGGCCTGACCAGGTGTCTGCGGTGGACAGCTACTACTACGATGATGG
CTGCGAGCCCTGCGGGAACGACACCTTCAACCGAGAGCCATTCATTGTCAGGTTCTTCTCCCGGTTCACAGAGGTCAGGGAGTTTGCCA
TTGTTCCCCTGCATGCGGCCCCGGGGGACGCAGTAGCCGAGATCGACGCTCTCTATGACGTCTACCTGGATGTCCAAGAGAAATGGGGC
TTGGAGGACGTCATGTTGATGGGCGACTTCAATGCGGGCTGCAGCTATGTGAGACCCTCCCAGTGGTCATCCATCCGCCTGTGGACAAG
CCCCACCTTCCAGTGGCTGATCCCCGACAGCGCTGACACCACAGCTACACCCACGCACTGTGCCTATGACAGGATCGTGGTTGCAGGGA
TGCTGCTCCGAGGCGCCGTTGTTCCCGACTCGGCTCTTCCCTTTAACTTCCAGGCTGCCTATGGCCTGAGTGACCAACTGGCCCAAGCC
ATCAGTGACCACTATCCAGTGGAGGTGATGCTGAAGTGA SEQ ID NO: 19-a polynucleotide encoding human DNAse I mutant precursor of SEQ ID NO: 2
(secretory signal sequence underlined):
ATGAGGGGCATGAAGCTGCTGGGGGCGCTGCTGGCACTGGCGGCCCTACTGCAGGGGGCCGTGTCCCTGAAGATCGCAGCCTTCAACAT
CAGGACATTTGGGGAGGACCAAGATGTCCAATGCCACCCTCGTCAGCTACATTGTGCAGATCCTGAGCCGCTATGACATCGCCCTGGTCC
AGGAGGTCAGAGACAGCCACCTGACTGCCGTGGGGAAGCTGCTGGACAACCTCAATCAGGATGCACCAGACACCTATCACTACGTGGTC
AGTGAGCCACTGGGACGGAAGAGCTATAAGGAGCGCTACCTGTTCGTGTACAGGCCTGACCAGGTGTCTGCGGTGGACAGCTACTACTA
CGATGATGGCTGCGAGCCCTGCGGGAACGACACCTTCAACCGAGAGCCATTCATTGTCAGGTTCTTCTCCCGGTTCACAGAGGTCAGGG
AGTTTGCCATTGTTCCCCTGCATGCGGCCCCGGGGGACGCAGTAGCCGAGATCGACGCTCTCTATGACGTCTACCTGGATGTCCAAGAG
AAATGGGGCTTGGAGGACGTCATGTTGATGGGCGACTTCAATGCGGGCTGCAGCTATGTGAGACCCTCCCAGTGGTCATCCATCCGCCT
GTGGACAAGCCCCACCTTCCAGTGGCTGATCCCCGACAGCGCTGACACCACAGCTACACCCACGCACTGTGCCTATGACAGGATCGTGG
TTGCAGGGATGCTGCTCCGAGGCGCCGTTGTTCCCGACTCGGCTCTTCCCTTTAACTTCCAGGCTGCCTATGGCCTGAGTGACCAACTG
GCCCAAGCCATCAGTGACCACTATCCAGTGGAGGTGATGCTGAAGTGA SEQ ID NO: 20-a polynucleotide encoding the secretory signal sequence (SEQ ID NO: 6)
of human DNase I:
ATGAGGGGCATGAAGCTGCTGGGGGCGCTGCTGGCACTGGCGGCCCTACTGCAGGGGGCCGTGTCC SEQ ID NO: 21-a polynucleotide encoding the mature human DNAse I mutant (without
secretory signal sequence) of SEQ ID NO: 5:
CTGAAGATCGCAGCCTTCAACATCAGGACATTTGGGGAGGACCAAGATGTCCAATGCCACCCTCGTCAGCTACATTGTGCAGATCCTGAG
CCGCTATGACATCGCCCTGGTCCAGGAGGTCAGAGACAGCCACCTGACTGCCGTGGGGAAGCTGCTGGACAACCTCAATCAGGATGCAC
CAGACACCTATCACTACGTGGTCAGTGAGCCACTGGGACGGAAGAGCTATAAGGAGCGCTACCTGTTCGTGTACAGGCCTGACCAGGTG
TCTGCGGTGGACAGCTACTACTACGATGATGGCTGCGAGCCCTGCGGGAACGACACCTTCAACCGAGAGCCATTCATTGTCAGGTTCTT
CTCCCGGTTCACAGAGGTCAGGGAGTTTGCCATTGTTCCCCTGCATGCGGCCCCGGGGGACGCAGTAGCCGAGATCGACGCTCTCTATG
ACGTCTACCTGGATGTCCAAGAGAAATGGGGCTTGGAGGACGTCATGTTGATGGGCGACTTCAATGCGGGCTGCAGCTATGTGAGACCC
TCCCAGTGGTCATCCATCCGCCTGTGGACAAGCCCCACCTTCCAGTGGCTGATCCCCGACAGCGCTGACACCACAGCTACACCCACGCA
CTGTGCCTATGACAGGATCGTGGTTGCAGGGATGCTGCTCCGAGGCGCCGTTGTTCCCGACTCGGCTCTTCCCTTTAACTTCCAGGCTG
CCTATGGCCTGAGTGACCAACTGGCCCAAGCCATCAGTGACCACTATCCAGTGGAGGTGATGCTGAAGTGA SEQ ID NO: 22-a polynucleotide encoding human DNase I, wild-type (WT), precursor of
SEQ ID NO: 1:
ATGAGGGGCATGAAGCTGCTGGGGGCGCTGCTGGCACTGGCGGCCCTACTGCAGGGGGCCGTGTCCCTGAAGATCGCAGCCTTCAACAT
CCAGACATTTGGGGAGACCAAGATGTCCAATGCCACCCTCGTCAGCTACATTGTGCAGATCCTGAGCCGCTATGACATCGCCCTGGTCC
AGGAGGTCAGAGACAGCCACCTGACTGCCGTGGGGAAGCTGCTGGACAACCTCAATCAGGATGCACCAGACACCTATCACTACGTGGTC
AGTGAGCCACTGGGACGGAACAGCTATAAGGAGCGCTACCTGTTCGTGTACAGGCCTGACCAGGTGTCTGCGGTGGACAGCTACTACTA
CGATGATGGCTGCGAGCCCTGCGGGAACGACACCTTCAACCGAGAGCCAGCCATTGTCAGGTTCTTCTCCCGGTTCACAGAGGTCAGGG
AGTTTGCCATTGTTCCCCTGCATGCGGCCCCGGGGGACGCAGTAGCCGAGATCGACGCTCTCTATGACGTCTACCTGGATGTCCAAGAG
AAATGGGGCTTGGAGGACGTCATGTTGATGGGCGACTTCAATGCGGGCTGCAGCTATGTGAGACCCTCCCAGTGGTCATCCATCCGCCT
GTGGACAAGCCCCACCTTCCAGTGGCTGATCCCCGACAGCGCTGACACCACAGCTACACCCACGCACTGTGCCTATGACAGGATCGTGG TTGCAGGGATGCTGCTCCGAGGCGCCGTTGTTCCCGACTCGGCTCTTCCCTTTAACTTCCAGGCTGCCTATGGCCTGAGTGACCAACTG
GCCCAAGCCATCAGTGACCACTATCCAGTGGAGGTGATGCTGAAG SEQ ID NO: 23-a polynucleotide encoding the mature wild-type (WT) human DNase I of
SEQ ID NO: 4:
CTGAAGATCGCAGCCTTCAACATCCAGACATTTGGGGAGACCAAGATGTCCAATGCCACCCTCGTCAGCTACATTGTGCAGATCCTGAG
CCGCTATGACATCGCCCTGGTCCAGGAGGTCAGAGACAGCCACCTGACTGCCGTGGGGAAGCTGCTGGACAACCTCAATGAGGATGCAC
CAGACACCTATCACTACGTGGTCAGTGAGCCACTGGGACGGAACAGCTATAAGGAGCGCTACCTGTTCGTGTACAGGCCTGACCAGGTG
TCTGCGGTGGACAGCTACTACTACGATGATGGCTGCGAGCCCTGCGGGAACGACACCTTCAACCGAGAGCCAGCCATTGTCAGGTTCTT
CTCCCCGGTTCACAGAGGTCAGGGAGTTTGCCATTGTTCCCCTGCATGCGGCCCCGGGGGACGCAGTAGCCGAGATCGACGCTCTCTATG
ACGTCTACCTGGATGTCCAAGAGAAATGGGGCTTGGAGGACGTCATGTTGATGGGCGACTTCAATGCGGGCTGCAGCTATGTGAGACCC
TCCCAGTGGTCATCCATCCGCCTGTGGACAAGCCCCACCTTCCAGTGGCTGATCCCGACAGCGCTGACACCACAGCTACACCCACGCA
CTGTGCCTATGACAGGATCGTGGTTGCAGGGATGCTGCTCCGAGGCGCCGTTGTTCCCGACTCGGCTCTTCCCTTTAACTTCCAGGCTG
CCTATGGCCTGAGTGACCAACTGGCCCAAGCCATCAGTGACCACTATCCAGTGGAGGTGATGCTGAAG SEQ ID NO: 24-*Mus musculus* wild type DNase I, precursor; Genbank Accession No.
NP_034191.3; the secretory signal sequence is underlined:
<u>MRYTGLMGTLLTLVNLLQLAGT</u>LRIAAFNIRTFGETKMSNATLSVYFVKILSRYDIAVIQEVRDSHLVAVGKLLDELNRDKPDTYRYVV
SEPLGRKSYKEQYLFVYRPDQVSILDSYQYDDGCEPCGNDTFSREPAIVKFFSPYTEVQEFAIVPLHAAPTEAVSEIDALYDVYLDVWQ
KWGLEDIMFMGDFNAGCSYVTSSQWSSIRLRTSPIFQWLIPDSADTTVTSTHCAYDRIVVAGALLQAAVVPNSAVPFDFQAEYGLSNQL
AEAISDHYPVEVTLRKI SEQ ID NO: 25-secretory signal sequence of *Mus musculus* wild type DNase I
MRYTGLMGTLLTLVNLLQLAGT SEQ ID NO: 26-mature wild-type (WT) *Mus musculus* wild type DNase I
LRIAAFNIRTFGETKMSNATLSVYFVKILSRYDIAVIQEVRDSHLVAVGKLLDELNRDKPDTYRYVVSEPLGRKSYKEQYLFVYRPDQV
SILDSYQYDDGCEPCGNDTFSREPAIVKFFSPYTEVQEFAIVPLHAAPTEAVSEIDALYDVYLDVWQKWGLEDIMFMGDFNAGCSYVTS
SQWSSIRLRTSPIFQWLIPDSADTTVTSTHCAYDRIVVAGALLQAAVVPNSAVPFDFQAEYGLSNQLAEAISDHYPVEVTLRKI SEQ ID NO: 27-a polynucleotide encoding the secretory signal sequence of *Mus musculus*
wild type DNase I
ATGCGGTACACAGGGCTAATGGGAACACTGCTCACCTTGGTCAACCTGCTGCAGCTGGCTGGGACT SEQ ID NO: 28-a polynucleotide encoding the mature wild-type (WT) *Mus musculus* wild type
DNase I
CTGAGAATTGCAGCCTTCAACATTCGGACTTTTGGGGAGACTAAGATGTCCAATGCTACCCTCTCTGTATACTTTGTGAAAATCCTGAG
TCGCTATGACATCGCTGTTATCCAAGAGGTCAGAGACTCCCACCTGGTTGCTGTTGGGAAGCTCCTGGATGAACTCAATCGGGACAAAC
CTGACACCTACCGCTATGTAGTCAGTGAGCCGCTGGGCCGCAAAAGCTACAAGGAACAGTACCTTTTTGTGTACAGGCCTGACCAGGTG
TCTATTCTGGACAGCTATCAATATGATGGCTGTGAACCCTGTGGAAATGACACCTTCAGCAGAGAGCCAGCCATTGTTAAGTTCTT
TTCCCCATACACTGAGGTCCAAGAATTTGCGATCGTGCCCTTGCATGCAGCCCCAACAGAAGCTGTGAGTGAGATCGACGCCCTCTACG
ATGTTTACCTAGATGTCTGGCAAAAGTGGGGCCTGGAGGACATCATGTTCATGGGAGACTTCAATGCTGGCTGCAGCTACGTCACTTCC
TCCCAGTGGTCCTCCATTCGCCTTCGGACAAGCCCCATCTTCCAGTGGCTGATCCCTGACAGTGCGGACACCACAGTCACATCAACACA
CTGTGCTTATGACAGGATTGTGGTTGCTGGAGCTCTGCTCCAGGCTGCTGTTGTTCCCAACTCGGCTGTTCCTTTTGATTTCCAAGCAG
AATACGGACTTTCCAACCAGCTGGCTGAAGCCATCAGTGACCATTACCCAGTGGAGGTGACACTCAGAAAAATCTGA SEQ ID NO: 29-a polynucleotide encoding the *Mus musculus* wild type DNase I, precursor
ATGCGGTACACAGGGCTAATGGGAACACTGCTCACCTTGGTCAACCTGCTGCAGCTGGCTGGGACTCTGAGAATTGCAGCCTTCAACAT
TCGGACTTTTGGGGAGACTAAGATGTCCAATGCTACCCTCTCTGTATACTTTGTGAAAATCCTGAGTCGCTATGACATCGCTGTTATCC
AAGAGGTCAGAGACTCCCACCTGGTTGCTGTTGGGAAGCTCCTGGATGAACTCAATCGGGACAAACCTGACACCTACCGCTATGTAGTC
AGTGAGCCGCTGGGCCGCAAAAGCTACAAGGAACAGTACCTTTTTGTGTACAGGCCTGACCAGGTGTCTATTCTGGACAGCTATCAATA
TGATGATGGCTGTGAACCCTGTGGAAATGACACCTTCAGCAGAGAGCCAGCCATTGTTAAGTTCTTTTCCCCATACACTGAGGTCCAAG
AATTTGCGATCGTGCCCTTGCATGCAGCCCCAACAGAAGCTGTGAGTGAGATCGACGCCCTCTACGATGTTTACCTAGATGTCTGGCAA
AAGTGGGGCCTGGAGGACATCATGTTCATGGGAGACTTCAATGCTGGCTGCAGCTACGTCACTTCCTCCCAGTGGTCCTCCATTCGCCT
TCGGACAAGCCCCATCTTCCAGTGGCTGATCCCTGACAGTGCGGACACCACAGTCACATCAACACACTGTGCTTATGACAGGATTGTGG
TTGCTGGAGCTCTGCTCCAGGCTGCTGTTGTTCCCAACTCGGCTGTTCCTTTTGATTTCCAAGCAGAATACGGACTTTCCAACCAGCTG
GCTGAAGCCATCAGTGACCATTACCCAGTGGAGGTGACACTCAGAAAAATCTGA SEQ ID NO: 30-Complete sequence of ApoEHCR enhancer-hAAT promoter-hDNaseI
(hyperactive)correct leader-WPRE Xinact (VR-18013AD)
AGGCTCAGAGGCACACAGGAGTTTCTGGGCTCACCCTGCCCCCTTCCAACCCCTCAGTTCCCATCCTCCAGCAGCTGTTTGTGTGCTGC
CTCTGAAGTCCACACTGAACAAACTTCAGCCTACTCATGTCCCTAAAATGGGCAAACATTGCAAGCAGCAAACAGCAAACACACAGCCC
TCCCTGCCTGCTGACCTTGGAGCTGGGGCAGAGGTCAGAGACCTCTCTGGGCCCATGCCACCTCCAACATCCACTCGACCCCTTGGAAT
TTCGGTGGAGAGGAGCAGAGGTTGTCCTGGCGTGGTTTAGGTAGTGTGAGAGGGATCTTGCTACCAGTGGAACAGCCACTAAGGATTCT
GCAGTGAGAGCAGAGGGCCAGCTAAGTGGTACTCTCCCAGAGACTGTCTGACTCACGCCACCCCCTCCACCTTGGACACAGGACGCTGT
GGTTTCTGAGCCAGGTACAATGACTCCTTTCGGTAAGTGCAGTGGAAGCTGTACACTGCCCAGGCAAAGCGTCCGGCAGCGTAGGCGG
GCGACTCAGATCCCAGCCAGTGGACTTAGCCCCTGTTTGCTCCTCCGATAACTGGGGTGACCTTGGTTAATATTCACCAGCAGCCTCCC
CCGTTGCCCCTCTGGATCCACTGCTTAAATACGGACGAGGACAGGGCCCTGTCTCCTCAGCTTCAGGCACCACCACTGACCTGGGACAG
TGAATGCCGCCACCATGAGGGGCATGAAGCTGCTGGGGCGCTGCTGGCACTGCCGGCCCTACTGCAGGGGCCGTGTCCCTGAAGATC
GCAGCCTTCAACATCAGGACATTTGGGAGGACCAAGATGTCCAATGCCACCCTCGTCAGCTACATTGTGCAGATCCTGAGCCGCTATGA
CATCGCCCTGGTCCAGGAGGTCAGAGACAGCCACCTGACTGCCGTGGGGAAGCTGCTGGACAACCTCAATGAGGATGCACCAGACACCT
ATCACTACGTGGTCAGTGAGCCACTGGGACGGAAGACTATAAGGAGCGCTACCTGTTCGTGTACAGGCCTGACCAGGTGTCTGCGGTG
GACAGCTACTACTACGATGATGGCTGCGAGCCCTGCGGGAACGACACCTTCAACCGAGAGCCATTCATTGTCAGGTTCTTCTCCCCGGTT
CACAGAGGTCAGGGAGTTTGCCATTGTTCCCCTGCATGCGGCCCCGGGGGACGCAGTAGCCGAGATCGACGCTCTCTATGACGTCTACC
TGGATGTCCAAGAGAAATGGGGCTTGGAGGACGTCATGTTGATGGGCGACTTCAATGCGGGCTGCAGCTATGTGAGACCCTCCCAGTGG
TCATCCATCCGCCTGTGGACAAGCCCCACCTTCCAGTGGCTGATCCCGACAGCGCTGACACCACAGCTACACCCACGCACTGTGCCTA
TGACAGGATCGTGGTTGCAGGGATGCTGCTCCGAGGCGCCGTTGTTCCCGACTCGGCTCTTCCCTTTAACTTCCAGGCTGCCTATGGCC

```
TGAGTGACCAACTGGCCCAAGCCATCAGTGACCACTATCCAGTGGAGGTGATGCTGAAGTGAAGTGGCGGCCGCTCGAGCTAGCGGCCG
CTCTAGAAGATAATCAACCTCTGGATTACAAAATTTGTGAAAGATTGACTGGTATTCTTAACTATGTTGCTCCTTTTACGCTATGTGGA
TACGCTGCTTTAATGCCTTTGTATCATGCTATTGCTTCCCGTATGGCTTTCATTTTCTCCTCCTTGTATAAATCCTGGTTGCTGTCTCT
TTATGAGGAGTTGTGGCCCGTTGTCAGGCAACGTGGCGTGGTGTGCACTGTGTTTGCTGACGCAACCCCCACTGGTTGGGGCATTGCCA
CCACCTGTCAGCTCCTTTCCGGGACTTTCGCTTTCCCCCTCCCTATTGCCACGGCGGAACTCATCGCCGCCTGCCTTGCCCGCTGCTGG
ACAGGGGCTCGGCTGTTGGGCACTGACAATTCCGTGGTGTTGTCGGGGAAATCATCGTCCTTTCCTTGGCTGCTCGCCTGTGTTGCCAC
CTGGATTCTGCGCGGGACGTCCTTCTGCTACGTCCCTTCGGCCCTCAATCCAGCGGACCTTCCTTCCCGCGGCCTGCTGCCGGCTCTGC
GGCCTCTTCCGCGTCTTCGCCTTCGCCCTCAGACGAGTCGGATCTCCCTTTGGGCCGCCTCCCCGCATCGGACTAG (APOE HCR enhancer: bases 1-320; human alpha-1-antitrypsin promoter: bases 321-717;
Kozak sequence: bases 718-726; human DNaseI hyperactive variant with natural full correct
leader sequence: bases 727-1575; WPRE X protein inactivated: bases 1576-2212)

SEQ ID NO: 31-Complete sequence of ApoEHCR enhancer-hAAT promoter-hDNaseI wild
type-WPRE Xinact (VR-18014AD)
AGGCTCAGAGGCACACAGGAGTTTCTGGGCTCACCCTGCCCCCTTCCAACCCCTCAGTTCCCATCCTCCAGCAGCTGTTTGTGTGCTGC
CTCTGAAGTCCACACTGAACAAACTTCAGCCTACTCATGTCCCTAAAATGGGCAAACATTGCAAGCAGCAAACAGCAAACACACAGCCC
TCCCTGCCTGCTGACCTTGGAGCTGGGGCAGAGGTCAGAGACCTCTCTGGGCCCATGCCACCTCCAACATCCACTCGACCCCTTGGAAT
TTCGGTGGAGAGGAGCAGAGGTTGTCCTGGCGTGGTTTAGGTAGTGTGAGAGGGATCTTGCTACCAGTGGAACAGCCACTAAGGATTCT
GCAGTGAGAGCAGAGGGCCAGCTAAGTGGTACTCTCCCAGAGACTGTTGCTACCACCCCCTCCACCTTGGACACAGGACGCTGT
GGTTTCTGAGCCAGGTACAATGACTCCTTTCGGTAAGTGCAGTGGAAGCTGTACACTGCCCAGGCAAAGCGTCCGGGCAGCGTAGGCGG
GCGACTCAGATCCCAGCCAGTGGACTTAGCCCCTGTTTGCTCCTCCGATAACTGGGGTGACCTTGGTTAATATTCACCAGCAGCCTCCC
CCGTTGCCCCTCTGGATCCACTGCTTAAATACGGACGAGGACAGGGCCCTGTCTCCTCAGCTTCAGGCACCACCACTGACCTGGGACAG
TGAATGCCGCCACCATGAGGGGCATGAAGCTGCTGGGGGCGCTGCTGGCACTGGCGGCCCTACTGCAGGGGGCCGTGTCCCTGAAGATC
GCAGCCTTCAACATCCAGACATTTGGGGAGACAAGATGTCCAATGCCACCCTCGTCAGCTACATTGTGCAGATCCTGAGCCGCTATGA
CATCGCCCTGGTCCAGGAGGTCAGAGACAGCCACCTGACTGCCGTGGGGAAGCTGCTGGACAACCTCAATCAGGATGCACCAGACACCT
ATCACTACGTGGTCAGTGAGCCACTGGGACGGAACAGCTATAAGGAGCGCTACCTGTTCGTGTACAGGCCTGACCAGGTGTCTGCGGTG
GACAGCTACTACTACGATGATGGCTGCGAGCCCTGCGGGAACGACACCTTCAACCGAGAGCCAGCCATTGTCAGGTTCTTCTCCCGGTT
CACAGAGGTCAGGGAGTTTGCCATTGTTCCCCTGCATGCGGCCCCGGGGGACGCAGTAGCCGAGATCGACGCTCTCTATGACGTCTACC
TGGATGTCCAAGAGAAATGGGGCTTGGAGGACGTCATGTTGATGGGCGACTTCAATGCGGGCTGCAGCTATGTGAGACCCTCCCAGTGG
TCATCCATCCGCCTGTGGACAAGCCCCACCTTCCAGTGGCTGATCCCGACAGCGCTGACACCACAGCTACACCCACGCACTGTGCCTA
TGACAGGATCGTGGTTGCAGGGATGCTGCTCCGAGGCGCCGTTGTTCCCGACTCGGCTCTTCCCTTTAACTTCCAGGCTGCCTATGGCC
TGAGTGACCAACTGGCCCAAGCCATCAGTGACCACTATCCAGTGGAGGTGATGCTGAAGTGAAGTGGCGGCCGCTCGAGCTAGCGGCCG
CTCTAGAAGATAATCAACCTCTGGATTACAAAATTTGTGAAAGATTGACTGGTATTCTTAACTATGTTGCTCCTTTTACGCTATGTGGA
TACGCTGCTTTAATGCCTTTGTATCATGCTATTGCTTCCCGTATGGCTTTCATTTTCTCCTCCTTGTATAAATCCTGGTTGCTGTCTCT
TTATGAGGAGTTGTGGCCCGTTGTCAGGCAACGTGGCGTGGTGTGCACTGTGTTTGCTGACGCAACCCCCACTGGTTGGGGCATTGCCA
CCACCTGTCAGCTCCTTTCCGGGACTTTCGCTTTCCCCCTCCCTATTGCCACGGCGGAACTCATCGCCGCCTGCCTTGCCCGCTGCTGG
ACAGGGGCTCGGCTGTTGGGCACTGACAATTCCGTGGTGTTGTCGGGGAAATCATCGTCCTTTCCTTGGCTGCTCGCCTGTGTTGCCAC
CTGGATTCTGCGCGGGACGTCCTTCTGCTACGTCCCTTCGGCCCTCAATCCAGCGGACCTTCCTTCCCGCGGCCTGCTGCCGGCTCTGC
GGCCTCTTCCGCGTCTTCGCCTTCGCCCTCAGACGAGTCGGATCTCCCTTTGGGCCGCCTCCCCGCATCGGACTAG (APOE HCR enhancer: bases 1-320; human alpha-1-antitrypsin promoter: bases 321-717;
Kozak sequence: bases 718-726; human DNaseI wild type with natural full correct leader
sequence: bases 727-1575; WPRE X protein inactivated: bases 1576-2212)

SEQ ID NO: 32-a polynucleotide encoding human DNase I, wild-type (WT), precursor of
SEQ ID NO: 1 with stop codon:
ATGAGGGGCATGAAGCTGCTGGGGGCGCTGCTGGCACTGGCGGCCCTACTGCAGGGGGCCGTGTCCCTGAAGATCGCAGCCTTCAACAT
CCAGACATTTGGGGAGACAAGATGTCCAATGCCACCCTCGTCAGCTACATTGTGCAGATCCTGAGCCGCTATGACATCGCCCTGGTCC
AGGAGGTCAGAGACAGCCACCTGACTGCCGTGGGGAAGCTGCTGGACAACCTCAATCAGGATGCACCAGACACCTATCACTACGTGGTC
AGTGAGCCACTGGGACGGAACAGCTATAAGGAGCGCTACCTGTTCGTGTACAGGCCTGACCAGGTGTCTGCGGTGGACAGCTACTACTA
CGATGATGGCTGCGAGCCCTGCGGGAACGACACCTTCAACCGAGAGCCAGCCATTGTCAGGTTCTTCTCCCGGTTCACAGAGGTCAGGG
AGTTTGCCATTGTTCCCCTGCATGCGGCCCCGGGGGACGCAGTAGCCGAGATCGACGCTCTCTATGACGTCTACCTGGATGTCCAAGAG
AAATGGGGCTTGGAGGACGTCATGTTGATGGGCGACTTCAATGCGGGCTGCAGCTATGTGAGACCCTCCCAGTGGTCATCCATCCGCCT
GTGGACAAGCCCCACCTTCCAGTGGCTGATCCCGACAGCGCTGACACCACAGCTACACCCACGCACTGTGCCTATGACAGGATCGTGG
TTGCAGGGATGCTGCTCCGAGGCGCCGTTGTTCCCGACTCGGCTCTTCCCTTTAACTTCCAGGCTGCCTATGGCCTGAGTGACCAACTG
GCCCAAGCCATCAGTGACCACTATCCAGTGGAGGTGATGCTGAAGTGA SEQ ID NO: 33-Kozak sequence
5'-GCCGCCACC-3'

SEQ ID NO: 34-Anc80L65 VP1 capsid protein
MAADGYLPDWLEDNLSEGIREWWDLKPGAPKPKANQQKQDDGRGLVLPGYKYLGPFNGLDKGEPVNAADAAALEHDKAYDQQLKAGDNP
YLRYNHADAEFQERLQEDTSFGGNLGRAVFQAKKRVLEPLGLVEEGAKTAPGKKRPVEQSPQEPDSSSGIGKKGQQPARKRLNFGQTGD
SESVPDPQPLGEPPAAPSGVGSNTMAAGGGAPMADNNEGADGVGNASGNWHCDSTWLGDRVITTSTRTWALPTYNNHLYKQISSQSGGS
TNDNTYFGYSTPWGYFDFNRFHCHFSPRDWQRLINNNWGFRPKKLNFKLFNIQVKEVTTNDGTTTIANNLTSTVQVFTDSEYQLPYVLG
SAHQGCLPPFPADVFMIPQYGYLTLNNGSQAVGRSSFYCLEYFPSQMLRTGNNFQFSYTFEDVPFHSSYAHSQSLDRLMNPLIDQYLYY
LSRTQTTSGTAGNRTLQFSQAGPSSMANQAKNWLPGPCYRQQRVSKTTNQNNSNFAWTGATKYHLNGRDSLVNPGPAMATHKDDEDKF
FPMSGVLIFGKQGAGNSNVDLDNVMITNEEEIKTTNPVATEEYGTVATNLQSANTAPATGTVNSQGALPGMVWQDRDVYLQGPIWAKIP
HTDGHFHPSPLMGGFGLKHPPPQILIKNTPVPANPPTTFSPAKFASFITQYSTGQVSVEIEWELQKENSKRWNPEIQYTSNYNKSTNVD
FAVDTNGVYSEPRPIGTRYLTRNL SEQ ID NO: 35-variant Anc80L65 VP1 capsid protein
MAADGYLPDWLEDNLSEGIREWWDLKPGAPKPKANQQKQDDGRGLVLPGYYLGPFNGLDKGEPVNAADAAALEHDKAYDQQLKAGDNPY
LRYNHADAEFQERLQEDTSFGGNLGRAVFQAKKRVLEPLGLVEEGAKTAPGKKRPVEQSPQEPDSSSGIGKKGQQPARKRLNFGQTGDS
ESVPDPQPLGEPPAAPSGVGSNTMAAGGGAPADNNEGADGVGNASGNWHCDSTWLGDRVITTSTRTWALPTYNNHLYKQISSQSGGSTN
DNTYFGYSTPWGYFDFNRFHCHFSPRDWQRLINNNWGFRPKKLNFKLFNIQVKEVTTNDGTTTIANNLTSTVQVFTDSEYQLPYVLGSA
```

Sequences

HQGCLPPFPADVFMIPQYGYLTLNNGSQAVGRSSFYCLEYFPSQMLRTGNNFQFSYTFEDVPFHSSYAHSQSLDRLMNPLIDQYLYYLS
RTQTTSGTAGNRTLQFSQAGPSSANQAKNWLPGPCYRQQRVSKTTNQNNNSNFAWTGATKYHLNGRDSLVNPGPAMATHKDDEDKFFPM
SGVLIFGKQGAGNSNVDLDNVITNEEEIKTTNPVATEEYGTVATNLQSANTAPATGTVNSQGALPGVWQDRDVYLQGPIWAKIPHTDGH
FHPSPLMGGFGLKEIPPPQILIKNTPVPANPPTTFSPAKFASFITQYSTGQVSVEIEELQKENSKRWNPEIQYTSNYNKSTNVDFAVDT
NGVYSEPRPIGTRYLTRNL

Definitions

The term "an enzyme which has a deoxyribonuclease (DNase) activity" is used herein to refer to an enzyme capable of hydrolytic cleavage of phosphodiester linkages in the DNA backbone.

As used herein, the terms "deoxyribonuclease" and "DNase" are used to refer to any enzyme that catalyzes the hydrolytic cleavage of phosphodiester linkages in the DNA backbone. A wide variety of deoxyribonucleases is known and can be used in the methods of the present invention. Non-limiting examples of DNases useful in the methods of the present invention include, e.g., DNase I (e.g., recombinant human DNase I (rhDNase I) or bovine pancreatic DNase I), analogues of DNase I (such as, e.g., DNase X, DNase gamma, and DNAS1L2), DNase II (e.g., DNase II-alpha, DNase II-beta), phosphodiesterase I, lactoferrin, and acetylcholinesterase. Also encompassed by the present invention are DNase enzymes which have an extended half-life (e.g., albumin and/or Fc fusions, or protected from binding to actin by modification of actin binding-site; see, e.g., Gibson et al., (1992) J. Immunol. Methods, 155, 249-256). The actin binding site of DNase I can be mutated, for example, at the following residues: Gln-9, Glu-13, Thr-14, His-44, Asp-53, Tyr-65, Val-66, Val-67, Glu-69, Asn-74, Ala-114 of recombinant human DNase I (SEQ ID NO: 4). For example, in human DNase I hyperactive variant comprising the sequence of SEQ ID NO: 5, the Ala-114 residue is mutated. Exemplary mutations include H44C, H44N, L45C, V48C, G49C, L52C, D53C, D53R, D53K, D53Y, D53A, N56C, D58S, D58T, Y65A, Y65E, Y65R, Y65C, V66N, V67E, V67K, V67C, E69R, E69C, A114C, H44N:T46S, D53R:Y65A, D53R:E69R, H44A:D53R: Y65A, H44A:Y65A:E69R, H64N:V66S, H64N:V66T, Y65N:V67S, Y65N:V67T, V66N:S68T, V67N:E69S, V67N:E69T, S68N:P70S, S68N:P70T, S94N:Y96S, S94N: Y96T (in the sequence of SEQ ID NO: 4). Also encompassed are mutations in DNase I with increased DNase I activity. Non-limiting examples of such mutations are, e.g., Q9R, E13R, E13K, T14R, T14K, H44R, H44K, N74K, and A114F of recombinant human DNase I (SEQ ID NO: 4). For example, a combination of the Q9R, E13R, N74K and A114F mutations is found in the hyperactive DNase I comprising the sequence of SEQ ID NO: 5. DNase I cleaves DNA preferentially at phosphodiester linkages adjacent to a pyrimidine nucleotide, yielding 5'-phosphate-terminated polynucleotides with a free hydroxyl group on position 3', on average producing tetranucleotides. DNase I acts on single-stranded DNA, double-stranded DNA, and chromatin.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, up to ±10%, up to ±5%, and up to ±1% of a given value. Alternatively, particularly with respect to biological systems or processes, the term can mean within an order of magnitude, such as within 2-fold, of a value. Where particular values are described in the application and claims, unless otherwise stated, the term "about" is implicit and in this context means within an acceptable error range for the particular value.

The terms "extracellular DNA", "cell-free DNA" and "cfDNA" are used interchangeably to refer to extracellular DNA (e.g., of eukaryotic, archaeal, or prokaryotic origin) found in blood, cerebrospinal fluid (CSF) or intestine of a patient.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The terms "individual", "subject", "animal", "patient", and "mammal" are used interchangeably to refer to mammals, including humans, veterinary animals (e.g., cats, dogs, cows, horses, sheep, pigs, etc.) and experimental animal models of diseases (e.g., mice, rats).

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

As used herein the term "therapeutically effective" applied to dose or amount refers to that quantity of a compound or pharmaceutical composition that is sufficient to result in a desired activity upon administration to a subject in need thereof. Note that when a combination of active ingredients is administered (e.g., a combination of DNase and another compound) the effective amount of the combination may or may not include amounts of each ingredient that would have been effective if administered individually.

As used herein, the term "promoter" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "tissue specific" promoter may be preferentially active in specific types of tissues or cells.

The term "liver-specific expression" as used herein refers to a predominant or exclusive expression in the liver, i.e., expression to a substantially greater extent than in other tissues and organs.

The term "liver-specific promoter" is used herein to refer to a promoter which is predominantly or exclusively active in a liver cell (e.g., hepatocyte) and directs/initiates transcription in the liver to a substantially greater extent than in other tissues and organs. In this context, the term "predominantly" means that at least 50% of said promoter-driven expression, more typically at least 90% of said promoter-driven expression (such as 100% of said promoter expression) occurs in liver cells. The ratio of liver expression to non-liver expression can vary between different liver-specific promoters. In some embodiments, a liver-specific promoter may preferentially direct/initiate transcription in a particular liver cell type (e.g., hepatocytes, Kupffer cells, endothelial cells, etc.). Some liver-specific promoters useful in the expression cassettes of the invention include at least one, typically several, hepatic nuclear factor binding sites. Liver-specific promoters useful in the expression cassettes of the invention can be constitutive or inducible promoters. Some non-limiting examples of hepatic promoters useful in the expression cassettes of the invention include: albumin promoter (Alb), human alpha-1 anti-trypsin (hAAT) promoter, thyroxine binding globulin (TBG), Apolipoprotein E hepatic control region promoter, Apolipoprotein A-II (APOA2) promoter, serpin peptidase inhibitor, Glade A, member 1 (SERPINA1) (hAAT) promoter, cytochrome P450 family 3, subfamily A polypeptide 4 (CYP3A4) promoter, microRNA 122 (miR-122) promoter, liver-specific IGF-II promoter P1, murine transthyretin (MTTR) promoter, alpha-fetoprotein (AFP) promoter, lecithin-cholesterol acyl transferase (LCAT) promoter, apolipoprotein H (ApoH) promoter, and mouse prealbumin gene promoter.

Non-limiting examples of liver-specific promoters include, e.g., albumin promoter (Alb), human alpha-1 anti-trypsin (hAAT) promoter, thyroxine binding globulin (TBG) promoter, Apolipoprotein E hepatic control region promoter, Apolipoprotein A-II (APOA2) promoter, serpin peptidase inhibitor, Glade A, member 1 (SERPINA1) (hAAT) promoter, cytochrome P450 family 3, subfamily A polypeptide 4 (CYP3A4) promoter, microRNA 122 (miR-122) promoter, Liver-specific IGF-II promoter P1, murine transthyretin (MTTR) promoter, the alpha-fetoprotein (AFP) promoter, a thyroid hormone-binding globulin promoter, an alcohol dehydrogenase promoter, the factor VIII (FVIII) promoter, a HBV basic core promoter (BCP) and PreS2 promoter, a phosphoenol pyruvate carboxykinase (PEPCK) promoter, an Hepatic Control Region (HCR)-ApoCII hybrid promoter, an AAT promoter combined with the mouse albumin gene enhancer (Ealb) element, a low density lipoprotein promoter, a pyruvate kinase promoter, a phosphenol pyruvate carboxykinase promoter, a lecithin-cholesterol acyl transferase (LCAT) promoter, an apolipoprotein H (ApoH) promoter, the transferrin promoter, a transthyretin promoter, an alpha-fibrinogen and beta-fibrinogen promoters, an alpha 1-antichymotrypsin promoter, an alpha 2-HS glycoprotein promoter, an haptoglobin promoter, a ceruloplasmin promoter, a plasminogen promoter, promoters of the complement proteins (e.g., C1q, C1r, C2, C3, C4, C5, C6, C8, C9, complement Factor I, and Factor H), C3 complement activator and the [alpha]1-acid glycoprotein promoter. Additional tissue-specific promoters may be found in the Tissue-Specific Promoter Database, TiProD (Nucleic Acids Research, J4:D104-D107 (2006).

In some embodiments, e.g., when liver targeting is mediated by a capsid protein, a nucleic acid encoding an enzyme which has a DNase activity can be operably linked to a promoter that allows for efficient systemic expression (e.g., CMV promoter, chicken beta actin promoter (CBA), EF1a promoter).

The term "portal vein cancer" is used herein to refer to a cancer (e.g., carcinoma, sarcoma, or lymphoma) that has originated in, or metastasized to, an organ or tissue that drains to the portal vein. Non-limiting examples of such organs and tissues are shown in FIG. 1 and include, e.g., liver, colon, small and large intestine, stomach, spleen, pancreas, and gall bladder.

The term "neurodegeneration" is used herein to refer to a separate clinical pathological condition with progressive loss of structure and/or function of neurons, including death of neurons. The neurodegeneration can be primary or secondary. Non-limiting examples of diseases involving primary neurodegeneration include, e.g., Alzheimer's disease (AD), Mild Cognitive Impairment (MCI), Parkinson's disease (PD), Huntington's disease (HD), prion-caused diseases, frontotemporal dementia (FTD), frontotemporal dementia with parkinsonism-17 (FTDP-17), Lewy body dementia, vascular dementias, Amyotrophic Later Sclerosis (ALS), chronic traumatic encephalopathy (CTE), progressive supranuclear palsy (PSP), multiple system atrophy (MSA), corticobasal degeneration (CBD), agyrophilic grain disease (AGD), Pick's disease, olivopontocerebellar atrophy (OPCA), senile dementia of the Alzheimer type, progressive supranuclear palsy (Steel-Richardson-Olszewski), corticodentatonigral degeneration, Hallervorden-Spatz disease, progressive familial myoclonic epilepsy, striatonigral degeneration, torsion dystonia (e.g., torsion spasm; dystonia musculorum deformans), spasmodic torticollis and other dyskinesis, familial tremor, Gilles de la Tourette syndrome, cerebellar cortical degeneration, spinocerebellar degeneration (e.g., Friedreich's ataxia and related disorders), Shy-Drager syndrome, spinal muscular atrophy, primary lateral sclerosis, hereditary spastic paraplegia, peroneal muscular atrophy (Charcot-Marie-Tooth), hypertrophic interstitial polyneuropathy (Dejerine-Sottas), chronic progressive neuropathy, pigmentary degeneration of the retina (retinitis pigmentosa), and hereditary optic atrophy (Leber's disease). Secondary neurodegeneration is caused primarily by necrosis. Non-limiting examples of conditions, which may result in secondary neurodegeneration, include destruction of neurons by neoplasm, edema, hemorrhage, stroke, trauma, immune attack, hypoxia, poisoning, metabolic defects, and infections.

The phrase "pharmaceutically acceptable", as used in connection with compositions of the invention, refers to molecular entities and other ingredients of such compositions that are physiologically tolerable and do not typically produce untoward reactions when administered to a subject (e.g., a mammal such as a human). As used herein, the term "pharmaceutically acceptable" means approved by a regulatory agency of the Federal or a state government or listed in the U.S. Pharmacopeia or other generally recognized pharmacopeia for use in mammals, and more particularly in humans.

The terms "cytostatic and/or cytotoxic chemotherapy" and "chemotherapy" are used interchangeably herein to refer to a therapy involving administering of a cytostatic and/or cytotoxic agent.

The terms "anti-cancer agent" and "anti-cancer chemotherapeutic agent" are used herein to refer to any chemical compound, which is used to treat cancer. Anti-cancer chemotherapeutic agents are well known in the art (see, e.g., Gilman A. G., et al., The Pharmacological Basis of Therapeutics, 8th Ed., Sec 12:1202-1263 (1990)). Specific examples of chemotherapeutic agents are provided throughout the specification.

The term "side effect of a chemotherapy" as used herein refers to an undesirable and unintended, although not necessarily unexpected, result of a chemotherapy.

As used herein, the terms "radiotherapy", "radiation therapy", and "RT" are used interchangeably to refer to the medical use of ionizing radiation as part of a cancer treatment to damage the DNA of malignant cells, either directly or by creating charged particles within the affected cells that damage the DNA. Commonly used types of radiation therapy encompassed by the present invention include, e.g., external beam radiation therapy (EBRT or XRT), brachytherapy/sealed source radiation therapy, and systemic radioisotope therapy/unsealed source radiotherapy The terms "side effect of a radiotherapy" or "side effect of a radiation therapy" as used herein refer to an undesirable and unintended, although not necessarily unexpected, result of a radiation therapy. Which side effects develop depend on the area of the body being treated, the dose given per day, the total dose given, the patient's general medical condition, and other treatments given at the same time, and may include, e.g., skin irritation or damage, fatigue, nausea, vomiting, fibrosis, bowel damage, memory loss, infertility, or a second cancer.

The term "catabolic state" as used herein refers to a condition characterized by a rapid weight loss and loss of fat and skeletal muscle mass, which may occur in a background of chemotherapy or chemoradiation therapy. Associated clinical events include, for example, immunosuppression, muscle weakness, predisposition to pulmonary embolism, thrombophlebitis, and altered stress response.

As used herein, the terms "viral vector" and "viral construct" refer to a recombinant viral construct that comprises one or more heterologous nucleotide sequences (e.g., a nucleotide sequence encoding an enzyme which has a DNase activity). In some embodiments, the viral vector is replication deficient. In some embodiments, viral structural and non-structural coding sequences are not present in the viral vector and are provided during viral vector production in trans by a vector, such as a plasmid, or by stably integrating the sequences into a packaging cell line. Depending on the virus, a viral vector can be packaged within a capsid (e.g., an AAV vector) and/or a lipid envelope (e.g., a lentiviral vector).

The term "polyadenylation signal", as used herein, relates to a nucleic acid sequence that mediates the attachment of a polyadenine stretch to the 3' terminus of the mRNA. Non-limiting examples of polyadenylation signals which can be used on the expression constructs of the invention include, e.g., the SV40 early polyadenylation signal, the SV40 late polyadenylation signal, the HSV thymidine kinase polyadenylation signal, the protamine gene polyadenylation signal, the adenovirus 5 EIb polyadenylation signal, the bovine growth hormone polyadenylation signal, the human variant growth hormone polyadenylation signal and the like.

As used in this specification and the appended claims, the singular forms "a," "an," and "the" include plural references unless the context clearly dictates otherwise.

In accordance with the present invention there may be employed conventional pharmacology and molecular biology techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M J. Gait ed. 1984); *Nucleic Acid Hybridization* (B. D. Hames & S. J. Higgins eds. (1985)); *Transcription and Translation* (B. D. Hames & S. J. Higgins, eds. (1984)); *Animal Cell Culture* (R. I. Freshney, ed. (1986); *Immobilized Cells and Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994); among others.

DNase Enzyme Targeting to Liver

The inventors have unexpectedly found that targeting expression of an enzyme which has a DNase activity to the liver can bring about an enhanced clearance of disease-associated cfDNA from the entire circulation, and especially from the porto-sinusoidal circulation. As demonstrated in the Examples section, below, cfDNA can accumulate in the liver, particularly in the periendothelial space and the space of Disse. Degradation of such reservoir of cfDNA via localized expression of an enzyme which has DNase activity can lower the overall level of cfDNA in the circulation.

As discussed throughout the application, an enzyme which has DNase activity can be efficiently expressed in liver cells through the use of viral vectors (e.g., adeno-associated viral (AAV) vectors, retroviral vectors (e.g., lentiviral vectors), or adenoviral vectors), liposomes, nanoparticles carrying a DNase transgene, or naked DNA. An adult human liver receives nearly one fourth of the cardiac output of blood, filters approximately 1 L of blood per minute, and accounts for 10-15% of the blood volume at any given moment. Such active circulation allows for rapid accumulation of high levels of vector particles within the liver. Vector particles can pass through the fenestrated endothelium along hepatic sinusoids directly to the hepatocytes. Such hepatocytes can be transfected by the vector particles and go on to produce DNase. The produced DNase is secreted into the periendothelial space and the space of Disse, where it can efficiently degrade the concentrated pool of cfDNA.

The inventors have found that transfection of liver cells to express an enzyme which has DNase activity provides a surprisingly greater reduction in cfDNA, along with substantial and surprising improvement in diseases and conditions associated with high levels of cfDNA in the bloodstream.

In some embodiments, expression of DNase enzyme in the liver is accomplished by use of nucleic acid expression cassettes that are predominantly expressed in the liver. In some embodiments, such expression cassettes can comprise one or more of the following elements: (a) a hepatic locus control element; (b) a hepatic promoter located 3' to the hepatic locus control element; (c) a coding sequence located 3' to the hepatic promoter, said coding sequence encoding a polypeptide, e.g. a deoxyribonuclease; (d) a polyadenylation signal located 3' to the coding sequence; and (e) an intron located 3' to the hepatic promoter and 5' to the polyadenylation signal. The elements (a), (b), (c), (d) and (e) can be operably linked to express the polypeptide encoded by the coding sequence. In some embodiments, the expression cassettes of the invention direct expression of a therapeutic amount of a polypeptide in liver cells for a period of at least 100 days (such as at least 200 days, at least 300 days, at least 400 days, or at least 500 days). In some embodiments, the polypeptide is a DNase. The DNase may be any DNase described herein, e.g., DNase I.

The polyadenylation signal may be operably linked to the nucleic acid encoding DNase. Non-limiting examples of polyadenylation signals include, e.g., the SV40 early polyadenylation signal, the SV40 late polyadenylation signal, the HSV thymidine kinase polyadenylation signal, the protamine gene polyadenylation signal, the adenovirus 5 EIb polyadenylation signal, the bovine growth hormone polyadenylation signal, the human variant growth hormone polyadenylation signal and the like.

In another aspect, the invention provides vectors that comprise a nucleic acid expression cassette that is predominantly expressed in the mammalian liver. Such expression cassette can comprise, e.g.: (a) a hepatic locus control element; (b) an hepatic promoter located 3' to the hepatic locus control element; (c) a coding sequence located 3' to the hepatic promoter, said coding sequence encoding a polypeptide, e.g. a deoxyribonuclease; (d) a polyadenylation signal located 3' to the coding sequence; and (e) an intron located 3' to the hepatic promoter and 5' to the polyadenylation signal. Elements (a), (b), (c), (d) and (e) are operably linked to express the polypeptide encoded by the coding sequence. Some vectors of the invention are episomal vectors, and some vectors of the inventions are integrating vectors such as integrating viral vectors. In some embodiments, the polypeptide is a deoxyribonuclease (DNase). The DNase may be any DNase described herein, e.g., DNase I.

In another aspect, the present invention provides methods for treating a disease or condition associated with increased levels of cfDNA. The disease or condition may be any disease or condition described herein or in any of U.S. Pat. Nos. 7,612,032; 8,388,951; 8,431,123; 8,535,663; 8,710,012; 8,796,004; 8,871,200; 8,916,151; 9,072,733; 9,248,166; 9,770,492; U.S. Pat. Appl. Pub. Nos. US20170056482, US20170100463, US20150110769, and Int. Appl. Pub. No. WO2016/190780, all of which are incorporated by reference herein in their entireties. In one embodiment, the method comprises the steps of: (1) introducing into the liver of a subject a vector comprising a nucleic acid expression cassette, said expression cassette comprising: (a) a liver-specific promoter; (b) a coding sequence located 3' to the liver-specific promoter, said coding sequence encoding an enzyme which has a DNase activity (e.g., any DNAs described herein); (c) a polyadenylation signal located 3' to the coding sequence; and optionally (d) an intron located 3' to the hepatic promoter and 5' to the polyadenylation signal. Elements (a), (b), (c), and (d) are operably linked to express the polypeptide encoded by the coding sequence; and (2) expressing a therapeutic amount of said polypeptide in the liver. In some embodiments of the methods of this aspect of the invention, a therapeutic amount of the polypeptide is expressed for at least 100 days (such as at least 200 days, at least 300 days, at least 400 days, or at least 500 days).

The nucleic acid expression vectors and cassettes of this aspect of the invention are predominantly expressed in the liver, e.g., at least 50% of the expression of the encoded polypeptide occurs within the liver. More typically, at least 90% of the expression occurs within the liver. Some of the expression vectors and cassettes of this aspect of the invention are exclusively expressed within the liver.

Hepatic locus control elements may be incorporated into the expression cassettes of the invention that are capable of enhancing the expression of nucleic acid molecules in liver cells, and confer copy number dependent, position independent expression on the expression cassette. Some hepatic locus control regions useful in the expression cassettes of the invention include, e.g., a matrix attachment region and/or a liver-specific enhancer element.

In addition to a promoter, an expression cassette and/or a vector may contain one or more additional transcription initiation, termination, and/or enhancer sequences; RNA processing signals (such as splicing and polyadenylation (poly A) signals); sequences that stabilize cytoplasmic mRNA; sequences that enhance translation efficiency (e.g., Kozak consensus sequence, such as 5'-GCCGCCACC-3' [SEQ ID NO: 33]); sequences that enhance protein stability; and sequences that enhance secretion of the encoded polypeptide. Examples of suitable polyA sequences include, e.g., SV40, SV50, bovine growth hormone (bGH), human growth hormone, and synthetic polyAs. Examples of suitable enhancers include, e.g., the alpha fetoprotein enhancer, the TTR minimal promoter/enhancer, LSP (TH-binding globulin promoter/alpha 1-microglobulin/bikunin enhancer), the Serpinl enhancer, amongst others. In one embodiment, the expression cassette comprises one or more expression enhancers. In one embodiment, the expression cassette contains two or more expression enhancers. These enhancers may be the same or may differ from one another. For example, an enhancer may include an Alpha mic/bik enhancer. This enhancer may be present in two copies which are located adjacent to one another. Alternatively, the dual copies of the enhancer may be separated by one or more sequences.

In still another embodiment, the expression cassette further contains an intron (e.g., the Promega intron, a truncated chimeric intron (T-chimeric intron), introns described in Int. Pat. Appl. Pub. No. WO 2011/126808).

Optionally, one or more sequences may be selected to stabilize mRNA. An example of such a sequence is a modified WPRE sequence, which may be engineered upstream of the polyA sequence and downstream of the coding sequence (see, e.g., MA Zanta-Boussif, et al, Gene Therapy (2009) 16: 605-619).

The enhancer may be an ApoE enhancer element of approximately 155 bp derived from apolipoprotein E or ApoE. ApoE is an apolipoprotein that mediates binding, internalization and catabolism of lipoprotein particles and is a ligand for the low-density lipoprotein (ApoB/E) receptor and for the ApoE receptor of hepatic tissues. The genetic enhancer associated with the ApoE gene is a eukaryotic control element that can increase transcription of a nucleic acid specifically in the liver.

The enhancer may include an element from a hepatic control region (e.g., HCR-1 or HCR-2) associated with the ApoE gene. For example, sequence from HCR-1 is found in the sequence of SEQ ID NO: 17.

In yet another embodiment, the expression cassette and/or vector further contains a post-transcriptional regulatory element (PRE). An exemplary post-transcriptional regulatory element is the Woodchuck hepatitis virus post-transcriptional regulatory element (WPRE). For example, a sequence from the WPRE is shown in SEQ ID NO: 16. The WPRE may be effective to increase expression of the protein (e.g., DNase). The WPRE may be modified so as not to produce an active form of a truncated X protein that is encoded in the WPRE. One such modified WPRE is provided in at least the sequence of SEQ ID NO: 16 and in the ApoEHCR enhancer: hAAT promoter>hDNaseI (hyperactive)correct leader-WPRE Xinact (bases 1576-2212 of SEQ ID NO: 30; see also FIGS. 10A and 10B).

In some embodiments, the cassettes of the invention direct the expression of a therapeutic amount of the polypeptide encoded by the coding sequence for an extended period, typically greater than 200 days, and in some instances greater than 500 days. Expression of the polypeptide encoded by the coding sequence can be measured by any art-recognized means, such as, e.g., by antibody-based assays, such as a Western Blot or an ELISA assay. Again, by way of non-limiting example, expression of the polypeptide encoded by the coding sequence within the expression cassette can be measured in a bioassay that detects an enzymatic or biological activity of the polypeptide.

Upon entry into the liver cells (e.g., hepatocytes), the vectors can remain episomal (i.e., do not integrate into the genome of a host cell), or can integrate into the host cell genome. Non-limiting examples of episomal vectors include adenoviral vectors, and examples of vector that integrate into the host cell genome include retroviral vectors.

In some embodiments of the invention, the expression vectors comprising a nucleotide sequence encoding an enzyme which has DNase activity, are delivered to cells in the form of liposomes in which the DNA is associated with one or more lipids, such as DOTMA (1,2-diolcyloxypropyl-3-trimethyl ammonium bromide) and DOPE (dioleoylphosphatidylethanolamine). In some embodiments, cationic liposomes containing DOTMA are effective to target expression vectors of the invention to the liver. In some embodiments, lactoferrin and/or poly L-lysine and/or polyethylenemine and/or chitosan is conjugated to an expression vector, with the conjugate effectively targeted to the liver after direct introduction into a subject.

In some embodiments, the liposomes have dimensions smaller than the fenestrations of the endothelial layer lining hepatic sinusoids in the liver.

In some embodiments, the expression vector is packaged into a nanovector or is encapsulated by a nanovector.

In some embodiments, the expression vector is packaged into phosphoramidite nanoparticles.

Various devices have been developed for enhancing the availability of the nucleic acids of the invention encoding enzymes which has DNase activity to the target cells, including, e.g., catheters or implantable materials containing DNA (G. D. Chapman et al., *Circulation Res.* 71:27-33 (1992)) and needle-free, jet injection devices which project a column of liquid directly into the target tissue under high pressure (P. A. Furth et al., *Anal Biochem.* 20:365-368 (1992); (H. L. Vahlsing et al., *J. Immunol. Meth.* 175:11-22 (1994); (F. D. Ledley et al., *Cell Biochem.* 18A:226 (1994)).

Another approach to targeted liver delivery of the nucleic acids of the invention encoding enzymes which has DNase activity is the use of molecular conjugates, which consist of protein or synthetic ligands to which a nucleic acid-binding agent has been attached for the specific targeting of nucleic acids to cells (R. J. Cristiano et al., *Proc. Natl. Acad. Sci. USA* 90:11548-52 (1993); B. A. Bunnell et al., *Somat. Cell Mol. Genet.* 18:559-69 (1992); M. Cotten et al., *Proc. Natl. Acad. Sci. USA* 89:6094-98 (1992)). This gene delivery system has been shown to be capable of targeted delivery to many cell types through the use of different ligands (R. J. Cristiano et al., *Proc. Natl. Acad. Sci. USA* 90:11548-52 (1993)). For example, lipofection and malaria circumsporozoite protein have been used for the liver-specific delivery of genes (Z. Ding et al., *J. Biol. Chem.* 270:3667-76 (1995)).

Preferred routes of administration for the expression vectors of the invention are intrahepatic, intravenous, and intra-arterial administration. However, other routes of administration allowing liver targeting can be also employed such as, e.g., enteral (e.g., oral), intramuscular, intraperitoneal, etc.

The expression vectors of the invention can be introduced directly into the liver by any art-recognized means, such as by direct injection into the liver, portal vein injection, or tail vein injection.

The expression vectors of the invention may be delivered by (1) creating an access site in an artery of a mammal, (2) introducing a guidewire into the artery, (3) introducing a sheath over the guidewire into the artery, (4) advancing a catheter through the sheath into the liver, (5) infusing the expression vector, e.g., rAAV virions, through the catheter into the liver, (6) removing the catheter and the sheath from the artery, and (7) repairing the access site. The catheter may be introduced into the target organ through an appropriate vein or artery. For example, the liver may be accessed via either the portal vein or the hepatic artery. An appropriate vein or artery may be accessed using techniques known in the art, such as the Seldinger technique. See, e.g., Conahan et al., (1977) JAMA 237:446-447, herein incorporated by reference. Other methods of accessing veins and arteries are also known. See, e.g., U.S. Pat. No. 5,944,695 herein incorporated by reference.

In certain other embodiments, occluding one or more of the blood vessels delivering blood to, or emptying blood from, the liver is conducted. The occluding device can be, for example, a balloon attached to the tip of a catheter. All of the arteries and veins entering or leaving the liver may be occluded so that the expression vector is delivered by way of asanguinous hepatic perfusion, whereby the liver is selectively perfused after excluding normal blood flow from the liver. This may be accomplished by clamping the hepatic artery, portal vein, suprahepatic vena cava, right suprarenal vein and infrahepatic vena cava to achieve the total vascular exclusion of the liver. The portal vein is then cannulated with a catheter of appropriate gauge, while an incision is made in the anterior wall of the infrahepatic vena cava, with a suction cannula placed into the vena cava to collect outflow. Liver perfusion, preferably single pass perfusion, is then performed using a pump. The flow rate may range from 0.1 ml/min per gram of liver to 10 ml/min per gram of liver. A rate of 1 ml/min per gram of liver is preferred, and may be increased to ensure satisfactory perfusion of the organ. After perfusion, the portal and caval vein incisions are sutured and the liver is revascularized. Cardoso, et al., Human Gene Therapy 4:411-418 at 412 (1993).

In other embodiments, expression vectors are delivered into the liver by injection into the hepatic artery.

In a liver organ, the parenchymal cells include hepatocytes, Kupffer cells and the epithelial cells that line the biliary tract and bile ductules. The major constituent of the liver parenchyma are polyhedral hepatocytes (also known as hepatic cells) that presents at least one side to a hepatic sinusoid and apposed sides to a bile canaliculus. Liver cells that are not parenchymal cells include cells within the blood vessels such as the endothelial cells or fibroblast cells.

In the liver, the hepatic vein is an efferent blood vessel since it normally carries blood away from the liver into the inferior vena cava. Also in the liver, the portal vein and hepatic arteries are afferent blood vessels in relation to the liver since they normally carry blood towards the liver.

A liver blood vessel includes the portal venous system which transports blood from the gastrointestinal tract and other internal organs (e.g. spleen, pancreas and gall bladder) to the liver. Another liver blood vessel is the hepatic vein. The hepatic vein may also be reached via the inferior vena cava or another blood vessel that ultimately connects to the liver. A needle or catheter may be used to inject the polynucleotide into the vascular system. The injection can be performed under direct observation following an incision and visualization of the tissues blood vessels. Alternatively, a catheter can be inserted at a distant site and threaded so that it resides in the vascular system that connects with the target tissue. In some embodiments, deep injection into the vena cava is performed. In another embodiment, the injection could be performed by using a needle that traverses the intact skin and enters a vessel that supplies or drains from the target tissue.

In some embodiments, the delivery is performed as follows. The liver and portal vein are visualized through a ventral midline incision. A vector/liposome/naked DNA in 1 ml of various solutions containing heparin to prevent clotting is injected into the portal vein using a needle over approximately 30 sec.

The efficiency of liver delivery, expression and secretion of the enzyme which has DNase activity can be determined, e.g., by assaying the level of the enzyme in the blood (e.g., blood obtained from the retro-orbital venous sinus), e.g., using immunological assays (e.g., assays with antibodies recognizing the enzyme such as, e.g., a radioimmune assay (RIA) (HGH-TGES 100T kit from Nichols Institute, San Juan Capistrano, Calif., USA)). In experimental animal models, the efficiency of liver delivery, expression and secretion of the enzyme which has DNase activity can be determined, e.g., by sacrificing the animals by cervical dislocation and the livers (average weight of 1.5 g) divided into six sections composed of two pieces of median lobe, two pieces of left lateral lobe, the right lateral lobe, and the caudal lobe plus a small piece of right lateral lobe. Each of the six sections may be placed separately into a homogenizing buffer. The homogenates may be centrifuged and the supernatant analyzed for the foreign gene product (i.e., enzyme which has DNase activity). Liver injections can be directed into the inferior cava which was clamped in two locations: proximal and distal to the entry of the hepatic vein into the inferior vena cava. Specifically, the downstream inferior vena cava clamp can be placed between the diaphragm and the entry point of the hepatic vein. The upstream inferior vena cava clamp can be placed just upstream of the entry point of the renal veins. Since the veins of other organs such as the renal veins enter the inferior vena cava at this location, not all of the injection fluid goes into the liver. In some of the animals that receive retrograde injections in the inferior vena cava, the hepatic artery, mesenteric artery, and portal vein can be clamped (occluded).

Parvovirus Vectors, Including Adeno-Associated Virus Vectors

In certain embodiments, the vector used in the invention is a parvovirus vector, such as an adeno-associated viral (AAV) vector. The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B 19 virus, and any other autonomous parvovirus now known or later discovered. Other autonomous parvoviruses are known to those skilled in the art. See, e.g., Bernard N. Fields et al., Virology, Vol. 2, Chapter 69 (4th ed., Lippincott-Raven Publishers).

In some embodiments, the parvovirus vector is a single-stranded parvovirus vector, such as an AAV vector. AAV (genus Dependovirus) normally infects humans (e.g., serotypes 1, 2, 3A, 3B, 4, 5, and 6) or primates (e.g., serotypes 1 and 4), or other warm-blooded animals (e.g., bovine, canine, equine, and ovine AAVs). Further information on parvoviruses and other members of the Parvoviridae is provided, e.g., in Kenneth I. Berns, "Parvoviridae: The Viruses and Their Replication," Chapter 69 in Fields Virology (3d Ed. 1996).

AAV vectors disclosed herein may be derived from any AAV serotype, including combinations of serotypes (e.g., "pseudotyped" AAV) or from various genomes (e.g., single-stranded or self-complementary). A "serotype" is traditionally defined on the basis of a lack of cross-reactivity between antibodies to one virus as compared to another virus. Such cross-reactivity differences are usually due to differences in capsid protein sequences/antigenic determinants (e.g., due to VP1, VP2, and/or VP3 sequence differences). Non-limiting examples of AAV serotypes which can be used to develop the AAV expression vectors of the invention include, e.g., AAV serotype 1 (AAV1), AAV2, AAV3 (including types 3A and 3B), AAV4, AAV5, AAV6, AAV7, AAV8, AAV9, AAV10, AAV11, AAV12, AAVrh10 (as disclosed, e.g., in U.S. Pat. No. 9,790,472, Int. Pat. Appl. Pub. No. WO2017180857 and WO2017/180861), AAVLK03 (as disclosed, e.g., in Wang et al., Mol. Ther., 2015, 23(12):1877-1887), AAVhu37 (as disclosed, e.g., in Int. Pat. Appl. Pub. No. WO2017180857), AAVrh64R1 (as disclosed, e.g., in Int. Pat. Appl. Pub. No. WO2017180857), Anc80 (based on a predicted ancestor of serotypes AAV1, AAV2, AAV8 and AAV9; see Zinn et al., Cell Rep., 2015, 12(67): 1056-1068), avian AAV, bovine AAV, canine AAV, equine AAV, ovine AAV, and any other AAV now known or later discovered. See, e.g., Fields et al., Virology, volume 2, chapter 69 (4th ed., Lippincott-Raven Publishers).

Recently, a number of putative new AAV serotypes and clades have been identified (see, e.g., Gao et al., (2004) J. Virology 78:6381-6388; Moris et al., (2004) Virology 33-: 375-383). The genomic sequences of the various serotypes of AAV and the autonomous parvoviruses, as well as the sequences of the terminal repeats, Rep proteins, and capsid subunits are known in the art, by way of example, Srivistava et al., (1983) J. Virology 45:555; Chiorini et al., (1998) J. Virology 71:6823; Chiorini et al, (1999) J. Virology 73:1309; Bantel-Schaal et al., (1999) J. Virology 73:939; Xiao et al., (1999) J. Virology 73:3994; Muramatsu et al., (1996) Virology 221: 208; Shade et al., (1986) J. Virol. 58:921; Gao et al., (2002) Proc. Nat. Acad. Sci. USA 99:11854; Moris et al., (2004) Virology 33-: 375-383; GenBank Accession number U89790; GenBank Accession number J01901; GenBank Accession number AF043303; GenBank Accession number AF085716; GenBank Accession number NC 006152; GenBank Accession number Y18065; GenBank Accession number NC 006260; GenBank Accession number NC_006261; International Patent Publication Nos. WO 00/28061, WO 99/61601, WO 98/11244; and U.S. Pat. No. 6,156,303, the disclosures of which are incorporated by reference herein for teaching parvovirus and AAV nucleic acid and amino acid sequences.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, VP2 and VP3) form the capsid. The terminal 145 nucleotides are self-complementary and are organized so that an energetically stable intramolecular duplex forming a T-shaped hairpin may be formed. These hairpin structures function as an origin for viral DNA replication, serving as primers for the cellular DNA polymerase complex. Following wtAAV infection in mammalian cells the Rep genes (i.e. Rep78 and Rep52) are expressed from the P5 promoter and the P19 promoter, respectively and both Rep proteins have a function in the replication of the viral genome.

In some embodiments, recombinant AAV (rAAV) vectors comprise one or more nucleotide sequences of interest that are flanked by at least one parvoviral or AAV inverted terminal repeat sequence (ITR). Such rAAV vectors can be replicated and packaged into viral particles when produced in a packaging cell that is expressing AAV rep and cap gene products (i.e. AAV Rep and Cap proteins). The terms "AAV Cap protein" or "AAV capsid protein", as used herein, refer to a polypeptide having at least one functional activity of a native AAV Cap protein (e.g., VP1, VP2, VP3). Examples of functional activities of Cap proteins (e.g., VP1, VP2, VP3) include the ability to induce formation of a capsid, facilitate accumulation of single-stranded DNA, facilitate AAV DNA packaging into capsids (i.e., encapsidation), bind to cellular receptors, and facilitate entry of the virion into host cells.

In some embodiments, the AAV vectors may comprise desired proteins or protein variants. A "variant" as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both.

AAV vectors are packaged into AAV viral capsids. The sequence of an AAV viral capsid protein defines numerous features of a particular AAV vector. For example, the capsid protein affects capsid structure and assembly, interactions with AAV nonstructural proteins such as Rep and AAP proteins, interactions with host body fluids and extracellular matrix, clearance of the virus from the blood, vascular permeability, antigenicity, reactivity to neutralizing antibodies, tissue/organ/cell type tropism, efficiency of cell attachment and internalization, intracellular trafficking routes, virion uncoating rates, among others. The sequence of a capsid protein (e.g., VP3) may be altered to enhance delivery to the liver.

AAV constructs may further comprise a sequence encoding one or more capsid proteins (VP1 and/or VP2, and/or VP3 capsid proteins, preferably just VP3 capsid protein) which package the above-mentioned polynucleotide sequence. The sequences coding for the capsid protein(s) for use in the context of the present invention may be taken from any of the known 42 serotypes, such as, e.g., AAV1, AAV2, AAV3, AAV4, AAV5, AAV6, AAV7, AAV8, AAV9, Anc80, or newly developed AAV-like particles obtained by, e.g., capsid shuffling techniques and/or use of AAV capsid libraries. For some non-limiting examples of capsid protein sequences, see, e.g., U.S. Pat. Nos. 9,790,472; 9,677,089; 7,282,199; Int. Pat. Appl. Publ. Nos. WO 2015/054653, WO2017/180857 (AAV8, AAV9, AAVrh10, AAVhu37, AAVrh64R1), WO2017/180861 (AAVrh10), WO2017/180854 (AAV8 mutants), and Wang et al., Mol. Ther., 2015, 23(12):1877-1887 (AAV8, AAVrh10, AAV3B, and AAVLK03). When the sequences encoding the capsid proteins derive from a different AAV serotype as the ITRs, the AAV construct is known as a "hybrid" parvovirus genome (i.e., in which the AAV capsid and the AAV terminal repeat(s) are from different AAV) as described in Int. Pat. Appl. Publ. No. WO and Chao et al., (2000) Molecular Therapy 2:619.

In some embodiments, the capsid protein(s) mediates efficient targeting of the AAV vector to the liver. In some embodiments, the capsid protein(s) mediate preferential targeting of the AAV vector to the liver. Some capsid proteins (e.g., VP3 of Anc80, AAV8 and AAV3B) are naturally liver-specific. The invention also encompasses the use of AAV capsid mutants which enhance liver targeting and/or liver specificity. Non-limiting examples of such point mutations to the AAV8 capsid sequence include, e.g., S279A, S671A, K137R, and T252A, as well as AAV8 capsid mutations disclosed in Int. Pat. Appl. Pub. No. WO2017/180854 (e.g., AAV3G1, AAVT20 or AAVTR1, VP3 mutations in amino acids 263-267 [e.g., 263NGTSG267→SGTH ("NGTSG" disclosed as SEQ ID NO: 39 and "SGTH" disclosed as SEQ ID NO: 40) or 263NGTSG267→SDTH ("NGTSG" disclosed as SEQ ID NO: 39 and "SDTH" disclosed as SEQ ID NO: 41)] and/or amino acids 457-459 [e.g., 457TAN459→SRP], and/or amino acids 455-459 [e.g., 455GGTAN459→DGSGL ("GGTAN" disclosed as SEQ ID NO: 42 and "DGSGL" disclosed as SEQ ID NO: 43)] and/or amino acids 583-597).

The AAV vectors disclosed herein include a nucleic acid encoding an enzyme which has a DNase activity, such as, e.g., DNase I. In various embodiments, the nucleic acid also may include one or more regulatory sequences allowing expression and secretion of the encoded enzyme, such as e.g., a promoter, enhancer, polyadenylation signal, an internal ribosome entry site (IRES), a sequence encoding a protein transduction domain (PTD), a secretory signal sequence, and the like. Thus, in some embodiments, the nucleic acid may comprise a promoter region operably linked to the coding sequence to cause or improve expression of the protein of interest in transfected cells. Such a promoter may be ubiquitous, cell- or tissue-specific, strong, weak, regulated, chimeric, etc., for example to allow efficient and stable production of the protein in the liver. The promoter may be homologous to the encoded protein, or heterologous, although generally promoters of use in the disclosed methods are functional in human cells. Examples of regulated promoters include, without limitation, Tet on/off element-containing promoters, rapamycin-inducible promoters, tamoxifen-inducible promoters, and metallothionein promoters. Other promoters that may be used include promoters that are tissue specific, e.g., for liver. Non-limiting examples of liver-specific promoters include, e.g., the albumin promoter (Alb), human alpha-1 anti-trypsin (hAAT) promoter, thyroxine binding globulin (TBG), apolipoprotein E hepatic control region promoter, apolipoprotein A-II (APOA2) promoter, serpin peptidase inhibitor, Glade A, member 1 (SERPINA1) (hAAT) promoter, cytochrome P450 family 3, subfamily A polypeptide 4 (CYP3A4) promoter, microRNA 122 (miR-122) promoter, liver-specific IGF-II promoter P1, murine transthyretin (MTTR) promoter, and the alpha-fetoprotein (AFP) promoter. Non-limiting examples of ubiquitous promoters include, e.g., viral promoters such as the CMV promoter, the RSV promoter, the SV40 promoter, etc., and cellular promoters such as the phosphoglycerate kinase (PGK) promoter, EF1a promoter, CMVE/CAG promoter system, and the β-actin promoter.

The AAV constructs of the invention may also contain non-resolvable terminal repeats. The expression "non-resolvable terminal repeat", as used herein, relates to terminal repeats which are not recognized by and resolved (i.e., "nicked") by the AAV Rep proteins, such that resolution of the terminal repeat is substantially reduced (e.g., by at least about 50%, 60%, 70%, 80%. 90%, 95%, 98% or greater as compared with a resolvable terminal repeat) or eliminated. Such non-resolvable terminal repeats may be naturally-occurring terminal repeat sequences (including altered forms thereof) and, for example, can be derived from a parvovirus, including an AAV, or can be from another virus or, as a further alternative, can be partially or completely synthetic. The non-resolvable terminal repeat may be a non-AAV viral sequence that is not recognized by the AAV Rep proteins, or it can be an AAV terminal repeat that has been modified (e.g., by insertion, substitution and/or deletion) so that it is no longer recognized by the AAV Rep proteins. Further, a non-resolvable terminal repeat can be any terminal repeat that is non-resolvable under the conditions used to produce the virus vector. Further, an AAV terminal repeat can be modified so that resolution by the AAV Rep proteins is substantially reduced or eliminated. The non-resolvable terminal repeat can be any inverted repeat sequence that forms a hairpin structure and cannot be nicked by the AAV Rep proteins.

The inverted terminal repeats (ITR) are typically present in at least two copies in the AAV vector, typically flanking the expression cassette containing the nucleotide sequence (s) encoding an enzyme which has a DNase activity. The ITRs typically will be at the 5' and 3' ends of the nucleotide sequence(s) encoding an enzyme which has a DNase activity, but need not be contiguous thereto. The ITRs can be the same or different from each other. The term "terminal repeat" includes any viral terminal repeat and/or partially or completely synthetic sequences that form hairpin structures and function as an inverted terminal repeat, such as the "double-D sequence" as described in U.S. Pat. No. 5,478,745 to Samulski et al. An "AAV terminal repeat" may be from any AAV, including but not limited to serotypes 1, 2, 3, 4, 5, 6, 7, 8, 9, 10, 11, 12, Anc80, or any other AAV now known or later discovered. The AAV terminal repeat need not have a wild-type sequence (e.g., a wild-type sequence may be altered by insertion, deletion, truncation or missense mutations), as long as the terminal repeat mediates the desired functions, e.g., replication, nicking, virus packaging, integration, and/or provirus rescue, and the like. The vector construct can comprise one or more (e.g., two) AAV terminal repeats, which may be the same or different. Further, the one or more AAV terminal repeats can be from the same AAV serotype as the AAV capsid, or can be different. In particular embodiments, the vector construct comprises an AAV1, AAV2, AAV3, AAV4, AAV5, AAV6, AAV7, AAV8, AAV9, AAV10, AAV11, AAV12, and/or Anc80 terminal repeat.

Parvoviral ITR nucleotide sequences are typically palindromic sequences, comprising mostly complementary, symmetrically arranged sequences also referred to as "A," "B," and "C" regions. The ITR functions as an origin of replication, a site having a "cis" role in replication, i.e., being a recognition site for trans acting replication proteins such as e.g. Rep 78 (or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. A parvovirus replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nucleotide sequence can be used in the context of the present invention. Two or another even number of regular ITRs can be used.

Functional ITR sequences are necessary for the replication, rescue and packaging of AAV virions. The ITR sequences may be wild type sequences or may have at least 80%, 85%, 90%, 95%, or 100% sequence identity with wild type sequences. The ITR sequences may be altered by for example in insertion, mutation, deletion or substitution of nucleotides, as long as they remain functional. In this context, functionality refers to the ability to direct packaging of the genome into the capsid shell and then allow for expression in the host cell to be transduced or target cell.

The AAV vector can comprise single stranded or double stranded (self-complementary) DNA. The single stranded nucleic acid molecule is either sense or antisense strand, as both polarities are equally capable of gene expression. The AAV vector may further comprise a marker or reporter gene, such as a gene for example encoding an antibiotic resistance gene, a fluorescent protein (e.g., GFP) or a gene encoding a chemically, enzymatically or otherwise detectable and/or selectable product (e.g., lacZ, aph, etc.) known in the art.

AAV expression vectors may comprise a nucleic acid that may include a secretory signal sequence allowing secretion of the encoded enzyme which has a DNase activity from the transduced cell. Non-limiting examples of such secretory signal sequences include, e.g., DNase I secretory signal sequence, IL2 secretory signal sequence, albumin secretory signal sequence, β-glucuronidase secretory signal sequence, alkaline protease secretory signal sequence, and fibronectin secretory signal sequence.

In some embodiments, an AAV8-based or an Anc80-based vector is used as the expression vector. The AAV8 and Anc80 vectors are particularly suited for liver targeting and expression. For example, both AAV8 and Anc80 vectors can transfect liver cells with greater efficiency as compared to an AAV2 vector. Both AAV8 and Anc80 also induce lower amounts of neutralizing antibodies than some of the other AAV vectors.

An AAV8 vector or an Anc80 vector comprising a nucleotide encoding for an enzyme which has a DNase activity can be administered intrahepatically (e.g., via direct organ injection) or systemically, e.g., by intravenous injection, with the AAV8 or Anc80 vector effective to transfect liver cells and mediate effective production of the encoded enzyme which has a DNase activity and its secretion in the periendothelial space and the space of Disse. In some embodiments, an Anc80 capsid protein (e.g., Anc80 VP1 capsid protein comprising the sequence SEQ ID NO: 3 or SEQ ID NO: 9, or an Anc80L65 VP1 capsid protein comprising the sequence of SEQ ID NO:34, or a variant Anc80L65 VP1 capsid protein comprising the sequence of SEQ ID NO: 35) is encoded by a nucleotide sequence in the expression vector. In some embodiments, an AAV8 capsid protein (e.g., AAV8 VP1 or AAV8 VP3) is encoded by a nucleotide sequence in the expression vector. Peripheral administration of the AAV vectors of the invention may include systemic injections, such as, e.g., intramuscular, intravenous, intraperitoneal, and intra-arterial injections.

The desired doses of the DNase enzyme encoding AAV vectors of the invention may be easily adapted by the skilled artisan, e.g., depending on the disease condition, the subject, the treatment schedule, etc. In some embodiments, from $10^5$ to $10^{14}$ recombinant viral particles are administered per dose, for example, from $10^6$ to $10^{11}$, from $10^7$ to $10^{11}$, or from $10^8$ to $10^{14}$. In other embodiments, exemplary doses for achieving therapeutic effects may include titers of at least about $10^5$, $10^6$, $10^7$, $10^8$, $10^9$, $10^{10}$ or $10^{11}$ recombinant viral particles or more.

The exogenous targeting sequence(s) may replace or substitute part or all of a major capsid subunit (e.g., VP3). As a further alternative, more than one exogenous targeting sequence, e.g., two, three, four, five or more sequences, may be introduced into the virion capsid. In alternative embodiments, insertions and substitutions within the minor capsid subunits (e.g., VP1 and VP2) may be undertaken. For AAV capsids, insertions or substitutions in VP2 or VP3 may be undertaken.

The native virion tropism may be reduced or abolished by insertion or substitution of the amino acid sequence. Alternatively, the insertion or substitution of the exogenous amino acid sequence may target the virion to a particular cell type(s). The exogenous targeting sequence may be any amino acid sequence encoding a protein or peptide that alters the tropism of the virion. In particular embodiments, the targeting peptide or protein may be naturally occurring or, alternately, completely or partially synthetic. Exemplary peptides and proteins include ligands and other peptides that bind to cell surface receptors present in liver cells include ligands capable of binding the Sr—B1 receptor for apolipoprotein E, galactose- and lactose-specific lectins, low density lipoprotein receptor ligands, asialoglycoprotein (galactose-terminal) ligands and the like.

Alternatively, the exogenous targeting sequence may be an antibody or an antigen-recognizing moiety thereof. The term "antibody" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. Also encompassed by the term "antibody" are bispecific or "bridging" antibodies as known by those skilled in the art. Antibody fragments within the scope of the present invention include, for example, Fab, F(ab')2, and Fc fragments, and the corresponding fragments obtained from antibodies other than IgG. Such fragments may be produced by known techniques. The exogenous amino acid sequence inserted into the virion capsid may be one that facilitates purification or detection of the virion. For example, the exogenous amino acid sequence may include a poly-histidine sequence that is useful for purifying the virion over a nickel column, as is known to those skilled in the art or an antigenic peptide or protein that may be employed to purify the virion by standard immunopurification techniques. Alternatively, the amino acid sequence may encode a receptor ligand or any other peptide or protein that may be used to purify the modified virion by affinity purification or any other techniques known in the art (e.g., purification techniques based on differential size, density, charge, or isoelectric point, ion-exchange chromatography, or peptide chromatography).

Alternatively, the exogenous targeting sequence may be an antibody or an antigen-recognizing moiety thereof. The term "antibody" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. Also encompassed by the term "antibody" are bispecific or "bridging" antibodies as known by those skilled in the art. Antibody fragments within the scope of the present invention include, for example, Fab, F(ab')2, and Fc fragments, and the corresponding fragments obtained from antibodies other than IgG. Such fragments may be produced by known techniques.

The exogenous amino acid sequence inserted into the virion capsid may be one that facilitates purification or detection of the virion. According to this aspect of the invention, it is not necessary that the exogenous amino acid sequence also alters the virion of the modified parvovirus. For example, the exogenous amino acid sequence may include a poly-histidine sequence that is useful for purifying the virion over a nickel column, as is known to those skilled in the art or an antigenic peptide or protein that may be employed to purify the virion by standard immunopurification techniques. Alternatively, the amino acid sequence may encode a receptor ligand or any other peptide or protein that may be used to purify the modified virion by affinity purification or any other techniques known in the art (e.g., purification techniques based on differential size, density, charge, or isoelectric point, ion-exchange chromatography, or peptide chromatography).

Adenovirus Vectors

Adenovirus genome is a linear, 36-Kb double-stranded DNA containing multiple, heavily spliced transcripts. At either end of the genome are inverted terminal repeats (ITRs). Genes are divided into early (E1-E4) and late (L1-L5) transcripts.

In some embodiments, recombinant adenovirus vectors have two genes deleted: E1 and E3 (dE1/E3). Deletion of E1 makes the viral vector replication-deficient. E1 can be supplied by the adenovirus packaging cell lines (e.g., T 293 or 911). E3 is involved in evading host immunity and is not essential for virus production. Deletion of E1 and E3 results in a transgene packaging capacity of >8 Kb. In some embodiments, Constructs contain left and right arms to facilitate homologous recombination of the transgene into the adenoviral plasmid.

Any of the accepted human adenovirus types may be used, such as, e.g., an adenoviral vector based on Ad5. Ad5-based vectors use the Coxsackie-Adenovirus Receptor (CAR) to enter cells. In some embodiments, human adenovirus Type 5 (dE1/E3) is used as a vector. Most adenovirus vectors are engineered such that a transgene replaces the Ad E1a, E1b, and/or E3 genes; subsequently the replication defective vector is propagated in human 293 cells that supply deleted gene function in trans. Adenovirus vectors can transduce multiple types of tissues in vivo, including nondividing, differentiated cells such as those found in the liver. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Hepatitis B Vectors and Other Hepatotropic Vectors

In some embodiments, liver-specific delivery and expression of an enzyme which has a DNase activity can be achieved by the use of viral vectors which naturally target hepatocytes. Vectors derived from hepatotropic viruses, such as hepatitis B viruses (HBV) or other viruses from the hepadnaviridae family, can be administered via circulation and target hepatocytes using the same receptors as the wild-type viruses. Hepatitis B virus (HBV) is the prototype of the hepadnaviridae, a family of a small enveloped DNA virus with pronounced host and tissue specificity (Ganem, 1996). Hepadnaviruses have been found in mammals, e.g., human (HBV), woodchuck (WHV) and ground squirrels (GSHV), as well as in birds, e.g., Pekin ducks (DHBV) and grey herons (HHBV).

In one embodiment of the present invention, the HBV vectors retain all cis-acting elements essential for viral genome replication. However, the present invention does not limit the position of the two novel cis-acting elements (i.e., α element and β element) at the indicated position on the map. In one embodiment, it is contemplated that in order to accommodate a larger insertion without exceeding the packaging size limit, the position of novel cis-acting elements could be changed without compromising vector function.

In one embodiment of the method, a sequence encoding an enzyme which has a DNase activity is inserted between the α element and DR2 of an HBV vector. In another embodiment of the method, it is contemplated that a sequence encoding an enzyme which has a DNase activity is inserted between 5' epsilon and the α element of an HBV vector.

Naked DNA Delivery

In some embodiments, an expression vector comprising a sequence encoding an enzyme which has a DNase activity is administered to the subject as a naked DNA. Such naked DNA can be delivered, e.g., into a liver blood vessel at distal or proximal points.

Enveloped Viral Vectors

In various embodiments of the invention, an enveloped viral particle can be used for liver delivery of a nucleic acid encoding an enzyme which has a DNase activity.

In some embodiments, the viral particle described herein is derived from a virus of the family Retroviridae. In one specific embodiment, the viral particle described herein is a retroviral particle. In another specific embodiment, the viral particle described herein is a lentiviral particle. Compared to other gene transfer systems, lentiviral and retroviral vectors offer a wide range of advantages, including their ability to transduce a variety of cell types, to stably integrate transferred genetic material into the genome of the targeted host cell, and to express the transduced gene at significant levels. Vectors derived from the gamma-retroviruses, for example, the murine leukemia virus (MLV), have been used in clinical gene therapy trials (Ross et al., Hum. Gen Ther. 7:1781-1790, 1996).

In one specific embodiment, the at least one viral element associated with a nucleotide of interest is a retroviral element. In another specific embodiment, the at least one viral element associated with a nucleotide of interest is a lentiviral element. In one specific embodiment, the at least one viral element associated with a nucleotide of interest is a Psi (ψ) packaging signal. In one specific embodiment, the lentiviral particle does not contain gp120 surface envelope protein and/or gp41 transmembrane envelope protein. In another specific embodiment, the lentiviral particle contains a mutant gp120 surface envelope protein and/or a mutant gp41 transmembrane envelope protein.

In some embodiments, the viral particles described herein are replication deficient and only contain an incomplete genome of the virus from which they are derived. For example, in some embodiments, the lentiviral and retroviral particles do not comprise the genetic information of the gag, env, or pol genes (which may be involved in the assembly of the viral particle), which is a known minimal requirement for successful replication of a lentivirus or retrovirus. In these cases, the minimal set of viral proteins needed to assemble the vector particle are provided in trans by means of a packaging cell line. In one specific embodiment, env, tat, vif, vpu and nef genes are lacking in lentiviral particles derived from HIV-1 and are provided in trans or are made inactive by the use of frame shift mutation(s).

In some embodiments, the RNA molecule incorporated into the lentiviral or retroviral particles (and encoding an enzyme which has a DNase activity) comprises the psi packaging signal and LTRs. To achieve expression of the nucleotide sequence encoding an enzyme which has a DNase activity in liver cells, such sequence is usually placed under the control of a non-limiting examples of ubiquitous promoters include, e.g., viral promoters such as the CMV promoter, the RSV promoter, the SV40 promoter, etc., and cellular promoters such as the phosphoglycerate kinase (PGK) promoter, EF1a promoter, CMVE/CAG promoter system, and the β-actin promoter.

In some embodiments of lentiviral and retroviral particles, the RNA molecule together with the gag and pol encoded proteins, provided in trans by the packaging cell line, are then assembled into the vector particles, which then infect cells, reverse-transcribe the RNA molecule that comprises a nucleotide sequence encoding an enzyme which has a DNase activity under the control of a promoter, and either integrate said genetic information into the genome of the target cells or remain episomal (if one or more of the components required for integration are disrupted). If the genetic information for the gag and pol encoded proteins is not present on the transduced RNA molecule, the vector particles are replication deficient, i.e., no new generation of said vector particles will thus be generated by the transduced cell, thus ensuring safety in clinical applications.

In some embodiments of any of the above methods, the one or more viral elements encodes Human Immunodeficiency Virus (HIV) component(s), Bovine Immunodeficiency Virus (BIV) component(s), Feline Immunodeficiency Virus (FIV) component(s), Simian Immunodeficiency Virus (SIV) component(s), Equine Infectious Anemia Virus (EIAV) component(s), Murine Stem Cell Virus (MSCV) component(s), Murine Leukemia Virus (MLV) component(s), Avian leukosis virus (ALV) component(s), Feline leukemia virus (FLV) component(s), Bovine leukemia virus (BLV) component(s), Human T-lymphotropic virus (HTLV) component(s), feline sarcoma virus component(s), avian reticuloendotheliosis virus component(s), caprine arthritis encephalitis virus (CAEV) component(s), and/or Visna-Maedi virus (VMV) component(s).

In conjunction with the viral particles described herein, described herein are methods for detecting and/or isolating cells. In some embodiments, such method uses viral particles comprising a selectable marker (e.g., neomycin resistance) and/or a reporter (e.g., GFP or eGFP) as a nucleotide sequence of interest allowing target cells to be selected using, e.g., selection compound exposure or fluorescent activated cell sorting (FACS).

In some embodiments, the retroviral vectors described herein are derived from murine leukemia virus (MLV). Retroviral vectors encoding MLV are widely available to those skilled in the art, such as PINCO (Grignani et al., 1998) or the pBabe vector series (Morgenstern and Land, 1990).

In some embodiments, the lentiviral particles described herein are derived from a lentivirus such as human immunodeficiency virus (HIV). Suitable vectors encoding HIV and other useful viruses can be readily identified and/or prepared by the skilled person.

In one specific embodiment, the transfer vector comprises: a cytomegalovirus (CMV) enhancer/promoter sequence; the R and U5 sequences from the HIV 5' LTR; the HIV-1 flap signal; an internal enhancer; an internal promoter; a nucleotide sequence of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR.

The invention also contemplates enveloped viral vectors comprising a heterologous targeting sequence or molecule inserted or substituted into the native envelope. The heterologous targeting sequence or molecule may confer an altered tropism towards liver or increase the efficiency of liver delivery of the vector.

Methods and Regimens for Administering Expression Vectors Encoding DNase Enzyme

In the methods of the invention, expression vectors comprising a nucleic acid encoding and enzyme which has a DNase activity can be administered to a patient at one time or over a series of treatments; once or several times per day.

The effective amount of expression vector to be administered will vary from patient to patient. Accordingly, effective amounts are best determined by the physician administering the compositions and appropriate dosages can be determined readily by one of ordinary skill in the art. Analysis of the blood (serum, plasma) or tissue levels of the vector-encoded enzyme which has a DNase activity and comparison to the initial level prior to administration can determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to weekly to monthly to annually to every several years.

Doses of an expression vector encoding for an enzyme which has a DNase activity depend on the type of condition to be treated, the severity and course of these side effects, the patient's clinical history, discretion of the attending physician, and response to a prior treatment such as, e.g., chemotherapy, or radiation therapy, and DNase protein therapy. In some embodiments, the effective amount of expression vector is the amount which results in DNase protein level in hepatic portal vein which is from 0.5 to 100 mg/L or from 1000 to 200000 Kunitz units (KU)/L, from 0.5 to 50 mg/L or from 1000 to 100000 Kunitz units (KU)/L, from 1.5 to 50 mg/L or from 3000 to 100000 KU/L, from 10 to 50 mg/L or from 20000 to 100000 KU/L.

The administration of an expression vector, e.g., AAV- or viral-vector, encoding for DNase enzyme, and/or DNase enzyme, according to the methods of the invention can be performed by any suitable route, including, e.g., intravenous, intra-arterial and intrahepatic administration.

Cancer Treatment

In one aspect is provided a method for treating or ameliorating cancer in a subject suffering from a cancer, which method comprises administering to the subject a therapeutically effective amount of an expression vector encoding an enzyme which has a DNase activity (e.g., DNase I such as, e.g., human recombinant DNase I or bovine pancreatic DNase I), analogues of DNase I (such as, e.g., DNase X, DNase gamma, or DNAS1L2), DNase II (e.g., DNase II-alpha, DNase II-beta), phosphodiesterase I, lactoferrin, or acetylcholinesterase). In some embodiments, the DNase enzyme comprises the sequence set forth in SEQ ID NO: 1 (wild-type precursor sequence comprising the secretory signal sequence). In some embodiments, the DNase enzyme comprises the sequence set forth in SEQ ID NO: 2 (precursor mutant sequence comprising the secretory signal sequence and also comprising mutations weakening actin-mediated inhibition). In some embodiments, the DNase enzyme comprises the sequence set forth in SEQ ID NO: 4 (wild-type mature sequence without the secretory signal sequence). In some embodiments, the DNase enzyme comprises the sequence set forth in SEQ ID NO: 5 (mature mutant sequence without the secretory signal sequence and comprising mutations weakening actin-mediated inhibition). In some embodiments, the DNase enzyme is expressed under the control of a liver-specific promoter or a liver-specific enhancer element.

The amount and manner of administration of the expression vectors of the invention should be effective to treat a cancer, e.g., by one or more of reducing tumor size, reducing the rate of tumor growth, reducing the rate of metastasis, enhancing the therapeutic effects of chemotherapy and/or radiotherapy, prolonging lifespan, reducing the rate of cancer- or treatment-associated weight loss, or increasing the rate of weight gain.

In some embodiments, the administration of an expression vector encoding an enzyme which has a DNase activity can be combined with administration of the same enzyme as protein (e.g., intravenously, intra-arterially, intrahepatically, intramuscularly, intraperitoneally, enterally, etc.). The enzyme can be, e.g., any one of DNase enzymes (e.g., DNase I (e.g., human recombinant DNase I or bovine pancreatic DNase I), analogues of DNase I (such as, e.g., DNase X, DNase gamma, or DNAS1L2), DNase II (e.g., DNase II-alpha, DNase II-beta), phosphodiesterase I, lactoferrin, or acetylcholinesterase).

The methods of treatment using the vectors of the invention can be used in subjects suffering from a broad range of cancers. The present invention is particularly useful for treating "portal vein cancers", which include any carcinoma, sarcoma, melanoma, or lymphoma originating in or having metastasized to organs, tissues and structures that drain to the portal vein (see FIG. 1). Non-limiting examples of portal vein cancers include, e.g., peritoneal carcinomatosis, lymphomas (e.g., B cell lymphoma, T cell lymphoma, non-Hodgkins lymphomas, Hodgkins lymphoma), stomach cancers, colon cancers, intestinal cancers, colorectal cancers, pancreatic cancers, liver cancers, splenic cancers, cancers of the bile duct, cancers of the gall bladder, sarcomas in a tissue draining to the portal vein (e.g., an angiosarcoma, endotheliosarcoma, hemangiosarcoma, leiomyosarcoma, other sarcomas, and epithelial carcinoma in such tissue), and liver metastatic diseases of any origin.

Non-limiting examples of other cancers which can be treated by the methods of the invention include, e.g., breast cancer, prostate cancer, multiple myeloma, transitional cell carcinoma, lung cancer (e.g., non-small cell lung cancer (NSCLC)), renal cancer, thyroid cancer, leukemia (e.g., chronic myeloid leukemia, acute myeloid leukemia, chronic lymphocytic leukemia, acute lymphocytic leukemia), head and neck cancer, esophageal cancer, rectal cancer, ovarian cancer, uterine endometrial cancer, vaginal cancer, cervical cancer, bladder cancer, neuroblastoma, sarcoma, osteosarcoma, malignant melanoma, squamous cell cancer, bone cancer (including both primary bone cancers (e.g., osteosarcoma, chondrosarcoma, Ewing's sarcoma, fibrosarcoma, malignant fibrous histiocytoma, adamantinoma, giant cell tumor, and chordoma) and secondary (metastatic) bone cancers), soft tissue sarcoma, basal cell carcinoma, angiosarcoma, hemangiosarcoma, myxosarcoma, liposarcoma, osteogenic sarcoma, angiosarcoma, endotheliosarcoma, lymphangiosarcoma, lymphangioendotheliosarcoma, synovioma, testicular cancer, uterine cancer, mesothelioma, leiomyosarcoma, rhabdomyosarcoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, choriocarcinoma, seminoma, embryonal carcinoma, Wilms' tumor, epithelial carcinoma, glioma, glioblastoma, astrocytoma, medulloblastoma, craniopharyngioma, ependymoma, pinealoma, hemangioblastoma, acoustic neuroma, oligodendroglioma, meningioma, retinoblastoma, medullary carcinoma, thymoma, sarcoma, etc.

For combination cancer treatments, an expression vector, e.g., AAV vector or lentiviral vector or adenoviral vector encoding an enzyme which has a DNase activity can be administered before, with, or after a chemotherapeutic agent (or a radiation therapy).

In some embodiments, the methods of the invention are used to prevent a cancer in a patient, e.g. a patient with a high risk of predisposition to cancer.

In some embodiments, the methods of the invention are used to prevent a cancer following a positive result from a blood-based DNA screening test (e.g., liquid biopsy) for the detection of predisposition to a cancer.

In some embodiments, the methods of the invention are used to prevent a cancer following the evaluation of a tumor susceptibility gene. Examples of tumor susceptibility genes include, but are not limited to, ABL1 (ABL), ABL2(ABLL, ARG), AKAP13 (HT31, LBC. BRX), ARAF1, ARHGEF5 (TIM), ATF1, AXL, BCL2, BRAF (BRAF1, RAFB1), BRCA1, BRCA2(FANCD1), BRIP1, CBL (CBL2), CSF1R (CSF-1, FMS, MCSF), DAPK1 (DAPK), DEK (D6S231E), DUSP6(MKP3,PYST1), EGF, EGFR (ERBB, ERBB1), ERBB3 (HER3), ERG, ETS1, ETS2, EWSR1 (EWS, ES, PNE), FES (FPS), FGF4 (HSTF1,KFGF), FGFR1, FGFR10P (FOP), FLCN, FOS (c-fos), FRAP1, FUS (TLS), HRAS, GLI1, GLI2, GPC3, HER2 (ERBB2, TKR1, NEU), HGF (SF), IRF4 (LSIRF, MUM1), JUNB, KIT(SCFR), KRAS2 (RASK2), LCK, LCO, MAP3K8(TPL2, COT, EST), MCF2 (DBL), MDM2, MET(HGFR, RCCP2), MLH type genes, MMD, MOS (MSV), MRAS (RRAS3), MSH type genes, MYB (AMV), MYC, MYCL1 (LMYC), MYCN, NCOA4 (ELE1, ARA70, PTC3), NF1 type genes, NMYC, NRAS, NTRK1 (TRK, TRKA), NUP214 (CAN, D9S46E), OVC, TP53 (P53), PALB2, PAX3 (HUP2), STAT1, PDGFB (SIS), PIM genes, PML (MYL), PMS (PMSL) genes, PPM1D (WIP1), PTEN (MMAC1), PVT1, RAF1 (CRAF), RB1 (RB), RET, RRAS2 (TC21), ROS1 (ROS, MCF3), SMAD type genes, SMARCB1(SNF5, INI1), SMURF1, SRC (AVS), STAT1, STAT3, STATS, TDGF1 (CRGF), TGFBR2, THRA (ERBA, EAR7 etc.), TFG (TRKT3), TIF1 (TRIM24, TIF1A), TNC (TN, HXB), TRK, TUSC3, USP6 (TRE2), WNT1 (INT1), WT1, and VHL.

The susceptibility gene can be evaluated by one or more of Next-generation sequencing, whole genome sequencing, exome sequencing, an ELISA-based method, and PCR amplification. Other methods can be used to evaluate the susceptibility gene as well.

In another aspect, the invention provides a method for treating or ameliorating a cancer in a subject in need thereof, said method comprising administering to the subject an expression vector comprising a nucleic acid encoding an enzyme which has a deoxyribonuclease (DNase) activity, wherein said expression vector provides synthesis of the DNase enzyme in the liver of said subject. In some embodiments, the cancer is accompanied by an increase in the total level or relative content of cell free DNA (cfDNA) of microbial origin in blood of said subject. In several embodiments, the method comprises detecting the level of cfDNA of microbial origin or the ratio of the cfDNA of microbial origin to the total level of cfDNA in blood of the subject. Non-limiting examples of methods of detecting the cfDNA of microbial origin include, e.g., PCR, RT-PCR, next-generation sequencing (NGS) and whole genome sequencing (WGS). In some embodiments, cfDNA of microbial origin can be detected, e.g., using PCR or RT-PCR of 16S ribosomal RNA, 16S ribosomal DNA or Intergenic Spacer Region. In some embodiments, determining the total level or relative content of cfDNA of microbial origin includes comparing the level of cfDNA of microbial origin or the ratio of the cfDNA of microbial origin to the total level of cfDNA in blood of the subject to a control level or ratio (e.g., a predetermined standard or a corresponding level or ratio determined using age-matched cancer-free subjects).

In one embodiment of any of the methods of the invention, the subject is human.

Amelioration of Toxicity of Cancer Chemotherapy or Radiation Therapy

In one aspect, the invention provides a method for preventing or ameliorating a toxicity, or a condition, associated with a cytostatic and/or cytotoxic chemotherapy in a subject suffering from a cancer and receiving or deemed to receive said chemotherapy, which method comprises administering to the subject a therapeutically effective amount of an expression vector encoding for an enzyme which has a DNase activity (e.g., DNase I (e.g., human recombinant DNase I or bovine pancreatic DNase I), analogues of DNase I (such as, e.g., DNase X, DNase gamma, or DNAS1L2), DNase II (e.g., DNase II-alpha, DNase II-beta), phosphodiesterase I, lactoferrin, or acetylcholinesterase). In some embodiments, the DNase enzyme comprises the sequence set forth in SEQ ID NO: 1 (wild-type precursor sequence comprising the secretory signal sequence). In some embodiments, the DNase enzyme comprises the sequence set forth in SEQ ID NO: 2 (precursor mutant sequence comprising the secretory signal sequence and also comprising mutations weakening actin-mediated inhibition). In some embodiments, the DNase enzyme comprises the sequence set forth in SEQ ID NO: 4 (wild-type mature sequence without the secretory signal sequence). In some embodiments, the DNase enzyme comprises the sequence set forth in SEQ ID NO: 5 (mature mutant sequence without the secretory signal sequence and comprising mutations weakening actin-mediated inhibition). In some embodiments, the DNase enzyme is expressed under the control of a liver-specific promoter and/or a liver-specific enhancer element.

The amount and manner of administration of the expression vector is effective to ameliorate at least one side effect of said chemotherapy.

The condition associated with a cytostatic and/or cytotoxic chemotherapy can include, e.g., (i) a catabolic state leading to body weight loss, (ii) bone marrow toxicity and/or catabolic changes in blood biochemistry, (iii) cardiotoxicity (e.g., myocardial necrosis), (iv) gastrointestinal toxicity, (v) suppression of immunity, (vi) neutropenia, and (vii) body weight loss.

In some embodiments, the cancer is associated with an increased level of cfDNA in blood or cerebrospinal fluid (CSF) or intestine of the patient, which level is higher than the control level (e.g., the level of cfDNA in blood or CSF or intestine of a healthy age-matched individual or an average level of cfDNA in blood or CSF or intestine of several healthy age-matched individuals).

In some embodiments, the effects of chemotherapy are associated with an increased level of cfDNA in blood or CSF, ascitic fluid, or intestine of the patient, which level is higher than the control level (e.g., the level of cfDNA in blood or cerebrospinal fluid or intestine of an age-matched individual with a similar cancer profile who does not receive chemotherapy, or an average level of cfDNA in blood or CSF or intestine of several age-matched individuals who have cancer but do not receive chemotherapy).

In a further aspect, the invention provides a method for increasing the efficacy of a cytostatic and/or cytotoxic chemotherapy in a subject suffering from a cancer and receiving or deemed to receive said chemotherapy, which method comprises administering to the subject a therapeutically effective amount of an expression vector (e.g., Anc80 or AAV8 AAV vector or lentiviral vector or adenoviral vector) encoding an enzyme which has a DNase activity (e.g., DNase I (e.g., human recombinant DNase I or bovine pancreatic DNase I), analogues of DNase I (such as, e.g., DNase X, DNase gamma, or DNAS1L2), DNase II (DNase II-alpha, DNase II-beta), phosphodiesterase I, lactoferrin, or acetylcholinesterase). The amount and manner of administration of the expression vector is effective to prevent or ameliorate at least one side effect of said chemotherapy, and to prevent or ameliorate toxicity associated with said chemotherapy. In some embodiments, any one of DNase enzyme (e.g., DNase I (e.g., human recombinant DNase I or bovine pancreatic DNase I), analogues of DNase I (such as, e.g., DNase X, DNase gamma, or DNAS1L2), DNase II (e.g., DNase II-alpha, DNase II-beta), phosphodiesterase I, lactoferrin, or acetylcholinesterase) is also administered, e.g., intravenously.

The expression vectors of the invention can be used to ameliorate toxicity and/or increase efficacy of a wide range of different chemotherapeutic agents. Non-limiting examples of such agents include anti-metabolites such as pyrimidine analogs (e.g., 5-fluorouracil [5-FU], floxuridine, capecitabine, gemcitabine and cytarabine) and purine analogs, folate antagonists and related inhibitors (e.g., mercaptopurine, thioguanine, pentostatin and 2-chlorodeoxyadenosine (cladribine)); antiproliferative/antimitotic agents including natural products such as *vinca* alkaloids (e.g., vinblastine, vincristine, and vinorelbine), microtubule disruptors such as taxanes (e.g., paclitaxel, docetaxel), vincristin, vinblastin, nocodazole, epothilones and navelbine, epidipodophyllotoxins (e.g., etoposide, teniposide), DNA damaging agents (e.g., actinomycin, amsacrine, anthracyclines, bleomycin, busulfan, camptothecin, carboplatin, chlorambucil, cisplatin, nedaplatin, cyclophosphamide, cytoxan, dactinomycin, daunorubicin, doxorubicin, epirubicin, aclarubicin, purarubicin, hexamethyhnelamineoxaliplatin, iphosphamide, melphalan, merchlorehtamine, mitomycin, mitoxantrone, nitrosourea, nimustine, ranimustine, estramustine, plicamycin, procarbazine, taxol, taxotere, teniposide, triethylenethiophosphoramide and etoposide (VP16)); antibiotics (e.g., dactinomycin (actinomycin D), daunorubicin, doxorubicin (adriamycin), idarubicin, anthracyclines, mitoxantrone, bleomycins, plicamycin (mithramycin), pleomycin, peplomycin, mitomycins (e.g., mitomycin C), actinomycins (e.g., actinomycin D), zinostatinsimalamer); enzymes (e.g., L-asparaginase); neocarzinostatin; antiplatelet agents; antiproliferative/antimitotic alkylating agents such as nitrogen mustards (e.g., mechlorethamine, cyclophosphamide and analogs, imidazol carboxamide, melphalan, chlorambucil, nitrogen mustard-N-oxide hydrochloride, ifosfamide), ethylenimines and methylmelamines (e.g., hexamethylmelamine, thiotepa, carboquone, triethylene thiophospharamide), alkyl sulfonates (e.g., busulfan, isoprosulfan tosylate), nitrosoureas (e.g., carmustine (BCNU) and analogs, streptozocin), trazenes-dacarbazinine (DTIC); epoxide type compounds (e.g., mitobronitol); antiproliferative/antimitotic antimetabolites such as folic acid analogs (e.g., methotrexate); platinum coordination complexes (e.g., cisplatin, carboplatin), procarbazine, hydroxyurea, mitotane, aminoglutethimide; hormones, hormone analogs (e.g., estrogen, tamoxifen, goserelin, bicalutamide, nilutamide) and aromatase inhibitors (e.g., letrozole, anastrozole); antisecretory agents (e.g., breveldin); immunosuppressives (e.g., cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blockers; nitric oxide donors; antisense oligonucleotides; antibodies (e.g., trastuzumab); cell cycle inhibitors and differentiation inducers (e.g., tretinoin); mTOR inhibitors, topoisomerase inhibitors (e.g., doxorubicin (adriamycin), amsacrine, camptothecin, daunorubicin, dactinomycin, eniposide, epirubicin, etoposide, idarubicin, mitoxantrone, topotecan, irinotecan); growth factor signal transduction kinase inhibitors; mitochondrial dysfunction inducers; chromatin disruptors; sobuzoxane; tretinoin; pentostatin; flutamide; porphimer natrium; fadrozole; procarbazine; aceglatone; radioimmunotherapy (RIT) compounds (e.g., Ibritumomab tiuxetan, Iodine ($^{131}$I) tositumomab); and targeted radionuclide therapy (TRT) compounds (e.g., samarium-153-EDTMP, strontium-89-chloride).

Non-limiting examples of side effects of cytostatic and/or cytotoxic chemotherapy which can be prevented or ameliorated by administering an expression vector according to the methods of the invention include, for example, bone marrow toxicity, neutropenia, myelopathy (e.g., leukopenia, granulocytopenia, lymphopenia, thrombocytopenia, erythropenia); hematopathy (e.g., plasma fibrinogenopenia); catabolic changes in blood biochemistry; gastrointestinal disorders (e.g., nausea, vomiting, anorexia, body weight loss, heavy feeling of stomach, diarrhea, constipation, stomatitis, esophagitis); pulmonary insufficiency (e.g., chronic pneumonia, lung fibrosis, ARDS, ALS, lung emboli); dermatopathy (e.g., keratinization, pachymenia, chromatosis, epilation, rash, nail alternation, cancer-induced alopecia); nervous system disorders (e.g., paresthesia, depression, deep areflexia, neuroparalysis, auditory disorder, allolalia, disorientation, neurologic manifestation, cerebellar ataxia, somnolence, coma, vertigo, frequency of micturition, frequency of defecation desire); endocrine disorders (e.g., pituitary disorder, adrenal disorder, hyperglycemia, hypoglycemia); genital disorders (e.g., hyposexuality, oligospermia, gynecomastia, menstrual disorder); cardiovascular disorders (e.g., myocardial necrosis, cardiomyopathy, arrhythmia, low blood pressure, tachycardia, cardiac failure); hepatopathy, pancreatic disorder, nephropathy, bladder trouble, hyperuricemia, decrease of immunocompetence, and infection.

The expression vectors of the invention can be also used to ameliorate toxicity and increase efficacy of various types of radiation therapy, including, for example, external beam radiation therapy (EBRT or XRT), brachytherapy/sealed source radiation therapy, and systemic radioisotope therapy/unsealed source radiotherapy. Non-limiting examples of side effects of radiotherapy which can be prevented or ameliorated by administering an expression vector according to the methods of the invention include, for example, skin irritation or damage, fatigue, nausea, vomiting, fibrosis, bowel damage, memory loss, infertility, and a second cancer.

The expression vectors of the invention can be used to increase efficacy of cancer immunotherapy, including, for example, antibodies (Naked monoclonal antibodies, Conjugated monoclonal antibodies, Chemolabeled antibodies, Bispecific monoclonal antibodies), cancer vaccines, Immune checkpoint inhibitors (Drugs that target PD-1 or PD-L1, CTLA-4), Non-specific cancer immunotherapies and adjuvants, CAR-T therapies.

Neurodegeneration Treatment

In one aspect, the invention provides a method for treating or ameliorating neurodegeneration. The term "neurodegeneration" is used herein to refer to a separate clinical pathological condition with progressive loss of structure and/or function of neurons, including death of neurons. The neurodegeneration can be primary or secondary.

In some embodiments, the neurodegeneration is associated with an increased level of cfDNA (e.g., microbial DNA or human DNA) in blood or cerebrospinal fluid (CSF) or intestine of a patient, which level is higher than the control level (e.g., the level of cfDNA in blood or CSF or intestine of a healthy age-matched individual or an average level of cfDNA in blood or cerebrospinal fluid or intestine of several healthy age-matched individuals). In one embodiment, the neurodegeneration is associated with a neurodegenerative disorder. Non-limiting examples of encompassed neurodegenerative disorders include, e.g., Alzheimer's disease (e.g., late-onset Alzheimer's disease), Mild Cognitive Impairment (MCI), Parkinson's disease, Amyotrophic Lateral Sclerosis (ALS), and Huntington's disease (HD), prion-caused diseases, progressive supranuclear palsy (PSP), progressive supranuclear palsy (Steel-Richardson-Olszewski), corticobasal degeneration (CBD), chronic traumatic encephalopathy (CTE), multiple system atrophy (MSA), agyrophilic grain disease (AGD), Pick disease (PiD), frontotemporal dementia (FTD), frontotemporal dementia with parkinsonism-17 (FTDP-17), multiple sclerosis, CADASIL Syndrome, ankylosing spondylitis, Dentatorubro-pallido-Luysian atrophy, Kennedy disease, Friedreich's ataxia, cerebellar ataxia, spinocerebellar ataxia, Lewy body dementia, vascular dementias, familial Danish dementia, familial British dementia, spinal muscular atrophy, olivopontocerebellar atrophy (OPCA), senile dementia of the Alzheimer type, corticodentatonigral degeneration, Hallervorden-Spatz disease, progressive familial myoclonic epilepsy, striatonigral degeneration, torsion dystonia (e.g., torsion spasm; dystonia musculorum deformans), spasmodic torticollis and other dyskinesis, familial tremor, Gilles de la Tourette syndrome, cerebellar cortical degeneration, spinocerebellar degeneration (e.g., Friedreich's ataxia and related disorders), Shy-Drager syndrome, primary lateral sclerosis, hereditary spastic paraplegia, peroneal muscular atrophy (Charcot-Marie-Tooth), hypertrophic interstitial polyneuropathy (Dejerine-Sottas), chronic progressive neuropathy, pigmentary degeneration of the retina (retinitis pigmentosa), and hereditary optic atrophy (Leber's disease), secondary neurodegeneration caused by necrosis (e.g., destruction of neurons by neoplasm, edema, hemorrhage, stroke, trauma, immune attack, hypoxia, poisoning, metabolic defects, and infections), and various taupathies (e.g., Primary age-related tauopathy (PART)/Neurofibrillary tangle-predominant senile dementia, with NFTs similar to AD, but without plaques, CTE, Lytico-Bodig disease, Ganglioglioma and gangliocytoma, Meningioangiomatosis, Postencephalitic parkinsonism, Subacute sclerosing panencephalitis). In some one embodiments, the neurodegeneration is associated with a nervous system dysfunction such as, e.g., schizophrenia or bipolar disorder, depressive disorder, autism, autism spectrum disorders, Chronic Fatigue Syndrome, Obsessive-Compulsive Disorder, generalized anxiety disorder (GAD), major depressive disorder (MDD), or social anxiety disorder (SAD). In some embodiments, the neurodegenerative disorder is caused by, secondary to, or associated with, amyloidosis. In some embodiments, the neurodegenerative disorder is a protein-misfolding associated disease. In some embodiments, the neurodegenerative disorder is caused by, secondary to, or associated with diabetes, rheumatoid arthritis, systemic lupus erythematosus (SLE), gout, metabolic syndrome, an amyloidosis (e.g., hereditary cerebral hemorrhage with amyloidosis, primary systemic amyloidosis, secondary systemic amyloidosis, serum amyloidosis, senile systemic amyloidosis, hemodialysis-related amyloidosis, Finnish hereditary systemic amyloidosis, Atrial amyloidosis, Lysozyme systemic amyloidosis, Insulin-related amyloidosis, Fibrinogen a-chain amyloidosis), asthma, or prion disease.

In some embodiments, the neurodegeneration is caused by, secondary to, or associated with the formation of a misfolded protein due to the presence of DNA (e.g., human, microbial, cell-free, or intracellular). In some embodiments, the neurodegeneration is caused by the formation of a misfolded protein due to the presence of DNA (e.g., human, microbial, cell-free or intracellular).

In some embodiments, the neurodegeneration is caused by, secondary to, or associated with the formation of a misfolded protein including, but not limited to, β-amyloid, Tau protein, α-synuclein, SOD1, TDP-43, IAPP, ADan, ABri, Fused in sarcoma (FUS) protein, Notch3, Glial fibrillary acidic protein, Seipin, Transthyretin, Serpins, Apolipoproteins, Amyloid β peptide, Lactoferrin, Galectin-7 Corneodesmosin.

In some embodiments, the methods of the invention can be used to prevent development of a neurodegenerative disease or another disease associated with protein misfolding following the evaluation of the presence of, or activity of, a disease-associated susceptibility gene. Examples of disease-associated susceptibility genes, include, but are not limited to, ADAR1, MDA5 (IFIH1), RNAseH subunits, SamHD1, TREX, TBK1, Optineurin, P62 (sequestosome 1), Progranulin, TDP43, FUS, VCP, CHMP2B, Profilin-1, Amyloid-β, Tau, α-synuclein, PINK, Parkin, LRRK2, DJ-1, GBA, ATPA13A2, EXOSCIII, TSEN2, TBC1D23, Riskfactor alleles, PLCG2, TREM2, APOE, TOMM40, IL-33, Glucocerebrosidase, Ataxin2, C9orf72, SOD1, and FUS. The susceptibility gene can be evaluated by one or more of Next-generation sequencing, whole genome sequencing, exome sequencing, an ELISA-based method, and PCR amplification. Other methods can be used to evaluate the susceptibility gene as well.

In one embodiment of the above methods, prevention or treatment of the misfolded protein aggregate formation in mammalian biological fluids and tissues is achieved by the use of expression vectors disclosed herein, including those comprising the sequence of SEQ ID NO: 30 (ApoEHCR enhancer-hAAT promoter-hDNaseI (hyperactive)correct leader-WPRE Xinact) or SEQ ID NO: 31 (ApoEHCR enhancer-hAAT promoter-hDNaseI wild type-WPRE Xinact5653). In the sequence of SEQ ID NO: 30, bases 1-320 correspond to the APOE HCR enhancer, bases 321-717 correspond to the human alpha-1-antitrypsin promoter, bases 718-726 correspond to the Kozak sequence, bases 727-1575 correspond to human DNaseI hyperactive variant with natural full correct leader sequence, and bases 1576-2212 correspond to the inactivated WPRE X protein. In the sequence of SEQ ID NO: 31, bases 1-320 correspond to the APOE HCR enhancer, bases 321-717 correspond to the human alpha-1-antitrypsin promoter, bases 718-726 correspond to the Kozak sequence, bases 727-1575 correspond to human DNaseI wild type with natural full correct leader sequence, and bases 1576-2212 correspond to the inactivated WPRE X protein.

As described in Int. Pat. Appl. Pub. No. WO 2016/190780, cfDNA from the intestine, blood and CSF of patients suffering from neurodegeneration causes neuronal cell death and apoptosis, and treatment with recombinant DNase protein destroying such cfDNA improves the nervous system function in these patients. As shown in the Examples section below, the use of the vectors of the invention for liver-specific expression of DNase, provides a further treatment improvement as compared to DNase protein administration.

The assessment of treatment efficacy for neurodegeneration and neuroinflammation can be performed using any methods known in the art, e.g., according to widely accepted clinical diagnostic criteria of cognitive decline such as MMSE, PANSS, physical function, and/or functional tasks (see, e.g., Holmes et al., (1999) The British Journal of Psychiatry, 174(1), 45-50; Os et al., (2006) Acta Psychiatrica Scandinavica, 113(2), 91-95; O'Shea et al., (2002) Physical therapy, 82(9), 888-897; Rochester et al., Arch. Phys. Med. Rehabil. (2004) 85(10), 1578-1585).

In some embodiments of the invention, the neurodegeneration is caused by, or aggravated by, increased intestinal permeability and translocation of gut bacteria and DAMPs of microbial origin including microbial cfDNA. Such cfDNA may trigger neuroinflammation and a spectrum of neurodegenerative diseases. cfDNA originating from digestive tract microbiota are subject to "first pass" through porto-sinusoidal circulation in the liver. The NLRP3 inflammasome is considered a key contributor to the development of neuroinflammation. For example, the NLRP3 inflammasome can undergo significant upregulation in the brain, e.g., brain cortical tissue. Aberrant activation of NLRP3 inflammasome signaling has been demonstrated to contribute to pathology in a broad spectrum of neurological diseases (Song, 2017).

In some embodiments, the invention provides a method for treating neurodegeneration in a subject suffering from neurodegeneration, which method comprises administering to the subject a therapeutically effective amount of an expression vector encoding an enzyme which has a DNase activity (e.g., DNase I (e.g., human recombinant DNase I or bovine pancreatic DNase I), analogues of DNase I (such as, e.g., DNase X, DNase gamma, or DNAS1L2), DNase II (e.g., DNase II-alpha, DNase II-beta), phosphodiesterase I, lactoferrin, or acetylcholinesterase). The amount and manner of administration of the expression vector (e.g., AAV vector or lentiviral vector or adenoviral vector or liposome or naked DNA) should be effective to treat one or more symptoms or effects from such neurodegeneration.

Without wishing to be bound by theory, after a nucleic acid encoding an enzyme which has a DNase activity is delivered to the liver using the vectors of the invention, the enzyme becomes produced by liver cells and is secreted into the periendothelial space and the space of Disse, where the enzyme efficiently degrades the concentrated pool of cfDNA present therein.

In some embodiments, the use of the expression vectors of the invention is combined with the administration (e.g., intravenous, intra-arterial, intrahepatic, intramuscular, intraperitoneal, or enteral administration) of a DNase protein (e.g., DNase I (e.g., human recombinant DNase I or bovine pancreatic DNase I), analogues of DNase I (such as, e.g., DNase X, DNase gamma, or DNAS1L2), DNase II (e.g., DNase II-alpha, DNase II-beta), phosphodiesterase I, lactoferrin, or acetylcholinesterase). Without wishing to be bound by theory, the systemic administration of a DNase protein in conjunction with the above described production of DNase in liver cells using the expression vectors of the invention more quickly degrades cfDNA in both the bloodstream and in any concentrated pool of cfDNA in the liver.

In some embodiments, the expression vectors encoding an enzyme which has a DNase activity can be administered in combination with other treatments useful for treatment of neurodegenerative diseases or other encompassed nervous system dysfunctions (e.g., bipolar disorder, migraine, schizophrenia, epilepsy). Non-limiting examples of such additional treatments include, e.g., histone acetyltransferase activators, cyclin-dependent protein kinase 5 inhibitors, neurotrophin mimetics, semaphorin-4D blockers, microsomal prostaglandin E synthase-1 inhibitors, levodopa, and N-methyl-d-aspartate (NMDA) receptor inhibitors (e.g., memantine).

Treatment of Delayed Hypersensitivity Reactions

In one aspect, the invention provides a method for treating a delayed hypersensitivity reaction (e.g., graft-versus host disease (GVHD)) in a subject in need thereof, which method comprises administering to the subject a therapeutically effective amount of an expression vector encoding an enzyme which has a DNase activity (e.g., DNase I such as, e.g., human recombinant DNase I or bovine pancreatic DNase I), analogues of DNase I (such as, e.g., DNase X, DNase gamma, or DNAS1L2), DNase II (e.g., DNase II-alpha, DNase II-beta), phosphodiesterase I, lactoferrin, or acetylcholinesterase). In some embodiments, the DNase enzyme comprises the sequence set forth in SEQ ID NO: 1

(wild-type precursor sequence comprising the secretory signal sequence). In some embodiments, the DNase enzyme comprises the sequence set forth in SEQ ID NO: 2 (precursor mutant sequence comprising the secretory signal sequence and also comprising mutations weakening actin-mediated inhibition). In some embodiments, the DNase enzyme comprises the sequence set forth in SEQ ID NO: 4 (wild-type mature sequence without the secretory signal sequence). In some embodiments, the DNase enzyme comprises the sequence set forth in SEQ ID NO: 5 (mature mutant sequence without the secretory signal sequence and comprising mutations weakening actin-mediated inhibition). In some embodiments, the DNase enzyme is expressed under the control of a liver-specific promoter or a liver-specific enhancer element.

Without wishing to be bound by theory, activation of neutrophils can release granule proteins together with double stranded DNA (dsDNA), to form extracellular fibers known as NETs. Complement is activated by NETs. Activation of complement can lead to the symptoms observed in delayed hypersensitivity reactions.

In some embodiments, the delayed hypersensitivity reaction is associated with an increased level of cfDNA in blood or CSF or intestine of the patient, which level is higher than the control level (e.g., the level of cfDNA in blood or cerebrospinal fluid or intestine of a healthy age-matched individual or an average level of cfDNA in blood or CSF or intestine of several healthy age-matched individuals). Administration of an expression vector encoding an enzyme which has a DNase activity could inhibit NET formation and lead to less activation of complement.

Without wishing to be bound by theory, the systemic administration of DNase enzyme in conjunction with the above described production of DNase in liver cells using expression vectors more quickly degrades cfDNA in both the bloodstream and in any concentrated pool of such cfDNA in the liver.

The expression vector encoding for DNase enzyme can also be administered in combination with one or more other treatments useful for treating a delayed hypersensitivity reaction such as, e.g., cyclosporine, tacrolimus (FK506), methylprednisolone, prednisone, ATG, sirolimus, mycophenolate mofetil, anti-interleukin-2 (IL-2) receptor, anti-CD5-specific immunotoxin, a pan T-cell ricin A-chain immunotoxin (XomaZyme), the addition of ex vivo cultured mesenchymal cells derived from unrelated donors to conventional steroid therapy, and any combinations thereof.

Treatment of Atherosclerosis

In one aspect is provided a method for treating atherosclerosis in a subject in need thereof, which method comprises administering to the subject a therapeutically effective amount of an expression vector encoding an enzyme which has a DNase activity (e.g., DNase I such as, e.g., human recombinant DNase I or bovine pancreatic DNase I), analogues of DNase I (such as, e.g., DNase X, DNase gamma, or DNAS1L2), DNase II (e.g., DNase II-alpha, DNase II-beta), phosphodiesterase I, lactoferrin, or acetylcholinesterase). In some embodiments, the DNase enzyme comprises the sequence set forth in SEQ ID NO: 1 (wild-type precursor sequence comprising the secretory signal sequence). In some embodiments, the DNase enzyme comprises the sequence set forth in SEQ ID NO: 2 (precursor mutant sequence comprising the secretory signal sequence and also comprising mutations weakening actin-mediated inhibition). In some embodiments, the DNase enzyme comprises the sequence set forth in SEQ ID NO: 4 (wild-type mature sequence without the secretory signal sequence). In some embodiments, the DNase enzyme comprises the sequence set forth in SEQ ID NO: 5 (mature mutant sequence without the secretory signal sequence and comprising mutations weakening actin-mediated inhibition). In some embodiments, the DNase enzyme is expressed under the control of a liver-specific promoter or a liver-specific enhancer element.

In some embodiments, atherosclerosis is associated with an increased level of cfDNA in blood or CSF or intestine of the patient, which level is higher than the control level (e.g., the level of cfDNA in blood or cerebrospinal fluid or intestine of a healthy age-matched individual or an average level of cfDNA in blood or cerebrospinal fluid or intestine of several healthy age-matched individuals).

The expression vector, e.g., Anc80 or another AAV- or lentiviral vector, encoding for DNase enzyme may be administered optionally with additional DNase enzyme. In some embodiments, any one of DNase enzyme (e.g., DNase I (e.g., human recombinant DNase I or bovine pancreatic DNase I), analogues of DNase I (such as, e.g., DNase X, DNase gamma, or DNAS1L2), DNase II (e.g., DNase II-alpha, DNase II-beta), phosphodiesterase I, lactoferrin, or acetylcholinesterase) is also administered, e.g., intravenously. Without wishing to be bound by theory, the systemic administration of DNase enzyme in conjunction with the above described production of DNase in liver cells more quickly degrades cfDNA in both the bloodstream and in any concentrated pool of such cfDNA in the liver.

The expression vector encoding for DNase enzyme can also be administered in combination with other treatments useful for treating atherosclerosis.

Pharmaceutical Compositions, Formulations and Dosage Forms

The AAV vectors disclosed herein may be administered in any suitable form, for instance, either as a liquid solution or suspension, as a solid form suitable for solution or suspension in liquid prior to injection. The vectors may be formulated with any appropriate and pharmaceutically acceptable excipient, carrier, adjuvant, diluent, etc. For instance, for injection, a suitable carrier or diluent may be an isotonic solution, a buffer, sterile and pyrogen-free water, or, for instance, a sterile and pyrogen-free phosphate-buffered saline solution. The expression vectors may be formulated in pharmaceutical compositions and dosage forms. Such pharmaceutical compositions and dosage forms can be formulated in any conventional manner using one or more physiologically acceptable carriers and/or excipients. The vector particles may be formulated for administration by, for example, injection. Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

Formulations also include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

The formulations used in the methods of the invention may conveniently be presented in unit dosage form and may be prepared by methods known in the art. The amount of active ingredients that can be combined with a carrier material to produce a single dosage form will vary depending upon the host being treated and the particular mode of administration. The amount of active ingredients that can be combined with a carrier material to produce a single dosage form will generally be that amount of the compound which produces a therapeutic effect.

Pharmaceutical compositions suitable for parenteral administration may further comprise one or more additional active ingredients (e.g., a DNase protein or another active compound) in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Limited Ability of DNase Enzyme to Digest Circulating Cell Free DNA (cfDNA) in Tumor Patients Nine patients with advanced metastatic disease who were admitted to the department of thoracic surgery of Kostushko Hospital (St. Petersburg, Russia) were given a 3-week course of intravenous treatment with bovine pancreatic DNase I protein which has specific activity of 2500 KU/mg (Samson, Russia). The treatment proceeded according following schedule: in week I, 300 mg was administered daily via six 30 minute IV infusions; in week II, 450 mg was administered daily via six 30 minute IV infusions; and in week III, 600 mg was administered daily via six 30 minute IV infusions.

Electrophoretic profiling of circulating cfDNA was performed for each patient before the first DNase I protein infusion, at the end of week II and immediately following last DNase I protein infusion. DNA was isolated from blood plasma using a classic phenol-chloroform method. Electrophoresis of blood cfDNA was performed on 1% agarose gel. DNA was visualized with ethidium bromide. The treatment efficacy was evaluated one week after the last DNase I protein infusion using a spiral CT scan based on RECIST criteria (see, e.g., RECIST 1.1, published in January 2009, irrecist.com). The patient summaries and individual blood electrophoretic data are presented in FIGS. 2A-2IJ. Overall, there was little decrease in the diameter of solid tumors according to the RECIST outcome (FIGS. 2A-2H). In most patients, there was still cfDNA in circulation after Week III.

Despite a continuous ascending high dose IV infusion of DNase I enzyme, only one patient with recurrent rectal carcinoma (PVIII) showed complete clearance of circulating cfDNA from plasma as measured by gel electrophoresis. Patient PVIII had a stable disease with no evidence of progression according RECIST criteria. Three other patients who qualified as stable disease patients according to RECIST criteria (PIX, PVII, PI) had little or no increase of circulating cfDNA from plasma as measured by gel electrophoresis.

Five patients who qualified as progressive disease patients according RECIST criteria (PII, PIII, PIV, PV, and PVI) had a substantial increase of circulating cfDNA from plasma as measured by gel electrophoresis. Also, in 8 out of 9 patients (88%), 3 week continuous intravenous infusions of ascending high doses of DNase enzyme failed to provide a therapeutically effective clearance of circulating cfDNA from plasma.

Example 2: Accumulation of Cell Free DNA in the Liver of Tumor Bearing Animals

Approximately $12 \times 10^6$ of LS174T human colon carcinoma cells were inoculated subcutaneously into the left flank of each of twelve female nu/nu mice (IBCH RAS breed) that were 8 weeks old. The mice received a single IV injection of 99 mTc labeled anti DNA antibodies according the following schedule: three mice received the injection at D5, three mice received the injection at D10, three mice received the injection at D15 and three mice received the injection at D25. Mice were sacrificed two hours following the injection and tissues and blood were collected for gamma counting.

AC-30-10 DNA binding antibodies (Genetex) were labeled with 99mTc as follows: solution of antibody in 0.3M citrate buffer (pH4.2) was mixed with 1 mCi of 99mTc-pertechnetate in 0.25 ml saline and mixed 10-mg/ml solution of SnCl2 dihydrate in 0.1N HCl. After 5 min incubation at room temperature, 1.9 ml of saline and 825 µl of IgM solution were added. The single injection doses were prepared as follows: 16.6 µCi (36852000 CPM approx. 0.047 µg of 99mTc-IgM) of 99mTc-IgM solution was mixed with 3.3 µg of unlabeled IgM and diluted with saline up to 100 µL volume. Gamma signal was quantified in each tissue using auto-gamma counter. Measurement was done in CMP units. Concentrations of 99mTc IgM was quantified based gamma counting data, tissue weight, specific radioactivity of the IgM preparations administered and 99mTc half-life.

The tissue distribution of radioactivity is presented in Table 1 below:

TABLE 1

Accumulation of anti-DNA antibodies in tissues of tumor bearing mice. (% of Injected dose/g of tissue).

|  | D 5 | D 10 | D 15 | D 25 |
|---|---|---|---|---|
| Brain | 0.020 ± 0.0 | 0.056 ± 0.04 | 0.078 ± 0.05 | 0.507 ± 0.36 |
| Spleen | 0.06 ± 0.02 | 0.154 ± 0.07 | 0.451 ± 0.18 | 0.501 ± 0.18 |
| Kidney | 0.21 ± 0.02 | 0.412 ± 0.26 | 2.44 ± 3.05 | 0.593 ± 0.15 |
| Liver | 1.07 ± 0.23 | 2.382 ± 0.97 | 3.542 ± 1.62 | 6.41 ± 3.76 |
| Tumor | 0.08 ± 0.02 | 0.257 ± 0.22 | 1.443 ± 0.79 | 3.374 ± 4.8 |
| Heart | 0.13 ± 0.16 | 0.323 ± 0.27 | 0.407 ± 0.31 | 0.334 ± 0.06 |
| Blood | 0.22 ± 0.02 | 0.384 ± 0.06 | 0.719 ± 0.64 | 1.123 ± 0.3 |

Figure 3:
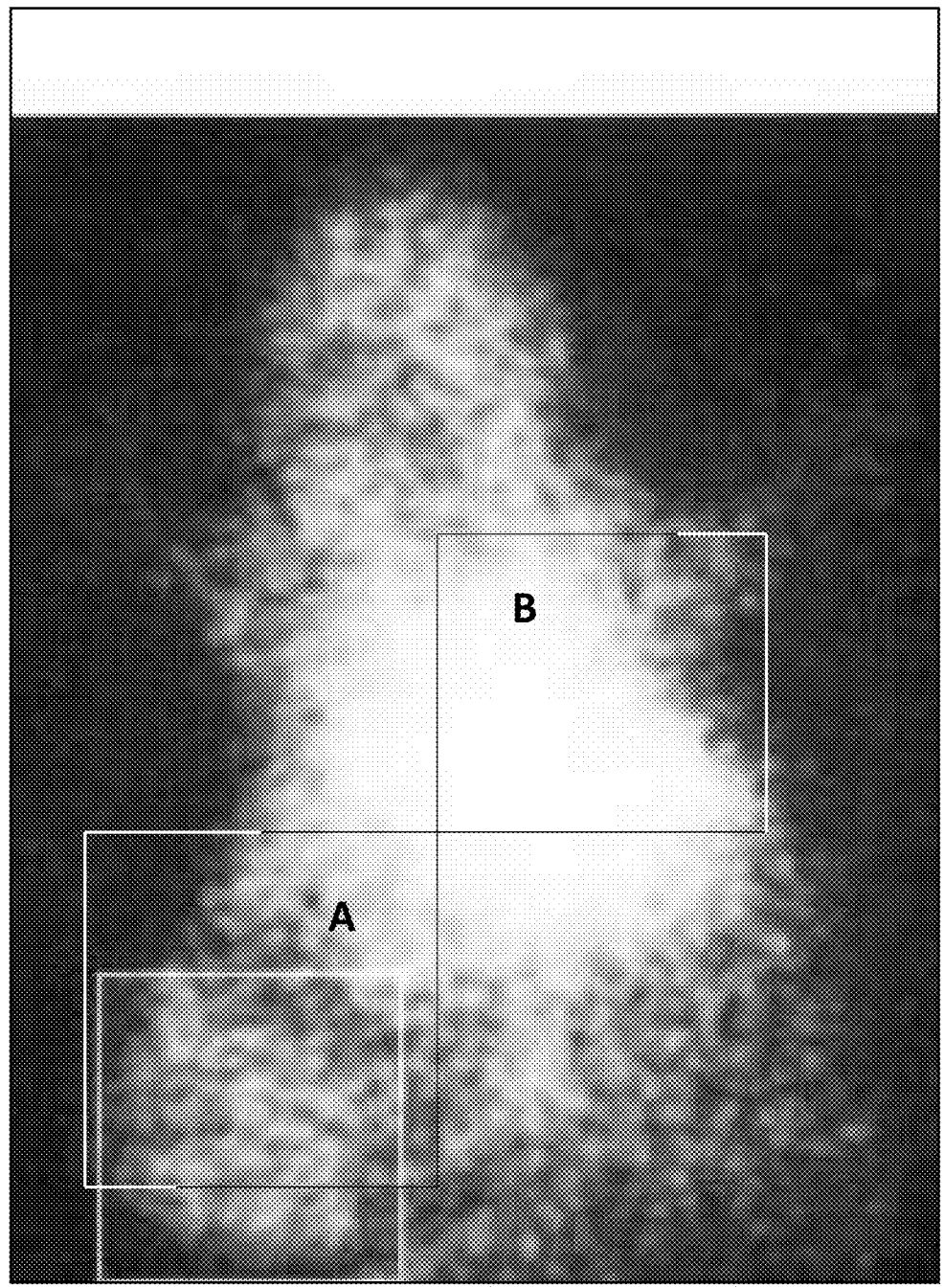
FIG. 3 shows a gamma-immunoscintigraphic image of a tumor-bearing mouse obtained at Day 15 one hour following injection of 99mTc labeled anti-DNA antibodies, with substantially more radioactivity observed in the liver zone (b) in the middle/right than in the tumor zone (a) in the lower left.

FIG. 3 shows a gamma-immunoscintigraphic image of a tumor-bearing mouse obtained at Day 15 one hour following injection of 99mTc labeled anti-DNA antibodies. The liver zone (b) in the middle-right portion of the image produced a radioactive signal that is greater than that of tumor zone (a) in the lower left portion of the image. Thus, the liver showed the most accumulation of circulating cfDNA.

Example 3: Sourcing of Tumor Originating cfDNA from Liver to Blood

Six 6-week-old female nude mice (IBCH RAS breed) were given subcutaneous injections with $2 \times 10^6$ of MCF-7 cells into the left flank. At Day 20 following the injection tumor was surgically removed. At Day 25 all mice were given anesthesia and 500 μl blood samples were taken from portal vein, hepatic artery and hepatic vein of each mouse. Plasma was separated from the blood cells by centrifugation at 2000 g for 10 minutes; the clear plasma phase on top was transferred to a new tube, and centrifuged at 14000 g. The supernatant was transferred to a fresh tube for DNA extraction. cfDNA was extracted from blood plasma samples using QIAamp DNA Blood Mini Kit according to manufacturer's instructions. The human beta globin sequence in cell free DNA was quantified in each sample using RT-PCR (iCycler iQ56 Bio-Rad) with human beta globin primer CAACTT-CATCCACGTTCACC (SEQ ID NO: 10). The Ct values of human beta globin sequence in blood plasma sampled from different vessels are presented at the Table 2 below:

TABLE 2

| Mouse No. | Portal vein | Hepatic artery | Hepatic vein |
|---|---|---|---|
| 1 | 29.49 ± 0.161 | 31.86 ± 0.817 | 23.59 ± 0.109 |
| 2 | 29.2 ± 0.379 | 28.62 ± 0.278 | 23.85 ± 0.218 |
| 3 | 29.94 ± 0.874 | 30.09 ± 0.347 | 24.22 ± 0.096 |
| 4 | →0 | →0 | →0 |
| 5 | 30.26 ± 0.21 | 29.42 ± 0.341 | 27.89 ± 0.112 |
| 6 | 30.44 ± 0.151 | 30.26 ± 0.176 | 25.78 ± 0.155 |

Even though the tumor was surgically removed, only in one mouse was the blood plasma free from circulating cfDNA of human origin. MCF-7 tumors do not produce metastasis when growing subcutaneously. The absence of metastatic nodules in liver or lungs was further confirmed by macroscopic and microscopic examination. Circulating cfDNA originating from the human tumor xenotransplant was detectable in the blood of mice, with the highest quantities detectable in the hepatic vein. These results confirm that liver sinusoids are a depot source of circulating cfDNA.

Figure 5A:
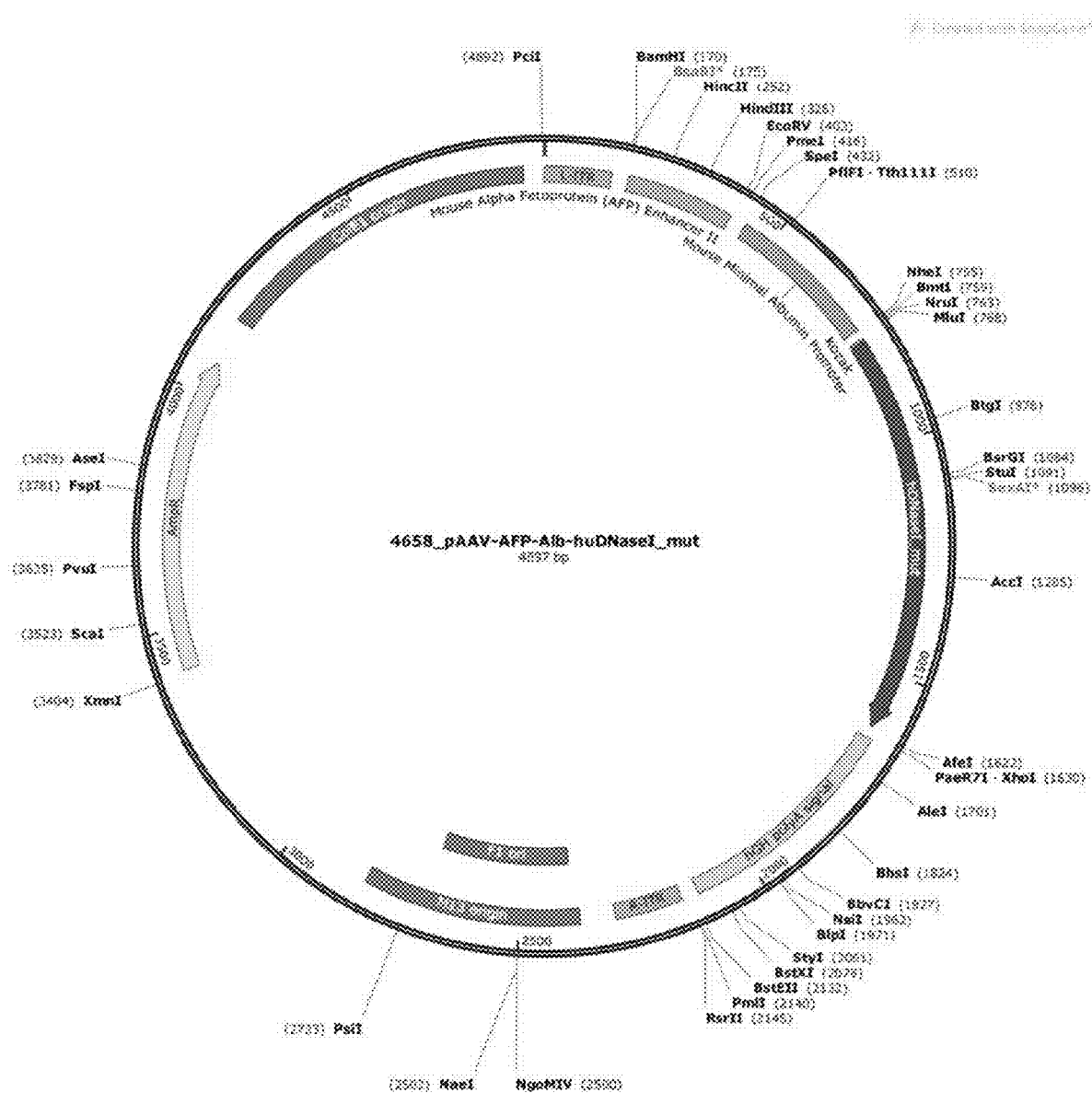
FIG. 5A shows a map of the mAFP/Alb AAV8 vector 4658_pAAV-AFP-Alb-huDNaseI_mut. The vector comprises (i) elements for propagation in bacteria, i.e., an AmpR marker, a colE1, F1 and M13 origins of replication, and (ii) the hDNAseI_mut sequence (SEQ ID NO: 2; hyperactive actin resistant DNase I mutant) operably linked to a mouse minimal albumin promoter, a mouse α-fetoprotein (AFP) enhancer II (with L-ITR), an hGH polyA signal, flanked by AAV8 L-ITR and R-ITR, an M13 origin of replication and an F1 origin of replication.
Figure 5B:
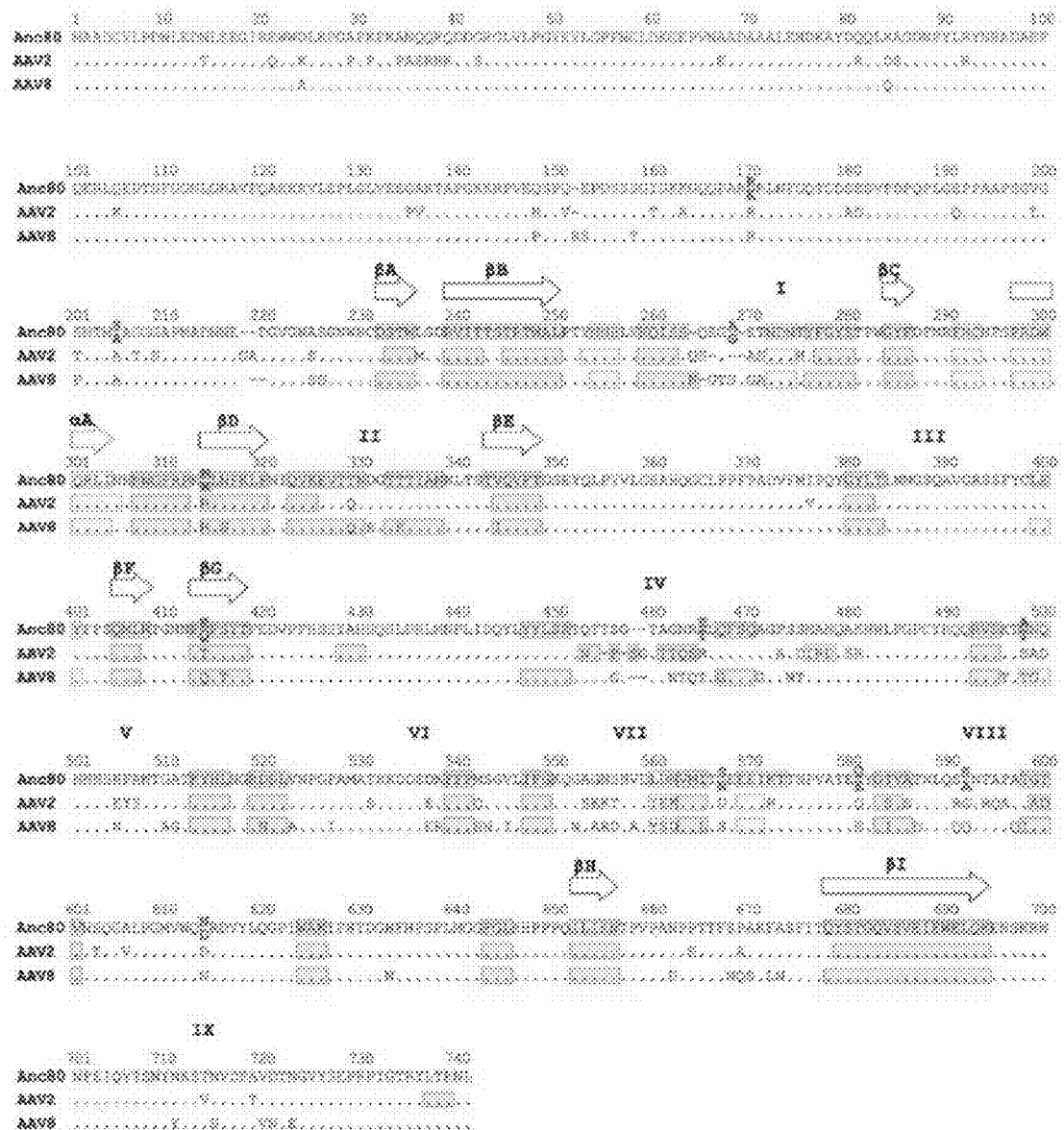
FIG. 5B shows the sequence alignment of Anc80 (SEQ ID NO: 36), AAV2 (SEQ ID NO: 37) and AAV8 (SEQ ID NO: 38) VP3 proteins (taken from Zinn et al., Cell Rep., 2015, 12(67): 1056-1068).

Example 4: Effects of Transgenic Delivery of DNase I and Intravenous Delivery of Recombinant DNase I Protein in a Pancreatic Cancer Model An AAV vector for liver specific transgenic expression of DNase I (4658_pAAV-AFP-Alb-huDNaseI_mut) was custom manufactured by Sirion Biotech (Martinsried, Germany). A vector map is shown in FIG. 5A. The AAV vector is based on AAV serotype 8 which effectively targets liver. The vector comprises the sequence set forth in SEQ ID NO: 2, which codes for a mutant human DNase I enzyme which comprises several mutations which make the enzyme less sensitive to actin inhibition and more catalytically active. The DNase I coding sequence further comprises a secretory signal sequence. The DNase I coding sequence is operably linked at the 5' end to mAFP/Alb enhancer/promoter system (liver-specific mouse alpha fetoprotein enhancer and liver-specific mouse minimal albumin promoter) and at the 3' end to hGH polyA signal. The expression cassette is further flanked by AA8 L-ITR and R-ITR.

The huDNaseI_mut expression cassette was cloned into an AAV transfer vector and produced in 293T cells via co-transfection of a transfer vector with AAV8 packaging plasmids. Viral particles were purified and concentrated up to $1 \times 10^{13}$ GC/ml and kept frozen in PBS.

A control vector identical to 4658_pAAV-AFP-Alb-huDNaseI_mut but with non-specific for liver CMVE/CAG promoter/enhancer system instead of the liver-specific mAFP/Alb enhancer/promoter system was also produced.

Human recombinant DNase I protein (rhDNaseI) was produced by Catalent (Madison, USA) and kept frozen at 10 mg/ml stock solution in 1 mM $CaCl_2$) and 150 mM NaCl.

56 female BALB/c nude mice (IBCH RAN) of 6-8 weeks age and 18-22 g weight were used in experiment. The mice were kept in individual ventilation cages at controlled temperature and humidity with four animals in each cage. Each mouse was inoculated subcutaneously at the right flank with MIA PaCa-2 pancreatic tumor cells ($1 \times 10^7$) in 0.2 ml of PBS supplemented with BD Matrigel (1:1) for tumor development. The treatments were started on day 17 after tumor inoculation when the average tumor size reached approximately 170 mm³. Each group consisted of eight tumor-bearing mice. The tested vectors and compositions were administered to the mice according to the predetermined regimen as shown in Table 3, below:

TABLE 3

Experimental Design

| Group | N$^a$ | Treatment | Dose, mg/kg | Route | Schedule |
|---|---|---|---|---|---|
| 1 | 8 | Vehicle control 0.9% NaCl | — | IP | BIW * 3 weeks |
| 2 | 8 | DNaseI_mut mAFP/Alb AAV8 + Gemcitabine | 1.00 × 10$^{11}$ GC/kg 60 mg/kg | IV IP | D 15 single dose BIW * 2 weeks |
| 3 | 8 | DNaseI_mut CMVE/CAG AAV8 + Gemcitabine | 1.00 × 10$^{11}$ GC/kg 60 mg/kg | IV IP | D 15 single dose BIW * 2 weeks |
| 4 | 8 | rhDNaseI protein + Gemcitabine | 5 mg/kg 60 mg/kg | IP IP | TD × 2 weeks BIW × 2 weeks |
| 5 | 8 | rhDNaseI protein + Gemcitabine | 15 mg/kg 60 mg/kg | IP IP | TD × 2 weeks BIW × 2 weeks |
| 6 | 8 | rhDNaseI protein + Gemcitabine | 50 mg/kg 60 mg/kg | IP IP | TD × 2 weeks BIW × 2 weeks |
| 7 | 8 | Gemcitabine | 60 mg/kg | IP | BIW × 2 weeks |

Tumor size was measured twice weekly in two dimensions using a caliper, and the volume was expressed in mm$^3$ using the formula: V=0.5 a×b$^2$ where a and b are the long and short diameters of the tumor, respectively. At the time of routine monitoring, the animals were checked daily for any effects of tumor growth and treatments on normal behavior such as mobility, food and water consumption by visual inspection only, loss or gain of body weight (measured twice weekly), eye/hair matting, and any other abnormal effects. On day 35, the study was terminated, the mice were humanely sacrificed by CO$_2$, and blood was sampled from the central and hepatic veins. Liver tissues were also sampled and immersed into formalin for fixing.

Circulating cfDNA was measured in plasma using a method described in H. Goldstein, "A rapid direct fluorescent assay for cell-free DNA quantification in biological fluids", Annals of Clinical Biochemistry, Vol 46, Issue 6, pp. 488-494. SYBR® Gold Nucleic Acid Gel Stain (Invitrogen) was diluted first at 1:1000 in dimethyl sulphoxide and then at 1:8 in phosphate-buffered saline. 10 μl of plasma samples were applied to 96-well plates. 40 μl of diluted SYBR® Gold was added to each well (final dilution 1:10,000) and fluorescence was measured with a 96 well fluorometer at an emission wavelength of 535 nm and an excitation wavelength of 485 nm.

Serum DNase I activity was measured using ORG590 (Orgentec) according to the manufacturer's protocol. Detection was performed using microplate photometer (Multiscan FC) at 450 nm with a correction wavelength of 620 nm. cfDNA in the liver tissue was quantified by immunohistochemistry (IHC) in liver paraffin slides using AC-30-10 mouse IgG DNA binding antibodies (Sigma) as primary antibodies and Novolink Polymer Detection Systems Novocastra (Leica Biosystems).

The mean tumor volume over time in female BALB/c nude mice bearing MIA PaCa-2 xenografts dosed with tested vectors and composition (as per Table 3) is shown in Table 4, below:

TABLE 4

The mean tumor volume over time

| Day | Group 1 | Group 2 | Group 3 | Group 4 | Group 5 | Group 6 | Group 7 |
|---|---|---|---|---|---|---|---|
| 17 | 172 ± 14 | 171 ± 15 | 171 ± 15 | 172 ± 15 | 170 ± 14 | 170 ± 14 | 170 ± 13 |
| 21 | 214 ± 18 | 147 ± 17 | 166 ± 14 | 207 ± 17 | 164 ± 16 | 202 ± 16 | 164 ± 14 |
| 24 | 242 ± 18 | 117 ± 16 | 161 ± 17 | 235 ± 18 | 193 ± 25 | 220 ± 14 | 197 ± 17 |
| 28 | 275 ± 18 | 86 ± 19 | 152 ± 20 | 274 ± 21 | 202 ± 37 | 239 ± 28 | 246 ± 10 |
| 31 | 299 ± 19 | 58 ± 11 | 119 ± 17 | 310 ± 31 | 189 ± 41 | 212 ± 23 | 220 ± 8 |
| 35 | 335 ± 32 | 44 ± 12 | 107 ± 19 | 368 ± 40 | 167 ± 36 | 197 ± 27 | 264 ± 14 |

The number of animals with body weight loss at Day 35 in each group of in female BALB/c nude mice bearing MIA PaCa-2 xenografts and dosed with tested vectors and composition (as per Table 3) is shown in Table 5, below:

TABLE 5

The number of animals with body weight loss at Day 35

| | Group 1 | Group 2 | Group 3 | Group 4 | Group 5 | Group 6 | Group 7 |
|---|---|---|---|---|---|---|---|
| BWL > 10% | 3 from 8 | 0 from 8 | 4 from 8 | 8 from 8 | 6 from 8 | 3 from 8 | 8 from 8 |
| BWL > 20% | 0 from 8 | 0 from 8 | 0 from 8 | 3 from 8 | 1 from 8 | 0 from 8 | 4 from 8 |

The results of quantification of circulating cfDNA in blood and DNase I enzymatic activity in central and hepatic vein are summarized in Table 6, below:

TABLE 6

| | Cell free DNA in blood ng/ml | DNase activity in blood mKuU/ml | DNase activity in hepatic vein mKuU/ml |
|---|---|---|---|
| Group 1 | 173 ± 5 | 1.75 | 1.55 |
| Group 2 | 27 ± 3 | 6.72 | 8.15 |
| Group 3 | 105 ± 8 | 5.78 | 5.35 |
| Group 6 | 133 ± 13 | 4.95 | 4.75 |
| Group 7 | 241 ± 11 | 1.15 | 1.05 |

The IHC microphotographs of liver tissue from different groups are presented in FIG. 4.

Data from the Tables 4-6, above, and FIG. 4 clearly show that liver-specific transgenic expression of DNase I enzyme in combination with chemotherapy not only produced significantly superior results in terms of antitumor efficacy but were also able to completely ameliorate chemotherapy-induced weight loss. Recombinant DNase I enzyme given twice daily in three ascending doses, as well as transgenic expression of DNase I which is not targeted to the liver, demonstrated significantly less antitumor efficacy and amelioration of chemotherapy-induced toxicity than liver-specific transgenic expression of DNase I. Mice treated with liver-specific DNaseI mAFP/Alb AAV8 vector had the lowest amount of circulating cfDNA, the lowest amount of cfDNA remaining in the liver, and the highest DNase I enzymatic activity in the hepatic vein.

Example 5: Effect of Transgenic Delivery of DNase I on Orthotopic and Non-Orthotopic Growth of Pancreatic Cancer Twelve 8-week old SCID mice (IBCH RAS) divided into 4 experimental groups were used in the experiment. Six mice received 4×10$^6$ MIA PaCa-2 pancreatic cancer cells expressing luciferase subcutaneously at the right femur in 100 μl of Matrigel (non-orthotopic model). Six mice were implanted in the body-tail of the pancreases with 4×10$^6$ MIA PaCa-2 pancreatic cancer cells expressing luciferase in 100 μl of Matrigel (orthotopic model). The next day, 3 mice with orthotopic MIA PaCa-2 implant received IV injection of mAFP/Alb AAV8 vector 4658_pAAV-AFP-Alb-huDNase-I_mut at 1.00×10$^{11}$ GC/kg dose and 3 mice with orthotopic MIA PaCa-2 implant received a placebo (PBS) injection. Three mice with non-orthotopic MIA PaCa-2 implant received an IV injection of DNaseI mAFP/Alb AAV8 vector at 1.00×10$^{11}$ GC/kg dose and three mice with non-orthotopic MIA PaCa-2 implant received a placebo (PBS) injection. Four weeks later at the end of the experiment, tumors were assessed by bioluminescence imaging using an AMI-1000 imaging system. The bioluminescence data are summarized in Table 7, below, with typical images presented in FIG. 6.

TABLE 7

| | Bioluminescence (ph/s/ROI) × 10$^8$ | | | |
|---|---|---|---|---|
| | Orthotopic MIA PaCa-2 | | Non-orthotopic MIA PaCa-2 | |
| | huDNaseI_mut mAFP/Alb AAV8 | Placebo | huDNaseI_mut mAFP/Alb AAV8 | Placebo |
| Mouse 1 | 0.0 | 1.13 | 1.71 | 5.8 |
| Mouse 2 | 0.0 | 1.41 | 2.13 | 6.1 |
| Mouse 3 | 0.0 | 1.74 | 1.05 | 5.65 |

Thus, transgenic delivery of DNase I enzyme to the liver completely blocks the development of tumor growth in an orthotopic fashion in an area drained by the portal vein, i.e., the pancreas. Development of same pancreatic cancer xenotransplant in non-orthotopic fashion was also significantly suppressed by injection of DNase I mAFP/Alb AAV8 but not to such an extent as to eliminate tumor growth completely.

Example 6: Effects of Liver and Pulmonary Delivery of DNase I Transgene on Growth of Breast Carcinoma in a Breast Cancer Model ADV-207186 vector was purchased from Vector Biolabs (Malvern, PA). A vector map is shown in FIG. 5C. This vector is based on human adenovirus Type 5 (dE1/E3) (which has a natural liver tropism) and contains wild-type human DNase I coding sequence which comprises a secretory signal sequence (SEQ ID NO:1). The DNase I coding sequence is operably linked at the 5' end to liver non-specific CMV promoter and at the 3' end to hGH polyA signal. The expression cassette is further flanked by ATT-L1 and ATT-L2.

MMTV-PyMT female mice IBCH RAS breed were used for the study. When each mouse developed at least three palpable tumors of at least 3 mm×5 mm, which typically occurred at 8 weeks of age, six mice were injected intravenously with of 0.2×10$^{11}$ PFU per mice of ADV-207186 and six mice were injected with 0.2×10$^{11}$ PFU per mice of ADV-207186 intranasally under anaesthesia. Mice were sacrificed at 14 weeks of age. Six mice were used as control. Tumor size was measured in two dimensions using a caliper, and the volume was expressed in mm$^3$ using the formula: V=0.5 a×b$^2$ where a and b are the long and short diameters of the tumor, respectively. TGI was calculated for each group using the formula: TGI (%)=[1−(Ti−T0)/(Vi−V0)]× 100; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start. Blood was sampled from the central vein at the termination of the study. Circulating cfDNA and serum DNase I activity were measured as described in Example 4. The data are reported in Table 8, below.

TABLE 8

| Treatment | Tumor Volume (mm$^3$) | TGI (%) | Cell free DNA, ng/ml | Serum DNase activity mKuU/ml |
|---|---|---|---|---|
| Control | 355 ± 32 | — | 137 ± 13 | 2.15 |
| DNase I Ad Type 5 (dE1/E3) AV IN | 209 ± 28 | 78 | 110 ± 7 | 4.95 |

TABLE 8-continued

| Treatment | Tumor Volume (mm³) | TGI (%) | Cell free DNA, ng/ml | Serum DNase activity mKuU/ml |
|---|---|---|---|---|
| DNase I Ad Type 5 (dE1/E3) AV IV | 54 ± 22 | 164 | 34 ± 11 | 5.2 |

The data show that targeting of the liver with an adenoviral vector harboring DNaseI transgene provides superior breast tumor growth inhibition and clearance of blood from circulating cfDNA as compared to the delivery of DNase I transgene to bronchoalveolar system, despite approximately the same level of DNase enzymatic activity in blood.

Example 7: Effects of Transgenic Expression of Actin Resistant Hyperactive DNase I in Liver and in Muscles on the Level of Microbial cfDNA and the Level of Neuroinflammation Increased intestinal permeability and translocation of gastrointestinal microbiota and damage-associated molecular patterns (DAMPs) of microbial origin, including microbial cfDNA, trigger neuroinflammation and spectra of neurodegenerative disease. cfDNA originating from gastrointestinal microbiota are subject to "first pass" through porto-sinusoidal circulation. The effects of muscle and liver delivery of hyperactive actin-resistant DNase I transgene, the effects of injections of wild-type DNase I protein on the level of microbial cfDNA in brain and liver, as well as the level of neuroinflammation in CSF and brain following bacteriophage-induced leaky gut syndrome were further investigated.

Healthy adult male Wistar rats (n=24; 12-week-old, 240-280 g) were maintained in individual cages in a P3 room under a 12-h light/dark cycle, at a temperature of 22 to 25° C. and 60±5% atmospheric humidity. All animals had free access to food and water according to the Guide for the Care and Use of Laboratory Animals.

Figure 9:
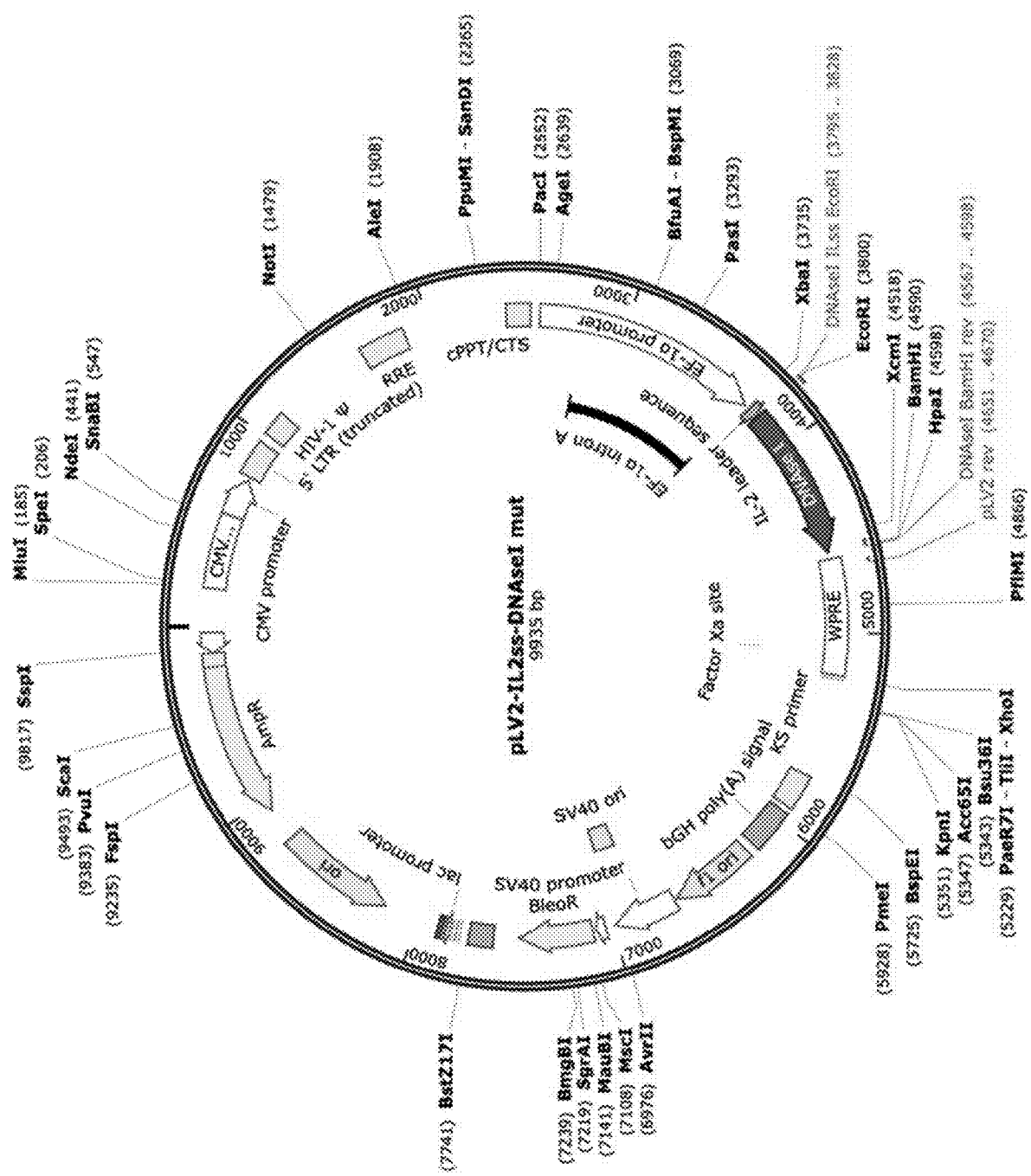
FIG. 9 shows a restriction map of the lentiviral vector pLV2-IL2ss-DNaseI mut used to deliver DNase I in Example 7. The vector comprises an AmpR marker, and origins of replication for F1 and SV40. The vector comprises an EF-1a promoter upstream of an IL-2 leader sequence upstream of DNAse I.

The DNA molecule coding for the hyperactive actin-resistant DNase I mutant (SEQ ID NO: 5) with DNase I secretory signal sequence replaced by the IL2 secretory signal sequence was synthesized (GeneCust) and cloned into the pLV2 lentiviral vector (Clontech) under the control of the EF1a promoter (not liver-specific). The resulting construct is pLV2-IL2ss-DNaseI mut and is shown in FIG. 9. The 293T lentiviral packaging cell line (Clontech) was cultured in DMEM (Gibco). HEK 293T cells were transfected with the pLV2-based lentiviral vector pLV2-IL2ss-DNAseI mut using Lipofectamine 2000 (Life Technology). 5 ml of supernatant was collected at 48 hours after transfection. Lentiviruses were collected by filtering through a 0.45 µm polyethersulfone membrane filter (Millipore), centrifugation during 30 m at 20,000 g. The resulting pellet was resuspended in 1 ml of PBS.

Leaky gut was induced in 24 rats using a bacteriophage cocktail against Enterobacteriaceae, Staphylococcaceae, and Streptococcaceae families so as to induce microbiota diseases. The cocktail included a *Salmonella* bacteriophage cocktail from Microgen (Moscow, Russia), containing bacteriophages against *S. paratyphi, S. typhimurium, S. heidelberg, S. newport, S. choleraesuis, S. oranienburg, S. infans, S. dublin, S. enteritidis, S. anatum,* and *S. newlands* and Pyobacteriophage phage cocktail from Microgen containing phages against seven bacterial species, *Staphylococcus aureus, Streptococcus pyogenes, Proteus mirabilis, Proteus vulgaris, Pseudomonas aeruginosa, Klebsiella pneumoniae,* and *Escherichia coli*. Phages (1.5 mL, 1×10⁶ plaque-forming units/mL of each phage cocktail) were added to drinking water according to the manufacturer's instruction and administered orally for 10 days. At day 7 of phage treatment, rats were randomized into 4 groups as follows: six rats received intrahepatic injection of 1.0×10¹² LVP in a volume of 200 µl; six rats received injection of 1.0×10¹² LVP in a volume of 200 µl into a thigh muscle; six rats received twice daily intravenous injections of recombinant DNase I protein at 50 mg/kg between day 7 and day 12. The remaining six rats were used as the untreated leaky gut control. An additional six healthy rats were used as a healthy control. At day 12, all rats were sacrificed and blood samples were collected for measurement of the DNase activity in blood. Brain autopsies were collected to perform NLRP3 inflammasome expression analysis and 16S universal bacterial RNA gene quantification.

The NLRP3 inflammasome is considered a key contributor to the development of neuroinflammation. Aberrant activation of NLRP3 inflammasome signaling has been demonstrated to contribute to pathology in a broad spectrum of neurological diseases (Song, 2017). NLRP3 expression was assessed by collection of 50 mg cortical tissue samples. RNA was isolated using the SV total RNA isolation system (Promega). Superscript III one-step RT-PCR system with platinum Taq DNA Polymerase (Invitrogen) was used for reverse transcriptase-PCR using 5'-GTTCTGAGCTC-CAACCATTCT-3' (SEQ ID NO: 11) as forward NLRP3 primer and 5'-CACTGTGGGTCCTTCATCTTT-3' (SEQ ID NO: 12) as reverse NLRP3 primer. 16S universal bacterial RNA gene primers (forward: 5'-TCGTCGGCAGCGTCA-GATGTGTATAAGAGACAGCCTACGGG-NGGCWGCAG-3' (SEQ ID NO: 13); reverse: 5'-GTCTCGTGGGCTCGGAGATGTGTATAAGA-GACAGGACTACHVGGGTATCTAATCC-3' (SEQ ID NO: 14)) were used to quantify presence of DNA of microbial origin in liver and brain. Gene expression analyses were done using the comparative Ct method.

Serum DNase I activity was measured using ORG590 (Orgentec) according to the manufacturer's protocol. Detection was performed using microplate photometer (Multiscan FC) at 450 nm with a correction wavelength of 620 nm. Results are summarized at the Table 9, below:

TABLE 9

| Group | Dnase activity in blood, mKuU/ml | Average ΔCt values for universal bacterial 16S from RT-PCR, liver | Average ΔCt values for universal bacterial 16S from RT-PCR, brain | Average ΔCt values for brain NLRP3 from RT-PCR |
|---|---|---|---|---|
| Healthy control | 4.35 | 28.315 | 28.723 | 18.992 |
| Leaky gut control | 2.33 | 24.617 | 26.315 | 17.352 |
| DNase I protein (wt) | 7.15 | 25.752 | 27.417 | 17.341 |

TABLE 9-continued

| Group | Dnase activity in blood, mKuU/ml | Average ΔCt values for universal bacterial 16S from RT-PCR, liver | Average ΔCt values for universal bacterial 16S from RT-PCR, brain | Average ΔCt values for brain NLRP3 from RT-PCR |
|---|---|---|---|---|
| Liver pLV2-IL2ss-DNaseI mut delivery | 9.73 | 27.717 | 28.212 | 18.882 |
| Muscle pLV2-IL2ss-DNaseI mut delivery | 8.77 | 25.112 | 27.573 | 17.931 |

The data show that induction of a leaky gut led to suppression of endogenous blood DNase enzyme activity, a significant increase of microbial cfDNA presence in liver and brain cortex and significant upregulation of NLRP3 inflammasome component in brain cortical tissue. Delivery of a hyperactive actin resistant DNase I lentiviral transgene to liver, as compared to the delivery of the same transgene to muscle tissue or to intravenous injections of DNase I protein, almost completely prevented increase of microbial cfDNA in liver and brain and brain inflammasome activation, despite maintaining of comparable DNase enzymatic activity in the central bloodstream.

Example 8: Effects of Transgenic Delivery of Hyperactive Actin Resistant DNase I and Intravenous Delivery of Recombinant DNase I Protein on GVHD The MHC class I and II disparate model, C57BL/6 (H-2b) to BALB/c (H-2d), was used to establish GVHD. All recipients were age-matched females with an age of 2-6 months at the time of bone marrow transplant (BMT). The single cell suspensions of bone marrow cells and splenocytes were prepared in saline for injection. To generate BMT chimeras, recipient BALB/c mice received 1200 rad TBI (137Cs source) split into 2 doses. The mice then received cells from C57BL/6 mice: $5 \times 10^6$ bone marrow cells and $10 \times 10^6$ splenocytes.

The experiments were designed to compare the following two treatments: wild-type mouse DNase I protein (50 mg/kg) daily and liver-specific wild-type mouse DNase I mAFP/Alb AAV8 vector as a single intravenous injection. Starting the same day as the BMT, recipients were treated with DNase I via IP route twice a day or by single intravenous delivery of DNase I mAFP/Alb AAV8 at $1.00 \times 10^{11}$ GC/kg dose. For histopathology mice were sacrificed on day 16 post-transplant. Tissues were placed in 10% formalin, embedded in paraffin, sectioned, and stained with hematoxilin and eosin. For quantification of donor-derived T cells spleen (SP), peripheral lymph nodes (PLN), mesenteric lymph nodes (MLN) and Peyer's patches (PP) were harvested from recipient mice on day 16 post transplantation. Cells recovered from these tissues were stained with CD3, CD4, CD8 and H-2db antibodies. The numbers of donor-derived T cells (H-2db+) and CD4+/H-2db+ and CD8+/H-2db+ subsets were determined by FACS. The survival data are presented in Table 10, below:

TABLE 10

| Treatment | D 0 | D 8 | D 16 | D 24 | D 32 |
|---|---|---|---|---|---|
| | | | Dead/alive | | |
| DNase I | 10/10 | 9/10 | 8/10 | 6/10 | 5/10 |
| DNase I mAFP/Alb AAV8 | 10/10 | 10/10 | 10/10 | 10/10 | 10/10 |

Data on liver histopathology in DNase I-treated and DNase I mAFP/Alb AAV8 treated recipient mice are presented in FIG. 7. The left panel shows lymphoplasmacytic infiltration of portal tracts, segmental loss of bile duct epithelial cells, areas of focal necrosis of hepatocytes, and significant amount of nucleiphilic material at the vascular interface in animals treated with DNase I protein only (and not DNaseI mAFP/Alb AAV8). The right panel shows that the livers from the animals treated with DNaseI mAFP/Alb AAV8 have much lower inflammatory cell density, no necrosis and much less nucleiphilic material at the vascular interface.

Figure 8:
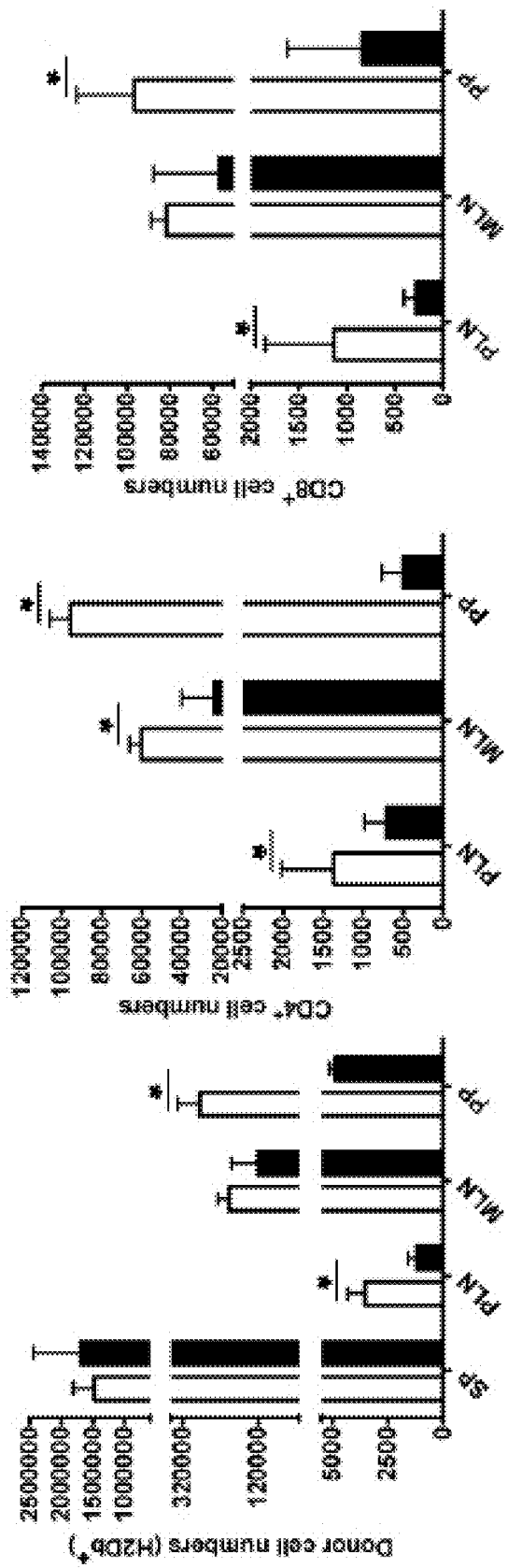
FIG. 8 shows a significant reduction in the total numbers of donor-derived T cells, donor-derived CD4+ and CD8+ T cells in the peripheral lymph nodes, mesenteric lymph nodes and Peyer's patches of DNase I mAFP/Alb AAV8-treated mice as compared with recombinant DNase I treated mice.

Data on donor-derived T cells in DNase I protein-treated and DNase I mAFP/Alb AAV8-treated recipient mice are presented in FIG. 8. In particular, FIG. 8 shows a significant reduction in the total numbers of donor-derived T cells, donor-derived CD4+ and CD8+ T cells in the peripheral lymph nodes (PLN), mesenteric lymph nodes (MLN) and Payer's patches (PP) in DNase I mAFP/Alb AAV8-treated recipients as compared with DNase I protein treated recipients.

The results show that liver-specific transgenic expression of DNase I enzyme results in doubling of animal survival comparing with DNase I protein treatment. Such survival benefit was accompanied with a significant reduction of total numbers of donor-derived T cells, donor-derived CD4+ and CD8+ T cells in the PLN, MLN and PP in DNase I mAFP/Alb AAV8 treated recipients as compared with DNase I protein treated recipients. In the liver, DNase I mAFP/Alb AAV8 treatment resulted in a significant reduction of lymphoplasmacytic infiltration of portal tracts, prevention of cell loss and clearance of vascular interface from nucleophilic material.

Example 9: Cloning of AAV Vector: ApoEHCR Enhancer-hAAT Promoter-hDNaseI (Hyperactive)Correct Leader-WPRE Xinact (VR-18013AD)

Figure 10B:
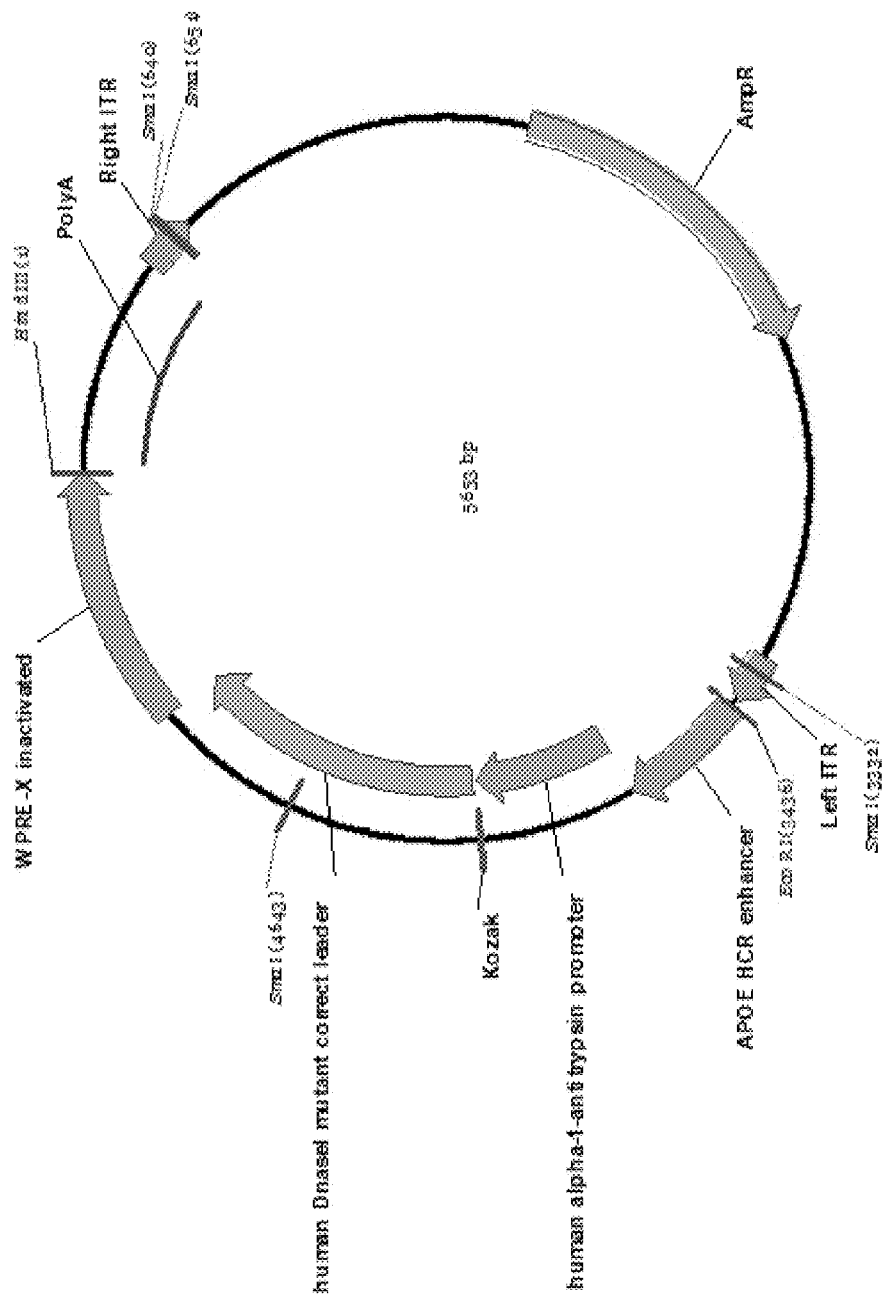
FIG. 10B shows a vector map of ApoEHCR enhancer:hAAT promoter>hDNaseI (hyperactive)correct leader-WPRE Xinact.
Figure 11:
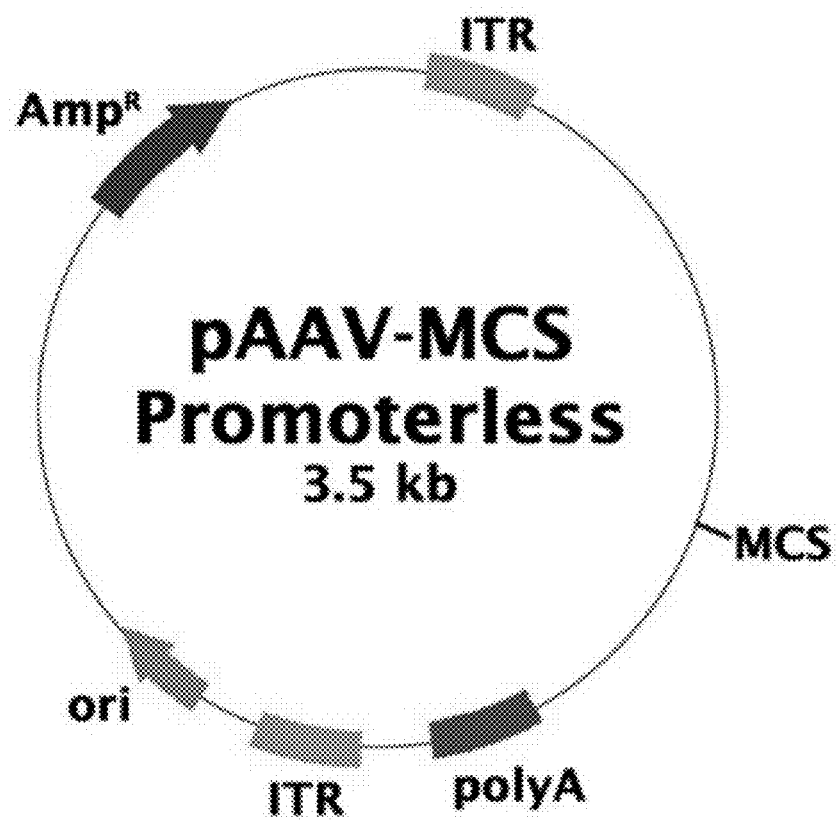
FIG. 11 shows a map of the pAAV-MCS Promoterless expression vector used for the preparation of ApoEHCR enhancer:hAAT promoter>hDNaseI (hyperactive)correct leader-WPRE Xinact.

An AAV Promoterless Expression Vector pAAV-MCS-Promoterless was obtained from Cell Bio labs (Cat no. VPK-411; FIG. 11). The ITR integrity was checked by performing a SmaI restriction enzyme digest followed by gel purification to assess for the presence of the following expected bands: 2681 bp, 666 bp, and 112 bp. The expected 11 bp band would not be seen. If the expected bands were present, the plasmid was amplified by growing in SURE cells (Agilent Technologies) or other similar bacteria. A 5' EcoRI site and a 3' HindIII site were added to the sequence of SEQ ID NO: 30 (ApoEHCR enhancer-hAAT promoter-hDNaseI (hyperactive)correct leader-WPRE Xinact). The polynucleotide of SEQ ID NO: 30 (with 5' EcoRI and 3' HindIII sites) was synthesized and then digested with EcoRI-HF and HindIII-HF (available from NEB). The 2.2 kb band was gel-extracted. The pAAV-MCS Promoterless vector was digested with EcoRI-HF and HindIII-HF, with the resulting 3.5 kb band gel extracted. The digested vector and the polynucleotide of SEQ ID NO: 30 (insert) were ligated for one hour at room temperature in a 3:1 insert to vector molar ratio. The ligated construct was transformed into SURE electrocompetent cells and plated on LB-Agar (Amp) plates. Colonies were selected and minipreps were prepared for screening. First, a SmaI digest was performed for ITR integrity to determine if the following expected bands were present: 2681 bp, 1650 bp, and 1311 bp. Then, an EcoRI-HF and HindIII-HF digest was performed to assess if the insert was present. If the insert was present, the following bands would be seen: 3435 bp and 2218 bp. A map of the VR-18013AD vector is shown in FIG. 10B.

Clones were selected if the expected bands were present in each of the SmaI digest and the EcoRI-HF and HindIII-HF digest. For selected clones, a glycerol stock was prepared for long-term storage. The plasmid was also amplified and sequenced. Clones comprising a plasmid with the correct sequence were then cultured and purified by endo-free Gigaprep (ALTA Biotech). The purified plasmid was suitable for packaging by MEE into AAV capsids.

Example 10: Cloning of AAV Vector: ApoEHCR Enhancer-hAAT Promoter-hDNaseI (Wild Type)-WPRE Xinact (VR-18014AD)

Figure 10C:
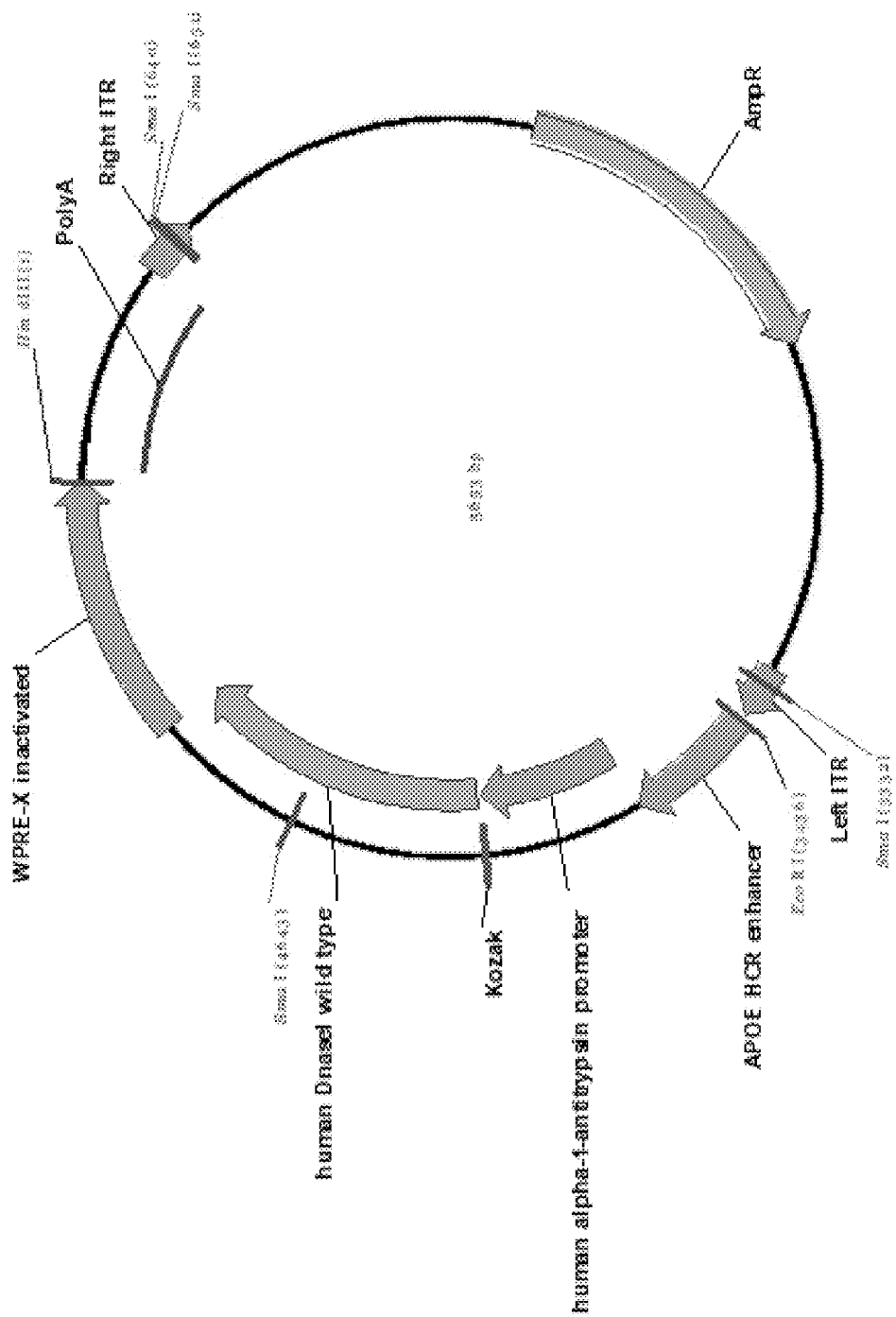
FIG. 10C shows a vector map of ApoEHCR enhancer:hAAT promoter>hDNaseI (wild-type)-WPRE Xinact.

An AAV Promoterless Expression Vector pAAV-MCS-Promoterless was obtained from Cell Bio labs (Cat no. VPK-411; FIG. 11). The ITR integrity was checked with SmaI digest and gel-purified to assess whether the plasmid produced the following expected bands: 2681 bp, 666 bp, and 112 bp. The expected 11 bp band would not be seen. If the expected bands were present, the plasmid was amplified by growing in SURE cells (Agilent Technologies) or other similar bacteria. A 5' EcoRI site and a 3' HindIII site were added to the sequence of SEQ ID NO: 31 (ApoEHCR enhancer-hAAT promoter-hDNaseI (wild type)-WPRE Xinact). The polynucleotide of SEQ ID NO: 31 (with 5' EcoRI and 3' HindIII sites) was synthesized and then digested with EcoRI-HF and HindIII-HF (available from NEB). The 2.2 kb band was gel-extracted. The pAAV-MCS Promoterless vector was digested with EcoRI-HF and HindIII-HF, with the resulting 3.5 kb band gel extracted. The digested vector and the polynucleotide of SEQ ID NO: 31 (insert) were ligated for one hour at room temperature in a 3:1 insert to vector molar ratio. The ligated construct was transformed into SURE electrocompetent cells and plated on LB-Agar (Amp) plates. Colonies were selected and minipreps were prepared for screening. First, a SmaI digest was performed for ITR integrity to determine if the following expected bands were present: 2681 bp, 1650 bp, and 1311 bp. Then, an EcoRI-HF and HindIII-HF digest was performed to assess if the insert was present. If the insert was present, the following bands would be seen: 3435 bp and 2218 bp. A map of the VR-18014AD vector is shown in FIG. 10C.

Clones were selected if the expected bands were present for each of the SmaI digest and the EcoRI-HF and HindIII-HF digest. For selected clones, a glycerol stock was prepared for long-term storage. The plasmid was also amplified and sequenced. Clones comprising a plasmid with the correct sequence were then cultured and purified by endo-free Gigaprep (ALTA Biotech). The purified plasmid was suitable for packaging by MEE into AAV capsids.

Example 11: Manufacture of ApoEHCR Enhancer-hAAT Promoter-hDNaseI (Hyperactive)Correct Leader-WPRE Xinact (VR-18013AD) and ApoEHCR Enhancer-hAAT Promoter-hDNaseI (Wild Type)-WPRE Xinact AAV Vectors (VR-18014AD)

The VR-18013AD and VR-18014AD expression plasmids were manufactured by GenScript USA Inc. (Piscataway, NJ 08854, USA). The corresponding hDNAse I (hyperactive) VR-18013AD AAV vector and hDNAseI (wild-type) VR-18014AD AAV vectors were produced using large-scale polyethylenimine transfections of Anc80L65 AAV cis, AAV trans, and adenovirus helper plasmids in near-confluent monolayers of HEK293 cells with further purification on an iodixanol gradient at scale using traditional protocols. The purified ApoEHCR enhancer-hAAT promoter-hDNaseI (hyperactive)correct leader-WPRE Xinact (VR-18013AD; transgene cassette of VR-18013AD comprised the sequence of SEQ ID NO: 30; see vector map of FIG. 10B) and ApoEHCR enhancer-hAAT promoter-hDNaseI (wild type)-WPRE Xinact (VR-18014AD (map shown in FIG. 10C. the transgene cassette of the vector had the sequence (SEQ ID NO: 31).) vectors were reformulated in PBS supplemented with 35 mM NaCl and 0.001% PF68, and comprising $1.0 \times 10^{13}$ GC/ml (VR-18014AD) and $5.0 \times 10^{12}$ GC/ml (VR-18013AD).

Figure 12:
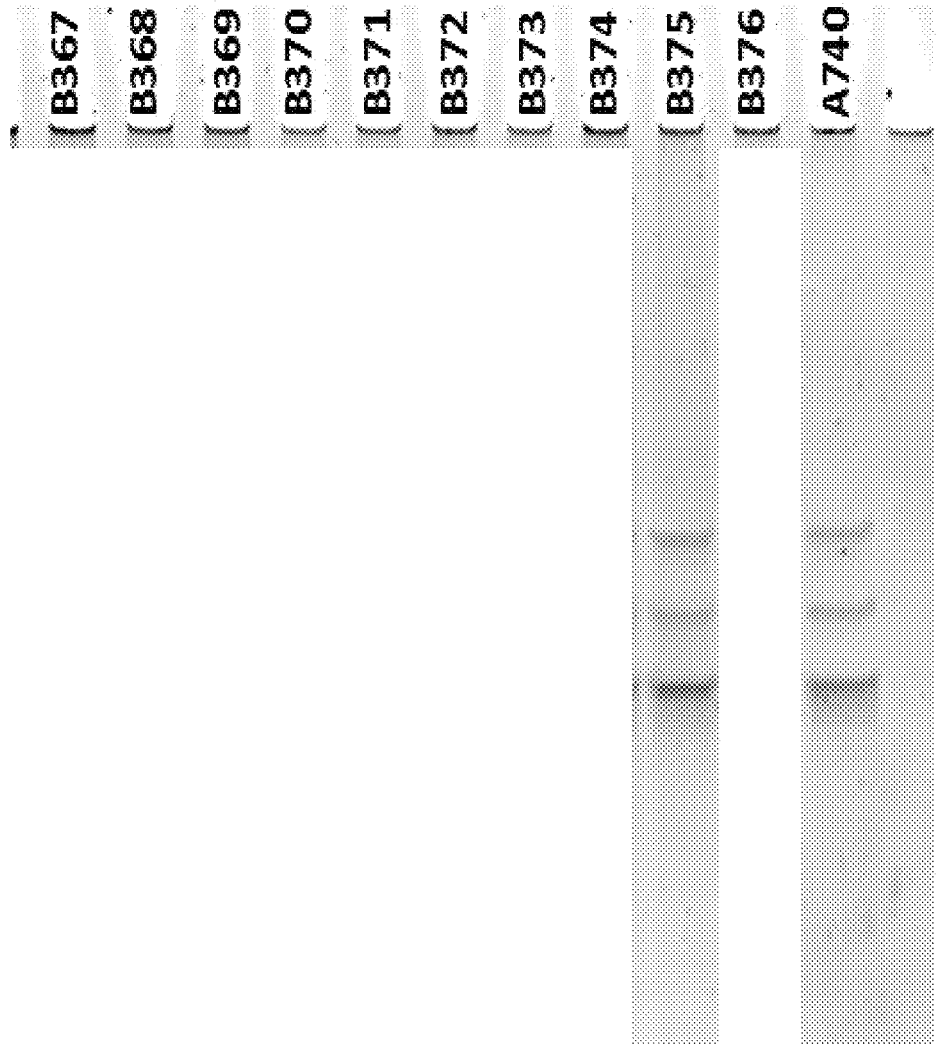
FIG. 12 shows the results of SDS-PAGE analysis of purified Anc80 VR-18013AD AAV vector. Three bands of 60, 72, and 90 kDa were observed in a ratio of about 1:1:10, which corresponds to the VP1-3 proteins.

The purified VR-18013AD AAV vector was analyzed by SDS-PAGE, with the results shown in FIG. 12. Three bands of 60, 72, and 90 kDa were observed in a ratio of about 1:1:10, which corresponds to the VP1-3 proteins.

For transduction, VR-18014AD and VR-18013AD were prepared as sterile, clear, colorless, highly purified solutions of recombinant VR-18014AD and VR-18013AD particles.

Example 12: Liver-Specific Transduction of AAV Vectors: ApoEHCR Enhancer-hAAT Promoter-hDNaseI (Hyperactive)Correct Leader-WPRE Xinact (VR-18013AD) and ApoEHCR Enhancer-hAAT Promoter-hDNaseI (Wild Type)-WPRE Xinact (VR-18014AD)

The transduction efficiency of the following two gene therapy vectors were studied: ApoEHCR enhancer-hAAT promoter-hDNaseI (hyperactive)correct leader-WPRE Xinact and ApoEHCR enhancer-hAAT promoter-hDNaseI (wild type)-WPRE Xinact. These gene therapy vector candidates were studied in vitro using HEP G2 human hepatoma derived cell line (ATCC HB-8065) and SK-HEP1 human hepatic adenocarcinoma of endothelial origin (ATCC HTB-52).

Cells were seeded to 48 well plates at $5 \times 10^5$ cell/ml. and grown in DMEM Adv, 10% FBS media. 24 h. post seed wells were supplemented with VR-18013AD or VR-18014AD using MOI $10^4$ GC/cell, $10^5$ GC/cell and $10^6$ GC/cell or blank control. Each well was in triplicate.

The DNase activity was analyzed using fluorescent probe (Terekhov et al., PNAS 2017; pnas.org/content/pnas/114/10/2550.full.pdf) representing hairpin oligonucleotide labeled with fluorescent dye and quencher. The increase in fluorescence was monitored using Variscan Flash plate reader (Thermo Scientific). The culture medium was diluted from 20 to 200 folds by reaction buffer 20 mM Tris-HCl pH 7.5, 1 mM $MnCl_2$ and 0.3 mM $CaCl_2$. 0.25 µM concentration of florescent probe was used. Complete hydrolysis of florescent probe in reaction conditions resulted in 28 RFU fluorescence under assay conditions. The background probe fluorescence was below 0.3 RFU. Calibration curve for DNase concentration estimation was obtained using serial dilution of pure DNase I Pulmozyme "Dornase alfa" (Roche). The DNase concentration in samples was estimated using linear regression. The data are shown in FIGS. 13A and 13B.

Figure 13A:
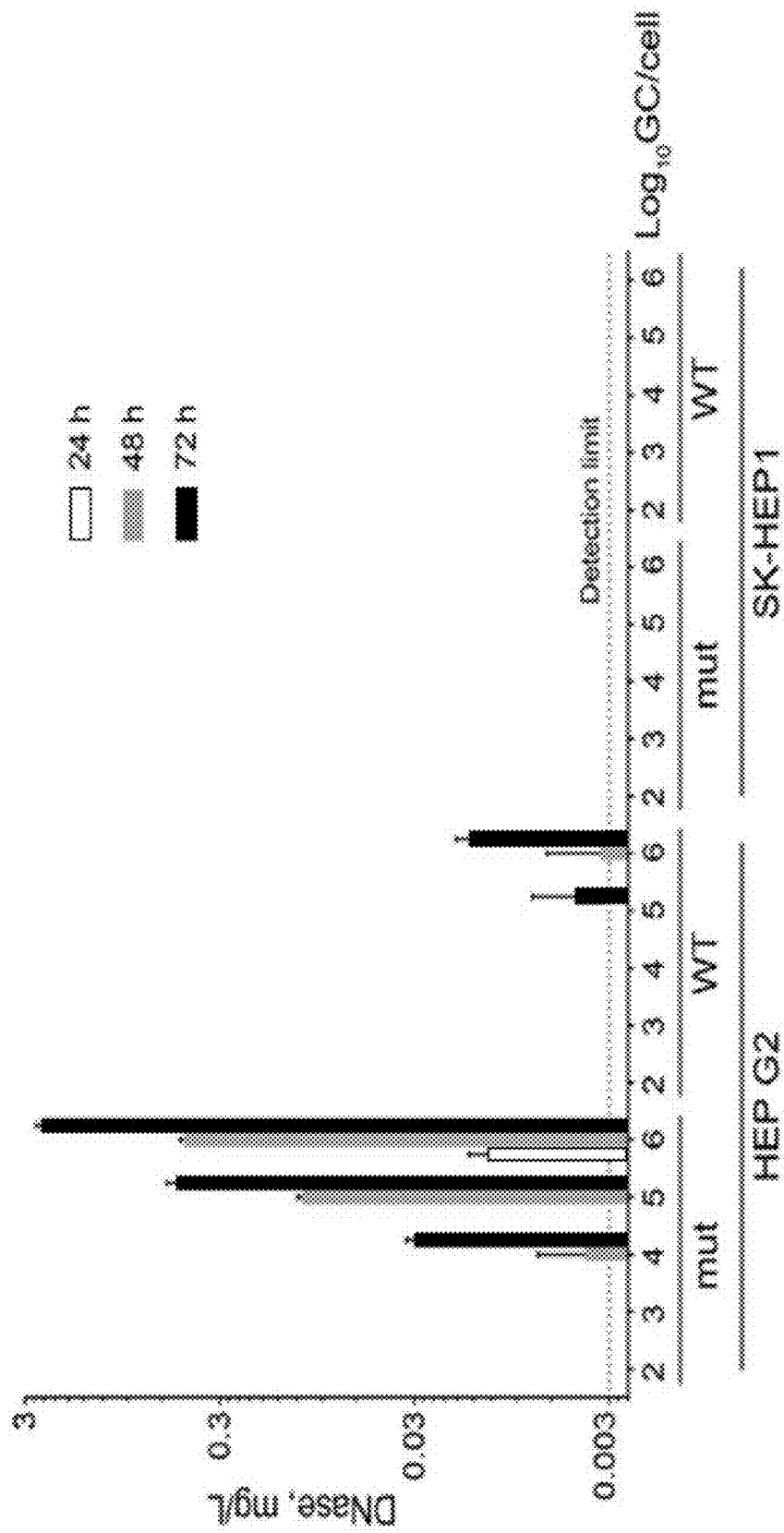

The data in FIGS. 13A and 13B show that ApoEHCR enhancer-hAAT promoter-hDNaseI (hyperactive)correct leader-WPRE Xinact (VR-18013AD) and ApoEHCR enhancer-hAAT promoter-hDNaseI (wild type)-WPRE Xinact (VR-18014AD) vectors efficiently transduce cells of hepatocyte origin only and trigger high yield expression and secretion of biologically enhanced DNase I enzyme or wild type DNase I enzyme from transduced G2 cells. DNase concentration estimation was obtained using serial dilution of pure DNase I Pulmozyme "Dornase alfa" (Roche). Transduction appears to be safe for cells since during 72 hours of observation there were no any signs of cell death even at highest VR-18013AD and VR-18014AD doses of $10^6$ GC/cell and no morphologic difference between any of transduced cells versus control cells.

Example 13: ApoEHCR Enhancer-hAAT Promoter-hDNaseI (Hyperactive)Correct Leader-WPRE Xinact (VR-18013AD) for Treatment of Alzheimer's Disease The therapeutic effect of single IV injection of VR-18013AD (ApoEHCR enhancer-hAAT promoter-hDNaseI (hyperactive)correct leader-WPRE Xinact) was studied in 3xTg-AD mice expressing three mutant human transgenes: presenilin (PS)1 (M146V), βAPP (Swedish mutation) and tau (P301L). These transgenic mice develop both amyloid and tau pathologies.

The effect of VR-18013AD on learning and memory deficits was evaluated by performing the following behavioral tests: 1) the Y-maze alternation test, which measures the spatial working memory and is dependent on the integrity of the limbic and non-limbic pathways; and 2) Contextual fear conditioning (CFC), which is highly dependent on hippocampal and amygdala function, but also on the cortex.

The objective of the study was to quantify the effect of a single VR-18013AD IV injection on amyloid deposition and tau phosphorylation in 3xTg-AD via immunohistochemistry. The impact of VR-18013AD on tau hyperphosphorylation was studied in 3xTg-AD mice using the AT8 mAb antibody specific for pSer202/Thr205 epitopes, which are among the earliest phosphorylated tau epitopes in patients with AD. Total tau was also determined in treated and untreated 3xTg-AD mice. Overactive microglia can induce highly-detrimental neurotoxic effects; hence the attenuation of the microglial response has been proposed as a potential therapeutic approach in AD.

The design of experiment is summarized in Table 11 below:

TABLE 11

| Study Procedures | D 0 | D 30 | D 60-D 180 | D 180 |
|---|---|---|---|---|
| VR-18013AD or PBS Injection | X | | | |
| *Y-maze alternation test | | X | | |
| *CFC test | | X | | |
| *Quantification of Abeta | | | | X |
| *Total and phosphorylated tau | | | | X |
| *Microglial activation | | | | X |

Figure 14:
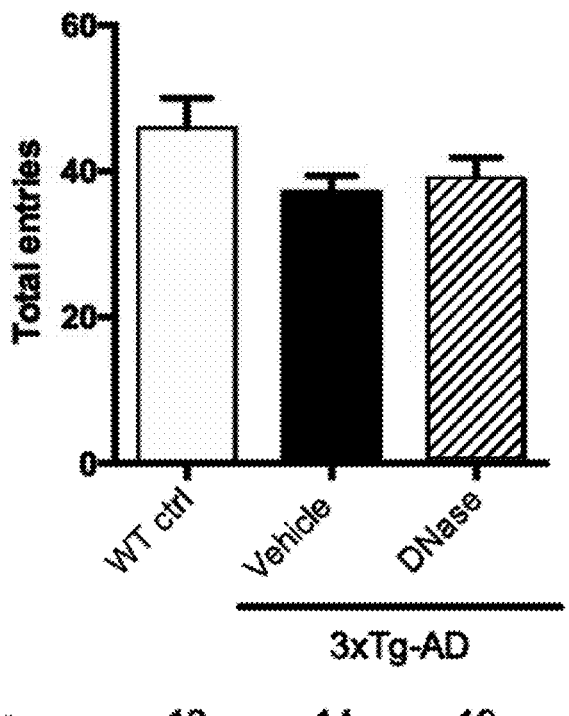
FIG. 14 shows the results of a Y Maze behavioral test.
Figure 15:
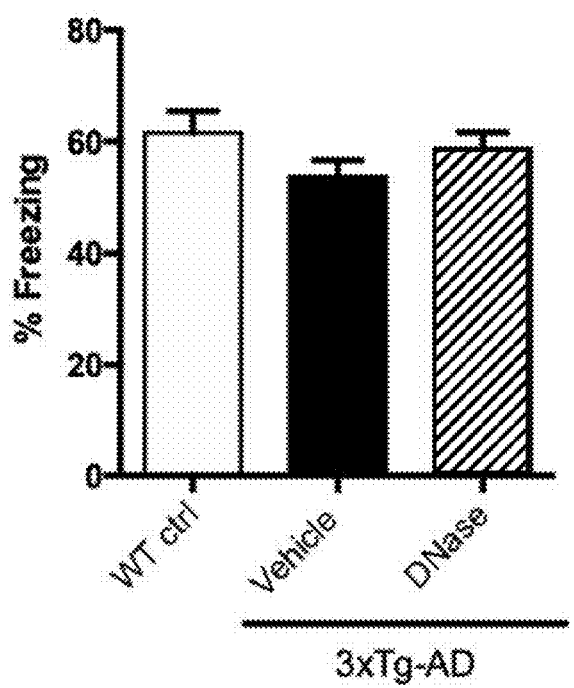
FIG. 15 shows the results of a contextual fear condition test.
Figure 16:
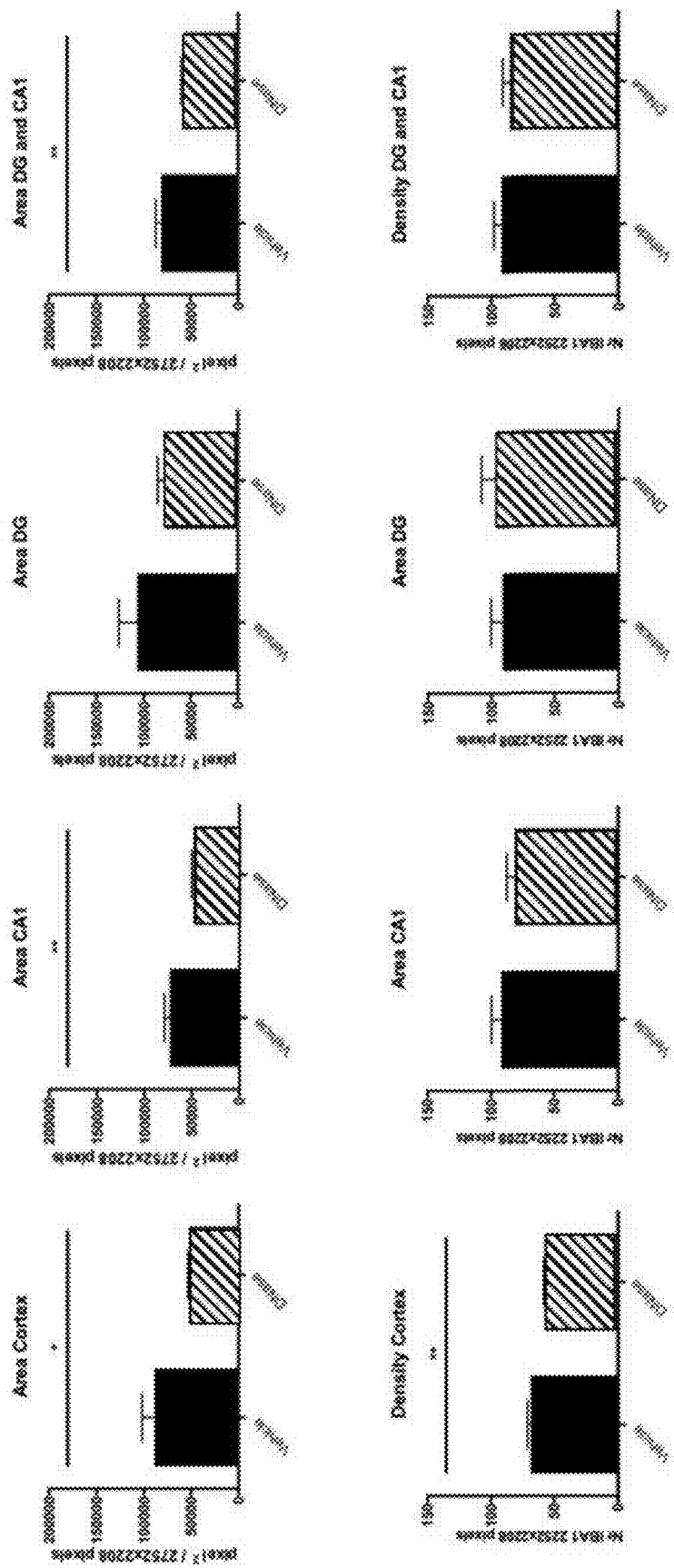
FIG. 16 shows that microglia activation was significantly reduced in VR-18013AD treated 3xTg-AD mice as compared with 3xTg-AD control mice, especially in cortical area of brain.

At day 0 the following groups of mice received treatment: (a) 13 six-month old wild type (WT) mice was injected with phosphate buffered saline (PBS); (b) 15 six-month old 3xTg-AD mice were injected with phosphate buffered saline (PBS) only; and (c) 10 six-month-old 3xTg-AD mice injected with VR-18013AD at $1.0 \times 10^{11}$ GC/per mouse dose. The data are summarized as follows. In FIG. 14, the Y Maze behavioral test shows a slight improvement in VR-18013AD treated 3xTg-AD mice vs 3xTg-AD control mice. In FIG. 15, the results of the contextual fear condition test shows a slight improvement in VR-18013AD treated 3xTg-AD mice as compared with 3xTg-AD control mice. The data of FIG. 16 show that microglia activation was significantly reduced in VR-18013AD treated 3xTg-AD mice as compared with 3xTg-AD control mice, especially in cortical area of brain.

Figure 17:
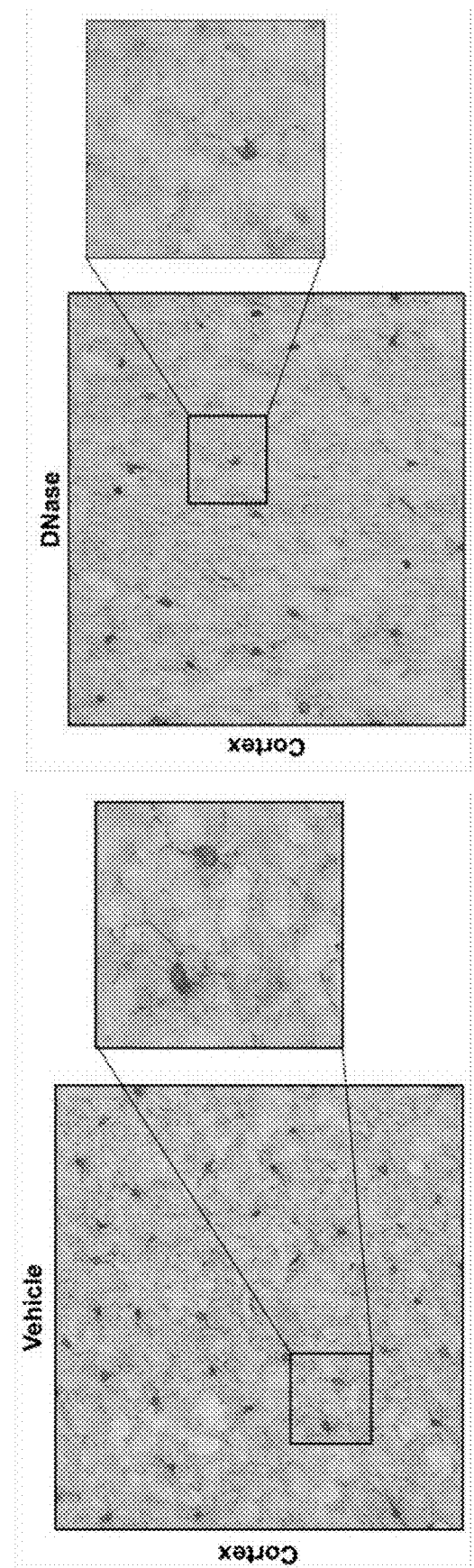
FIG. 17 shows data indicating a significant reduction of microglia activation in the cortical brain area of VR-18013AD treated 3xTg-AD mice vs 3xTg-AD control mice.
Figure 20:
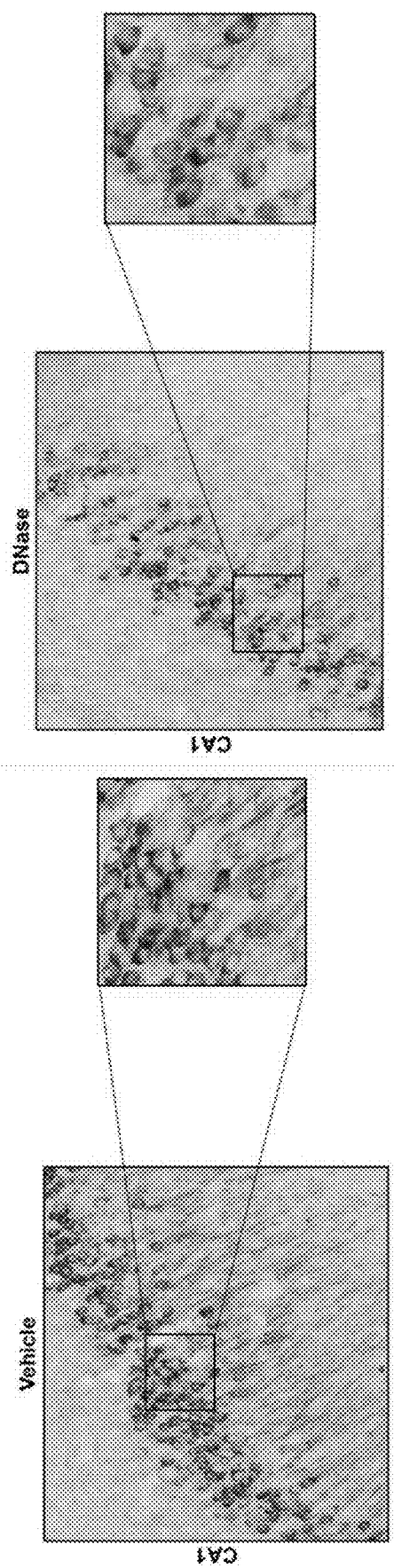
FIG. 20 shows data indicating a significant reduction of p-tau reduction in hippocampal region after VR-18013AD treated treatment.

The data of FIG. 17 show that there is a significant reduction of microglia activation in the cortical brain area of VR-18013AD treated 3xTg-AD mice vs 3xTg-AD control mice. The data of FIG. 18 show that treatment with VR-18013AD significantly reduces amyloid deposition in VR-18013AD treated 3xTg-AD mice vs 3xTg-AD control mice. The data of FIG. 19 show that treatment with VR-18013AD significantly reduces hyperphosphorylated Tau deposition in VR-18013AD treated 3xTg-AD mice vs 3xTg-AD control mice. The photographs in FIG. 20 show significant reduction of p-tau in hippocampal region after VR-18013AD treated treatment. In summary, a single IV injection of VR-18013AD shows significant therapeutic activity in an Alzheimer's disease mouse model.

Example 14: VR-18014AD as Treatment of Peritoneal Carcinomatosis

Figure 21:
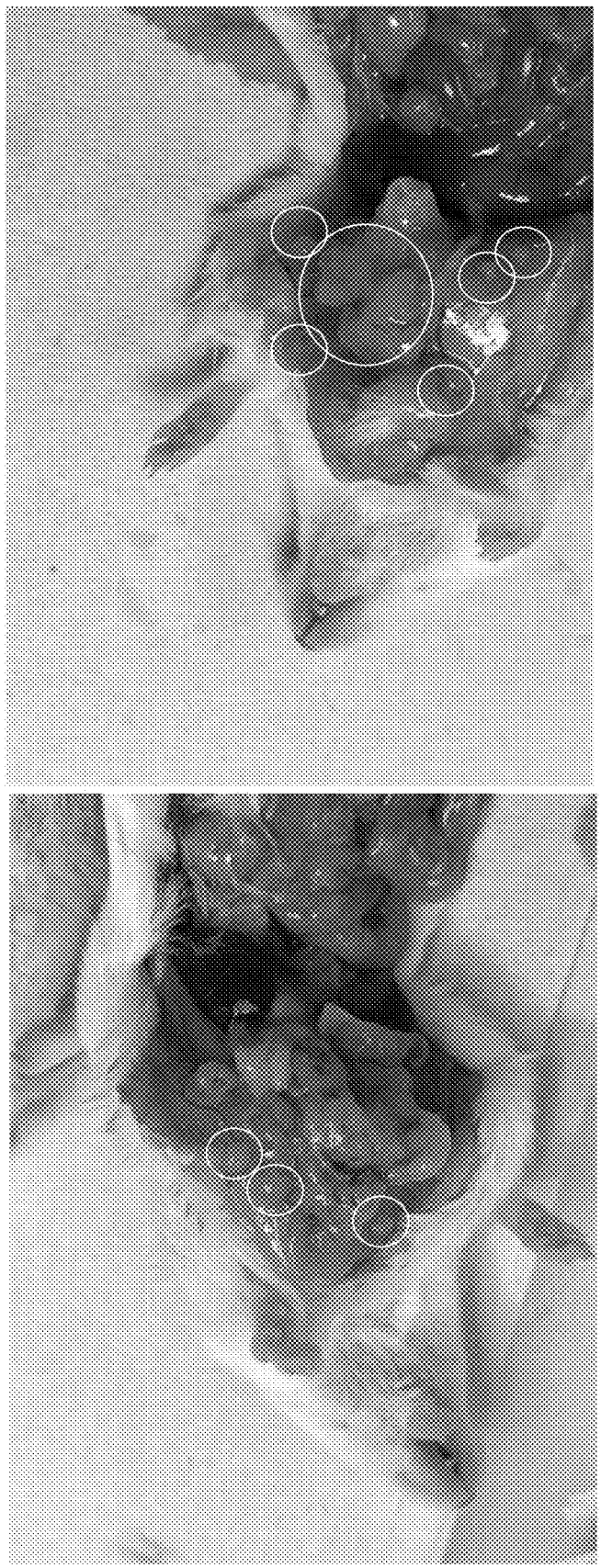
FIG. 21 shows a typical morphometric image of control (single IV injection of PBS) and VR-18014AD (single IV injection of VR-18014AD at $1.0 \times 10^{11}$ GC/per mouse dose) treated mice.

Twelve BALB/c mice (20-22 g) of the IBCH RAS breed were housed at a controlled temperature of 20-22° C. At day 1, mice were injected intraperitoneally with 200 µl of a cell suspension comprising $5 \times 10^5$ CT26 NNMU induced undifferentiated colon carcinoma cells. At day 6 following tumor transplant, mice were randomly assigned to the control group (six mice, single IV injection of PBS) or the treatment group (six mice, single IV injection of VR-18014AD at $1.0 \times 10^{11}$ GC/per mouse dose). A morphometric assessment and measurement of the number of tumor nodes in each group were performed on day 16 after tumor cell inoculation following mice euthanasia. Mice from the control group had 14-22 tumor nodes per mouse, with part of the nodes forming agglomerates. In contrast, VR-18014AD treated mice had just 2-5 nodes of smaller size with no signs of agglomerate formation. Typical morphometric images of control and VR-18014AD-treated mice are shown in FIG. 21.

Example 15: CfDNA Extracted from Mice with Induced Leaky Gut Triggers Tau Aggregation, and Liver-Specific DNase Gene Transfer Suppresses the Ability of cfDNA to Induce Tau Aggregation Aggregated tau protein is associated with over 20 neurological disorders, including Alzheimer's disease. Leaky gut was induced in 18 rats as specified in Example 7. The tested vectors and compositions were administered to the mice according to a predetermined regimen as shown in Table 12 below:

TABLE 12

| Treatment group | Number of animals | Leaky gut induction | Treatment | Euthanasia and blood sampling |
|---|---|---|---|---|
| VR-18013AD $10^{12}$ GC/kg single IV | 3 | D 0 | D 5 | D 9 |
| VR-18013AD $10^{10}$ GC/kg single IV | 3 | D 0 | D 5 | D 9 |
| VR-18014AD $10^{12}$ GC/kg single IV | 3 | D 0 | D 5 | D 9 |
| VR-18014AD $10^{10}$ GC/kg single IV | 3 | D 0 | D 5 | D 9 |
| ADV-207186 $0.2 \times 10^{12}$ PFU/kg single IV | 3 | D 0 | D 5 | D 9 |
| Liver pLV2-IL2ss-DNaseI mut $1.0 \times 10^{13}$ LVP/kg | 3 | D 0 | D 5 | D 9 |
| Control (PBS single IV) | 3 | D 0 | D 5 | D 9 |
| DNase I 50 mg/kg single dose IV | 3 | D 0 | D 8 | D 9 | cfDNA extraction was performed as follows. Peripheral blood samples (5 ml) were collected through cardiopuncture in cell free DNA BCT tubes. Plasma was separated from the cellular fraction with a first centrifugation at 800 g at 4° C. for 10 min. The plasma was further centrifuged at 13,000 g at 4° C. for 10 min to pellet and remove any remaining cells, and then stored in 1 ml aliquots at −80° C. until DNA extraction.

For cfDNA extraction, QIAamp Circulating Nucleic Acid (Qiagen) was used following the manufacturer's protocol.

An evaluation of cfDNA on Tau aggregation was performed. Full-length human Tau (4R2N) was used. For the assay, a solution comprising 1 mg/ml of Tau monomer in the presence of 2.5 µM heparin in 100 mM HEPES pH 7.4, 100 mM NaCl was incubated in the presence of 25 µl of extracted cfDNA at 20° C. with cyclic agitation (1 min shaking at 500 rpm followed by 29 min without shaking). The total sample volume was 200 µl; the solution also comprised 5 µM Thioflavin T. Aggregation was followed over time by ThT fluorescence (excitation 435 nm, emission 485 nm).

The results are summarized in Table 13 below, with both mean and SEM of three replicates indicated:

The data of Table 13 clearly demonstrate that liver-specific transgenic expression of DNase I enzyme significantly suppress the ability of cfDNA extracted from blood of animals with leaky gut to promote Tau aggregation while injections of recombinant DNaseI enzyme as well as use of non-liver specific transgenic expression of DNase I enzyme are much less effective.

REFERENCES

Song, L. et al., "NLRP3 Inflammasome in Neurological Diseases, from Functions to Therapies" Front. Cell. Neurosci., 2017, Vol. 11, No. 63.
Fleischhacker M. et al., "Circulating nucleic acids (CNAs) and cancer: a survey" Biochim Biophys Acta, 2007, 1775(1): 181-232.
Demers, M. at al., "Cancers predispose neutrophils to release extracellular DNA traps that contribute to cancer-associated thrombosis" PNAS, 2012, 109(32):13076-13081.
Garcia-Olmo D. C. and Garcia-Olmo, D. "Biological role of cell-free nucleic acids in cancer: the theory of genometastasis" Crit Rev Oncolog., 2013, 18:153-161.
Sawyers 2008 C. L., "The cancer biomarker problem" Nature, 2008, 452(7187):548-552.
Butt A. N. et al. Overview of circulating nucleic acids in plasma/serum. Ann. N.Y. Acad. Sci 2008, 1137:236-242.
Schwarzenbach H. et al., "Detection and monitoring of cell-free DNA in blood of patients with colorectal cancer" Ann. N.Y. Acad. Sci., 2008, 1137:190-196.
Zenaro E, et al., Neutrophils promote Alzheimer's disease-like pathology and cognitive decline via LFA-1 integrin. Nat Rev Nephrol., 2015, Author manuscript; available in PMC 2017 Jul. 14.
Fushi, W. et al., "Extracellular DNA in Pancreatic Cancer Promotes Cell Invasion and Metastasis" Cancer Res., 2013, 73:4256-4266.
Tohme, S. et al., "Neutrophil Extracellular Traps Promote the Development and Progression of Liver Metastases after Surgical Stress" Cancer Res., 2016 Mar. 15, 76(6): 1367-1380.

TABLE 13

| | Aggregation, ThT fluorescence | | | | | | | |
|---|---|---|---|---|---|---|---|---|
| Time (h) | VR-18013AD $10^{10}$ GC/kg single IV | VR-18013AD $10^{12}$ GC/kg single IV | VR-18014AD $10^{10}$ GC/kg single IV | VR-18014AD $10^{12}$ GC/kg single IV | ADV-207186 $0.2 \times 10^{12}$ PFU/kg single IV | Liver pLV2-IL2ss-DNaseI mut $1.0 \times 10^{13}$ L VP/kg | Control (PBS single IV) | DNase I 50 mg/kg single dose IV |
| 24 | 0 | 0 | 0 | 0 | 0 | 0 | 0 | 0 |
| 48 | 0 | 0 | 0 | 0 | 16 ± 4 | 0 | 12 ± 2 | 8 ± 2 |
| 72 | 0 | 0 | 0 | 0 | 18 ± 2 | 0 | 16 ± 5 | 13 ± 4 |
| 96 | 0 | 0 | 0 | 0 | 48 ± 7 | 0 | 34 ± 6 | 39 ± 9 |
| 120 | 0 | 0 | 0 | 0 | 52 ± 12 | 0 | 45 ± 11 | 44 ± 7 |
| 144 | 0 | 0 | 0 | 0 | 60 ± 9 | 0 | 67 ± 8 | 53 ± 5 |
| 168 | 0 | 0 | 0 | 0 | 96 ± 18 | 0 | 88 ± 12 | 74 ± 6 |
| 192 | 4 ± 3 | 0 | 0 | 0 | 121 ± 25 | 0 | 109 ± 10 | 92 ± 12 |
| 216 | 8 ± 4 | 10 ± 2 | 15 ± 5 | 7 ± 2 | 143 ± 38 | 13 ± 5 | 158 ± 24 | 116 ± 18 |
| 240 | 22 ± 4 | 12 ± 5 | 34 ± 9 | 15 ± 3 | 237 ± 42 | 27 ± 5 | 249 ± 38 | 162 ± 29 |
| 264 | 42 ± 14 | 27 ± 5 | 49 ± 9 | 30 ± 4 | 275 ± 43 | 39 ± 7 | 286 ± 42 | 191 ± 44 |
| 288 | 56 ± 4 | 39 ± 8 | 65 ± 11 | 36 ± 3 | 364 ± 58 | 46 ± 7 | 351 ± 41 | 249 ± 36 |
| 312 | 75 ± 6 | 54 ± 8 | 89 ± 13 | 44 ± 10 | 384 ± 49 | 52 ± 11 | 336 ± 34 | 285 ± 31 |
| 336 | 98 ± 8 | 67 ± 10 | 109 ± 15 | 76 ± 8 | 360 ± 62 | 95 ± 138 | 342 ± 53 | 302 ± 44 |

Patutina, O. et al., Inhibition of metastasis development by daily administration of ultralow doses of RNase A and DNase I. *Biochimie.*, 2011 April, 93(4): 689-96.

Dan Li, DNase I Treatment Reduces GVHD in Mice. Biology of Blood and Marrow Transplantation, Volume 21, Issue 2, Page S339.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A method for inhibiting growth of a primary tumor in a subject having a cancer accompanied by accumulation of cell free DNA (cfDNA) in the hepatic porto-sinusoidal circulation of the subject, said method comprising administering to the subject a therapeutically effective amount of a recombinant adeno-associated virus (rAAV) expression vector comprising (i) a capsid protein and (ii) a nucleic acid comprising a promoter operably linked to a nucleotide sequence encoding an enzyme which has a deoxyribonuclease (DNase) activity, wherein the promoter is a liver-specific promoter, wherein the nucleic acid comprises the sequence of SEQ ID NO: 30 or SEQ ID NO: 31, and wherein the administration of the rAAV vector results in inhibiting growth of the primary tumor in the subject.

2. A method for inhibiting growth of a primary tumor in a subject having a cancer accompanied by accumulation of cell free DNA (cfDNA) in the hepatic porto-sinusoidal circulation of the subject, said method comprising administering to the subject an expression vector comprising a nucleic acid comprising a promoter operably linked to a sequence encoding an enzyme which has a deoxyribonuclease (DNase) activity, wherein the promoter is a liver specific promoter and/or wherein the vector comprises one or more molecules capable of targeting of the nucleic acid to liver cells, wherein the nucleic acid comprises the sequence of SEQ ID NO: 30 or SEQ ID NO: 31, and wherein the administration of the vector results in inhibiting growth of the primary tumor in the subject.

3. The method of claim 2, wherein the subject is human.

4. The method of claim 2, wherein the subject has an elevated level of cell-free DNA (cfDNA) in the bloodstream as compared to a level of cfDNA in the bloodstream of a normal healthy subject.

5. The method of claim 1, wherein the cancer is selected from the group consisting of a peritoneal carcinomatosis, a lymphoma, a stomach cancer, a colon cancer, an intestinal cancer, a colorectal cancer, a pancreatic cancer, a liver cancer, a cancer of the bile duct, a cancer of the gall bladder, a sarcoma, a breast cancer, a lung cancer, and a brain cancer.

6. The method of claim 1, wherein the AAV is from serotype 8 or Anc 80.

* * * * *